United States Patent
Hunag et al.

(10) Patent No.: US 8,129,394 B2
(45) Date of Patent: Mar. 6, 2012

(54) HETEROARYL-SUBSTITUTED IMIDAZOLE COMPOUNDS AND USES THEREOF

(75) Inventors: Zilin Hunag, San Leandro, CA (US); Jeff Jin, San Ramon, CA (US); Timothy Machajewski, Martinez, CA (US); William R. Antonios-McCrea, Moraga, CA (US); Maureen McKenna, Pinole, CA (US); Daniel Poon, Piedmont, CA (US); Paul A. Renhowe, Emeryville, CA (US); Martin Sendzik, San Mateo, CA (US); Cynthia Shafer, Moraga, CA (US); Aaron Smith, Union City, CA (US); Yongjin Xu, Castro Valley, CA (US); Qiong Zhang, Union City, CA (US); Zheng Chen, Fremont, CA (US)

(73) Assignee: Novartis AG, Basel (CH)

( * ) Notice: Subject to any disclaimer, the term of this patent is extended or adjusted under 35 U.S.C. 154(b) by 280 days.

(21) Appl. No.: 12/383,035

(22) Filed: Mar. 19, 2009

(65) Prior Publication Data

US 2010/0003246 A1    Jan. 7, 2010

Related U.S. Application Data

(60) Provisional application No. 61/038,723, filed on Mar. 21, 2008, provisional application No. 61/208,458, filed on Feb. 24, 2009.

(51) Int. Cl.
| | |
|---|---|
| A61K 31/4965 | (2006.01) |
| A61K 31/505 | (2006.01) |
| A01N 43/54 | (2006.01) |
| C07D 403/00 | (2006.01) |
| C07D 401/00 | (2006.01) |
| C07D 405/00 | (2006.01) |
| C07D 409/00 | (2006.01) |
| C07D 411/00 | (2006.01) |
| C07D 413/00 | (2006.01) |
| C07D 417/00 | (2006.01) |
| C07D 419/00 | (2006.01) |

(52) U.S. Cl. .................. 514/255.05; 514/275; 544/295; 544/331

(58) Field of Classification Search .................. None
See application file for complete search history.

(56) References Cited

U.S. PATENT DOCUMENTS

| | | |
|---|---|---|
| 5,717,100 A | 2/1998 | Selnick et al. |
| 2003/0166633 A1 | 9/2003 | Gaster et al. |
| 2005/0282805 A1 | 12/2005 | Hangeland et al. |

FOREIGN PATENT DOCUMENTS

| | | |
|---|---|---|
| DE | 21 55 558 A1 | 6/1972 |
| EP | 1 232 153 B1 | 11/2004 |
| EP | 1 721 905 A1 | 11/2006 |
| JP | 02 188579 | 7/1990 |
| JP | 03 157383 | 7/1991 |
| JP | 2007 246520 | 9/2007 |
| WO | WO 01/66540 | 9/2001 |
| WO | WO 02/39954 | 5/2002 |
| WO | WO 2005/047266 A1 | 5/2005 |
| WO | WO 2005/103028 | 11/2005 |

OTHER PUBLICATIONS

Deng, et. al., Journal of Medicinal Chemistry (2006), 49(2), 490-500.*

Kim, Heon-Gon et al., "Synthesis of Heteroaryl Substituted Imidazole Derivatives" Bull. Korean Chem. Soc. 2000 21(3):345-347.

Krayushkin, M.M. et al., "Photochromic Dihetarylethenes 7.* Synthesis . . ." Russian Chemical Bulletin, International Edition Jan. 2001 50(1):116-121.

Kim, Dae-Kee et al., "Systhesis and Biological Evaluation of 4(5)-(6-Alkylpyridin-2-yl)Imidazoles . . ." J. Med. Chem. 2007 50:3143-3147.

* cited by examiner

Primary Examiner — Jeffrey Murray
(74) Attorney, Agent, or Firm — Michael G. Smith

(57) ABSTRACT

Novel imidazole compounds of the general formula

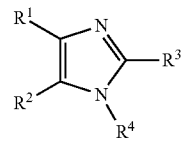

are disclosed, wherein $R^1$ and $R^2$ comprise heteroaryl groups. These compounds and compositions containing them are useful in methods to treat Raf kinase-mediated disorders such as cancer.

13 Claims, No Drawings

HETEROARYL-SUBSTITUTED IMIDAZOLE COMPOUNDS AND USES THEREOF

RELATED APPLICATIONS

This application claims benefit of priority to U.S. Provisional Ser. No. 61/038,723, filed Mar. 21, 2008, and U.S. Provisional Ser. No. 61/208,458, filed Feb. 24, 2009, the contents of which are incorporated herein by reference in their entirety.

FIELD OF THE INVENTION

The present invention relates to new substituted heterocyclic compounds and pharmaceutically acceptable salts thereof, compositions of the new compounds together with pharmaceutically acceptable carriers, and uses of the new compounds, either alone or in combination with at least one additional therapeutic agent, in the prophylaxis or treatment of cancer and other disorders mediated by Raf kinase.

BACKGROUND OF THE INVENTION

The Raf serine/threonine kinases are essential components of the Ras/Mitogen-Activated Protein Kinase (MAPK) signaling module that controls a complex transcriptional program in response to external cellular stimuli. Raf genes code for highly conserved serine-threonine-specific protein kinases which are known to bind to the Ras oncogene. They are part of a signal transduction pathway believed to consist of receptor tyrosine kinases, p21 Ras, Raf protein kinases, Mek kinases and ERK (MAPK) kinases, which ultimately phosphorylate transcription factors. In this pathway Raf kinases are activated by Ras and phosphorylate and activate two isoforms of Mitogen-Activated Protein Kinase (called Mek1 and Mek2), that are dual specificity threonine/tyrosine kinases. Both Mek isoforms activate Mitogen Activated Kinases 1 and 2 (MAPK, also called Extracellular Ligand Regulated Kinase 1 and 2 or Erk1 and Erk2). The MAPKs phosphorylate many substrates, including transcription factors, and in so doing set up their transcriptional program. Raf kinase participation in the Ras/MAPK pathway influences and regulates many cellular functions such as proliferation, differentiation, survival, oncogenic transformation and apoptosis.

Both the essential role and the position of Raf in many signaling pathways have been demonstrated from studies using deregulated and dominant inhibitory Raf mutants in mammalian cells as well as from studies employing biochemical and genetic techniques to model organisms. In many cases, the activation of Raf by receptors that stimulate cellular tyrosine phosphorylation is dependent on the activity of Ras, indicating that Ras functions upstream of Raf. Upon activation, Raf then phosphorylates and activates Mek, resulting in the propagation of the signal to downstream effectors, such as MAPK (mitogen-activated protein kinase) (Crews et al. (1993) Cell 74:215).

Raf kinase has three distinct isoforms, Raf-1 (c-Raf), a-Raf, and b-Raf, distinguished by their ability to interact with Ras, to activate MAPK kinase pathway, tissue distribution and sub-cellular localization (Marias et. al., Biochem. J. 351: 289-305, 2000; Weber et. al., Oncogene 19:169-176, 2000; Pritchard et. al., Mol. Cell. Biol. 15:6430-6442, 1995).

Activating mutation of one of the Ras genes can be seen in ~20% of all tumors and the Raf/MEK/ERK pathway is activated in ~30% of all tumors (Bos et. al., Cancer Res. 49:4682-4689, 1989) (Hoshino et. al., Oncogene 18:813-822, 1999). Recent studies have shown that b-Raf mutation in the skin nevi is a critical step in the initiation of melanocytic neoplasia (Pollock et. al., Nature Genetics 25: 1-2, 2002). Furthermore, most recent studies indicate that activating mutation in the kinase domain of b-Raf occurs in ~66% of melanomas, 12% of colon carcinoma and 14% of liver cancer (Davies et. al., Nature 417:949-954, 2002) (Yuen et. al., Cancer Research 62:6451-6455, 2002) (Brose et. al., Cancer Research 62:6997-7000, 2002).

Inhibitors of Raf/MEK/ERK pathway at the level of Raf kinases can potentially be effective as therapeutic agents against tumors with over-expressed and/or mutated receptor tyrosine kinases, activated intracellular tyrosine kinases, tumors with aberrantly expressed Grb2 (an adapter protein that allows stimulation of Ras by the Sos exchange factor) as well as tumors harboring activating mutations of Ras or Raf. In the early clinical trials inhibitors of Raf-1 kinase that also inhibit b-Raf have shown promise as therapeutic agents in cancer therapy (Crump, Current Pharmaceutical Design 8: 2243-2248, 2002; Sebastien et. al., Current Pharmaceutical Design 8: 2249-2253, 2002).

Disruption of Raf expression in cell lines through the application of RNA antisense technology has been shown to suppress both Ras and Raf-mediated tumorigenicity (Kolch et al., Nature 349:416-428, 1991; Monia et al., Nature Medicine 2(6):668-675, 1996).

Several Raf kinase inhibitors have been described as exhibiting efficacy in inhibiting tumor cell proliferation in vitro and/or in vivo assays (see, e.g., U.S. Pat. Nos. 6,391,636, 6,358,932, 6,037,136, 5,717,100, 6,458,813, 6,204,467, and 6,268,391). Other patents and patent applications suggest the use of Raf kinase inhibitors for treating leukemia (see, e.g., U.S. Pat. Nos. 6,268,391, 6,204,467, 6,756,410, and 6,281,193; and abandoned U.S. Patent Application Nos. 20020137774 and 20010006975), or for treating breast cancer (see, e.g., U.S. Pat. Nos. 6,358,932, 5,717,100, 6,458,813, 6,268,391, 6,204,467 and 6,911,446).

SUMMARY OF THE INVENTION

The present invention provides novel compounds and methods for their use, including methods of treating cancer and other conditions mediated by Raf kinase.

In one aspect, the present invention embraces compounds having the formula I:

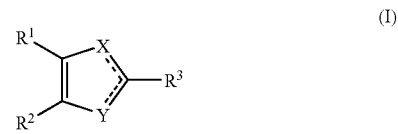

wherein:

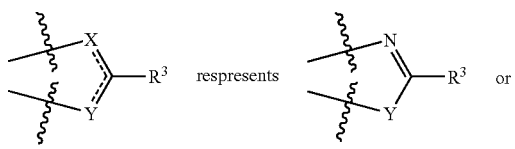 respresents

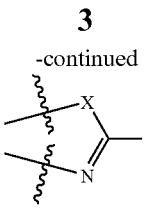

X or Y, whichever is present, is selected from the group consisting of NR⁴, O, and S;

R¹ is optionally substituted heteroaryl or optionally substituted heterocyclyl;

R² is optionally substituted heteroaryl, or optionally substituted heterocyclyl;

R³ is optionally substituted alkyl, optionally substituted aryl, optionally substituted heteroaryl, optionally substituted cycloalkyl, or optionally substituted heterocyclyl; and R⁴ is hydrogen or optionally substituted alkyl, including tautomers of the central imidazole ring when X or Y is NH or a stereoisomer or pharmaceutically acceptable salt thereof.

These compounds are further described herein.

In another aspect, the invention provides a compound of the following Formula (VI):

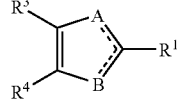

or a pharmaceutically acceptable salt thereof, wherein:

one of A or B is N and the other of A or B is NR²;

one of dashed lines ---- represent a single bond and the other represents a double bond, so the central ring is an imidazole;

R¹ is selected from H, C$_{1-3}$ alkyl, cyclopropyl, phenyl, (4-OH)-phenyl, (4-CH$_3$O)-phenyl, (4-CF$_3$O)-phenyl, (4-F)-phenyl, (4-alkylsulfonyl)piperazin-1-yl, and —O—(CH$_2$)$_{1-4}$—NR$_{10}$R$_{11}$;

R² is selected from H and C$_{1-2}$ alkyl;

R³ is selected from:

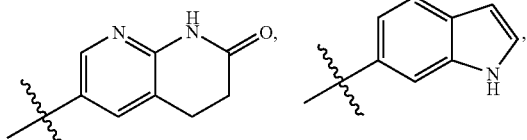

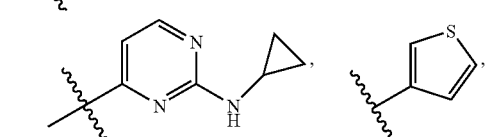

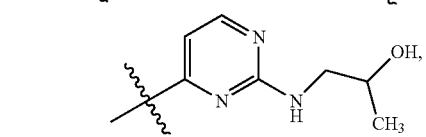

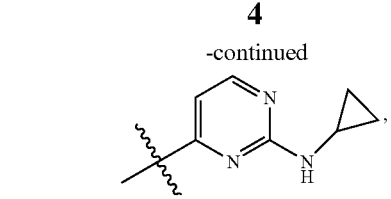

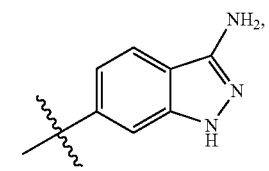

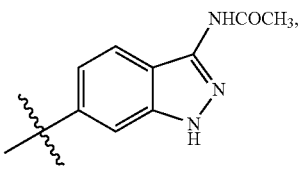

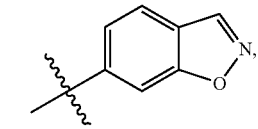

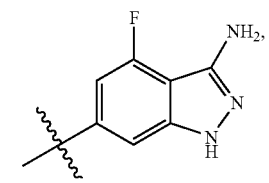

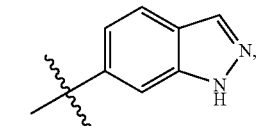

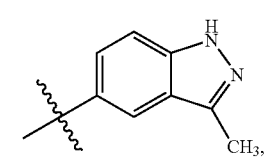

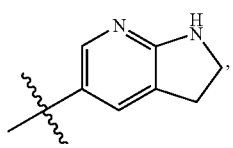

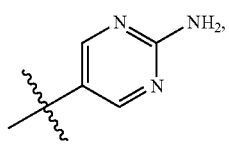

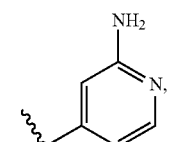

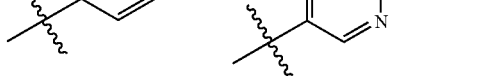

-continued
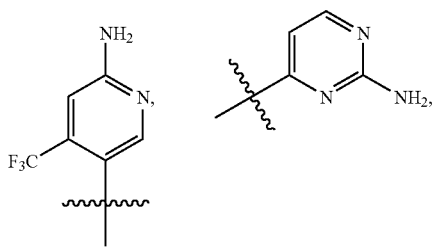
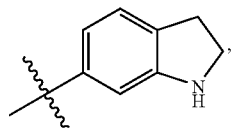
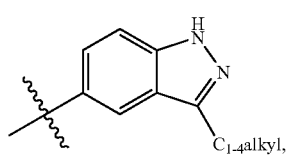
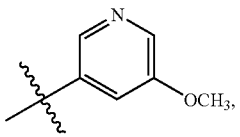
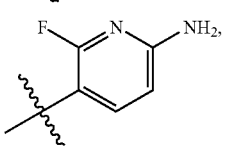
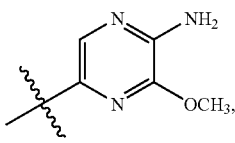
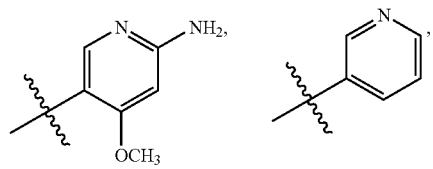
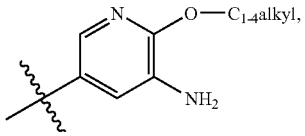
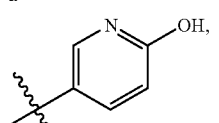
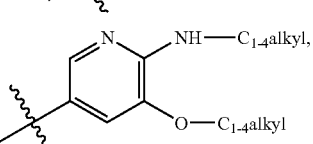
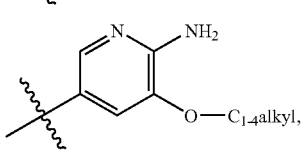
-continued
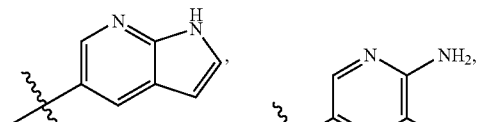
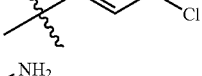
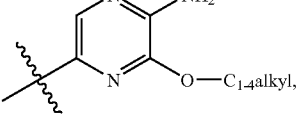
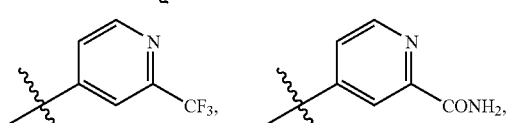
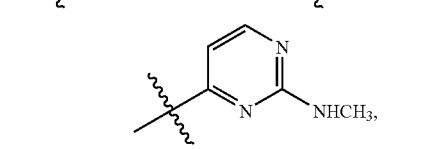
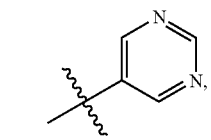
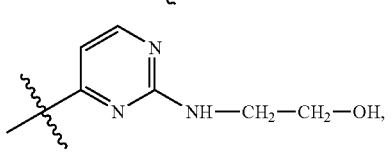
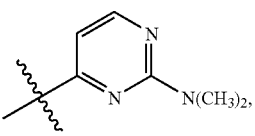
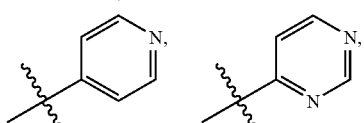
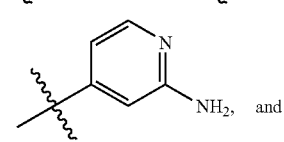
and
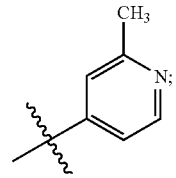
$R^4$ is selected from:
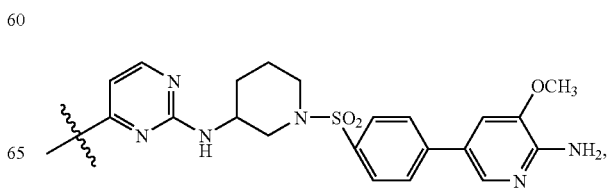

-continued

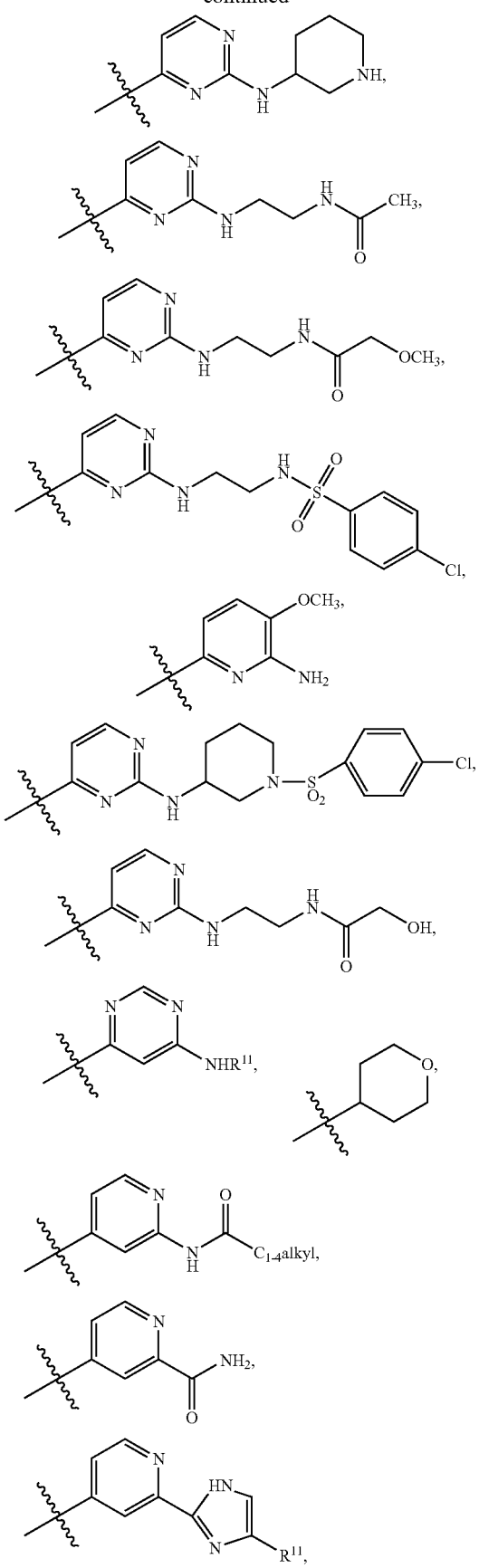

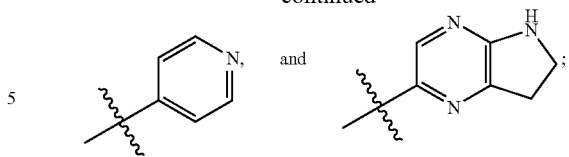

and $R^{10}$ and $R^{11}$ independently are selected from H and $C_{1-4}$ alkyl.

In another aspect provided is a compound of Formula (VII) or a pharmaceutically acceptable salt thereof:

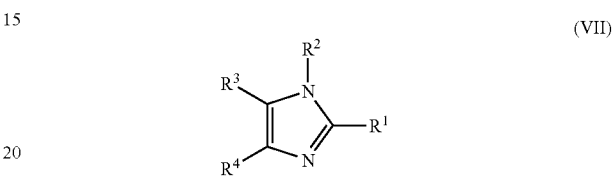

(VII)

wherein $R^1$, $R^2$, $R^3$, and $R^4$ are as defined for Formula (VI).

In another aspect of the present invention are provided formulations comprising any of the compounds described herein and a pharmaceutically acceptable carrier.

In certain embodiments of the present invention are provided formulations comprising an effective amount of a compound of any one of the compounds described herein and a pharmaceutically acceptable carrier.

In certain embodiments of the present invention are provided formulations comprising any one of the compounds described herein admixed with at least one pharmaceutically acceptable excipient.

In certain embodiments, the excipient is selected from the group consisting of corn starch, potato starch, tapioca starch, starch paste, pre-gelatinized starch, sugars, gelatin, natural gums, synthetic gums, sodium alginate, alginic acid, tragacanth, guar gum, cellulose, ethyl cellulose, cellulose acetate, carboxymethyl cellulose calcium, sodium carboxymethylcellulose, methyl cellulose, hydroxypropyl methylcellulose, microcrystalline cellulose, magnesium aluminum silicate, polyvinyl pyrrolidone, talc, calcium carbonate, powdered cellulose, dextrates, kaolin, mannitol, silicic acid, sorbitol, agar-agar, sodium carbonate, croscarmellose sodium, crospovidone, polacrilin potassium, sodium starch glycolate, clays, sodium stearate, calcium stearate, magnesium stearate, stearic acid, mineral oil, light mineral oil, glycerin, sorbitol, mannitol, polyethylene glycol, other glycols, sodium lauryl sulfate, hydrogenated vegetable oil, peanut oil, cottonseed oil, sunflower oil, sesame oil, olive oil, corn oil, soybean oil, zinc stearate, sodium oleate, ethyl oleate, ethyl laureate, silica, and combinations thereof.

In certain embodiments of the present invention are provided formulations described herein which further comprise at least one additional agent for the treatment or prevention of cancer. In some variations, the additional therapeutic agent is selected from an anticancer compound, an analgesic, an antiemetic, an antidepressant, an anti-inflammatory agent, a different Raf kinase inhibitor, an inhibitor of MEK, mTOR, PI3K, CDK9, PAK, Protein Kinase C, a MAP kinase, a MAPK Kinase, ERK, irinotecan, topotecan, gemcitabine, 5-fluorouracil, leucovorin, carboplatin, cisplatin, oxaliplatin, taxanes, tezacitabine, cyclophosphamide, vinca alkaloids, imatinib, anthracyclines, rituximab and trastuzumab.

In another aspect of the present invention methods are provided to treat cancer, comprising administering to a subject in need of such treatment an effective amount of any one of the compounds or pharmaceutical compositions described herein. In certain embodiments of the present invention, the cancer is selected from the group consisting of lung carcinoma, pancreatic carcinoma, bladder carcinoma, colon carcinoma, myeloid disorders, prostate cancer, thyroid cancer, melanoma, and adenomas.

In certain embodiments of the present invention, the methods described herein further comprise administering to the individual at least one additional agent for the treatment or prevention of cancer. In some variations, the additional agent is selected from an anticancer compound, an analgesic, an antiemetic, an antidepressant, an anti-inflammatory agent, a different Raf kinase inhibitor, an inhibitor of MEK, mTOR, PI3K, CDK9, PAK, Protein Kinase C, a MAP kinase, a MAPK Kinase, ERK, irinotecan, topotecan, gemcitabine, 5-fluorouracil, leucovorin, carboplatin, cisplatin, oxaliplatin, taxanes, tezacitabine, cyclophosphamide, vinca alkaloids, imatinib, anthracyclines, rituximab, and trastuzumab.

In certain embodiments of the present invention, the additional therapeutic agent is administered to the subject concurrently with the compound.

In another aspect of the present invention are provided methods for the treatment or prevention of a condition mediated by Raf kinase, comprising administering to a subject in need thereof an effective amount of any of the compounds or pharmaceutical compositions described herein. In some variations, the Raf kinase is a mutant b-Raf kinase.

In another aspect of the present invention is any one of the compounds described herein for use as a medicament, or for the manufacture of a medicament, or use of a compound as described herein as a medicament for treating cancer.

In another aspect of the present invention is the use of one or more of any one of the compounds described herein for the manufacture of a medicament for the treatment or prevention of a condition characterized by Raf kinase activity. In some variations, the condition is cancer.

DETAILED DESCRIPTION OF CERTAIN EMBODIMENTS

Abbreviations and Definitions

Where linking groups are specified by their conventional chemical formula herein, written from left to right, they equally encompass the chemically identical substituents that would result from writing the structure from right to left, e.g., —CH$_2$O— is intended to include —OCH$_2$— for this purpose only.

As used herein, "hydrocarbyl" refers to a residue which contains only carbon and hydrogen, unless otherwise described as 'substituted'. The residue may be aliphatic or aromatic, straight-chain, cyclic, branched, saturated or unsaturated, or any combination of these. The hydrocarbyl residue, when so described, however, may contain heteroatoms in addition to or instead of the carbon and hydrogen members of the hydrocarbyl group itself. Thus, when specifically noted as containing heteroatoms the hydrocarbyl group may contain heteroatoms within the "backbone" of the hydrocarbyl residue, and when optionally substituted, the hydrocarbyl residue may also have one or more carbonyl groups, amino groups, hydroxyl groups and the like in place of one or more hydrogens of the parent hydrocarbyl residue.

The term "alkyl," by itself or as part of another substituent, means, unless otherwise stated, a fully saturated straight-chain (linear; unbranched) or branched chain, or combination thereof, having the number of carbon atoms specified, if designated (i.e. $C_1$-$C_{10}$ means one to ten carbons). Examples include, but are not limited to, groups such as methyl, ethyl, n-propyl, isopropyl, n-butyl, t-butyl, isobutyl, sec-butyl, homologs and isomers of, for example, n-pentyl, n-hexyl, n-heptyl, n-octyl, and the like. If no size is designated, the alkyl groups mentioned herein contain 1-10 carbon atoms, typically 1-8 carbon atoms, and often 1-6 or 1-4 carbon atoms.

The term "alkenyl" refers to unsaturated aliphatic groups including straight-chain (linear; unbranched), branched-chain groups, and combinations thereof, having the number of carbon atoms specified, if designated, which contain at least one double bond (—C=C—). All double bonds may be independently either (E) or (Z) geometry, as well as mixtures thereof. Examples of alkenyl groups include, but are not limited to, —CH$_2$—CH=CH—CH$_3$; —CH=CH—CH=CH$_2$ and —CH$_2$—CH=CH—CH(CH$_3$)—CH$_2$—CH$_3$. If no size is specified, the alkenyl groups discussed herein contain 2-6 carbon atoms.

The term "alkynyl" refers to unsaturated aliphatic groups including straight-chain (linear; unbranched), branched-chain groups, and combinations thereof, having the number of carbon atoms specified, if designated, which contain at least one carbon-carbon triple bond (—C≡C—). Examples of alkynyl groups include, but are not limited to, —CH$_2$—C≡C—CH$_3$; —C≡C—C≡CH and —CH$_2$—C≡C—CH(CH$_3$)—CH$_2$—CH$_3$. If no size is specified, the alkynyl groups discussed herein contain 2-6 carbon atoms.

Alkynyl and alkenyl groups can contain more than one unsaturated bond, or a mixture of double and triple bonds, and can be otherwise substituted as described for alkyl groups.

The terms "alkoxy," "alkenyloxy," and "alkynyloxy" refer to —O-alkyl, —O-alkenyl, and —O-alkynyl, respectively.

The term "cycloalkyl" by itself or in combination with other terms, represents, unless otherwise stated, cyclic versions of alkyl, alkenyl, or alkynyl, or mixtures thereof. Additionally, cycloalkyl may contain fused rings, but excludes fused aryl and heteroaryl groups, and cycloalkyl groups can be substituted unless specifically described as unsubstituted. Examples of cycloalkyl include, but are not limited to, cyclopropyl, cyclobutyl, cyclopentyl, cyclohexyl, 1-cyclohexenyl, 3-cyclohexenyl, cycloheptyl, norbornyl, and the like. If no ring size is specified, the cycloalkyl groups described herein contain 3-8 ring members, or 3-6 ring members.

As used herein "loweralkyl" includes both substituted or unsubstituted straight or branched chain alkyl groups having from 1 to 6 carbon atoms. Representative loweralkyl groups include, for example, methyl, ethyl, propyl, isopropyl, n-butyl, tert-butyl, neopentyl, trifluoromethyl, pentafluoroethyl and the like. Loweralkyl groups may be substituted, such as with halo, hydroxy, amino, nitro and/or cyano groups, and the like. Representative of halo-substituted and hydroxy-substituted loweralkyl include chloromethyl, trichloromethyl, chloroethyl, hydroxyethyl, and the like. Other suitable substituted loweralkyl moieties include, for example, aralkyl, aminoalkyl, aminoaralkyl, carbonylaminoalkyl, alkylcarbonylaminoalkyl, arylcarbonylaminoalkyl, aralkylcarbonylaminoalkyl, aminoalkoxyalkyl and arylaminoalkyl.

The term "heterocyclic" or "heterocyclyl," by itself or in combination with other terms, represents a cycloalkyl radical containing at least one annular carbon atom and at least one annular heteroatom selected from the group consisting of O, N, P, Si and S, preferably from N, O and S, wherein the ring is not aromatic but can contain unsaturations. The nitrogen and sulfur atoms in a heterocyclic group may optionally be oxidized and the nitrogen heteroatom may optionally be quaternized. In many embodiments, the annular heteroatoms are selected from N, O and S. The heterocyclic groups discussed herein, if not otherwise specified, contain 3-10 ring members, and at least one ring member is a heteroatom selected from N, O and S; commonly not more than three of these heteroatoms are included in a heterocyclic group, and generally not more than two of these heteroatoms are present in a single ring of the heterocyclic group. The heterocyclic group can be fused to an additional carbocyclic, heterocyclic, or aryl ring. A heterocyclic group can be attached to the remainder of the molecule at an annular carbon or annular heteroatom, and the heterocyclic groups can be substituted as described for alkyl groups. Additionally, heterocyclic may contain fused rings, but excludes fused systems containing a heteroaryl group as part of the fused ring system. Examples of heterocyclic groups include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, 1,2,3,4-tetrahydropyridyl, dihydroindole (indoline), tetrahydrofuran-3-yl, tetrahydrothien-2-yl, tetrahydrothien-3-yl, 1-piperazinyl, 2-piperazinyl, and the like.

As with other moieties described herein, heterocycloalkyl moieties can be unsubstituted, or substituted with various substituents known in the art, e.g., hydroxy, halo, oxo (C=O), alkylimino (RN=, wherein R is a loweralkyl or loweralkoxy group), amino, alkylamino, dialkylamino, acylaminoalkyl, alkoxy, thioalkoxy, polyalkoxy, loweralkyl, cycloalkyl or haloalkyl. Non-limiting examples of substituted heterocycloalkyl groups include the following, where each moiety may be attached to the parent molecule at any available valence:

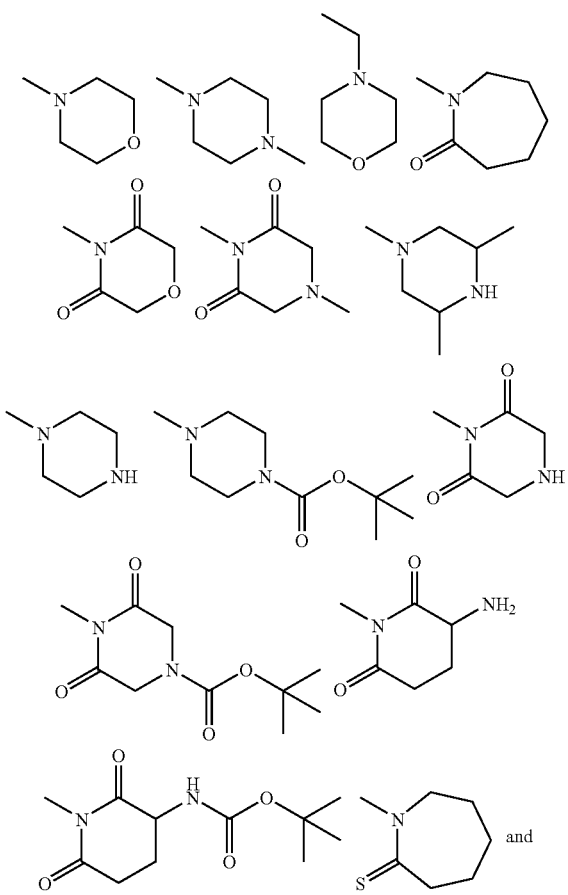

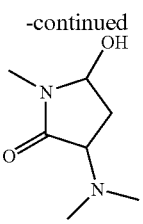

Also included within heterocyclic are piperidine, morpholine, thiomorpholine, piperazine, pyrrolidine, tetrahydrofuran, oxetane, oxepane, oxirane, tetrahydrothiofuran, thiepane, thiirane, and optionally substituted versions of each of these.

The terms "cycloalkyloxy" and "heterocycloalkyloxy" refer to —O-cycloalkyl and —O-heterocycloalkyl groups, respectively (e.g., cyclopropoxy, 2-piperidinyloxy, and the like).

The terms "cyclylalkyl" and "heterocyclylalkyl" designate an alkyl-substituted cycloalkyl group and alkyl-substituted heterocycloalkyl, respectively, where the alkyl moiety is attached to the parent structure. Non-limiting examples include cyclopropyl-ethyl, cyclobutyl-propyl, cyclopentyl-hexyl, cyclohexyl-isopropyl, 1-cyclohexenyl-propyl, 3-cyclohexenyl-t-butyl, cycloheptyl-heptyl, norbornyl-methyl, 1-piperidinyl-ethyl, 4-morpholinyl-propyl, 3-morpholinyl-t-butyl, tetrahydrofuran-2-yl-hexyl, tetrahydrofuran-3-yl-isopropyl, and the like. Cyclylalkyl and heterocyclylalkyl also include substituents in which at least one carbon atom is present in the alkyl group and wherein another carbon atom of the alkyl group has been replaced by, for example, an oxygen, nitrogen or sulfur atom (e.g., cyclopropoxymethyl, 2-piperidinyloxy-t-butyl, and the like).

The term "aryl" means, unless otherwise stated, an aromatic hydrocarbon group which can be a single ring or multiple rings (e.g., from 1 to 3 rings) which are fused together. Aryl may contain fused rings, wherein one or more of the rings is optionally cycloalkyl, but not including heterocyclic or heteroaromatic rings; a fused system containing at least one heteroaromatic ring is described as a heteroaryl group, and a phenyl ring fused to a heterocyclic ring is described herein as a heterocyclic group. Examples of aryl groups include, but are not limited to, phenyl, 1-naphthyl, 2-naphthyl, tetrahydronaphthyl and the like.

The term "heteroaryl" as used herein refers to groups comprising a single ring or two or three fused rings, where at least one of the rings is an aromatic ring that contain from one to four heteroatoms selected from N, O, and S as ring members (i.e., it contains at least one heteroaromatic ring), wherein the nitrogen and sulfur atoms are optionally oxidized, and the nitrogen atom(s) are optionally quaternized. A heteroaryl group can be attached to the remainder of the molecule through an annular carbon or annular heteroatom, and it can be attached through any ring of the heteroaryl moiety, if that moiety is bicyclic or tricyclic. Heteroaryl may contain fused rings, wherein one or more of the rings is optionally cycloalkyl or heterocycloalkyl or aryl, provided at least one of the rings is a heteroaromatic ring. Non-limiting examples of heteroaryl groups are 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below.

Aryl or heteroaryl groups commonly contain up to four substituents per ring (0-4), and sometimes contain 0-3 or 0-2 substituents. The terms "aryloxy" and "heteroaryloxy" refer to aryl and heteroaryl groups, respectively, attached to the remainder of the molecule via an oxygen linker (—O—).

The term "arylalkyl" or: "aralkyl" designates an alkyl-linked aryl group, where the alkyl portion is attached to the parent structure and the aryl is attached to the alkyl portion of the arylalkyl moiety. Examples are benzyl, phenethyl, and the like. "Heteroarylalkyl" or "heteroaralkyl" designates a heteroaryl moiety attached to the parent structure via an alkyl residue. Examples include furanylmethyl, pyridinylmethyl, pyrimidinylethyl, and the like. Aralkyl and heteroaralkyl also include substituents in which at least one carbon atom of the alkyl group is present in the alkyl group and wherein another carbon of the alkyl group has been replaced by, for example, an oxygen atom (e.g., phenoxymethyl, 2-pyridylmethoxy, 3-(1-naphthyloxy)propyl, and the like).

The terms "halo" or "halogen," by themselves or as part of another substituent, mean, unless otherwise stated, a fluorine, chlorine, bromine, or iodine atom. Additionally, terms such as "haloalkyl," are meant to include monohaloalkyl and perhaloalkyl. For example, the term "halo($C_1$-$C_4$)alkyl" is meant to include, but not be limited to, trifluoromethyl, 2,2,2-trifluoroethyl, 4-chlorobutyl, 3-bromopropyl, and the like. The prefix "perhalo" refers to the respective group wherein all available valences are replaced by halo groups. For example "perhaloalkyl" includes —$CCl_3$, —$CF_3$, —$CCl_2CF_3$, and the like. The terms "perfluoroalkyl" and "perchloroalkyl" are a subsets of perhaloalkyl wherein all available valences are replaced by fluoro and chloro groups, respectively. Non limiting examples of perfluoroalkyl include —$CF_3$ and —$CF_2CF_3$. Non limiting examples of perchloroalkyl include —$CCl_3$ and —$CCl_2CCl_3$.

"Amino" refers herein to the group —$NH_2$ or —NRR', where R and R' are each independently selected from hydrogen or an alkyl (e.g., lower alkyl). The term "arylamino" refers herein to the group —NRR' where R is aryl and R' is hydrogen, alkyl, or an aryl. The term "aralkylamino" refers herein to the group —NRR' where R is an aralkyl and R' is hydrogen, an alkyl, an aryl, or an aralkyl. "Substituted amino" refers to an amino wherein at least one of R and R' is not H, i.e., the amino has at least one substituent group on it.

The term "alkoxyalkyl" refers to the group -$alk_1$-O-$alk_2$ where $alk_1$ is alkyl or alkenyl, and $alk_2$ is alkyl or alkenyl. The term "loweralkoxyalkyl" refers to an alkoxyalkyl where $alk_1$ is loweralkyl or loweralkenyl, and $alk_2$ is loweralkyl or loweralkenyl. The term "aryloxyalkyl" refers to the group -alkyl-O-aryl. The term "aralkoxyalkyl" refers to the group -alkyl-O-aralkyl.

The term "alkoxyalkylamino" refers herein to the group —NR-(alkoxyalkyl), where R is hydrogen, aralkyl, or alkyl.

The term "aminocarbonyl" refers herein to the group —C(O)—$NH_2$, i.e., it is attached to the base structure through the carbonyl carbon atom. "Substituted aminocarbonyl" refers herein to the group —C(O)—NRR' where R is alkyl and R' is hydrogen or an alkyl. The term "arylaminocarbonyl" refers herein to the group —C(O)—NRR' where R is an aryl and R' is hydrogen, alkyl or aryl. "Aralkylaminocarbonyl" refers herein to the group —C(O)—NRR' where R is aralkyl and R' is hydrogen, alkyl, aryl, or aralkyl.

"Aminosulfonyl" refers herein to the group —S(O)$_2$—$NH_2$. "Substituted aminosulfonyl" refers herein to the group —S(O)$_2$—NRR' where R is alkyl and R' is hydrogen or an alkyl. The term "aralkylaminosulfonlyaryl" refers herein to the group -aryl-S(O)$_2$—NH-aralkyl.

"Carbonyl" refers to the divalent group —C(O)—.

"Carbonyloxy" refers generally to the group —C(O)—O—. Examples in include, —C(O)—O—R where R is H, alkyl, cycloalkyl, aryl, or aralkyl. The term "carbonyloxycycloalkyl" refers generally herein to both a "carbonyloxycarbocycloalkyl" and a "carbonyloxyheterocycloalkyl", i.e., where R is a carbocycloalkyl or heterocycloalkyl, respectively. The term "arylcarbonyloxy" refers herein to the group —C(O)—O-aryl, where aryl is a mono- or polycyclic, carbocycloaryl or heterocycloaryl. The term "aralkylcarbonyloxy" refers herein to the group —C(O)—O-aralkyl.

The term "sulfonyl" refers herein to the group —$SO_2$—. "Alkylsulfonyl" refers to a substituted sulfonyl of the structure —$SO_2R$ in which R is alkyl. Alkylsulfonyl groups employed in compounds of the present invention are typically loweralkylsulfonyl groups having from 1 to 6 carbon atoms in R. Thus, exemplary alkylsulfonyl groups employed in compounds of the present invention include, for example, methylsulfonyl (i.e., where R is methyl), ethylsulfonyl (i.e., where R is ethyl), propylsulfonyl (i.e., where R is propyl), and the like. The term "arylsulfonyl" refers herein to the group —$SO_2$-aryl. The term "aralkylsulfonyl" refers herein to the group —$SO_2$-aralkyl. The term "sulfonamido" refers herein to —$SO_2NH_2$, or to —$SO_2NRR'$ if substituted.

As used herein, the term "carbonylamino" refers to the divalent group —NH—C(O)— in which the hydrogen atom of the amide nitrogen of the carbonylamino group can be replaced by an alkyl, aryl, or aralkyl group. Such groups include moieties such as carbamate esters (—NH—C(O)—O—R) and amides —NH—C(O)R, where R is a straight or branched chain alkyl, cycloalkyl, or aryl or loweraralkyl. The term "loweralkylcarbonylamino" refers to alkylcarbonylamino where R is a loweralkyl having from 1 to about 6 carbon atoms in its backbone structure. The term "arylcarbonylamino" refers to group —NH—C(O)—R where R is an aryl. Similarly, the term "aralkylcarbonylamino" refers to carbonylamino where R is an aralkyl. As used herein, the term "aminocarbonyl" refers to the divalent group —C(O)—NH— in which the hydrogen atom of the amide nitrogen of the carbonylamino group can be replaced by an alkyl, aryl, or aralkyl group, as described above.

As used herein, the term "guanidino" or "guanidyl" refers to moieties derived from guanidine, $H_2N$—C(=NH)—$NH_2$. Such moieties include those bonded at the nitrogen atom carrying the formal double bond (the "2"-position of the guanidine, e.g., diaminomethyleneamino, ($H_2N$)$_2$C=NH—) and those bonded at either of the nitrogen atoms carrying a formal single bond (the "1-" and/or "3"-positions of the guanidine, e.g., $H_2N$—C(=NH)—NH—). The hydrogen atoms at any of the nitrogens can be replaced with a suitable substituent, such as loweralkyl, aryl, or loweraralkyl.

As used herein, the term "amidino" refers to the moieties R—C(=N)—NR'— (the radical being at the "$N^1$" nitrogen) and R(NR')C=N— (the radical being at the "$N^2$" nitrogen), where R and R' can be hydrogen, alkyl, aryl, or aralkyl.

Unless otherwise stated, each radical/moiety described herein (e.g., "alkyl," "cycloalkyl," "heterocycloalkyl," "aryl," "heteroaryl," "alkoxy," etc.) is meant to include both substituted and unsubstituted forms.

"Optionally substituted" as used herein indicates that the particular group or groups being described may have no non-hydrogen substituents (i.e., it can be unsubstituted), or the group or groups may have one or more non-hydrogen substituents. If not otherwise specified, the total number of such substituents that may be present is equal to the number of H atoms present on the unsubstituted form of the group being described. Typically, a group will contain up to three (0-3) substituents. Where an optional substituent is attached via a double bond, such as a carbonyl oxygen (=O), the group takes up two available valences on the group being substituted, so the total number of substituents that may be included is reduced according to the number of available valences. Suitable substituent groups include, for example, hydroxyl, nitro, amino, imino, cyano, halo, thio, sulfonyl, thioamido, amidino, imidino, oxo, oxamidino, methoxamidino, imidino, guanidino, sulfonamido, carboxyl, formyl, loweralkyl, loweralkoxy, loweralkoxyalkyl, alkylcarbonyl, aminocarbonyl, arylcarbonyl, aralkylcarbonyl, carbonylamino, heteroarylcarbonyl, heteroaralkylcarbonyl, alkylthio, aminoalkyl, cyanoalkyl, aryl and the like. Deuterium, when introduced into a compound at levels at least 5× above natural abundance, can also be considered a substituent for purposes of describing the compounds herein. Note that because deuterium is an isotope of hydrogen that does not substantially change the shape of the molecule, deuterium is exempt from the typical numerical limitations placed on numbers of substituents: deuterium (D) can be included in place of hydrogen (H) in addition to other substituents and should not be counted in the numerical limitations that apply to other substituents.

A substituent group can itself be substituted by the same groups described herein for the corresponding type of structure. The group substituted onto the substituted group can be carboxyl, halo, nitro, amino, cyano, hydroxyl, loweralkyl, loweralkenyl, loweralkynyl, loweralkoxy, aminocarbonyl, —SR, thioamido, —SO$_3$H, —SO$_2$R or cycloalkyl, where R is typically hydrogen or loweralkyl.

When the substituted substituent includes a straight chain group, the substituent can occur either within the chain (e.g., 2-hydroxypropyl, 2-aminobutyl, and the like) or at the chain terminus (e.g., 2-hydroxyethyl, 3-cyanopropyl, and the like). Substituted substituents can be straight chain, branched or cyclic arrangements of covalently bonded carbon or heteroatoms (N, O or S).

Alkyl, alkenyl and alkynyl groups are often substituted to the extent that such substitution makes sense chemically. Typical substituents include, but are not limited to, halo, D, =O, =N—CN, =N—O, =NR, OR, NR$_2$, SR, SO$_2$R, SO$_2$NR$_2$, NRSO$_2$R, NRCONR$_2$, NRCOOR, NRCOR, CN, COOR, CONR$_2$, OOCR, COR, and NO$_2$, wherein each R is independently H, C1-C8 alkyl, C2-C8 heteroalkyl, C1-C8 acyl, C2-C8 heteroacyl, C2-C8 alkenyl, C2-C8 heteroalkenyl, C2-C8 alkynyl, C2-C8 heteroalkynyl, C6-C10 aryl, or C5-C10 heteroaryl, and each R is optionally substituted with halo, =O, =N—CN, =N—OR', =NR', OR', NR'$_2$, SR', SO$_2$R', SO$_2$NR'$_2$, NR'SO$_2$R', NR'CONR'$_2$, NR'COOR', NR'COR', CN, COOR', CONR'$_2$, OOCR', COR', and NO$_2$, wherein each R' is independently H, D, C1-C8 alkyl, C2-C8 heteroalkyl, C1-C8 acyl, C2-C8 heteroacyl, C6-C10 aryl or C5-C10 heteroaryl. Alkyl, alkenyl and alkynyl groups can also be substituted by C1-C8 acyl, C2-C8 heteroacyl, C6-C10 aryl or C5-C10 heteroaryl, each of which can be substituted by the substituents that are appropriate for the particular group.

While "alkyl" as used herein includes cycloalkyl and cycloalkylalkyl groups, the term "cycloalkyl" may be used herein to describe a carbocyclic non-aromatic group that is connected via a ring carbon atom, and "cycloalkylalkyl" may be used to describe a carbocyclic non-aromatic group that is connected to the molecule through an alkyl linker. Similarly, "heterocyclyl" may be used to describe a non-aromatic cyclic group that contains at least one heteroatom as a ring member and that is connected to the molecule via a ring atom, which may be C or N; and "heterocyclylalkyl" may be used to describe such a group that is connected to another molecule through a linker. The sizes and substituents that are suitable for the cycloalkyl, cycloalkylalkyl, heterocyclyl, and heterocyclylalkyl groups are the same as those described above for alkyl groups. As used herein, these terms also include rings that contain a double bond or two, as long as the ring is not aromatic.

"Heteroalkyl", "heteroalkenyl" and "heteroalkynyl", like other 'heteroforms' of groups described herein, as used herein, refer to an alkyl, alkenyl or alkynyl group wherein at least one carbon of the alkyl, alkenyl or alkynyl has been replaced by a heteroatom selected from O, S and N. Typically only one, or 1-2 heteroatoms are incorporated into these groups in place of carbon atoms.

Aryl and heteroaryl moieties may be substituted with a variety of substituents including C1-C8 alkyl, C2-C8 alkenyl, C2-C8 alkynyl, C5-C12 aryl, C1-C8 acyl, and heteroforms of these, each of which can itself be further substituted. Other substituents for aryl and heteroaryl moieties include halo, D, OR, NR$_2$, SR, SO$_2$R, SO$_2$NR$_2$, NRSO$_2$R, NRCONR$_2$, NRCOOR, NRCOR, CN, COOR, CONR$_2$, OOCR, COR, and NO$_2$, wherein each R is independently H, D, C1-C8 alkyl, C2-C8 heteroalkyl, C2-C8 alkenyl, C2-C8 heteroalkenyl, C2-C8 alkynyl, C2-C8 heteroalkynyl, C6-C10 aryl, C5-C10 heteroaryl, C7-C12 arylalkyl, or C6-C12 heteroarylalkyl, and each R is optionally substituted as described above for alkyl groups. The substituent groups on an aryl or heteroaryl group may of course be further substituted with the groups described herein as suitable for each type of such substituents or for each component of the substituent. Thus, for example, an arylalkyl substituent may be substituted on the aryl portion with substituents described herein as typical for aryl groups, and it may be further substituted on the alkyl portion with substituents described herein as typical or suitable for alkyl groups.

In general, any alkyl, alkenyl, alkynyl, acyl, or aryl or arylalkyl group, or any heteroform thereof, that is contained in a substituent may itself optionally be substituted by additional substituents. The nature of these substituents is similar to those recited with regard to the primary substituents themselves if the substituents are not otherwise described. Thus, where an embodiment of, for example, R$^7$ is alkyl, this alkyl may optionally be substituted by the remaining substituents listed as embodiments for R$^7$ where this makes chemical sense, and where this does not undermine the size limit provided for the alkyl per se; e.g., alkyl substituted by alkyl or by alkenyl would simply extend the upper limit of carbon atoms for these embodiments, and is not included. However, alkyl substituted by aryl, amino, alkoxy, =O, and the like would be included within the scope of the invention, and the atoms of these substituent groups are not counted in the number used to describe the alkyl, alkenyl, etc. group that is being described. Where no number of substituents is specified, each such alkyl, alkenyl, alkynyl, acyl, or aryl group may be substituted with a number of substituents according to its available valences; in particular, any of these groups may be substituted with fluorine atoms at any or all of its available valences, for example.

As used herein, "isomer" includes all stereoisomers of the compounds referred to in the formulas herein, including enantiomers, diastereomers, as well as all conformers, rotamers, and tautomers, unless otherwise indicated. The invention includes all enantiomers of any chiral compound disclosed, in either substantially pure levorotatory or dextrorotatory form, or in a racemic mixture, or in any ratio of enantiomers. For compounds disclosed as an (R)-enantiomer, the invention also includes the (S)-enantiomer; for compounds disclosed as the (S)-enantiomer, the invention also includes the (R)-enantiomer. The invention includes any diastereomers of the compounds referred to in the above formulas in diastereomerically pure form and in the form of mixtures in all ratios.

Unless stereochemistry is explicitly indicated in a chemical structure or chemical name, the chemical structure or chemical name is intended to embrace all possible stereoisomers, conformers, rotamers, and tautomers of the compound depicted. For example, a compound containing a chiral carbon atom is intended to embrace both the (R) enantiomer and the (S) enantiomer, as well as mixtures of enantiomers, including racemic mixtures; and a compound containing two chiral carbons is intended to embrace all enantiomers and diastereomers (including (R,R), (S,S), (R,S), and (R,S) isomers).

In all uses of the compounds of the formulas disclosed herein, the invention also includes use of any or all of the stereochemical, enantiomeric, diastereomeric, conformational, rotomeric, tautomeric, solvate, hydrate, polymorphic, crystalline form, non-crystalline form, salt, pharmaceutically acceptable salt, metabolite and prodrug variations of the compounds as described.

"Protecting group" refers to a chemical group that exhibits the following characteristics: 1) is stable to the projected reactions for which protection is desired; 2) is removable from the protected substrate to yield the desired functionality; and 3) is removable by reagents compatible with the other functional group(s) present or generated in such projected reactions. Selection of suitable protecting groups for use in the methods described herein is within the ordinary skill level in the art. Examples of suitable protecting groups can be found in Greene et al. (1991) PROTECTIVE GROUPS IN ORGANIC SYNTHESIS, 3rd Ed. (John Wiley & Sons, Inc., New York). Amino protecting groups include, but are not limited to, mesitylenesulfonyl (Mts), benzyloxycarbonyl (CBz or Z), t-butyloxycarbonyl (Boc), t-butyldimethylsilyl (TBS or TBDMS), 9-fluorenylmethyloxycarbonyl (Fmoc), tosyl, benzenesulfonyl, 2-pyridyl sulfonyl, or suitable photolabile protecting groups such as 6-nitroveratryloxy carbonyl (Nvoc), nitropiperonyl, pyrenylmethoxycarbonyl, nitrobenzyl, α-,α-dimethyl-dimethoxybenzyloxycarbonyl (DDZ), 5-bromo-7-nitroindolinyl, and the like. Hydroxyl protecting groups include, but are not limited to, Fmoc, TMS, TBS, TBDPS, TES, acetyl, benzoyl, photolabile protecting groups (such as nitroveratryl oxymethyl ether (Nvom)), SEM, MOM (methoxy methyl ether), and MEM (methoxyethoxymethyl ether), NPEOC (4-nitrophenethyloxycarbonyl) and NPEOM (4-nitrophenethyloxymethyloxycarbonyl).

As used herein, the term "carboxy-protecting group" refers to a carbonyl group which has been esterified with one of the commonly used carboxylic acid protecting ester groups employed to block or protect the carboxylic acid function while reactions involving other functional sites of the compound are carried out. In addition, a carboxy protecting group can be attached to a solid support whereby the compound remains connected to the solid support as the carboxylate until cleaved by hydrolytic methods to release the corresponding free acid. Representative carboxy-protecting groups include, for example, loweralkyl esters, secondary amides and the like.

Certain compounds of the present invention can exist in unsolvated forms as well as solvated forms (i.e., solvates). Compounds of the invention may also include hydrated forms (i.e., hydrates). In general, the solvated and hydrated forms are equivalent to unsolvated forms for purposes of biological utility and are encompassed within the scope of the present invention. The invention also includes all polymorphs, including crystalline and non-crystalline forms. In general, all physical forms are equivalent for the uses contemplated by the present invention and are intended to be within the scope of the present invention.

The invention includes all salts of the compounds described herein, as well as methods of using such salts of the compounds. The invention also includes all non-salt forms of any salt of a compound named herein, as well as other salts of any salt of a compound named herein. In one embodiment, the salts of the compounds comprise pharmaceutically acceptable salts. "Pharmaceutically acceptable salts" are those salts which retain the biological activity of the free compounds and which can be administered as drugs or pharmaceuticals to humans and/or animals. The desired salt of a basic functional group of a compound may be prepared by methods known to those of skill in the art by treating the compound with an acid. Examples of inorganic acids include, but are not limited to, hydrochloric acid, hydrobromic acid, sulfuric acid, nitric acid, and phosphoric acid. Examples of organic acids include, but are not limited to, formic acid, acetic acid, propionic acid, glycolic acid, hippuric acid, pyruvic acid, oxalic acid, maleic acid, malonic acid, succinic acid, fumaric acid, tartaric acid, citric acid, benzoic acid, cinnamic acid, mandelic acid, sulfonic acids, and salicylic acid. The desired salt of an acidic functional group of a compound can be prepared by methods known to those of skill in the art by treating the compound with a base. Examples of inorganic salts of acid compounds include, but are not limited to, alkali metal and alkaline earth salts, such as sodium salts, potassium salts, magnesium salts, and calcium salts; ammonium salts; and aluminum salts. Examples of organic salts of acid compounds include, but are not limited to, procaine, dibenzylamine, N-ethylpiperidine, N,N'-dibenzylethylenediamine, and triethylamine salts.

Pharmaceutically acceptable metabolites and prodrugs of the compounds referred to in the formulas herein are also embraced by the invention. The term "pharmaceutically acceptable prodrugs" as used herein refers to those prodrugs of the compounds of the present invention which are, within the scope of sound medical judgment, suitable for use in contact with the tissues of humans and lower animals without undue toxicity, irritation, allergic response, and the like, commensurate with a reasonable benefit/risk ratio, and effective for their intended use, as well as the zwitterionic forms, where possible, of the compounds of the invention. The term "prodrug" refers to compounds that are rapidly transformed in vivo to yield the parent compound of the above formula, for example by hydrolysis in blood. A thorough discussion is provided in T. Higuchi and V. Stella, PRO-DRUGS AS NOVEL DELIVERY SYSTEMS, Vol. 14 of the A.C.S. Symposium Series, and in Edward B. Roche, ed., BIOREVERSIBLE CARRIERS IN DRUG DESIGN, American Pharmaceutical Association and Pergamon Press, 1987.

Pharmaceutically acceptable esters of the compounds referred to in the formulas herein are also embraced by the invention. As used herein, the term "pharmaceutically acceptable ester" refers to esters, which hydrolyze in vivo and include those that break down readily in the human body to leave the parent compound or a salt thereof. Suitable ester groups include, for example, those derived from pharmaceutically acceptable aliphatic carboxylic acids, particularly alkanoic, alkenoic, cycloalkanoic and alkanedioic acids, in which each alkyl or alkenyl moiety advantageously has not more than 6 carbon atoms. Examples of particular esters include formates, acetates, propionates, butyrates, acrylates and ethylsuccinates.

The invention further provides deuterated versions of the above-described compounds. As used herein, "deuterated version" refers to a compound in which at least one hydrogen atom is enriched in the isotope deuterium beyond the natural rate of deuterium occurrence. Typically, the hydrogen atom is enriched to be at least 50% deuterium, frequently at least 75% deuterium, and preferably at least about 90% deuterium. Optionally, more than one hydrogen atom can be replaced by deuterium. For example, a methyl group can be deuterated by replacement of one hydrogen with deuterium (i.e., it can be —CH$_2$D), or it can have all three hydrogen atoms replaced with deuterium (i.e., it can be —CD$_3$). In each case, D signifies that at least 50% of the corresponding H is present as deuterium.

A substantially pure compound means that the compound is present with no more than 15% or no more than 10% or no more than 5% or no more than 3% or no more than 1% of the total amount of compound as impurity and/or in a different form. For instance, substantially pure S,S compound means that no more than 15% or no more than 10% or no more than 5% or no more than 3% or no more than 1% of the total R,R; S,R; and R,S forms are present.

As used herein, "therapeutically effective amount" indicates an amount that results in a desired pharmacological and/or physiological effect for the condition. The effect may be prophylactic in terms of completely or partially preventing a condition or symptom thereof and/or may be therapeutic in terms of a partial or complete cure for the condition and/or adverse effect attributable to the condition. Therapeutically effective amounts of the compounds of the invention generally include any amount sufficient to detectably inhibit Raf activity by any of the assays described herein, by other Raf kinase activity assays known to those having ordinary skill in the art or by detecting an inhibition or alleviation of symptoms of cancer.

As used herein, the term "pharmaceutically acceptable carrier," and cognates thereof, refers to adjuvants, binders, diluents, etc. known to the skilled artisan that are suitable for administration to an individual (e.g., a mammal or non-mammal). Combinations of two or more carriers are also contemplated in the present invention. The pharmaceutically acceptable carrier(s) and any additional components, as described herein, should be compatible for use in the intended route of administration (e.g., oral, parenteral) for a particular dosage form. Such suitability will be easily recognized by the skilled artisan, particularly in view of the teaching provided herein. Pharmaceutical compositions described herein include at least one pharmaceutically acceptable carrier or excipient; preferably, such compositions include at least one carrier or excipient other than or in addition to water.

As used herein, the term "pharmaceutical agent" or "additional pharmaceutical agent," and cognates of these terms, are intended to refer to active agents other than the claimed compounds of the invention, for example, drugs, which are administered to elicit a therapeutic effect. The pharmaceutical agent(s) may be directed to a therapeutic effect related to the condition that a claimed compound is intended to treat or prevent (e.g., conditions mediated by Raf kinase, including, but not limited to those conditions described herein (e.g., cancer)) or, the pharmaceutical agent may be intended to treat or prevent a symptom of the underlying condition (e.g., tumor growth, hemorrhage, ulceration, pain, enlarged lymph nodes, cough, jaundice, swelling, weight loss, cachexia, sweating, anemia, paraneoplastic phenomena, thrombosis, etc.) or to further reduce the appearance or severity of side effects of administering a claimed compound.

A "Raf inhibitor compound" is used herein to refer to a compound that reduces or eliminates the activity of Raf Kinase. This inhibition of Raf kinase can be produced in vitro or in vivo. In some embodiments, the Raf inhibitor compound reduces or eliminates the activity of Raf Kinase in a reversible or irreversible manner. In some embodiments, the Raf inhibitor compound exhibits an IC$_{50}$ with respect to Raf Kinase activity of no more than about 100 μM and more typically not more than about 50 μM, as measured in the Raf/Mek Amplified Luminescence Proximity Homogeneous Assay described generally hereinbelow. Preferred isoforms of Raf Kinase in which the compounds of the present invention will be shown to inhibit, include a-Raf, b-Raf, b-Raf (V599E) and c-Raf (Raf-1). "IC$_{50}$" is that concentration of inhibitor which reduces the activity of an enzyme (e.g., Raf kinase) to half-maximal level. Representative compounds of the present invention have been shown to exhibit inhibitory activity against Raf. In some embodiments, compounds of the present invention exhibit an IC$_{50}$ with respect to Raf of no more than about 10 μM, or no more than about 7.5 μM, or no more than about 5 μM, or no more than about 2.5 μM, or not more than about 1 μM, or not more than about 750 nM, or not more than about 500 nM, or not more than about 200 nM, or not more than about 100 nM, or not more than about 50 nM, or not more than about 20 nM, or not more than about 10 mM, or not more than about 5 nM, or not more than about 1 nM, as measured in the Raf kinase assays described herein.

The term "cancer" or "cancer disorder" refers to cancer diseases that can be treated by the inhibition of Raf kinase, including, for example, solid cancers, such as carcinomas (e.g., of the lungs, pancreas, thyroid, bladder or colon), myeloid disorders (e.g., myeloid leukemia) and adenomas (e.g., villous colon adenoma). In some embodiments, the cancer of interest for this invention will be a cancer that expresses a mutated version of b-Raf.

When used with respect to methods of treatment/prevention and the use of the compounds and formulations thereof described herein, an individual "in need thereof" may be an individual who has been diagnosed with or previously treated for the condition to be treated. With respect to prevention, the individual in need thereof may also be an individual who is at risk for a condition (e.g., a family history of the condition, life-style factors indicative of risk for the condition, etc.). Typically, when a step of administering a compound of the invention is disclosed herein, the invention further contemplates a step of identifying an individual or subject in need of the particular treatment to be administered or having the particular condition to be treated.

In some embodiments, the individual is a mammal, including, but not limited to, bovine, horse, feline, rabbit, canine, rodent, or primate. In some embodiments, the mammal is a primate. In some embodiments, the primate is a human. In some embodiments, the individual is human, including adults, children and premature infants. In some embodiments, the individual is a non-mammal. In some variations, the primate is a non-human primate such as chimpanzees and other apes and monkey species. In some embodiments, the mammal is a farm animal such as cattle, horses, sheep, goats, and swine; pets such as rabbits, dogs, and cats; laboratory animals including rodents, such as rats, mice, and guinea pigs; and the like. Examples of non-mammals include, but are not limited to, birds, and the like. The term "individual" does not denote a particular age or sex.

In some variations, the individual has been identified as having one or more of the conditions described herein. Identification of the conditions as described herein by a skilled physician is routine in the art (e.g., via blood tests, X-rays, CT scans, endoscopy, biopsy, etc.) and may also be suspected by the individual or others, for example, due to tumor growth, hemorrhage, ulceration, pain, enlarged lymph nodes, cough, jaundice, swelling, weight loss, cachexia, sweating, anemia, paraneoplastic phenomena, thrombosis, etc. In some embodiments, the individual has further been identified as having a cancer that expresses a mutated Raf, such as a mutated b-Raf.

In some embodiments, the individual has been identified as susceptible to one or more of the conditions as described herein. The susceptibility of an individual may be based on any one or more of a number of risk factors and/or diagnostic approaches appreciated by the skilled artisan, including, but not limited to, genetic profiling, family history, medical history (e.g., appearance of related conditions), lifestyle or habits.

As used herein and in the appended claims, the singular forms "a", "an" and "the" include plural forms, unless the context clearly dictates otherwise.

Unless defined otherwise or clearly indicated by context, all technical and scientific terms used herein have the same meaning as commonly understood by one of ordinary skill in the art to which this invention belongs.

Raf Kinase Inhibitors

The compounds described herein are effective to treat cancers, as further discussed herein. Without being bound by theory, it is believed they are effective due to their inhibitory activity on Raf, and in some embodiments they are believed to be effective by inhibition of b-Raf, particularly certain mutated forms of b-Raf. Accordingly, the invention provides compounds that are inhibitors of Raf kinase and methods to use such compounds for the treatment of disorders associated with Raf activity, including cancers. In one aspect, the present invention provides compounds that inhibit or decrease the catalytic activity of a Raf kinase enzyme.

In one aspect, the compounds have the formula (I):

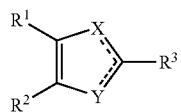

wherein:

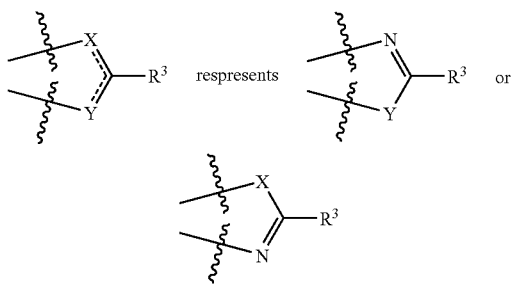

X or Y, whichever is present, is selected from the group consisting of $NR^4$, O, and S;

$R^1$ is optionally substituted heteroaryl or optionally substituted heterocyclyl;

$R^2$ is optionally substituted heteroaryl, or optionally substituted heterocyclyl;

$R^3$ is optionally substituted alkyl, optionally substituted aryl, optionally substituted heteroaryl, optionally substituted cycloalkyl, or optionally substituted heterocyclyl; and $R^4$ is hydrogen or optionally substituted alkyl, including tautomers of the central imidazole ring when X or Y is NH or a stereoisomer or pharmaceutically acceptable salt thereof.

In these compounds, one of X and Y is present, and can be $NR^4$, O or S. When X or Y is $NR^4$ where $R^4$ is H, this provides an imidazole as the central ring in Formula I, and that ring can exist as either of two tautomers (one where X is NH, and one where Y is NH). In that case it does not matter whether X or Y is NH, because the two tautomers are readily interconverted; indeed they are in equilibrium when the compound is dissolved in solution and the compound probably exists as a mixture of these tautomers whether in solid form, as an oil, or in solution. For other X or Y groups, the compound in which X is present differs from the one in which Y is present. For certain aspects of the present invention, it is preferred to have X present; for other aspects it is preferred to have Y present in the central ring.

$R^1$ is an optionally substituted heterocyclic or heteroaryl ring, which can be monocyclic or it can be a fused to a second ring to form a bicyclic or even a tricyclic ring system. In some embodiments, $R^1$ is an optionally substituted monocyclic heteroaryl containing up to three heteroatoms selected from N, O and S as ring members, exemplified by pyridine, pyrimidine, triazine, furan, thiophene, pyrazine, pyridazine, pyrrole, pyrazole, imidazole, oxazole, isoxazole, thiazole, or isothiazole, or triazole. Pyrazine and Pyridine are sometimes preferred. In some embodiments, $R^1$ is an optionally substituted bicyclic heteroaryl ring system, comprising phenyl, pyridyl, pyrazinyl, pyridazinyl, triazinyl, or pyrimidinyl fused to a second ring; the second ring can be a phenyl, pyrrole, pyrazole, triazole, imidazole, piperidine, piperidinone, pyrrolidine, pyrrolidinone, or the like; provided at least one of the two rings is a heteroaromatic ring (aromatic ring containing at least one N, O or S as a ring member). Typical examples of these bicyclic heteroaromatic groups include indole, benzimidazole, indazole, benzofuran, benzothiophene, quinoline, isoquinoline, quinoxaline, naphthyridine, benzopyrazole, benzoxazole, benzothiazole, benzisoxazole, and benzoisothiazole, for example. In some embodiments, the optionally substituted heteroaryl ring is a deuterated version of one of the above described rings.

In other embodiments, $R^1$ is optionally substituted heterocyclic group, which can be a heterocyclic ring fused to an additional aryl, cycloalkyl, or heterocyclyl ring, which is also optionally substituted. In some embodiments when $R^1$ is an optionally substituted heterocyclic ring fused to an optionally substituted phenyl, so $R^1$ can be an optionally substituted dihydroindole, dihydroindazole, dihydroindole, dihydroisoindole, tetrahydroquinoline, tetrahydroquinolinone, tetrahydroisoquinoline, or tetrahydroisoquinolinone, each of which can be linked to the central ring in Formula I through the heterocyclic ring or the phenyl portion of these $R^1$ groups.

Suitable substituents for $R^1$ include those described herein as generally suitable for heterocyclic groups. In particular, $R^1$ can be substituted with one or more halo (especially F or Cl), amino and substituted amino, aminocarbonyl, C1-C4 alkyl, C1-C4 alkoxy, =O (oxo), C1-C4 haloalkyl (e.g., $CF_3$), D, —OH, —CN, MeNH—, $Me_2N$—, acetyl, acetylamino, aminosulfonyloxy, C1-C4 alkoxycarbonyl, carboxyl, and combinations of these groups. Specific combinations of these groups of particular note include amino with C1-C4 alkoxy, amino with halo, C1-C4 alkoxy with halo, and the like.

In some embodiments, X or Y, whichever is present, is $NR^4$, and $R^4$ is H or Me.

In some of these embodiments, $R^4$ is hydrogen or an optionally substituted C1-C6 alkyl. In other embodiments, $NR^4$ is NH or NMe.

In other embodiments, X or Y, whichever is present, is O. In other embodiments, X or Y, whichever is present, is S.

In some of these embodiments, $R^1$ is optionally substituted pyridyl or pyrazinyl, including deuterated versions thereof. In certain embodiments, $R^1$ is optionally substituted 3-pyridyl. In other certain embodiments, $R^1$ is optionally substituted 2-pyrazinyl.

For $R^1$, sometimes 2-amino-3-methoxypyridin-5-yl or 2-amino-3-methoxypyrazin-5-yl is preferred.

In some of these embodiments, the optional substituents for $R^1$ are selected from the group consisting of halo, D, cyano, hydroxy, —C(O)R', —NR"C(O)R", —C(O)NR"$_2$, —OS(O)$_2$NR"$_2$, optionally substituted alkyl, optionally substituted amino, and optionally substituted C1-C4 alkoxy including C1-C4-haloalkoxy (e.g., —OCF$_3$, —OCF$_2$H, or —OCFH$_2$), and wherein R' is optionally substituted alkyl, and wherein each R" is independently hydrogen or optionally substituted C1-C4 alkyl. In some embodiments, one such substituent on $R^1$ is a deuterated version of one of these, e.g., —OCD$_3$, for example.

In some of these embodiments, $R^1$ is selected from:

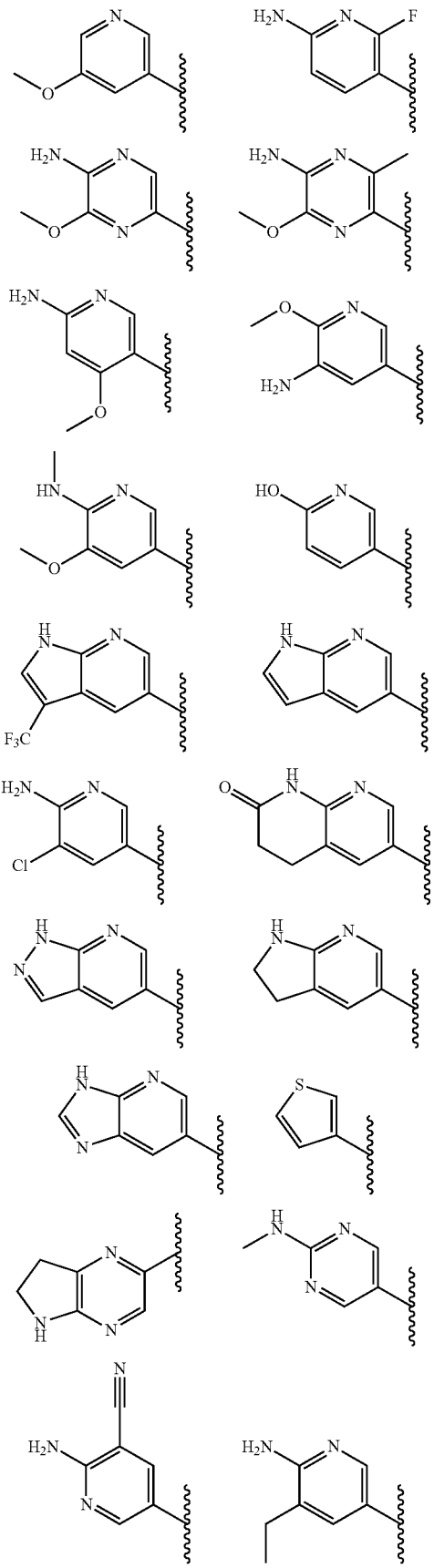

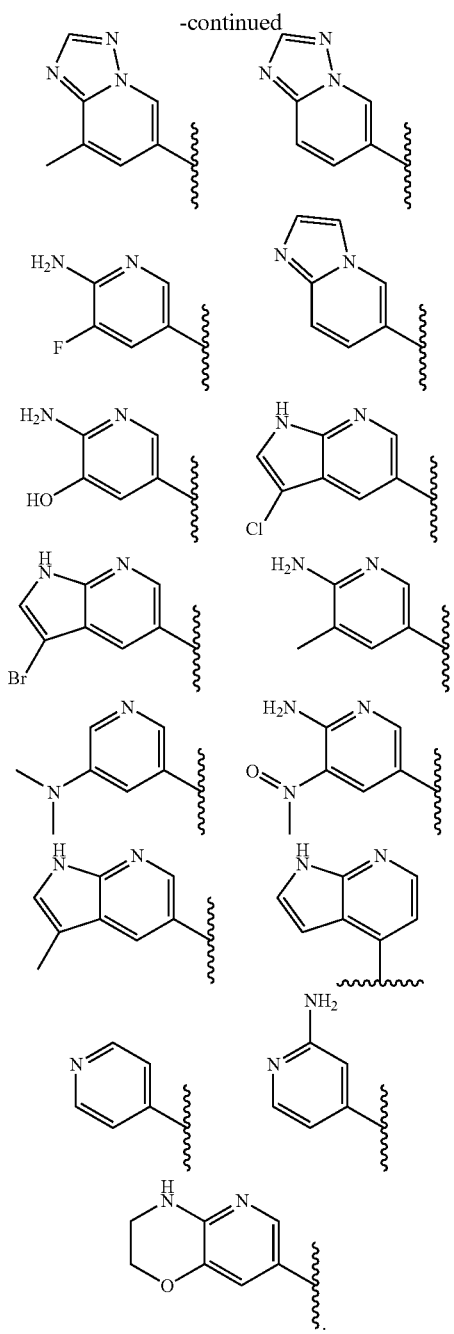

R² is optionally substituted heteroaryl, or optionally substituted heterocyclyl. R² can be an optionally substituted monocyclic ring such as pyridine, pyrimidine, furan, thiophene, thiazole, isothiazole, oxazole, isoxazole, pyrazolyl, imidazolyl, dihydropyranyl, tetrahydropyranyl, and the like. In some embodiments, R² can be an optionally substituted bicyclic group, comprising a phenyl, pyridyl or pyrimidinyl, for example, fused to an additional ring such as cyclopentyl, cyclohexyl, pyrrole, imidazole, pyrazole, piperidine, and the like; provided one ring of the bicyclic group contains a heteroatom as a ring member. R² can be attached to the base molecule through either ring of a bicyclic moiety, including through phenyl when R² comprises a phenyl ring fused to a heterocyclic ring or a heteroaromatic ring. Typical examples of these heteroaryl groups include optionally substituted indole, benzimidazole, indazole, benzofuran, benzothiophene, quinoline, isoquinoline, quinoxaline, naphthyridine, benzopyrazole, benzoxazole, benzothiazole, benzisoxazole, and benzoisothiazole, each of which can be linked to the central ring in Formula I through either ring of these bicyclic R² groups. One example of such bicyclic rings is pyrrolopyridine. In other embodiments, R² can be an optionally substituted heterocyclyl group such as tetrahydropyran, tetrahydrofuran, dihydropyran, piperidine, piperidinone, pyrrolidine, pyrrolidinone, dihydroindole, dihydroindazole, dihydroindole, dihydroisoindole, tetrahydroquinoline, tetrahydroquinolinone, tetrahydroisoquinoline, tetrahydroisoquinolinone, and the like.

In certain embodiments, the optional substituents for R² are selected from the group consisting of halo, D, cyano, hydroxy, —C(O)R', —NR"C(O)R', —C(O)NR"₂, —OS(O)₂NR"₂, optionally substituted alkyl, optionally substituted amino, and optionally substituted alkoxy, and wherein R' is H or optionally substituted alkyl, and wherein each R" is independently hydrogen or optionally substituted alkyl.

Some particularly suitable substituents for R² include halo (especially F and Cl), D, C1-C4 alkyl, amino, dimethylamino, methylamino, substituted amino, C1-C4 alkoxy, CN, —OH, optionally substituted phenyl or pyridyl, or optionally substituted phenylmethyl or pyridylmethyl groups. Preferred substituted amino groups can be of the formula —NH(CR'₂)₂₋₄—NH—C(═O)—R*, where each R' is independently H or Me, and R* represents H, C1-C4 alkyl, or C1-C4 alkoxy, where the C1-C4 alkyl or C1-C4 alkoxy can be substituted with up to three groups such as Halo, D, CN, NH₂, NMe₂, NHMe, OH, OMe, CF₃, OCF₃, ═O, and the like.

In some embodiments, R² contains at least one substituted amino group having the formula —NHR¹³, wherein R¹³ is optionally substituted alkyl or substituted aryl. In certain embodiments, the R¹³ optionally substituted alkyl group is sec-butyl, —CR₂CR₂NRC(O)CR₂OCR₃, or —CR₂CR₂NRC(O)OCR₃, wherein each R is independently hydrogen or C1-C6 alkyl, such as —CH₂CH₂NHC(O)CH₂OCH₃, —CH₂CH(CH₃)NHC(O)CH₂OCH₃, —CH₂CH(CH₃)NHC(O)CH(CH₃)OCH₃, or —CH₂CH(CH₃)NHC(O)OCH₃ and any enantiomers or diastereomers thereof. In some variations, the R¹³ substituted aryl group is —C₆H₄-o-OCH₃, —C₆H₄-m-OCF₃, —C₆H₄-m-CF₃, —C₆H₄-p-CF₃, or —C₆H₃-m-CF₃-p-Cl.

In some embodiments, the substituted amino on R² can be selected from acetylamino, 2-hydroxyethylamino, hydroxyacetylamino, acetylaminoethylamino, piperidinylamino, substituted piperidinylamino; or amino substituted with C1-C4 alkyl, C3-C6 cycloalkyl (e.g., cyclohexyl, cyclopropyl, cyclohexyl), C5-C6 heterocycloalkyl containing one or two heteroatoms selected from N, O and S as ring members, or phenyl optionally substituted with halo, C1-C4 alkyl, C1-C4 alkoxy; and the like. Specific embodiments of the substituted amino group include 2-methoxyethylamine, 2-hydroxyethylamine, cyclopropylamine, 2-(hydroxyacetylamino)ethyl, 3-piperidinylamino, 1-(4-chlorophenylsulfonyl)piperidine-3-ylamino, 1-(4-(2-amino-3-methoxypyridin-5-yl)phenyl)piperidinyl-3-ylamino, 2-(methoxyacetylamino)ethylamino, 2-(4-chlorophenylsulfonyl)aminoethylamino, cyclopropylamino, 2-hydroxypropylamino, 2-(cyclopropylsulfonyl)aminoethylamino, 2-(methylsulfonylamino)ethylamino, 1-(cyclopropylsulfonyl)piperidine-3-ylamino, 1-(methoxyacetyl)piperidine-3-ylamino, 1-(cyclopropylsulfonyl)piperidine-4-ylamino, isobutylamino, 3-methoxyphenylamino, isopropylamino, 2-methoxyethylamino, cyclopentylamino, cyclohexylamino, 2-(methoxyacetylamino)propylamino, 3-trifluoromethylphenylamino, 3-fluorophenylamino, ethylamino, propylamine, 2-butylamino, 3-methoxypropylamino, cyclopropylmethylamino, 2-(2,6-dimethylmorpholin-4-yl)pyridine-5-ylamino, 3-trifluormethoxyphenylamino, 4-methoxybenzylamino, 1-acetylpyrrolidin-3-ylamino, 2-(methylsulfonylamino)propylamino, 1,2-(difluorodioxolanyl)phen-4-ylamino, 4-trifluoromethylamino, 2-(2-methoxypropanoylamino)propylamine, 1-(methylsulfonyl)-pyrrolidin-3-ylamino, 2-(methoxyacetylamino)-1-methylethylamino, 2-(2-methopropanoylamino)-1-methylethylamino, 2-(trifluoracetylamino)ethylamino, 2,2,2-trifluorethylamino, 4-trifluoromethylphenylamino, 2-(methylaminocarbonylamino)propylamino, 4-chloro-3-trifluoromethylamino, 2-methoxypyridinyl-4-amino, 2-(methoxycarbonylamino)propylamino, 2-(isopropoxycarbonylamino)propylamino, 2-(isobutoxycarbonylamino)propylamino, and 2-(neopentyloxycarbonylamino)propylamine.

For the substituted phenyl or pyridyl groups in these $R^2$ substituents, the substitutents can be selected from halo, D, C1-C4 alkyl, C1-C4 alkoxy, CN, $CF_3$, amino, hydroxy, and the like.

In some embodiments, $R^2$ is optionally substituted pyridinyl or optionally substituted pyrimidinyl. In other embodiments, $R^2$ is optionally substituted 4-pyridinyl. In other embodiments, $R^2$ is optionally substituted 4-pyrimidinyl. In particular embodiments, $R^2$ can be 2-(substituted amino)-pyridin-4-yl or 2-(substituted amino)-pyrimidin-4-yl.

In some of these embodiments, $R^2$ is selected from

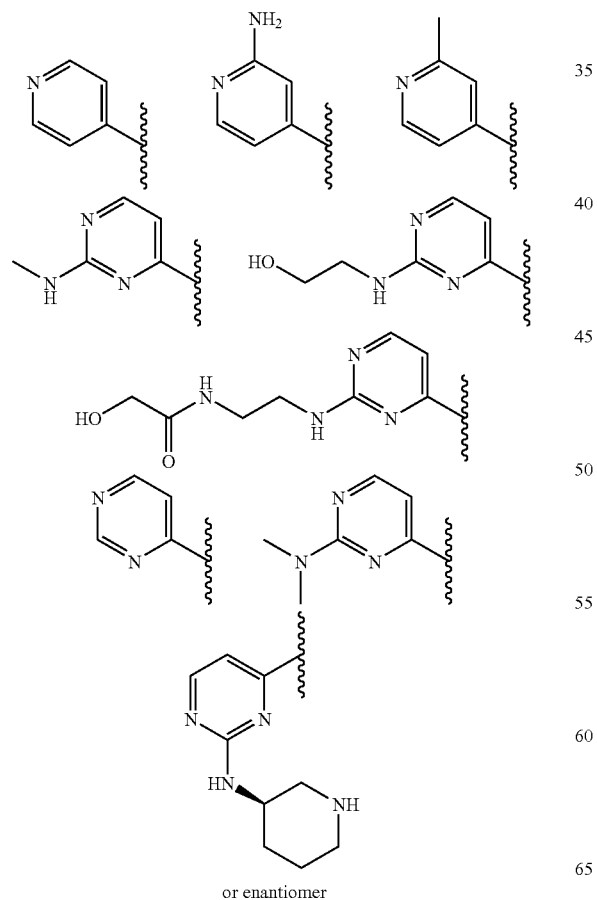

or enantiomer

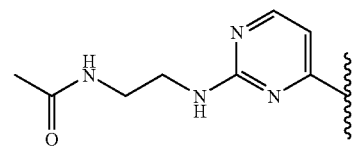

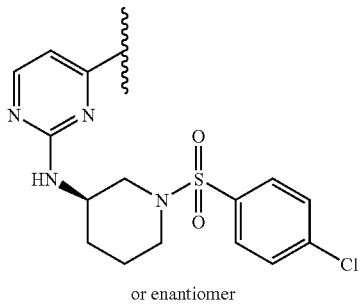

or enantiomer

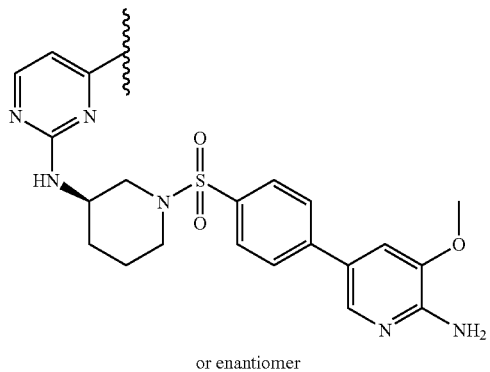

or enantiomer

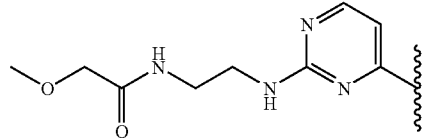

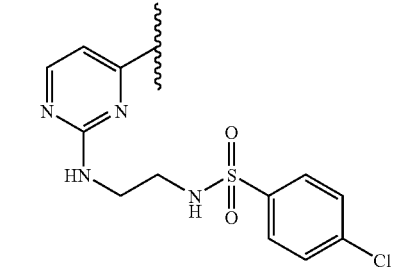

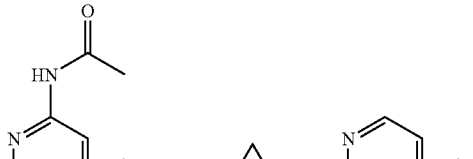

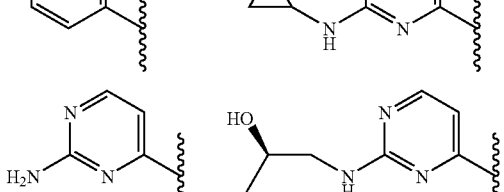

or enantiomer

-continued
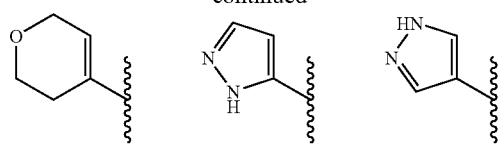
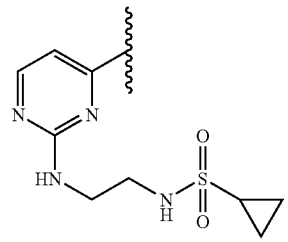
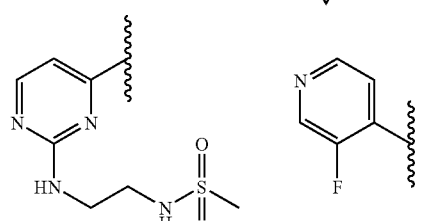
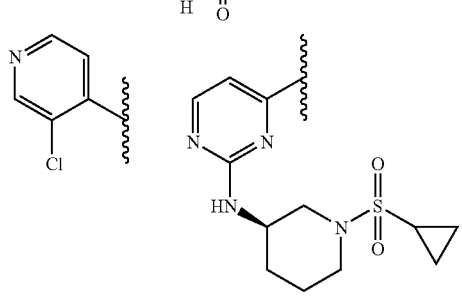
or enantiomer
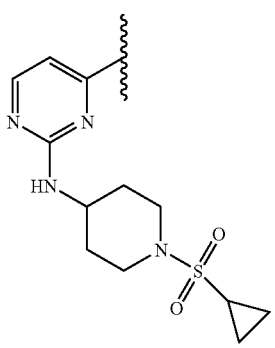
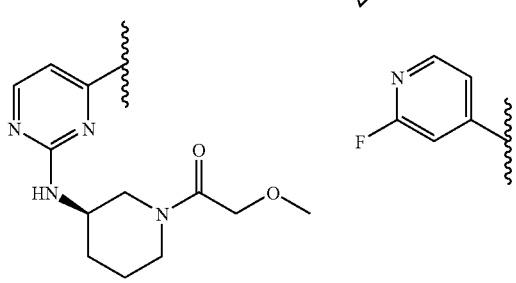
or enantiomer
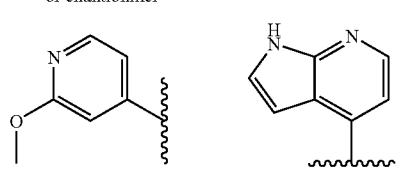
-continued
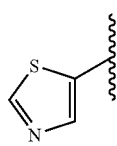 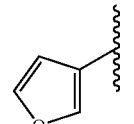 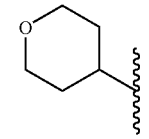
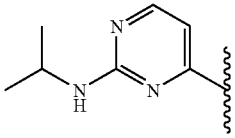
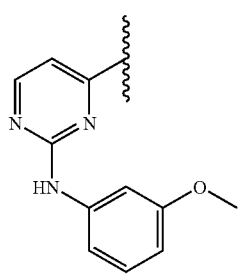
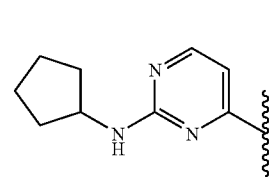
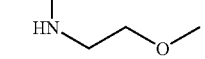
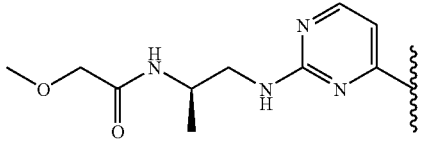
or enantiomer
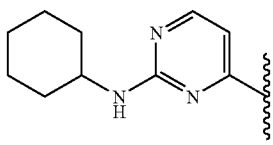
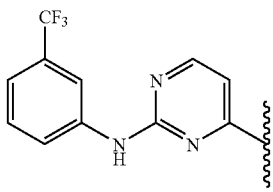
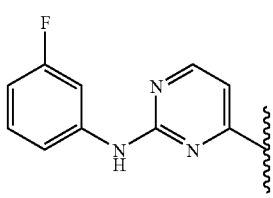
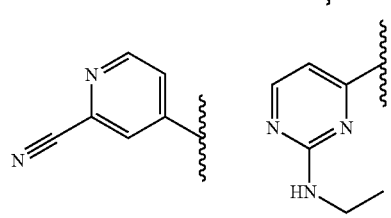

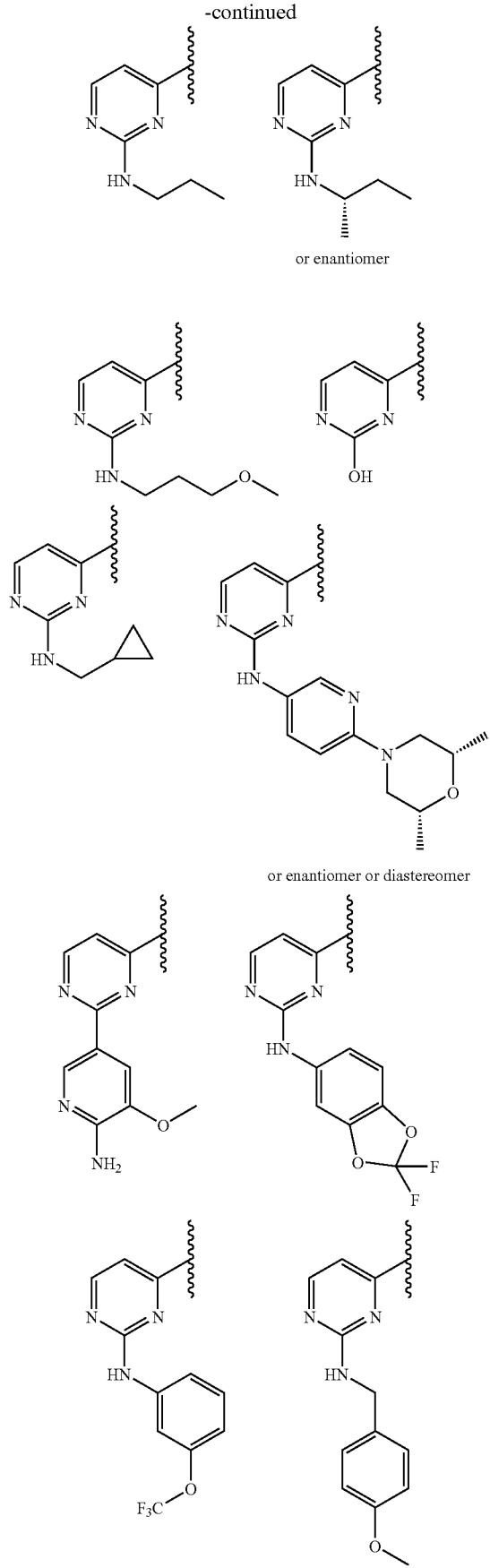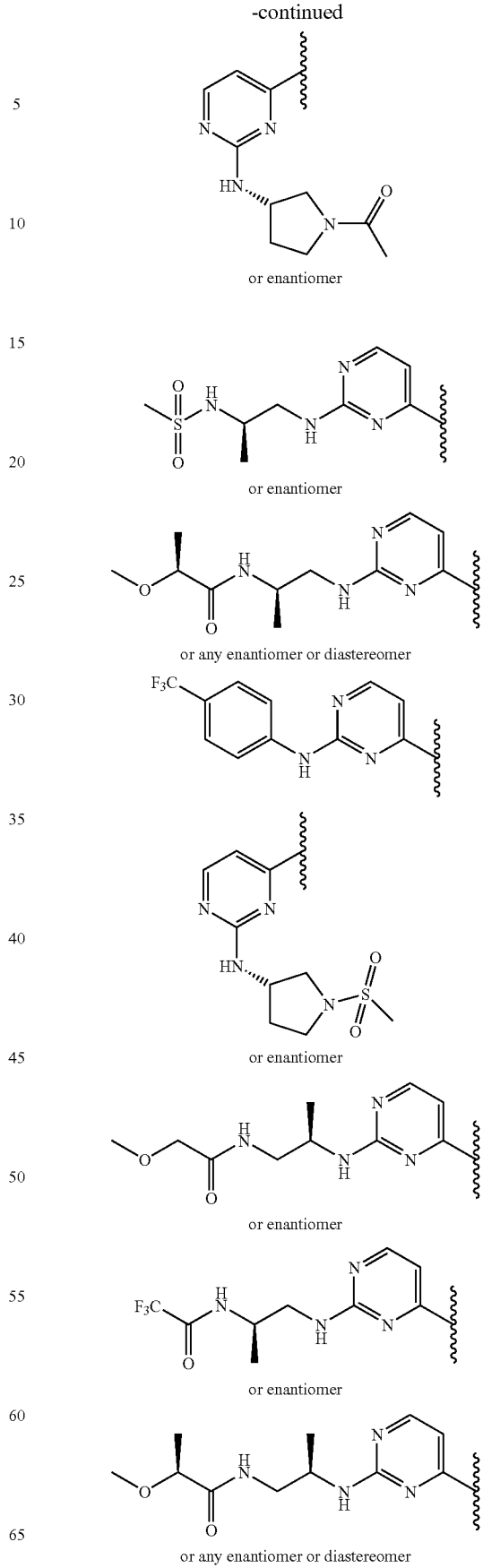

-continued

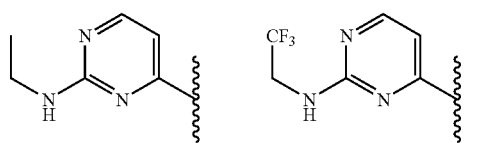

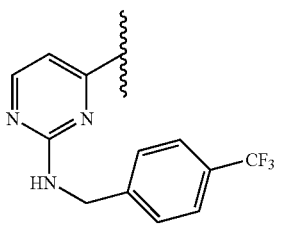

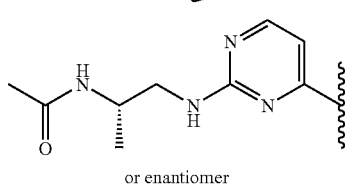

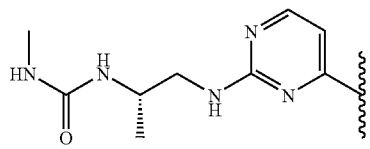
or enantiomer

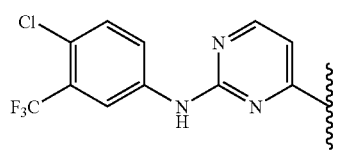
or enantiomer

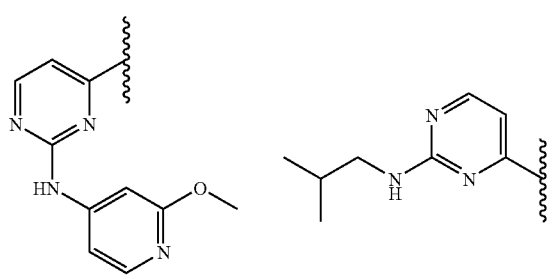

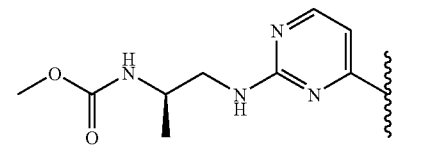

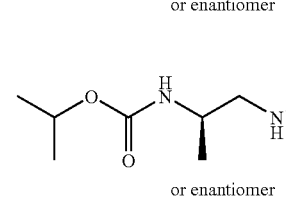
or enantiomer

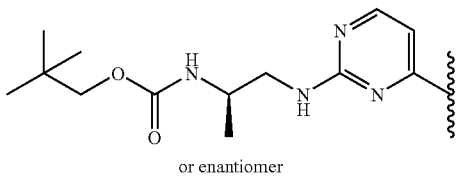
or enantiomer

-continued

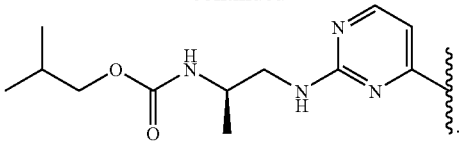
or enantiomer $R^3$ can be an optionally substituted alkyl, optionally substituted aryl, optionally substituted heteroaryl, optionally substituted cycloalkyl, or optionally substituted heterocyclyl group. In some embodiments, $R^3$ is optionally substituted C1-C6 alkyl, such as methyl, ethyl, propyl, isopropyl, t-butyl, neopentyl, and the like, or a deuterated version of one of these. These alkyl groups can be substituted with one or more groups, typically one to three groups, selected from oxo (═O), halo, D, R", OR", COOR", NR"$_2$, CONR"$_2$, CN, C3-C6 cycloalkyl, optionally substituted phenyl, and the like; where R" is H or C1-C4 alkyl individually at each occurrence, and where NR"$_2$ can represent pyrrolidine, piperidine, piperazine, or morpholine or an oxo- or methyl-substituted version of one of these heterocycles. In some embodiments, this alkyl is unsubstituted, or is substituted with OR" or NR"$_2$.

In other embodiments, $R^3$ is cycloalkyl, wherein the cycloalkyl can be a 3-8 membered ring of carbon atoms and can be substituted by up to three groups selected from oxo (═O), halo, D, CN, R", OR", COOR", NR"$_2$, CONR"$_2$, C3-C6 cycloalkyl, optionally substituted phenyl, and the like; where R" is H or C1-C4 alkyl or C1-C4 halomethyl individually at each occurrence, and where NR"$_2$ can represent pyrrolidine, piperidine, piperazine, or morpholine or an oxo- or methyl-substituted version of one of these heterocycles. The cycloalkyl can also contain a carbon-carbon double bond. Examples of suitable cycloalkyls include cyclopropyl, 1-cyanocyclopropyl, 1-trifluoromethylcyclopropyl, 1-chlorocyclopropyl, 1-methylcyclopropyl, cyclopentyl, cyclopentenyl, cyclohexyl, cyclohexenyl, cyclobutyl, and the like.

In other embodiments, $R^3$ is heterocyclyl, wherein the heterocyclic ring can be a 3-8 membered ring containing up to three heteroatoms selected from N, O and S as ring members, and can be substituted by up to three groups selected from oxo (═O), halo, D, R", OR", COOR", NR"$_2$, CONR"$_2$, SO$_2$R", SO$_2$NR"$_2$, C3-C6 cycloalkyl, optionally substituted phenyl, and the like; where R" is H or C1-C4 alkyl individually at each occurrence, and where NR"$_2$ can represent pyrrolidine, piperidine, piperazine, or morpholine or an oxo- or methyl-substituted version of one of these heterocycles. The heterocyclic ring can also contain a carbon-carbon double bond. Examples of suitable heterocyclic rings include pyrrolidine, piperidine, piperazine, tetrahydrofuran, tetrahydropyran, tetrahydropyridine, dihydropyridine, and the like.

In other embodiments, $R^3$ is aryl or heteroaryl, which can be unsubstituted or it can be substituted with up to three groups. Suitable aryl groups include phenyl, naphthyl and substituted versions of these. Suitable heteroaryl groups include pyrazole, pyridinyl, indolyl, quinolinyl, isoquinolinyl, benzopyrazolyl, and the like. Substituents for the aryl or heteroaryl in some embodiments can be selected from C1-C4 alkyl, C1-C4 alkoxy, CN, halo, D, CF$_3$, CHO, aminosulfonyl, aminocarbonyl, methylaminocarbonyl, dimethylaminocarbonyl, carboxyl, methoxycarbonyl, methylsulfonyl, trifluoromethoxy, substituted C1-C4 alkoxy (e.g., 2-dimethylaminoethyl), and the like.

In some of these embodiments, $R^3$ is optionally substituted phenyl, optionally substituted C1-C6 alkyl, optionally substituted C3-C6 cycloalkyl, optionally substituted heterocyclyl, or optionally substituted heteroaryl. In other embodiments, $R^3$ is unsubstituted phenyl or phenyl substituted with one, two or three substituents. In other embodiments, the optional substituents on the optionally substituted phenyl represented by $R^3$ are selected from the group consisting of halo, hydroxyl, cyano, formyl, optionally substituted pyridyl, optionally substituted C1-C6 alkyl, optionally substituted C1-C6 alkoxy, —C(O)OR', —S(O)$_2$R', —S(O)$_2$NR"$_2$, and —C(O)NR"$_2$, and wherein R' is optionally substituted C1-C4 alkyl and each R" is independently hydrogen or optionally substituted C1-C4 alkyl. In other embodiments, $R^3$ is substituted or unsubstituted C1-C6 alkyl. In other embodiments, $R^3$ is optionally substituted C3-C6 cycloalkyl. In other embodiments, $R^3$ is optionally substituted C3-C8 heterocyclyl.

In some of these embodiments, $R^3$ is selected from:

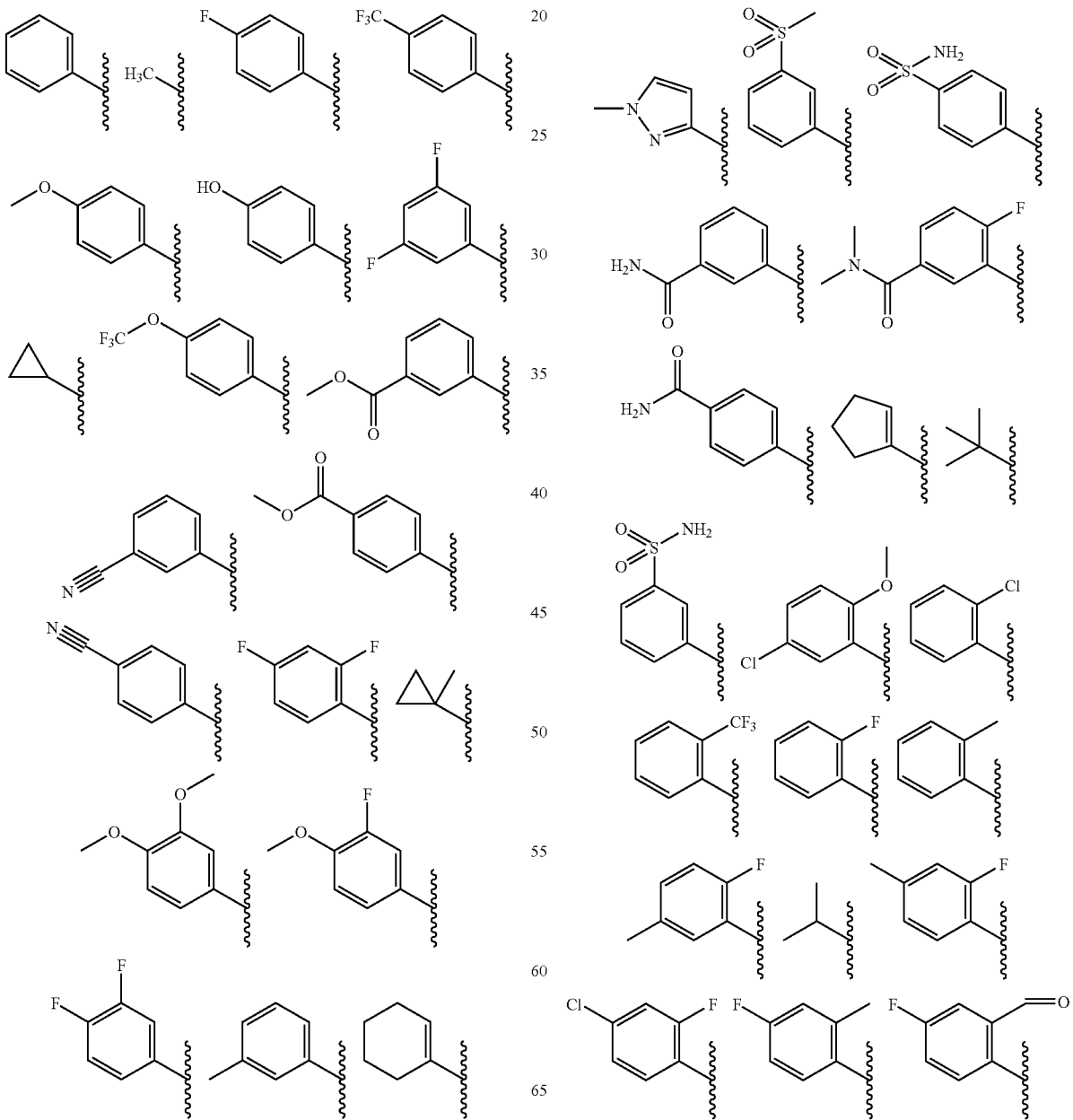

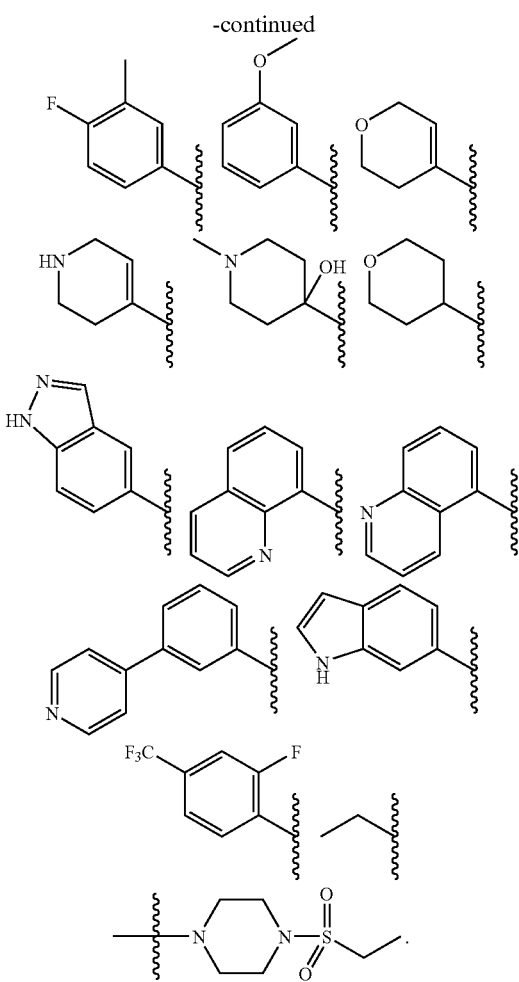

In some embodiments, $R^3$ is preferably not a perfluoralkyl group, or $R^3$ is not $CF_3$.

In certain embodiments of these compounds, X or Y, whichever is present, is $NR^4$.

In certain embodiments, $R^4$ is hydrogen or an optionally substituted C1-C6 alkyl. In certain embodiments, $NR^4$ is NH or NMe.

In certain embodiments, X or Y, whichever is present, is O. In certain embodiments, X or Y, whichever is present, is S.

In certain embodiments, the compound is of Formula II:

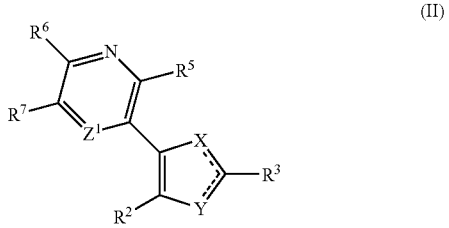

wherein $Z^1$ is $CR^8$ or N; and
$R^5$, $R^6$, $R^7$, and $R^8$ are independently selected from the group consisting of hydrogen, deuterium, halo, cyano, hydroxy, —C(O)R', —NR"C(O)R', —C(O)NR"$_2$, —OS(O)$_2$NR"$_2$, optionally substituted C1-C6 alkyl, optionally substituted amino, and optionally substituted C1-C6 alkoxy;

R' is optionally substituted alkyl and each R" is independently hydrogen or optionally substituted C1-C4 alkyl;
$R^2$, $R^3$, X and Y are as defined for Formula (I);
and any two of $R^6$, $R^7$ and $R^8$ that are attached to adjacent atoms of a ring in Formula II can be taken together to form an additional optionally substituted 5-6 membered ring.

These compounds include the pharmaceutically acceptable salts, and isomers, deuterated versions and tautomers, as discussed above for compounds of Formula (I). In these compounds, $R^2$ and $R^3$ can be selected from the specified $R^2$ and $R^3$ groups described above for Formula (I).

In certain embodiments of the compounds of Formula (II), $R^6$ is $NH_2$.

In certain embodiments, $R^7$ is —OMe or a deuterated version of —OMe, such as —OCD$_3$. In some embodiments, $R^5$ is H. In some embodiments, $R^5$ is Deuterium.

In certain embodiments, $Z^1$ is CH and $R^5$ is H. In other embodiments, $Z^1$ is N.

In certain embodiments, $R^2$ is optionally substituted pyridinyl or optionally substituted pyrimidinyl. In some variations, $R^2$ is optionally substituted 4-pyridinyl. In some variations, $R^2$ is optionally substituted 4-pyrimidinyl. Preferably, this ring is substituted by a substituted amino group that is 'meta' to the point of attachment of $R^2$ to the central ring of Formula (II).

$R^2$ can be an optionally substituted heteroaryl, or optionally substituted heterocyclyl. R can be a monocyclic heteroaromatic or heterocyclic group such as pyridine, pyrimidine, furan, thiophene, thiazole, isothiazole, oxazole, isoxazole, pyrazolyl, imidazolyl, dihydropyranyl, tetrahydropyranyl, and the like. In some embodiments, $R^2$ can be a bicyclic group, comprising a phenyl, pyridyl or pyrimidinyl, for example, fused to an additional ring such as cyclopentyl, cyclohexyl, pyrrole, imidazole, pyrazole, piperidine, and the like. One example of such bicyclic rings is pyrrolopyridine.

The optionally substituted heteroaryl or heterocyclyl groups of $R^2$ can be substituted with one to three groups such as halo (especially F and Cl), deuterium (D), C1-C4 alkyl, amino, substituted amino, C1-C4 alkoxy, CN, —OH, optionally substituted phenyl or pyridyl, or optionally substituted phenylmethyl or pyridylmethyl groups. Substituted amino is sometimes preferred. In some embodiments, the substituted amino is of the formula —NH(CR$^{12}$)$_{2-4}$—NH—C(=O)—R*, where each R' is independently H or Me, and R* represents H, C1-C4 alkyl, or C1-C4 alkoxy, where the C1-C4 alkyl or C1-C4 alkoxy can be substituted with up to three groups such as Halo, D, CN, NH$_2$, NMe$_2$, NHMe, OH, OMe, CF$_3$, OCF$_3$, =O, and the like. In some embodiments, at least one substituent on $R^2$, when $R^2$ is a six-membered ring, is at the position meta to the point where $R^2$ is attached to the central ring. In some embodiments, the substituent at this position is substituted amino. Thus $R^2$ can be 2-(substituted amino)-4-pyridyl or 2-(substituted amino)-4-pyrimidinyl.

In certain embodiments, $R^2$ is selected from

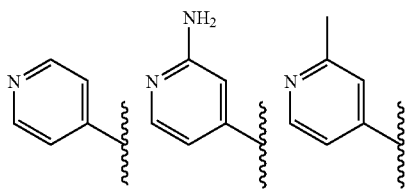

39
-continued
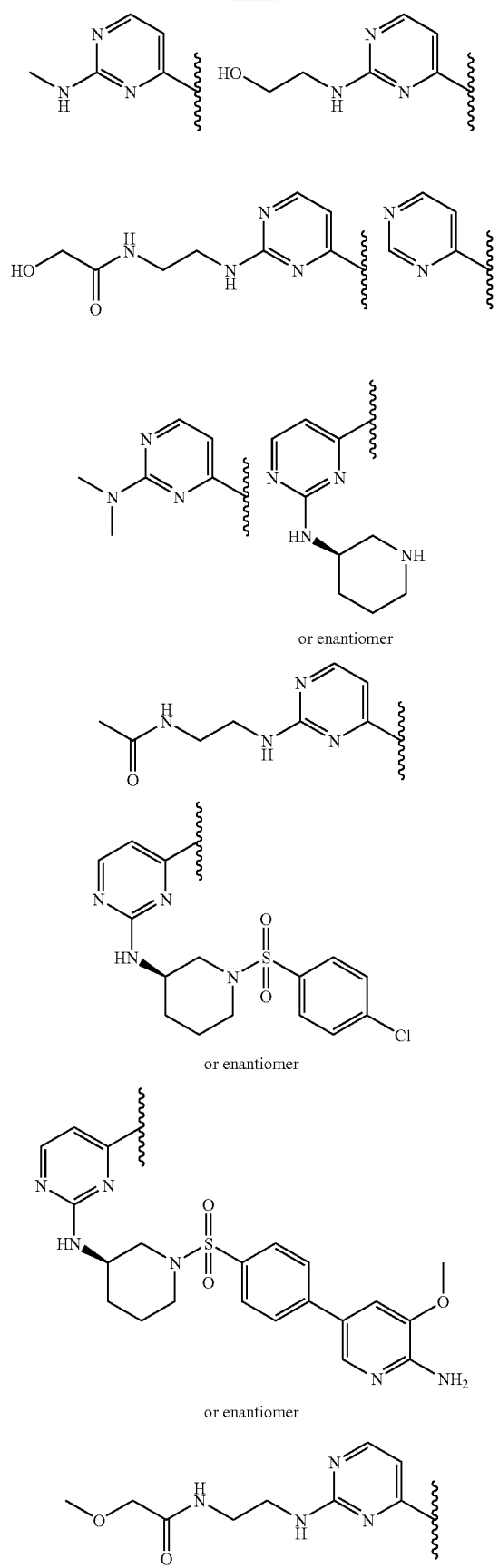
40
-continued
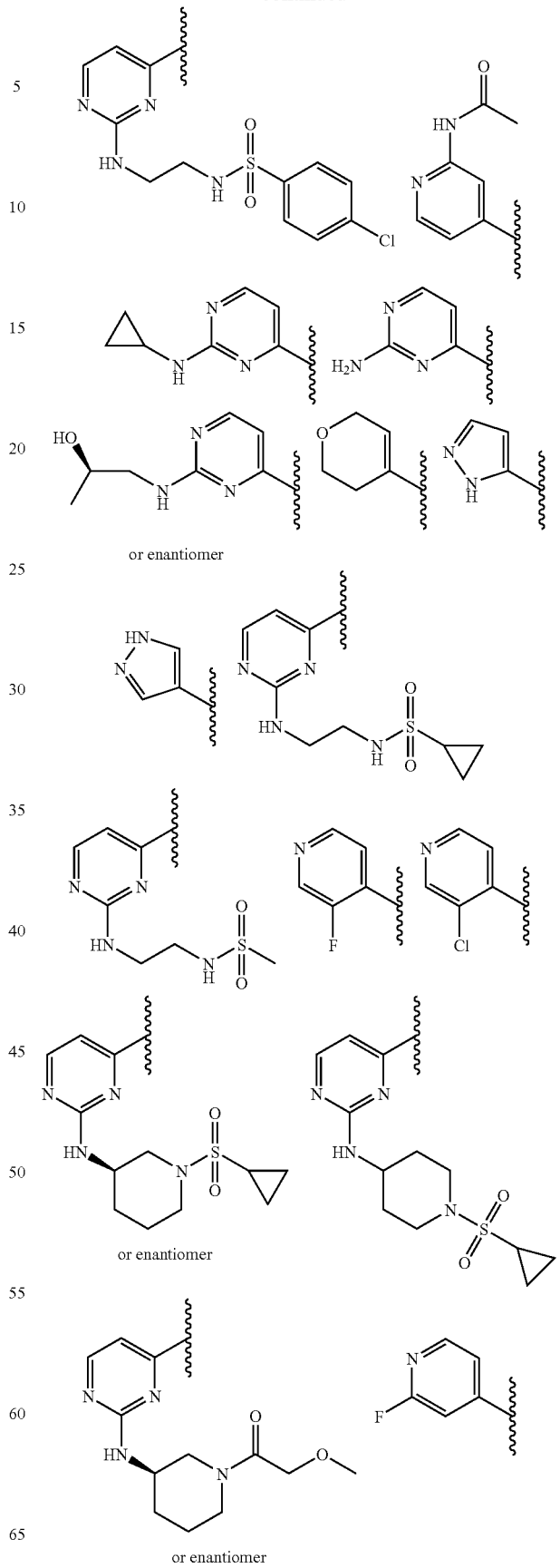

-continued
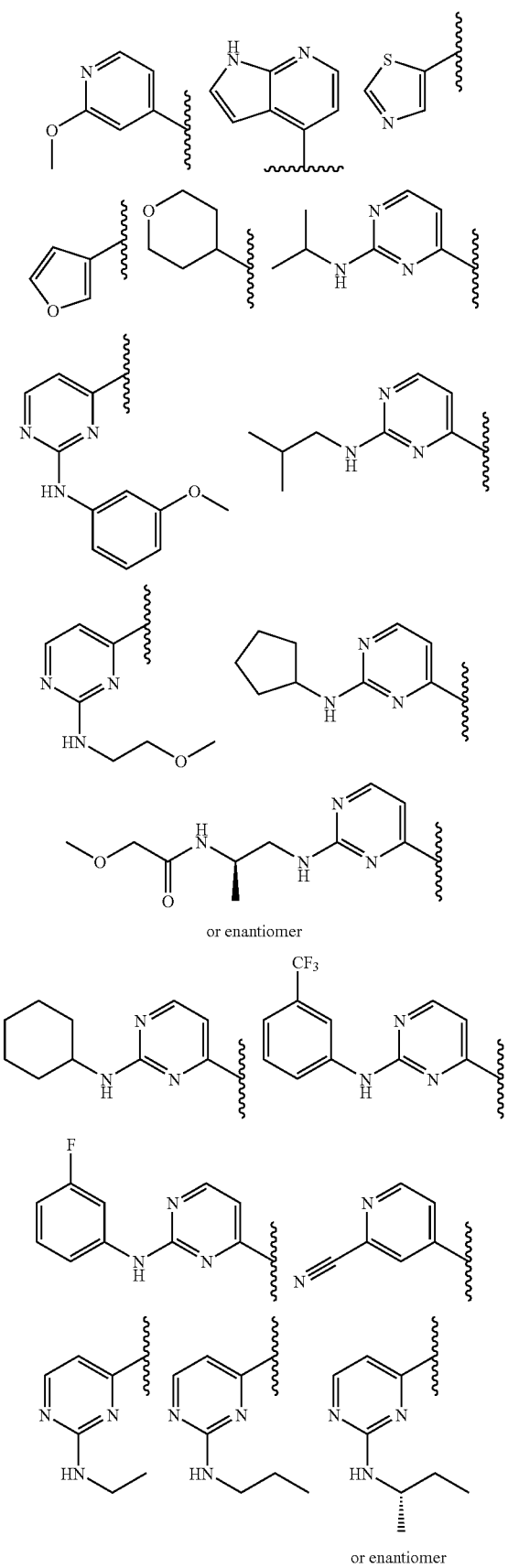
or enantiomer
-continued
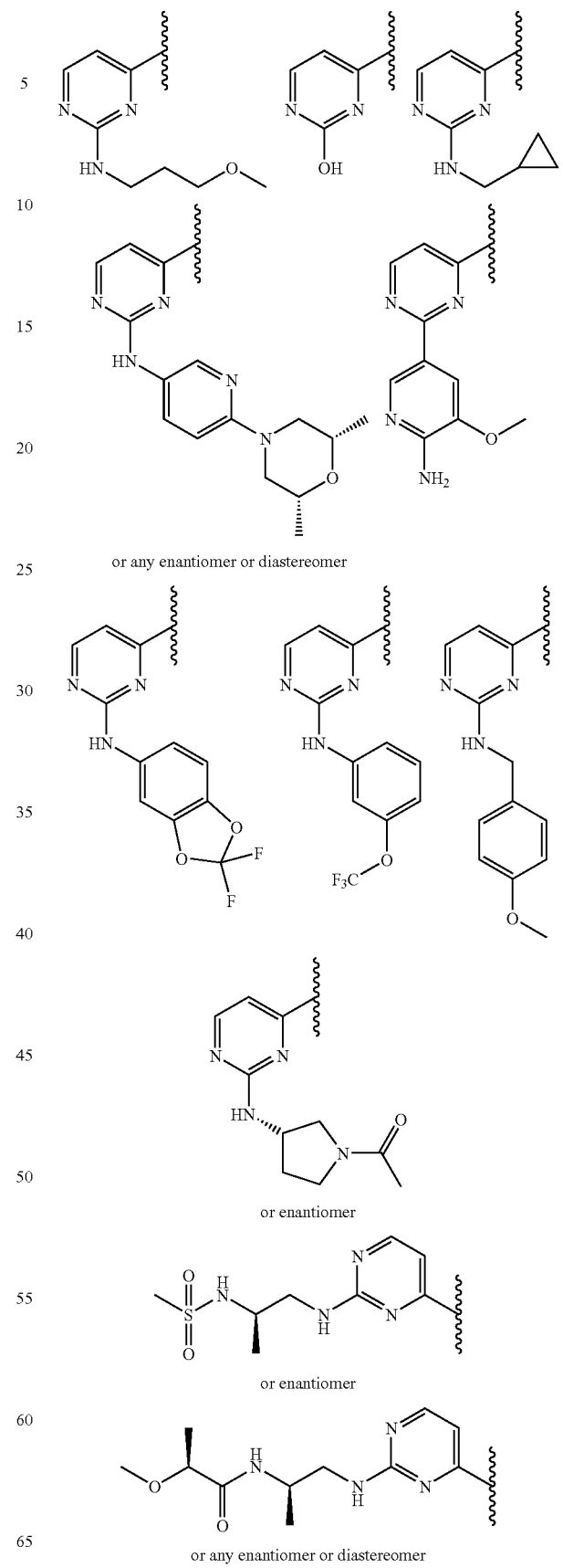
or any enantiomer or diastereomer -continued

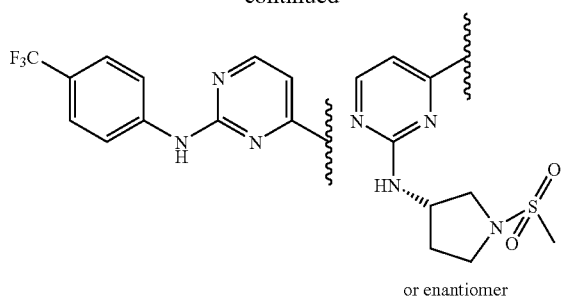
or enantiomer

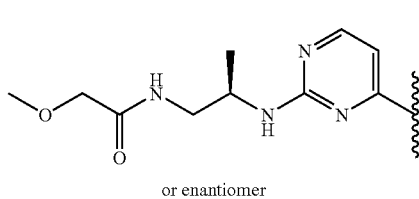
or enantiomer

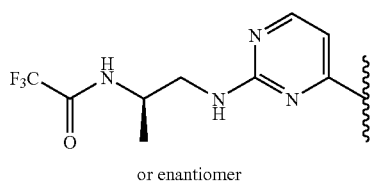
or enantiomer

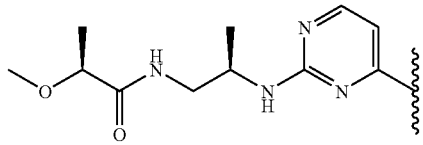
or any enantiomer or diastereomer

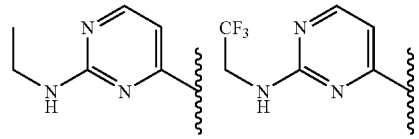

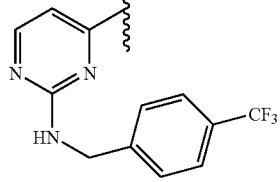

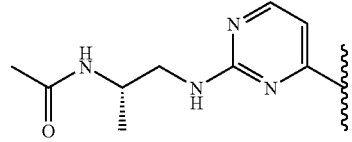
or enantiomer

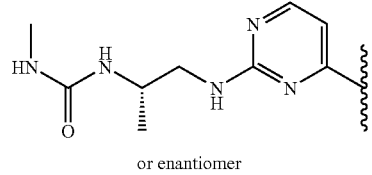
or enantiomer

-continued

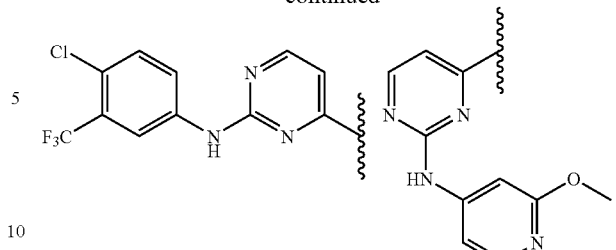

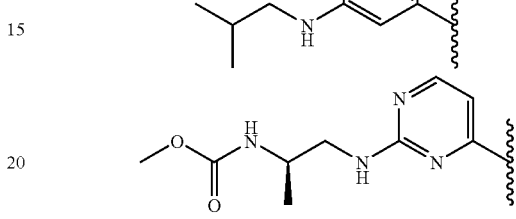
or enantiomer

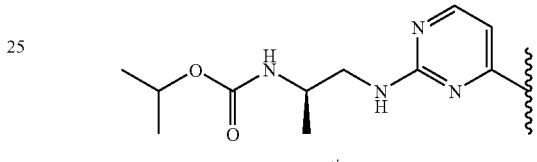
or enantiomer

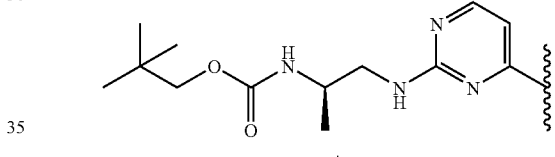
or enantiomer

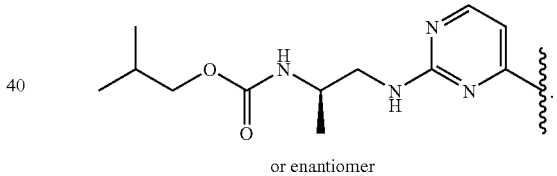
or enantiomer

In certain embodiments, the compound is of Formula (III):

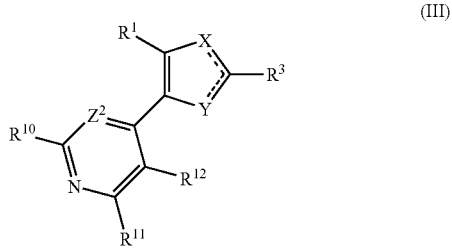

(III)

wherein $Z^2$ is $CR^9$ or N; and
$R^9$, $R^{10}$, $R^{11}$, and $R^{12}$ are independently selected from the group consisting of hydrogen, halo, D, cyano, hydroxy, —NR"C(O)R', optionally substituted alkyl, optionally substituted amino, optionally substituted heteroaryl, and optionally substituted alkoxy;
R' is optionally substituted C1-C4 alkyl and R" is hydrogen or optionally substituted C1-C4 alkyl;

and any two of $R^9$, $R^{10}$, $R^{11}$, and $R^{12}$ that are attached to adjacent atoms of a ring in Formula III can be taken together to form an additional optionally substituted 5-6 membered ring. $R^1$, $R^3$, X and Y in these compounds are as described for Formula (I).

These compounds include the pharmaceutically acceptable salts, and isomers and tautomers, as discussed above for compounds of Formula (I). In these compounds, $R^1$ and $R^3$ can be chosen from the specified $R^1$ and $R^3$ groups described above for Formula (I).

In some embodiments of the compounds of Formula (III), one or both of $R^{11}$ and $R^{12}$ is H, or one of them is D and one is H, or $R^{11}$ and $R^{12}$ taken together form a ring fused to the ring containing $Z^2$. $R^{10}$ can be H, or D, or it can be a substituent other than H or D. In certain embodiments, $R^{10}$ is selected from the group consisting of hydrogen, D, optionally substituted alkyl, and optionally substituted amino. In certain embodiments, $R^{10}$ is —$NHR^{13}$, wherein $R^{13}$ is selected from the group consisting of optionally substituted alkyl, optionally substituted heterocyclyl, —C(O)R', optionally substituted cycloalkyl, optionally substituted amino, optionally substituted aryl, and optionally substituted heteroaryl. In some embodiments, $R^{13}$ is a group of the formula —NH$(CR_{12})_{2-4}$—NH—C(=O)—R*, where each R' is independently H or Me, and R* represents H, C1-C4 alkyl, or C1-C4 alkoxy, where the C1-C4 alkyl or C1-C4 alkoxy can be substituted with up to three groups such as Halo, D, CN, $NH_2$, $NMe_2$, NHMe, OH, OMe, $CF_3$, $OCF_3$, =O, and the like. In selected embodiments, $R_{10}$ is —$NHR^{13}$ and $R^{11}$ and $R^{12}$ are both hydrogen.

In certain embodiments, $R^{13}$ is optionally substituted alkyl or substituted aryl. In certain embodiments, the $R^{13}$ optionally substituted alkyl group is sec-butyl, —$CR_2CR_2NRC(O)CR_2OCR_3$, or —$CR_2CR_2NRC(O)OCR_3$, wherein each R is independently hydrogen or C1-C6 alkyl, such as —$CH_2CH_2NHC(O)CH_2OCH_3$, —$CH_2CH(CH_3)NHC(O)CH_2OCH_3$, —$CH_2CH(CH_3)NHC(O)CH(CH_3)OCH_3$, or —$CH_2CH(CH_3)NHC(O)OCH_3$ and any enantiomers or diastereomers thereof. In some variations, the $R^{13}$ substituted aryl group is —$C_6H_4$-o-$OCH_3$, —$C_6H_4$-m-$OCF_3$, —$C_6H_4$-m-$CF_3$, —$C_6H_4$-p-$CF_3$, or —$C_6H_3$-m-$CF_3$-p-Cl.

In certain embodiments of Formula (II), $Z^2$ is CH. In other embodiments, $Z^2$ is N.

In certain embodiments of Formula (II), $R^{11}$ and $R^{12}$ are both H.

In certain embodiments of Formula (II), X or Y is $NR^4$, where $R^4$ is H.

In certain embodiments of Formula (II), $R^3$ is optionally substituted phenyl, optionally substituted C1-C6 alkyl, optionally substituted C3-C6 cycloalkyl, optionally substituted heterocyclyl, or optionally substituted heteroaryl. In some variations, $R^3$ is unsubstituted phenyl or phenyl substituted with one, two or three substituents. In some variations, the optional substituents on the optionally substituted phenyl represented by $R^3$ are selected from the group consisting of halo, hydroxyl, cyano, formyl, optionally substituted pyridyl, optionally substituted alkyl, optionally substituted alkoxy, —C(O)OR', —S(O)$_2$R', —S(O)$_2$NR"$_2$, and —C(O)NR"$_2$, and wherein R' is optionally substituted alkyl and each R" is independently hydrogen or optionally substituted alkyl. In some variations, $R^3$ is substituted or unsubstituted C1-C6 alkyl. In other embodiments, $R^3$ is optionally substituted C3-C6 cycloalkyl. In some variations, $R^3$ is optionally substituted heterocyclyl.

In certain embodiments of Formula (II), $R^3$ is selected from:

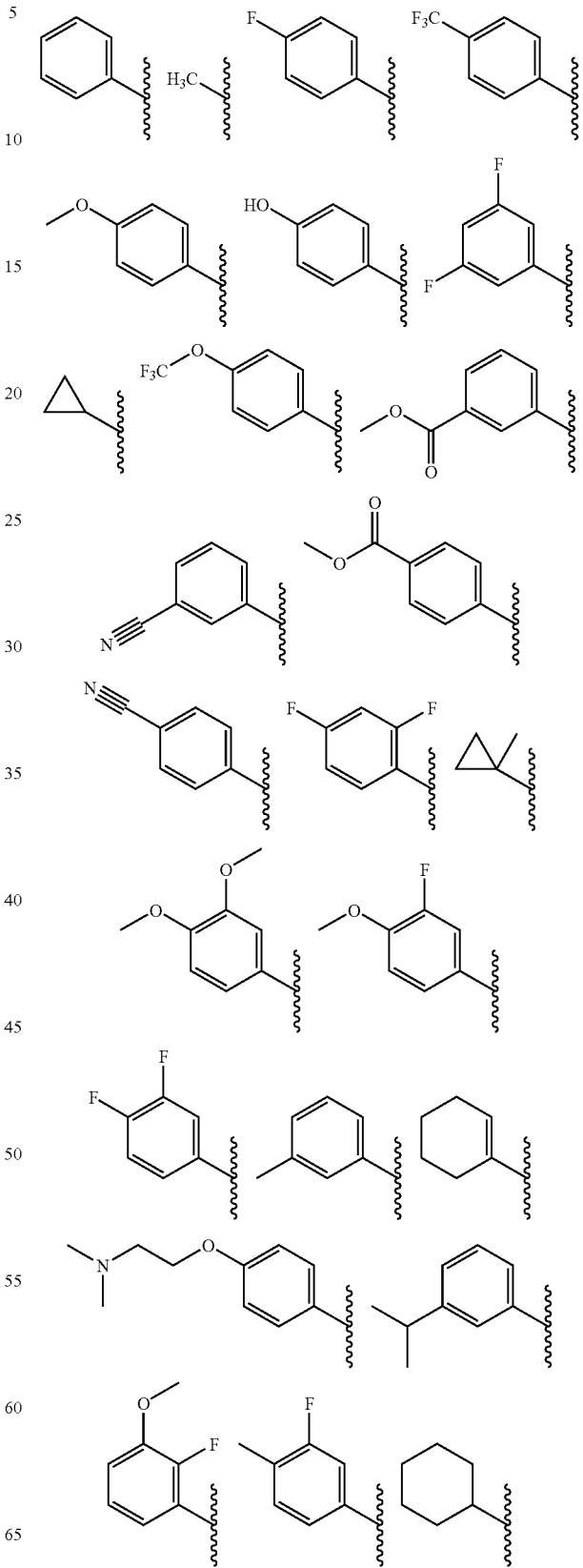

-continued

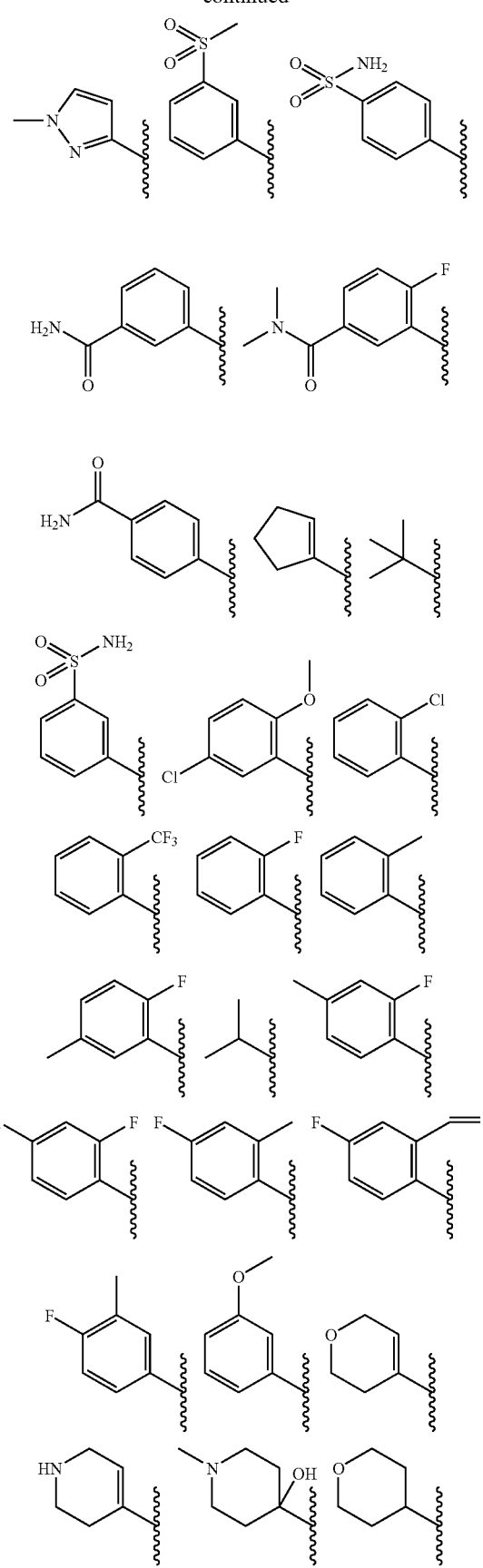

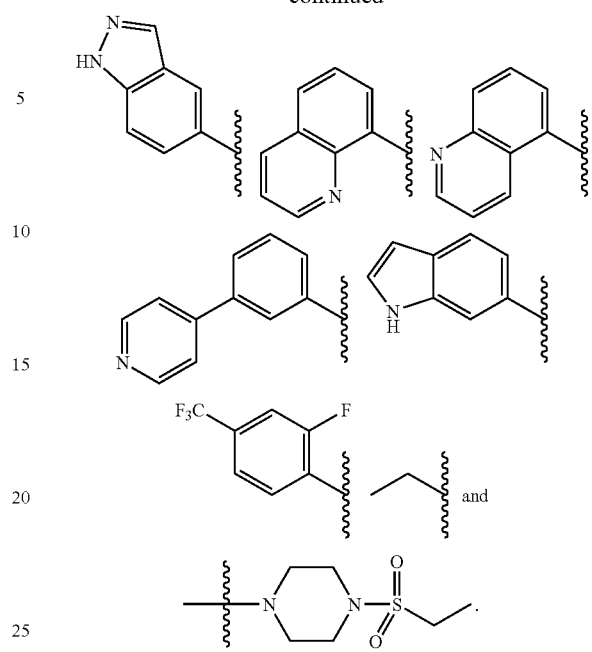

In certain embodiments of the compounds of Formulas (I)-(III), X is present, and X is NMe.

In certain embodiments of the compounds of Formulas (I)-(III), Y is present, and Y is NMe.

In certain embodiments of the compounds of Formulas (I)-(III), X is present, and X is O.

In certain embodiments of the compounds of Formulas (I)-(III), Y is present, and Y is O.

In certain embodiments of the compounds of Formulas (I)-(III), X is present, and X is S.

In certain embodiments of the compounds of Formulas (I)-(III), Y is present, and Y is S.

In another aspect, a compound of Formula IV is provided:

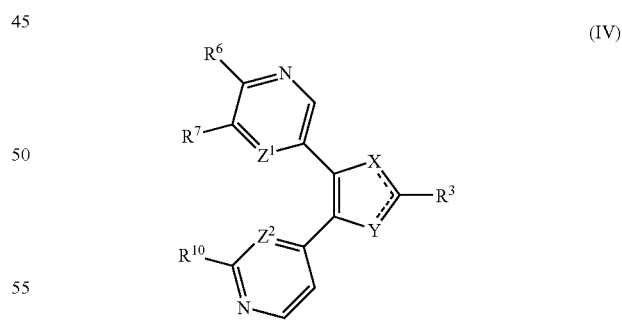

(IV)

wherein $Z^1$ and $Z^2$ are each independently N or CH or CD;

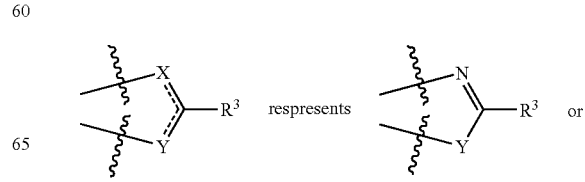

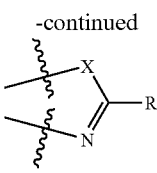

where X or Y, whichever is present, is selected from the group consisting of NR$^4$, O, and S;

R$^3$ is optionally substituted phenyl, or a C1-C6 hydrocarbyl group;

R$^4$ is H or optionally substituted C1-C6 alkyl;

R$^6$ is NHR$^{14}$, where R$^{14}$ is H or optionally substituted C1-C6 alkyl;

R$^7$ is H, D, halo, optionally substituted amino or optionally substituted C1-C4 alkoxy; and R$^{10}$ is NHR$^{15}$, wherein R$^{15}$ is selected from the group consisting of optionally substituted C1-C6 alkyl, optionally substituted heterocyclyl, —C(O)R', optionally substituted C3-C6 cycloalkyl, optionally substituted amino, optionally substituted aryl, and optionally substituted heteroaryl;

R' is H or optionally substituted C1-C4 alkyl;

or a pharmaceutically acceptable salt thereof, a deuterated version thereof, or a tautomer or stereoisomer thereof.

In certain embodiments of the compound of Formula (IV), X or Y, whichever is present, is NH or NMe. In alternative embodiments, X or Y is O. In other embodiments, X or Y is S.

In certain embodiments of the compound of Formula (IV), R$^6$ is NH$_2$.

In certain embodiments of the compound of Formula (IV), R$^7$ is OCH$_3$ or a deuterated version of —OCH$_3$ (e.g., —OCH$_2$D, —OCHD$_2$, —OCD$_3$).

In some embodiments of the compound of Formula (IV), R$^6$ is NH$_2$ and R$^7$ is —OCH$_3$.

In some embodiments of the compound of Formula (IV), R$^3$ is an unsubstituted alkyl such as Me, Et, nPr, iPr, or t-Bu, or cyclopropyl, 1-methylcyclopropyl, cyclopentyl, cyclopentenyl, or cyclohexyl; or R$^3$ is phenyl, which can be unsubstituted or it can be phenyl substituted with halo or CF$_3$ or C1-C4 alkyl or C1-C4 alkoxy.

In certain embodiments of the compound of Formula (IV), R$^{10}$ is NHR$^{15}$, where R$^{15}$ is optionally substituted alkyl or substituted aryl. R$^{10}$ can be a group of the formula —NH(CR'$_2$)$_{2-4}$—NH—C(=O)—R*, where each R' is independently H or Me, and R* represents H, C1-C4 alkyl, or C1-C4 alkoxy, where the C1-C4 alkyl or C1-C4 alkoxy can be substituted with up to three groups such as Halo, D, CN, NH$_2$, NMe$_2$, NHMe, OH, OMe, CF$_3$, OCF$_3$, =O, and the like.

Optionally, Z$^1$ and Z$^2$ are each CH, or CD. In other embodiments Z$^1$ is N and Z$^2$ is CH. In other embodiments, Z$^1$ is CH and Z$^2$ is N. In other embodiments, Z$^1$ and Z$^2$ are each N.

In certain embodiments of the compound of Formula (IV), the R$^{15}$ optionally substituted alkyl group is sec-butyl, —CR$_2$CR$_2$NRC(O)CR$_2$OCR$_3$, or —CR$_2$CR$_2$NRC(O)OCR$_3$, wherein R is independently at each occurrence hydrogen or C1-C6 alkyl, such as —CH$_2$CH$_2$NHC(O)CH$_2$OCH$_3$, —CH$_2$CH(CH$_3$)NHC(O)CH$_2$OCH$_3$, —CH$_2$CH(CH$_3$)NHC(O)CH(CH$_3$)OCH$_3$, or —CH$_2$CH(CH$_3$)NHC(O)OCH$_3$ and any enantiomers or diastereomers thereof. In some variations, the R$^{15}$ substituted aryl group is C$_6$H$_4$-o-OCH$_3$, —C$_6$H$_4$-m-OCF$_3$, —C$_6$H$_4$-m-CF$_3$, —C$_6$H$_4$-p-CF$_3$, or —C$_6$H$_3$-m-CF$_3$-p-Cl.

In certain embodiments, the compounds of the present invention include any one compound of Table 1, or a pharmaceutically acceptable salt, isomer, or solvate thereof; or a deuterated version thereof. In some variations, the compounds of the present invention include any one compound of any subset of compounds of Table 1, or a pharmaceutically acceptable salt, isomer, or solvate thereof. In some variations, the compounds of the present invention include any one of all the compounds of Table 1, or a pharmaceutically acceptable salt, isomer, or solvate thereof.

In certain embodiments, the compounds of the invention include, for example:

N-(2-(4-(5-(6-amino-5-methoxypyridin-3-yl)-2-(4-fluorophenyl)-1H-imidazol-4-yl)pyrimidin-2-ylamino)ethyl)-2-methoxyacetamide;

N-(2-(4-(4-(6-amino-5-methoxypyridin-3-yl)-2-(4-(trifluoromethyl)phenyl)-1H-imidazol-5-yl)pyrimidin-2-ylamino)ethyl)-2-methoxyacetamide;

(S)—N-(1-(4-(4-(6-amino-5-methoxypyridin-3-yl)-2-(4-fluorophenyl)-1H-imidazol-5-yl)pyrimidin-2-ylamino)propan-2-yl)-2-methoxyacetamide;

4-(4-(6-amino-5-methoxypyridin-3-yl)-2-tert-butyl-1H-imidazol-5-yl)-N-(3-(trifluoromethoxy)phenyl)pyrimidin-2-amine;

4-(4-(6-amino-5-methoxypyridin-3-yl)-2-tert-butyl-1H-imidazol-5-yl)-N-(3-(trifluoromethyl)phenyl)pyrimidin-2-amine;

(S)—N-(1-(4-(4-(5-amino-6-methoxypyrazin-2-yl)-2-(4-(trifluoromethyl)phenyl)-1H-imidazol-5-yl)pyrimidin-2-ylamino)propan-2-yl)-2-methoxyacetamide;

(S)—N-(1-(4-(4-(5-amino-6-methoxypyrazin-2-yl)-2-(4-fluorophenyl)-1H-imidazol-5-yl)pyrimidin-2-ylamino)propan-2-yl)-2-methoxyacetamide;

(S)—N-(1-(4-(4-(6-amino-5-methoxypyridin-3-yl)-2-(4-(trifluoromethyl)phenyl)-1H-imidazol-5-yl)pyrimidin-2-ylamino)propan-2-yl)-2-methoxyacetamide;

(S)—N-(1-(4-(4-(6-amino-5-methoxypyridin-3-yl)-2-tert-butyl-1H-imidazol-5-yl)pyrimidin-2-ylamino)propan-2-yl)-2-methoxyacetamide;

(S)—N-(1-(4-(4-(6-amino-5-methoxypyridin-3-yl)-2-(2-fluoro-4-(trifluoromethyl)phenyl)-1H-imidazol-5-yl)pyrimidin-2-ylamino)propan-2-yl)-2-methoxyacetamide;

(S)—N-(1-(4-(4-(5-amino-6-methoxypyrazin-2-yl)-2-tert-butyl-1H-imidazol-5-yl)pyrimidin-2-ylamino)propan-2-yl)-2-methoxyacetamide;

4-(4-(6-amino-5-methoxypyridin-3-yl)-2-tert-butyl-1H-imidazol-5-yl)-N-(4-(trifluoromethyl)phenyl)pyrimidin-2-amine;

4-(4-(6-amino-5-methoxypyridin-3-yl)-2-tert-butyl-1H-imidazol-5-yl)-N-(4-chloro-3-(trifluoromethyl)phenyl)pyrimidin-2-amine;

4-(4-(6-amino-5-methoxypyridin-3-yl)-2-tert-butyl-1-methyl-1H-imidazol-5-yl)-N-isobutylpyrimidin-2-amine;

4-(4-(6-amino-5-methoxypyridin-3-yl)-2-tert-butyl-1H-imidazol-5-yl)-N-(2-methoxypyridin-4-yl)pyrimidin-2-amine;

(S)-methyl 1-(4-(4-(5-amino-6-methoxypyrazin-2-yl)-2-tert-butyl-1H-imidazol-5-yl)pyrimidin-2-ylamino)propan-2-ylcarbamate;

(S)—N—((S)-1-(4-(4-(5-amino-6-methoxypyrazin-2-yl)-2-tert-butyl-1H-imidazol-5-yl)pyrimidin-2-ylamino)propan-2-yl)-2-methoxypropanamide;

4-(4-(6-amino-5-methoxypyridin-3-yl)-2-ethyl-1H-imidazol-5-yl)-N-(2-methoxypyridin-4-yl)pyrimidin-2-amine;

4-(4-(5-amino-6-methoxypyrazin-2-yl)-2-tert-butyl-1H-imidazol-5-yl)-N-(2-methoxypyridin-4-yl)pyrimidin-2-amine;

4-(4-(6-amino-5-methoxypyridin-3-yl)-2-methyl-1H-imidazol-5-yl)-N-(2-methoxypyridin-4-yl)pyrimidin-2-amine;

(S)—N-(1-(4-(4-(5-amino-6-methoxypyrazin-2-yl)-2-cyclopropyl-1H-imidazol-5-yl)pyrimidin-2-ylamino)propan-2-yl)-2-methoxyacetamide;

(S)-methyl 1-(4-(4-(5-amino-6-methoxypyrazin-2-yl)-2-(1-methylcyclopropyl)-1H-imidazol-5-yl)pyrimidin-2-ylamino)propan-2-ylcarbamate;

4-(4-(6-amino-5-methoxypyridin-3-yl)-2-(4-fluorophenyl)-1H-imidazol-5-yl)pyrimidin-2-amine;

(S)—N-(1-(4-(2-tert-butyl-4-(3-chloro-1H-pyrrolo[2,3-b]pyridin-5-yl)-1H-imidazol-5-yl)pyrimidin-2-ylamino)propan-2-yl)-2-methoxyacetamide;

(S)-methyl 1-(4-(4-(6-amino-5-methoxypyridin-3-yl)-2-(4-(trifluoromethyl)phenyl)-1H-imidazol-5-yl)pyrimidin-2-ylamino)propan-2-ylcarbamate;

3-methoxy-5-(2-phenyl-4-(pyridin-4-yl)-1H-imidazol-5-yl)pyridin-2-amine;

5-(2-(4-fluorophenyl)-5-(pyridin-4-yl)-1H-imidazol-4-yl)-3-methoxypyridin-2-amine;

3-methoxy-5-(4-(pyridin-4-yl)-2-(4-(trifluoromethyl)phenyl)-1H-imidazol-5-yl)pyridin-2-amine;

5-(2-(2,4-difluorophenyl)-4-(pyridin-4-yl)-1H-imidazol-5-yl)-3-methoxypyridin-2-amine;

3-methoxy-5-(2-phenyl-5-(pyridin-4-yl)oxazol-4-yl)pyridin-2-amine;

(S)—N-(1-(4-(4-(6-amino-5-methoxypyridin-3-yl)-2-(4-fluorophenyl)oxazol-5-yl)pyrimidin-2-ylamino)propan-2-yl)-2-methoxyacetamide; and (S)—N-(1-(4-(4-(5-amino-6-methoxypyrazin-2-yl)-2-(4-fluorophenyl)oxazol-5-yl)pyrimidin-2-ylamino)propan-2-yl)-2-methoxyacetamide.

In yet another aspect, the invention provides a compound of the following Formula (VI):

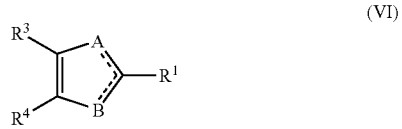

(VI)

or a pharmaceutically acceptable salt thereof, wherein:

one of A or B is N and the other of A or B is $NR_2$;

one of dashed lines ---- represent a single bond and the other represents a double bond, so the central ring is an imidazole;

$R^1$ is selected from H, $C_{1-3}$ alkyl, cyclopropyl, phenyl, (4-OH)-phenyl, (4-CH$_3$O)-phenyl, (4-CF$_3$O)-phenyl, (4-F)-phenyl, (4-alkylsulfonyl)piperazin-1-yl, and —O—(CH$_2$)$_{1-4}$—NR$_{10}$R$_{11}$;

$R^2$ is selected from H and $C_{1-2}$ alkyl;

$R^3$ is selected from:

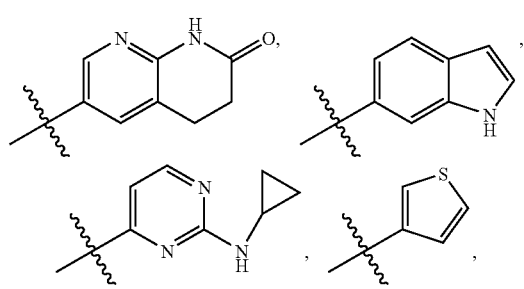

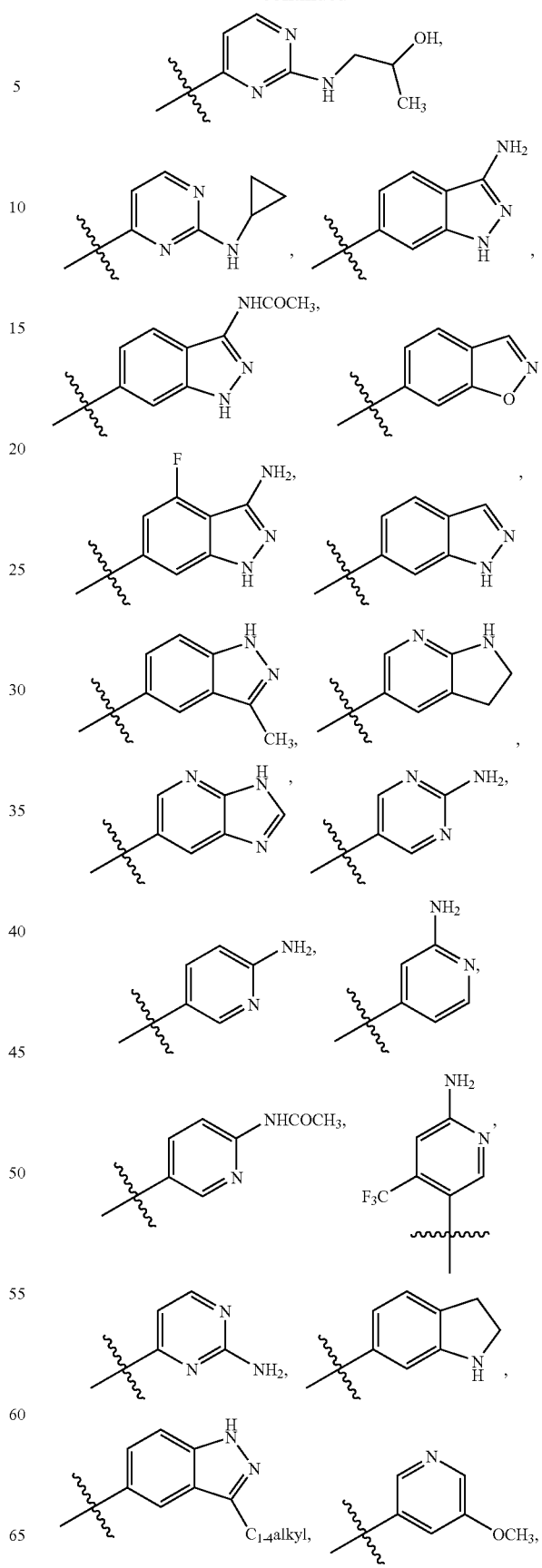

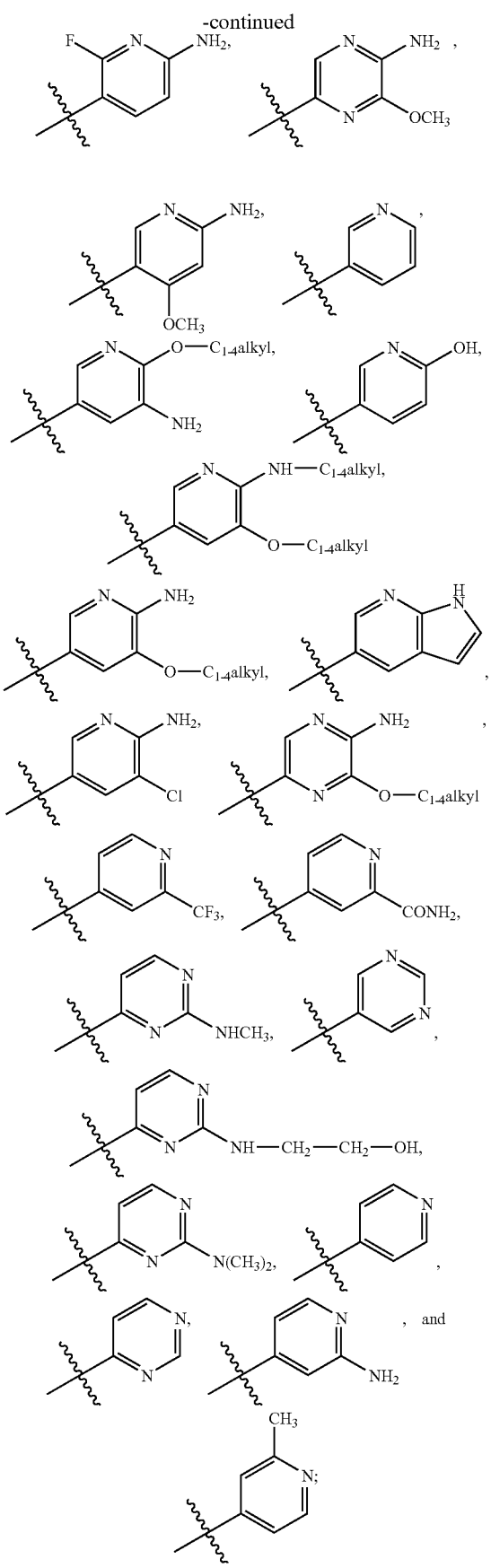
$R^4$ is selected from:
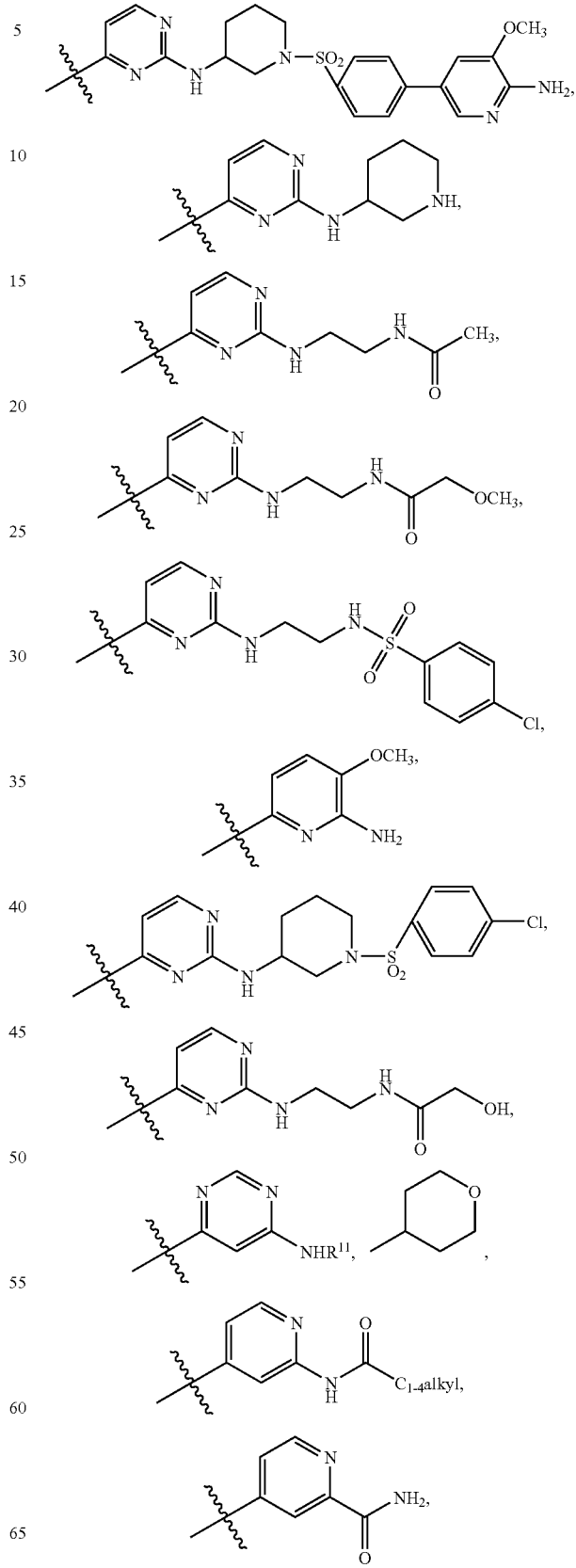

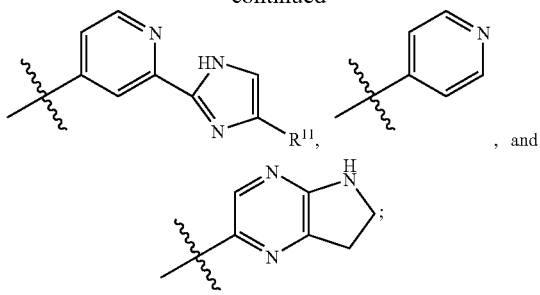

, and and $R^{10}$ and $R^{11}$ independently are selected from H and $C_{1-4}$ alkyl.

In another embodiment provided is a compound of Formula (VII) or a pharmaceutically acceptable salt thereof:

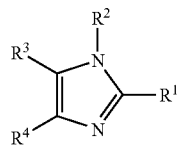

(VII)

wherein $R^1$, $R^2$, $R^3$, and $R^4$ are as defined for Formula (VI).

Various features relating to Formula (VI)-(VII) are given below. These features when referring to different substituents or variables can be combined with each other or with any other embodiments described in this application. In some aspects, provided are compounds of Formula (VI)-(VII) having one or more of the following features below.

In one embodiment:
$R^1$ is selected from H, $C_{1-3}$ alkyl, phenyl, and $—(CH_2)_{1-4}—NR^{10}R^{11}$;
$R^2$ is selected from H and $C_{1-2}$ alkyl;
$R^3$ is selected from:

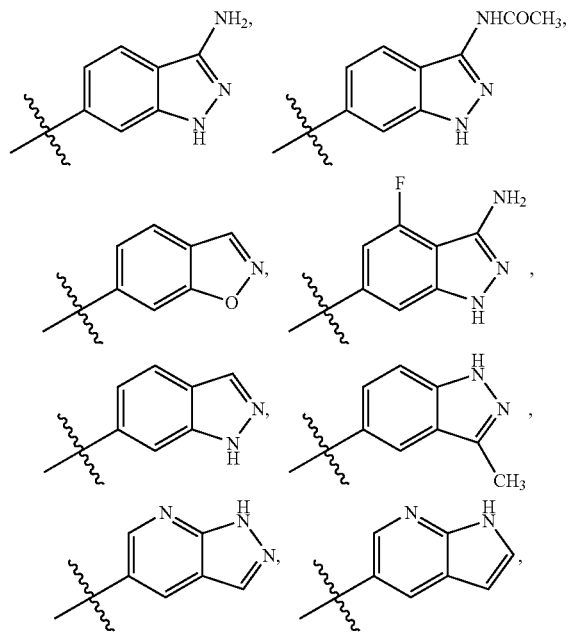

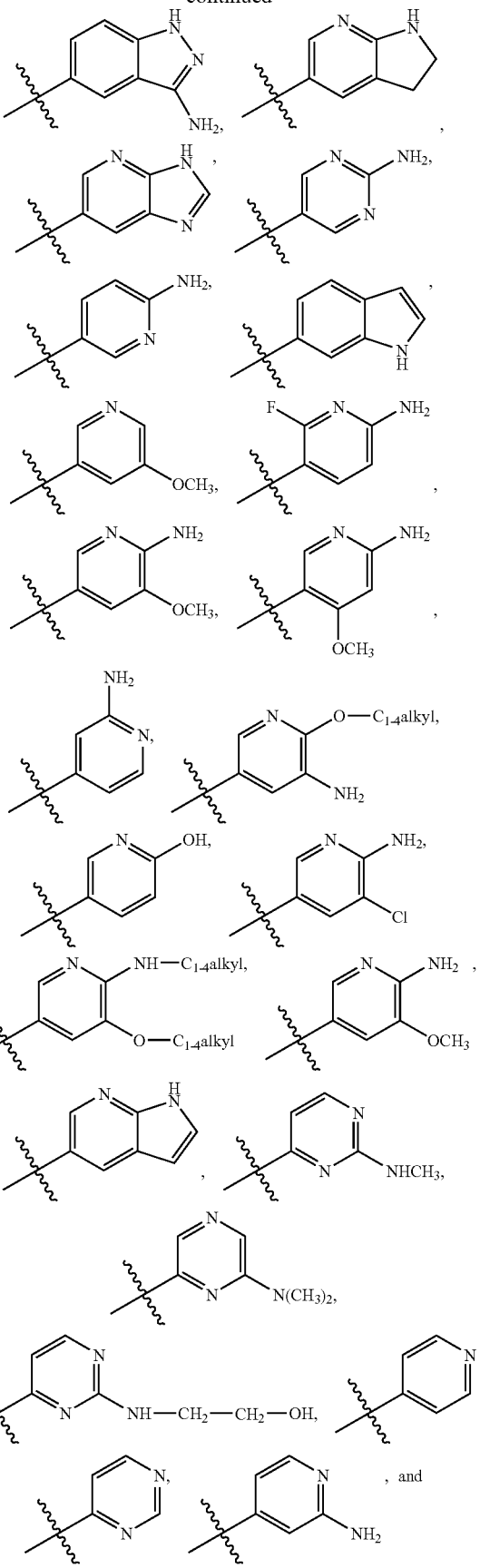

-continued
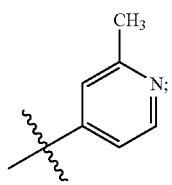
and R⁴ is selected from:
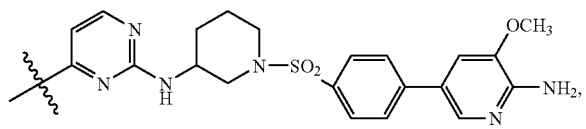
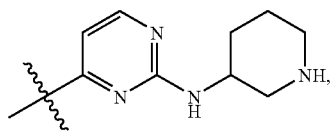
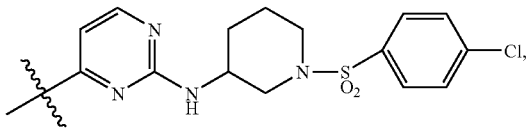
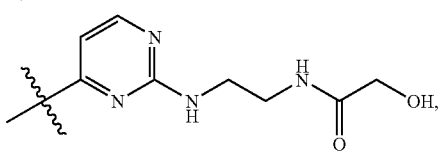
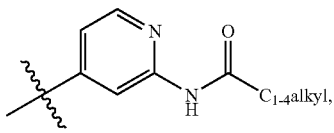
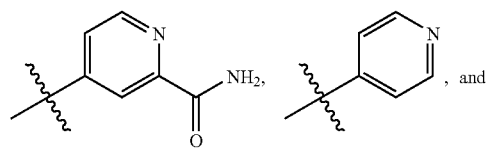
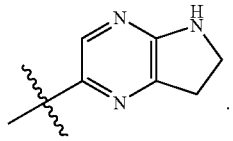
In another embodiment, R³ is selected from:
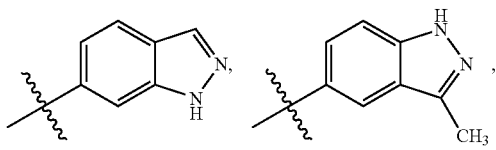
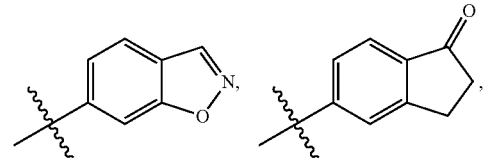
-continued
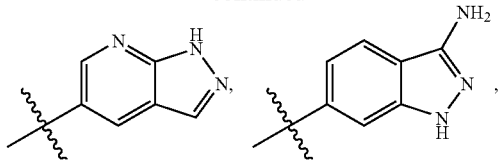
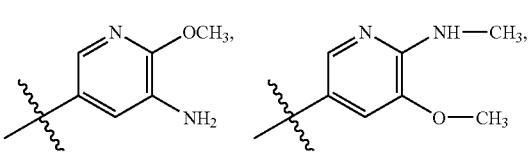
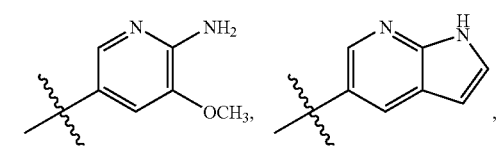
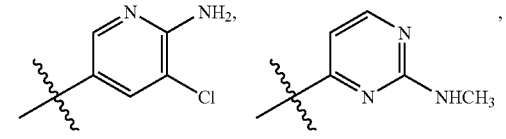
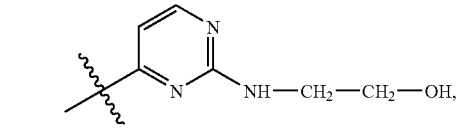
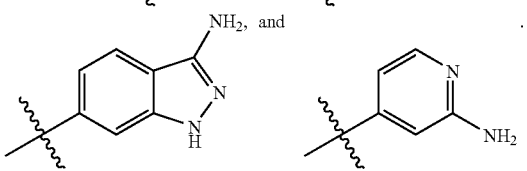

In another embodiment, R³ is selected from:

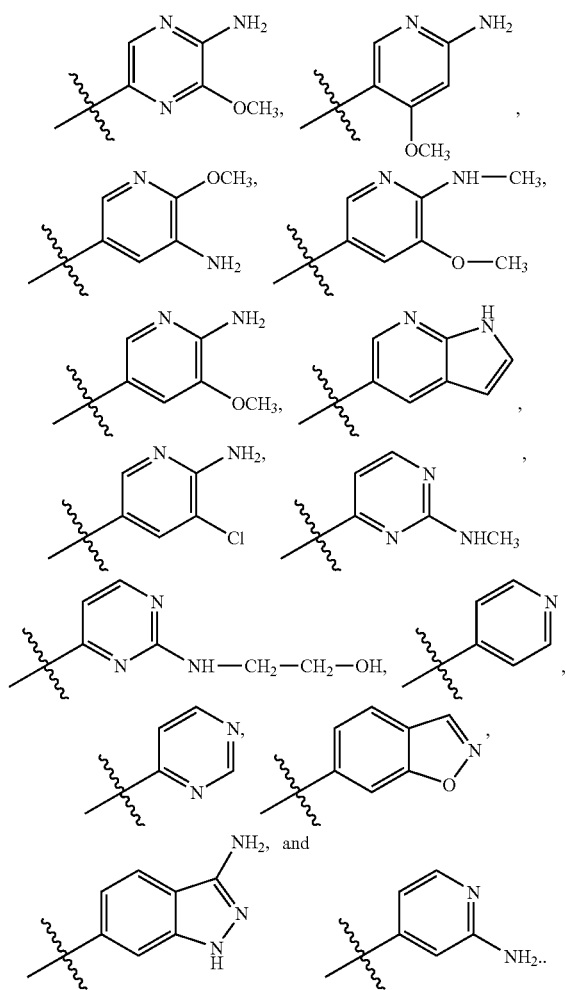

The invention also includes isotopically-labeled compounds, that are structurally identical to those disclosed above, except that one or more atom is/are replaced by an isotope, i.e., an atom having an atomic mass or mass number different from the atomic mass or mass number usually found in nature for the particular atom. Examples of isotopes that can be incorporated into compounds of the invention include isotopes of hydrogen, carbon, nitrogen, oxygen, phosphorous, sulfur, fluorine and chlorine, such as $^2H$, $^3H$, $^{13}C$, $^{14}C$, $^{15}N$, $^{18}O$, $^{17}O$, $^{31}P$, $^{32}P$, $^{35}S$, $^{18}F$ and $^{36}Cl$, respectively. Compounds of the present invention, tautomers thereof, prodrugs thereof, and pharmaceutically acceptable salts of the compounds and of the prodrugs that contain the aforementioned isotopes and/or other isotopes of other atoms are within the scope of this invention. Certain isotopically-labeled compounds of the present invention, for example those into which radioactive isotopes such as $^3H$ and $^{14}C$ are incorporated, are useful in drug and/or substrate tissue distribution assays. Tritiated, i.e., $^3H$, and carbon-14, i.e., $^{14}C$, isotopes are particularly preferred for their ease of preparation and detectability. These radiolabeled isotopically substituted compounds are useful with quite low amounts of the isotope incorporated, e.g., 0.01% isotopic substitution or more may provide a readily-detectable labeled species. Further, substitution with heavier isotopes such as deuterium, i.e., 2H, may afford certain therapeutic advantages resulting from greater metabolic stability, for example increased in vivo half-life or reduced dosage requirements and, hence, may be preferred in some circumstances. For deuterated compounds, it is typically desirable to incorporate at least 20% substitution of D for H; often at least 50% substitution of D for H; and preferably at least about 75% or at least about 90% replacement of D with H is provided. Isotopically labeled compounds of this invention and prodrugs thereof can generally be prepared by carrying out known or referenced procedures and by substituting a readily available isotopically labeled reagent for a non-isotopically labeled reagent.

The invention also provides pharmaceutical compositions comprising any of the compounds described above. In one aspect, the invention provides a pharmaceutical composition comprising a at least one compound of the invention as herein described, admixed with at least one pharmaceutically acceptable excipient. In certain embodiments, the excipient is selected from the group consisting of corn starch, potato starch, tapioca starch, starch paste, pre-gelatinized starch, sugars, gelatin, natural gums, synthetic gums, sodium alginate, alginic acid, tragacanth, guar gum, cellulose, ethyl cellulose, cellulose acetate, carboxymethyl cellulose calcium, sodium carboxymethylcellulose, methyl cellulose, hydroxypropyl methylcellulose, microcrystalline cellulose, magnesium aluminum silicate, polyvinyl pyrrolidone, talc, calcium carbonate, powdered cellulose, dextrates, kaolin, mannitol, silicic acid, sorbitol, agar-agar, sodium carbonate, croscarmellose sodium, crospovidone, polacrilin potassium, sodium starch glycolate, clays, sodium stearate, calcium stearate, magnesium stearate, stearic acid, mineral oil, light mineral oil, glycerin, sorbitol, mannitol, polyethylene glycol, other glycols, sodium lauryl sulfate, hydrogenated vegetable oil, peanut oil, cottonseed oil, sunflower oil, sesame oil, olive oil, corn oil, soybean oil, zinc stearate, sodium oleate, ethyl oleate, ethyl laureate, silica, and combinations thereof.

In some embodiments, the pharmaceutical composition of the invention further comprises an additional therapeutic agent. Examples of suitable additional therapeutic agents include an anticancer compound, an analgesic, an antiemetic, an antidepressant, and an anti-inflammatory agent.

The invention also provides methods to use the compounds described herein as pharmaceutical agents. These agents are typically used to treat a condition mediated by Raf kinase.

The invention thus provides a method to treat a condition mediated by Raf kinase, comprising administering to a subject in need thereof an effective amount of a compound of the invention as described herein, or a pharmaceutical composition containing at least one such compound. In some embodiments, the Raf kinase is a mutant b-Raf kinase.

In one embodiment, the compounds of the invention are used for treating cancer or for manufacturing a medicament, which can be a medicament for treating cancer. Specific cancers to be treated by the compounds or methods of the invention include, but are not limited to, lung carcinoma, pancreatic carcinoma, bladder carcinoma, colon carcinoma, myeloid disorders, prostate cancer, thyroid cancer, melanoma, and adenomas.

In one embodiment, the invention provides a method to treat cancer, comprising administering to a subject in need of such treatment an effective amount of a compound as described herein, or of a pharmaceutical composition containing at least one compound described herein. Cancers to be treated by these compounds and pharmaceutical compositions include lung carcinoma, pancreatic carcinoma, bladder carcinoma, colon carcinoma, myeloid disorders, melanomas, and adenomas. Treatment can further include administering to the subject an additional therapeutic agent, which can be an anticancer drug, a pain medication, an antiemetic, an antidepressant or an anti-inflammatory agent.

In certain embodiments, the additional therapeutic agent is a different Raf kinase inhibitor or an inhibitor of MEK, mTOR, PI3K, CDK9, PAK, Protein Kinase C, a MAP kinase, a MAPK Kinase, or ERK. This additional therapeutic agent can be administered to the subject concurrently with the compound of the invention, or the two can be administered separately but timed so that they act concurrently in the subject's body. In certain embodiments, the additional therapeutic agent is an anticancer drug selected from irinotecan, topotecan, gemcitabine, 5-fluorouracil, leucovorin carboplatin, cisplatin, oxaliplatin, taxanes, tezacitabine, cyclophosphamide, vinca alkaloids, imatinib, anthracyclines, rituximab and trastuzumab.

Conditions Mediated by Raf Kinase

Compounds and formulations discussed herein are useful for treatment or prevention of a condition mediated or characterized by Raf kinase, such as cancer. As used herein, "treatment or prevention of a condition mediated by Raf kinase" indicates administering one or more of the compounds discussed herein, with or without additional pharmaceutical agents, in order to reduce, eliminate, and/or prevent either the condition or one or more symptoms of the condition, or to retard the progression of the disease or of one or more symptoms of the condition, or to reduce the severity of the disease or of one or more symptoms of the condition.

In one aspect, the present invention provides methods of treating individuals suffering from a condition mediated or characterized by Raf kinase (AKA, a Raf related disorder), such as cancer. Thus, the present invention provides methods of treating an individual in need of such treatment comprising administering to the subject a therapeutically effective amount of a compound one or more of the compounds described herein, either alone or in combination with other anticancer agents.

In other aspects, the present invention provides methods for the treatment or prevention of a Raf related disorders in an individual in need of such treatment or prevention, comprising administering to said subject one or more of the compounds of the invention in an amount effective to reduce or prevent tumor growth in the individual.

Antiestrogens, such as tamoxifen, inhibit breast cancer growth through induction of cell cycle arrest, that requires the action of the cell cycle inhibitor p27Kip. Recently, it has been shown that activation of the Ras-Raf-MAP Kinase pathway alters the phosphorylation status of p27Kip such that its inhibitory activity in arresting the cell cycle is attenuated, thereby contributing to antiestrogen resistance (Donovan et al, *J. Biol. Chem.* 276:40888, 2001). As reported by Donovan et al., inhibition of MAPK signaling through treatment with MEK inhibitor changed the phosphorylation status of p27 in hormone refractory breast cancer cell lines and in so doing restored hormone sensitivity. Accordingly, in one aspect, the compounds of the invention may be used in the treatment of hormone dependent cancers, such as breast and prostate cancers, to reverse hormone resistance commonly seen in these cancers with conventional anticancer agents.

In yet other aspects, the present invention provides compounds which are inhibitors of the enzyme Raf kinase. Since the enzyme is a downstream effector of p21Ras, the instant inhibitors are useful in pharmaceutical compositions for human or veterinary use where inhibition of the Raf kinase pathway is indicated, e.g., in the treatment of tumors and/or cancerous cell growth mediated by Raf kinase. In particular, the compounds are useful in the treatment of an individual with, e.g., a solid tumor, since the progression of these cancers is dependent upon the Ras protein signal transduction cascade and therefore is susceptible to treatment by interruption of the cascade by inhibiting Raf kinase activity. Accordingly, the compounds of the invention are useful in treating cancers, such as, for example, carcinomas (e.g., of the lungs, pancreas, thyroid, bladder or colon, myeloid disorders (e.g., myeloid leukemia) or adenomas (e.g., villous colon adenoma).

In yet other aspects, the present invention provides methods for treating or preventing Raf kinase-related disorders in an individual in need of such treatment or prevention, comprising administering to said individual an amount of one or more compounds of the invention effective to reduce or prevent tumor growth in the subject, in combination with at least one additional agent for the treatment of cancer. A number of suitable anticancer agents to be used as combination therapeutics are contemplated for use in the methods of the present invention. Indeed, the present invention contemplates, but is not limited to, administration of numerous anticancer agents such as: agents that induce apoptosis; polynucleotides (e.g., ribozymes); polypeptides (e.g., enzymes); drugs; biological mimetics; alkaloids; alkylating agents; antitumor antibiotics; antimetabolites; hormones; platinum compounds; monoclonal antibodies conjugated with anticancer drugs, toxins, and/or radionuclides; biological response modifiers (e.g., interferons [e.g., IFN-a, etc.] and interleukins [e.g., IL-2, etc.], etc.); adoptive immunotherapy agents; hematopoietic growth factors; agents that induce tumor cell differentiation (e.g., all-trans-retinoic acid, etc.); gene therapy reagents; antisense therapy reagents and nucleotides; tumor vaccines; inhibitors of angiogenesis, and the like. Numerous other examples of chemotherapeutic compounds and anticancer therapies suitable for coadministration with the disclosed compounds of the invention are known to those skilled in the art.

In yet other aspects, anticancer agents to be used in combination with compounds of the present invention comprise agents that induce or stimulate apoptosis. Agents that induce apoptosis include, but are not limited to, kinase inhibitors (e.g., Epidermal Growth Factor Receptor [EGFR] kinase inhibitor, Vascular Growth Factor Receptor [VGFR] kinase inhibitor, Fibroblast Growth Factor Receptor [FGFR] kinase inhibitor, Platelet-derived Growth Factor Receptor [PGFR] I kinase inhibitor, and Bcr-Abl kinase inhibitors such as STI-571, Gleevec, and Glivec]); antisense molecules; antibodies [e.g., Herceptin and Rituxan]; anti-estrogens [e.g., raloxifene and tamoxifen]; anti-androgens [e.g., flutamide, bicalutamide, finasteride, aminoglutethamide, ketoconazole, and corticosteroids]; cyclooxygenase 2 (COX-2) inhibitors [e.g., Celecoxib, meloxicam, NS-398, and non-steroidal antiinflammatory drugs (NSAIDs)]; and cancer chemotherapeutic drugs [e.g., irinotecan (Camptosar), CPT-11, fludarabine (Fludara), dacarbazine (DTIC), dexamethasone, mitoxantrone, Mylotarg, VP-16, cisplatinum, 5-FU, Doxorubicin, Taxotere or taxol]; cellular signaling molecules; ceramides and cytokines; and staurosporine, and the like.

In certain embodiments, a Raf inhibitor compound of the invention can be combined with an inhibitor of MEK, ERK, PI3K, mTOR, or a dual PI3K-mTOR inhibitor. In addition, the compounds may be combined with inhibitors of VEGF, EGFR, FGFR, HER-2, FLT-3, or HDAC to provide compositions for treatment of certain disorders including cancers described herein.

In hematological cancers, such as chronic myelogenous leukemia (CML), chromosomal translocation is responsible for the constitutively activated Bcr-Abl tyrosine kinase. The afflicted patients are responsive to Gleevec, a small molecule tyrosine kinase inhibitor, as a result of inhibition of Abl kinase activity. However, many patients with advanced stage disease respond to Gleevec initially, but then relapse later due to resistance-conferring mutations in the Abl kinase domain. In vitro studies have demonstrated that Bcr-Abl employs the Raf kinase pathway to elicit its effects. In addition, inhibiting more than one kinase in the same pathway provides additional protection against resistance-conferring mutations. Accordingly, in another aspect of the invention, the compounds of the invention are used in combination with at least one additional agent, such as Gleevec, in the treatment of hematological cancers, such as chronic myelogenous leukemia (CML), to reverse or prevent resistance to the at least one additional agent.

In yet other aspects, the cancer to be treated is characterized by increased Raf kinase activity, for example, one which overexpresses wild-type b- or c-Raf kinase or that expresses an activating mutant Raf kinase, for example a mutant b-Raf kinase. Cancers wherein a mutated Raf kinase has been detected include melanoma, colorectal cancer, ovarian cancer, gliomas, anaplastic thyroid carcinoma, papillary thyroid carcinoma, Barrett's esophageal carcinoma, adenocarcinomas, sarcomas, breast cancer, liver cancer, acute myeloid leukemia, head and neck squamous cell carcinoma, lung cancer, gastric carcinoma, non-Hodgkins lymphoma, and cholangiocarcinoma. Mutated b-Raf kinase is especially prevalent in many melanomas. The mutations in b-Raf that have been detected in human cancers are point mutations that occur in the kinase domain and are clustered in exons 11 and 15 of the gene which contains several regulatory phosphorylation sites. The most prevalent mutation results in a V600E mutation in b-Raf. The V600E mutation was formerly designated V599E due to an error in the GenBank nucleotide sequence. Beeram, et al., *Journal of Clinical Oncology* (2005), 23 (27):6771-6790 and U.S. Pat. Application Nos. 20080176840, 20060293340, and 20060079494. In some embodiments, the invention thus provides a method to treat a condition mediated by the mutated b-Raf, (V600E).

In yet other aspects, a sample of diseased tissue may be taken from the patient, for example, as a result of a biopsy or resection, and tested to determine whether the tissue produces a mutant raf-kinase, such as a mutant b-Raf kinase or overexpresses a wild-type Raf kinase, such as wild-type b- or c-Raf kinase. If the test indicates that mutant Raf kinase is produced or that a Raf kinase is overproduced in the diseased tissue, the patient is treated by administration of an effective Raf-inhibiting amount of a Raf inhibitor compound described herein.

Tissue samples are tested by methods generally known in the art. For example, b-Raf mutations are detected by allele specific PCR, DHPLC, mass spectropscopy and overexpression of wild-type b- or c-Raf detected by immunohistochemistry, immunofluorescense, or Western blot analysis.

Formulations

The compounds described herein can be in formulations (including pharmaceutical compositions) by formulation with additives such as excipients (e.g., one or more excipients), antioxidants (e.g., one or more antioxidants), stabilizers (e.g., one or more stabilizers), preservatives (e.g., one or more preservatives), pH adjusting and buffering agents (e.g., one or more pH adjusting and/or buffering agents), tonicity adjusting agents (e.g., one or more tonicity adjusting agents), thickening agents (e.g., one or more thickening agents), suspending agents (e.g., one or more suspending agents), binding agents (e.g., one or more binding agents, viscosity-increasing agents (e.g., one or more viscosity-increasing agents), and the like, either alone or together with other anti-cancer agents, provided that the additional components are pharmaceutically acceptable for the particular condition to be treated. In some embodiments, the formulation may include combinations of two or more of the additional components as described herein (e.g., 2, 3, 4, 5, 6, 7, 8, or more additional components). In some embodiments, the additives include processing agents and drug delivery modifiers and enhancers, such as, for example, calcium phosphate, magnesium stearate, talc, monosaccharides, disaccharides, starch, gelatin, cellulose, methyl cellulose, sodium carboxymethyl cellulose, dextrose, hydroxypropyl-p-cyclodextrin, polyvinylpyrrolidinone, low melting waxes, ion exchange resins, and the like, as well as combinations of any two or more thereof. Other suitable pharmaceutically acceptable excipients are described in REMINGTON'S PHARMACEUTICAL SCIENCES, Mack Pub. Co., New Jersey (1991), and REMINGTON: THE SCIENCE AND PRACTICE OF PHARMACY, Lippincott Williams & Wilkins, Philadelphia, 20th edition (2003) and 21st edition (2005).

Some exemplary excipients may include corn starch, potato starch, tapioca starch, starch paste, pre-gelatinized starch, sugars, gelatin, natural gums, synthetic gums, sodium alginate, alginic acid, tragacanth, guar gum, cellulose, ethyl cellulose, cellulose acetate, carboxymethyl cellulose calcium, sodium carboxymethylcellulose, methyl cellulose, hydroxypropyl methylcellulose, microcrystalline cellulose, magnesium aluminum silicate, polyvinyl pyrrolidone, talc, calcium carbonate, powdered cellulose, dextrates, kaolin, mannitol, silicic acid, sorbitol, agar-agar, sodium carbonate, croscarmellose sodium, crospovidone, polacrilin potassium, sodium starch glycolate, clays, sodium stearate, calcium stearate, magnesium stearate, stearic acid, mineral oil, light mineral oil, glycerin, sorbitol, mannitol, polyethylene glycol, other glycols, sodium lauryl sulfate, hydrogenated vegetable oil, peanut oil, cottonseed oil, sunflower oil, sesame oil, olive oil, corn oil, soybean oil, zinc stearate, sodium oleate, ethyl oleate, ethyl laureate, silica, and combinations thereof.

The formulations may vary according to the condition to be treated, the amount of compound to be administered, the condition of the individual, and other variables that will readily be apparent to one of ordinary skill in the art in view of the teachings provided herein.

In some embodiments, the pH of the formulations may be from about 3.5 to about 9.5, or from about 4.5 to about 7.5, or from about 5.0 to about 7.0, from about 5.5 to about 7.0, from about 6.0 to about 7.0.

Administration and Dosage

The formulations comprising one or more compounds described herein may be administered in conjunction with one or more of the pharmaceutical agents as described herein and as known in the art, including one or more additional pharmaceutical agents to further reduce the occurrence and/or severity of symptoms and/or clinical manifestations thereof, as well as pharmaceutical agents that treat or prevent the underlying conditions, or in conjunction with (e.g., prior to, concurrently with, or after) additional treatment modalities. The formulations as described herein may be administered before, concurrently with, or after the administration of one or more of the pharmaceutical agents described herein. The compounds described herein may also be administered in conjunction with (e.g., prior to, concurrently with, or after) agents to alleviate the symptoms associated with either the condition or the treatment regimen.

While the compounds of the invention can be administered as the sole active pharmaceutical agent in a formulation, they can also be used in combination with one or more other agents used in the treatment of cancer. Representative agents useful in combination with the compounds of the invention for the treatment of cancer include, for example, irinotecan, topotecan, gemcitabine, 5-fluorouracil, leucovorin carboplatin, cisplatin, oxaliplatin, taxanes, tezacitabine, cyclophosphamide, vinca alkaloids, imatinib (Gleevec), anthracyclines, rituximab, trastuzumab, as well as other cancer chemotherapeutic agents.

The above compounds to be employed in combination with the compounds of the invention will be used in therapeutic amounts as indicated in the PHYSICIANS' DESK REFERENCE (PDR) 47th Edition (1993), or such therapeutically useful amounts as would be known to one of ordinary skill in the art.

The compounds of the invention and the other anticancer agents can be administered at the recommended maximum clinical dosage or at lower doses. Dosage levels of the active compounds in the compositions of the invention may be varied so as to obtain a desired therapeutic response depending on the route of administration, severity of the disease and the characteristics and response of the patient. The combination can be administered as separate compositions or as a single dosage form containing both agents. When administered as a combination, the therapeutic agents can be formulated as separate compositions, which are given at the same time or different times, or the therapeutic agents, can be given as a single composition.

As will be well appreciated by the skilled artisan, for particular conditions, different pharmaceutical agent(s) and/or additional treatment modality(ies) may be indicated.

The formulations and methods described herein may be used alone or in conjunction with (e.g., prior to, concurrently with, or after) other modes of treatments (e.g., adjunctive therapy with additional pharmaceutical agents described herein with reference to pharmaceutical formulations of the claimed compounds or known to the skilled artisan) used to treat or prevent the condition being treated/prevented and/or administration of an additional treatment modality, or combinations of the foregone). For example, in combination with one or more additional pharmaceutical agents as described herein and known to those of skill in the art and/or currently available treatment modalities, including, for example, surgery or radiotherapy. As used herein, the term "additional treatment modality" refers to treatment/prevention of the conditions described herein without the use of a pharmaceutical agent (e.g., surgery, radiotherapy, etc.). Where combinations of pharmaceutical agent(s) and/or additional treatment modality(ies) are used, they may be, independently, administered prior to, concurrently with, or after administration of one or more of the quinuclidine compound(s) (or formulation(s) thereof) as described herein.

The optimal combination of one or more additional treatment modalities and/or additional pharmaceutical agents in conjunction with administration of the formulations described herein, can be determined by an attending physician or veterinarian based on the individual and taking into consideration the various factors effecting the particular individual, including those described herein.

The formulations described herein will generally be used in an amount effective to achieve the intended result, for example in an amount effective to treat or prevent the particular condition being treated or prevented. The formulations may be administered therapeutically to achieve therapeutic benefit. By therapeutic benefit is meant eradication or amelioration of the underlying condition being treated and/or eradication or amelioration of one or more of the symptoms associated with the underlying condition such that the individual reports an improvement in feeling or condition, notwithstanding that the individual may still be afflicted with the underlying condition. Therapeutic benefit also includes halting or slowing the progression of the condition, regardless of whether improvement is realized.

The amount of the formulation administered in order to administer an effective amount will depend upon a variety of factors, including, for example, the particular condition being treated, the frequency of administration, the particular formulation being administered, the severity of the condition being treated and the age, weight and general health of the individual, the adverse effects experienced by the individual being treated, etc. Determination of an effective dosage is within the capabilities of those skilled in the art, particularly in view of the teachings provided herein. Dosages may also be estimated using in vivo animal models.

The compounds of the invention may be administered enterally (e.g., orally or rectally), parenterally (e.g., sublingually, by injection, or by inhalation (e.g., as mists or sprays)), or topically, in dosage unit formulations containing conventional nontoxic pharmaceutically acceptable carriers, adjuvants, and vehicles as desired. For example, suitable modes of administration include oral, subcutaneous, transdermal, transmucosal, iontophoretic, intravenous, intraarterial, intramuscular, intraperitoneal, intranasal (e.g., via nasal mucosa), subdural, rectal, gastrointestinal, and the like, and directly to a specific or affected organ or tissue. For delivery to the central nervous system, spinal and epidural administration, or administration to cerebral ventricles, can be used. Topical administration may also involve the use of transdermal administration such as transdermal patches or iontophoresis devices. The term parenteral as used herein includes subcutaneous injections, intravenous, intramuscular, intrasternal injection, or infusion techniques.

The compounds may be mixed with pharmaceutically acceptable carriers, adjuvants, and vehicles appropriate for the desired route of administration. In some embodiments, the route of administration is orally. In other embodiments, formulations are suitable for oral administration. The compounds described for use herein can be administered in solid form, in liquid form, in aerosol form, or in the form of tablets, pills, powder mixtures, capsules, granules, injectables, creams, solutions, suppositories, enemas, colonic irrigations, emulsions, dispersions, food premixes, and in other suitable forms. The route of administration may vary according to the condition to be treated. Additional methods of administration are known in the art.

Injectable preparations, for example, sterile injectable aqueous or oleaginous suspensions, may be formulated according to the known art using suitable dispersing or wetting agents and suspending agents. The sterile injectable preparation may also be a sterile injectable solution or suspension in a nontoxic parenterally acceptable diluent or solvent, for example, as a solution in propylene glycol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

Suppositories for rectal administration of the drug can be prepared by mixing the drug with a suitable nonirritating excipient such as cocoa butter and polyethylene glycols that are solid at room temperature but liquid at the rectal temperature and will therefore melt in the rectum and release the drug.

Solid dosage forms for oral administration may include capsules, tablets, pills, powders, and granules. In such solid dosage forms, the active compound may be admixed with at least one inert diluent such as sucrose, lactose, or starch. Such dosage forms may also comprise additional substances other than inert diluents, e.g., lubricating agents such as magnesium stearate. In the case of capsules, tablets, and pills, the dosage forms may also comprise buffering agents. Tablets and pills can additionally be prepared with enteric coatings.

Liquid dosage forms for oral administration may include pharmaceutically acceptable emulsions, solutions, suspensions, syrups, and elixirs containing inert diluents commonly used in the art, such as water. Such formulations may also comprise adjuvants, such as wetting agents, emulsifying and suspending agents, cyclodextrins, and sweetening, flavoring, and perfuming agents.

The compounds of the present invention can also be administered in the form of liposomes. As is known in the art, liposomes are generally derived from phospholipids or other lipid substances. Liposomes are formed by mono- or multi-lamellar hydrated liquid crystals that are dispersed in an aqueous medium. Any non-toxic, physiologically acceptable and metabolizable lipid capable of forming liposomes can be used. The present formulations in liposome form can contain, in addition to a compound of the present invention, stabilizers, preservatives, excipients, and the like. Suitable lipids are the phospholipids and phosphatidyl cholines (lecithins), both natural and synthetic. Methods to form liposomes are known in the art. See, for example, Prescott, Ed., METHODS IN CELL BIOLOGY, Volume XIV, Academic Press, New York, N.W., p. 33 et seq (1976).

The compounds can be administered in prodrug form. Suitable prodrug formulations include, but are not limited to, peptide conjugates of the compounds of the invention and esters of compounds of the inventions. Further discussion of suitable prodrugs is provided in H. Bundgaard, DESIGN OF PRODRUGS, New York: Elsevier, 1985; in R. Silverman, THE ORGANIC CHEMISTRY OF DRUG DESIGN AND DRUG ACTION, Boston: Elsevier, 2004; in R. L. Juliano (ed.), BIOLOGICAL APPROACHES TO THE CONTROLLED DELIVERY OF DRUGS (Annals of the New York Academy of Sciences, v. 507), New York: New York Academy of Sciences, 1987; and in E. B. Roche (ed.), DESIGN OF BIOPHARMACEUTICAL PROPERTIES THROUGH PRODRUGS AND ANALOGS (Symposium sponsored by Medicinal Chemistry Section, APhA Academy of Pharmaceutical Sciences, November 1976 national meeting, Orlando, Fla.), Washington: The Academy, 1977. In some variations, the compounds are administered in a form of pharmaceutically acceptable esters.

The frequency and duration of administration of the formulation will depend on the condition being treated, the condition of the individual, and the like. The formulation may be administered to the individual one or more times, for example, 2, 3, 4, 5, 10, 15, 20, or more times. The formulation may be administered to the individual, for example, once a day, 2 times a day, 3 times a day, or more than 3 times a day. The formulation may also be administered to the individual, for example, less than once a day, for example, every other day, every third day, every week, or less frequently. The formulation may be administered over a period of days, weeks, or months.

The amount of active ingredient that may be combined with the carrier materials to produce a single dosage form will vary depending upon the host to which the active ingredient is administered and the particular mode of administration. It will be understood, however, that the specific dose level for any particular individual will depend upon a variety of factors including the activity of the specific compound employed, the age, body weight, body area, body mass index (BMI), general health, sex, diet, time of administration, route of administration, rate of excretion, drug combination, and the type, progression, and severity of the particular disease undergoing therapy. The pharmaceutical unit dosage chosen is usually fabricated and administered to provide a defined final concentration of drug in the blood, tissues, organs, or other targeted region of the body. The therapeutically effective amount for a given situation can be readily determined by routine experimentation and is within the skill and judgment of the ordinary clinician.

Examples of dosages which can be used are a therapeutically effective amount within the dosage range of about 0.1 µg/kg to about 300 mg/kg, or within about 1.0 µg/kg to about 40 mg/kg body weight, or within about 1.0 µg/kg to about 20 mg/kg body weight, or within about 1.0 µg/kg to about 10 mg/kg body weight, or within about 10.0 µg/kg to about 10 mg/kg body weight, or within about 100 µg/kg to about 10 mg/kg body weight, or within about 1.0 mg/kg to about 10 mg/kg body weight, or within about 10 mg/kg to about 100 mg/kg body weight, or within about 50 mg/kg to about 150 mg/kg body weight, or within about 100 mg/kg to about 200 mg/kg body weight, or within about 150 mg/kg to about 250 mg/kg body weight, or within about 200 mg/kg to about 300 mg/kg body weight, or within about 250 mg/kg to about 300 mg/kg body weight. Other dosages which can be used are about 0.01 mg/kg body weight, about 0.1 mg/kg body weight, about 1 mg/kg body weight, about 10 mg/kg body weight, about 20 mg/kg body weight, about 30 mg/kg body weight, about 40 mg/kg body weight, about 50 mg/kg body weight, about 75 mg/kg body weight, about 100 mg/kg body weight, about 125 mg/kg body weight, about 150 mg/kg body weight, about 175 mg/kg body weight, about 200 mg/kg body weight, about 225 mg/kg body weight, about 250 mg/kg body weight, about 275 mg/kg body weight, or about 300 mg/kg body weight. Compounds of the present invention may be administered in a single daily dose, or the total daily dosage may be administered in divided dosage of two, three or four times daily.

For topical application, the formulation may be administered, for example transdermally at about 5 mg to about 100 mg over 24 hours. For IV administration, the formulation may be administered at a dosage of, for example, from about 0.1 mg per day to about 500 mg per day, typically from about 1 to about 200 mg/day. For oral administration, the formulation may be administered at a dosage of, for example, from about 1 mg per day to about 1500 mg per day, often from about 5 to about 250 mg/day.

When additional active agents are used in combination with the compounds of the present invention, the additional active agents may generally be employed in therapeutic amounts as indicated in the PHYSICIANS' DESK REFERENCE (PDR) 53rd Edition (1999), or such therapeutically useful amounts as would be known to one of ordinary skill in the art.

The compounds of the invention and the other therapeutically active agents can be administered at the recommended maximum clinical dosage or at lower doses. Dosage levels of the active compounds in the formulations of the invention may be varied so as to obtain a desired therapeutic response depending on the route of administration, severity of the disease and the response of the individual. When administered in combination with other pharmaceutical agents, the pharmaceutical agents can be formulated as separate formulations that are given at the same time or different times, or the pharmaceutical agents can be given as a single formulation.

Kits

The invention also provides articles of manufacture and kits containing materials useful for the treatment or prevention of a condition mediated by Raf kinase. The article of manufacture may comprise a container with a label. Suitable containers include, for example, bottles, vials, and test tubes.

The containers may be formed from a variety of materials such as glass or plastic. The container may hold a formulation having an active agent which is effective in treating or preventing conditions mediated by Raf kinase. The active agent in the formulation is one or more of the compounds of the invention. The label on the container may indicate that the formulation is used for treating or suppressing conditions mediated by Raf kinase, and may also indicate directions for either in vivo or in vitro use, such as those described above.

The invention also provides kits comprising any one or more of the compounds of the invention. In some embodiments, the kit of the invention comprises the container described above. In other embodiments, the kit of the invention comprises the container described above and a second container comprising a buffer. It may further include other materials desirable from a commercial and user standpoint, including other buffers, diluents, filters, needles, syringes, and package inserts with instructions for performing any methods described herein.

In other aspects, the kits may be used for any of the methods described herein, including, for example, to treat an individual with one or more conditions mediated by or characterized by Raf kinase, or to suppress one or more such conditions.

In certain embodiments the kits may include a dosage amount of at least one formulation as disclosed herein. Kits may also comprise a means for the delivery of the formulation thereof.

The kits may include other pharmaceutical agents for use in conjunction with the formulation described herein. In some variations, the pharmaceutical agent(s) may be one or more anti-cancer drug(s). These agents may be provided in a separate form, or mixed with the compounds of the present invention, provided such mixing does not reduce the effectiveness of either the pharmaceutical agent or formulation described herein and is compatible with the route of administration. Similarly the kits may include additional agents for adjunctive therapy or other agents known to the skilled artisan as effective in the treatment or prevention of the conditions described herein.

The kits may optionally include appropriate instructions for preparation and administration of the formulation, side effects of the formulation, and any other relevant information. The instructions may be in any suitable format, including, but not limited to, printed matter, videotape, computer readable disk, optical disc or directions to internet-based instructions.

In another aspect of the invention, kits for treating an individual who suffers from or is susceptible to the conditions described herein are provided, comprising a first container comprising a dosage amount of a composition as disclosed herein, and instructions for use. The container may be any of those known in the art and appropriate for storage and delivery of intravenous formulation. In certain embodiments the kit further comprises a second container comprising a pharmaceutically acceptable carrier, diluent, adjuvant, etc. for preparation of the formulation to be administered to the individual.

Kits may also be provided that contain sufficient dosages of the compounds described herein (including formulations thereof) to provide effective treatment for an individual for an extended period, such as 1-3 days, 1-5 days, a week, 2 weeks, 3 weeks, 4 weeks, 6 weeks, 8 weeks, 3 months, 4 months, 5 months, 6 months, 7 months, 8 months, 9 months or more.

Kits may also include multiple doses of the formulation and instructions for use and packaged in quantities sufficient for storage and use in pharmacies, for example, hospital pharmacies and compounding pharmacies.

The kits may include the composition as described herein packaged in either a unit dosage form or in a multi-use form. The kits may also include multiple units of the unit dose form.

In certain embodiments, are provided a formulation described herein in a unit dose form. In other embodiments a formulation may be provided in a multi-dose form (e.g., a blister pack, etc.).

The present invention also relates to the processes for preparing the compounds of the invention and to the synthetic intermediates useful in such processes, as described in detail below.

Synthetic Methods

Compounds of the invention may be prepared using a number of methods familiar to one of skill in the art. The discussion below is offered to illustrate certain of the diverse methods available for use in assembling the compounds of the invention. However, the discussion is not intended to define the scope of the reactions or reaction sequences that are useful in preparing compounds of the invention.

For compounds with the general structure as depicted by 4, the following synthetic approach may be employed

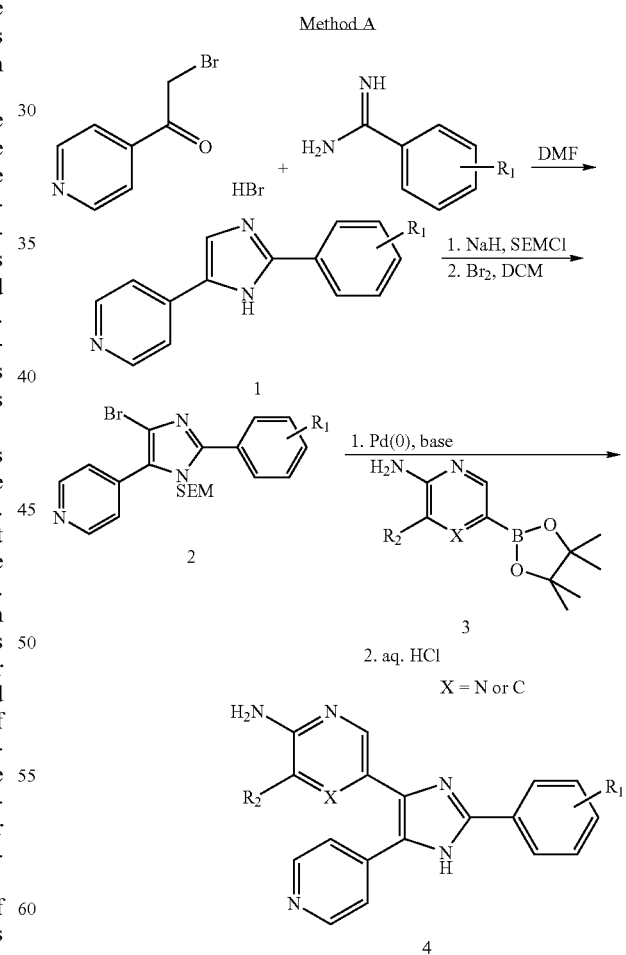

Condensation between a bromoketone and a substituted benzamidine furnishes the disubstituted imidazole 1. Prosaic SEM protection and bromination affords bromoimidazole 2 as a mixture regioisomers. Suzuki cross coupling with a substituted aminopyridine or pyrimidine boronate ester 3 and final deprotection results in the trisubstituted imidazole 4. Protection of the imidazole nitrogen is not restricted to the SEM group; other protecting group may be used (see Greene and Wuts, PROTECTIVE GROUPS IN ORGANIC SYNTHESIS, 2$^{nd}$ Edition, John Wiley & Sons).

An alternative approach to access analogs as represented by 4 is described in Method B.

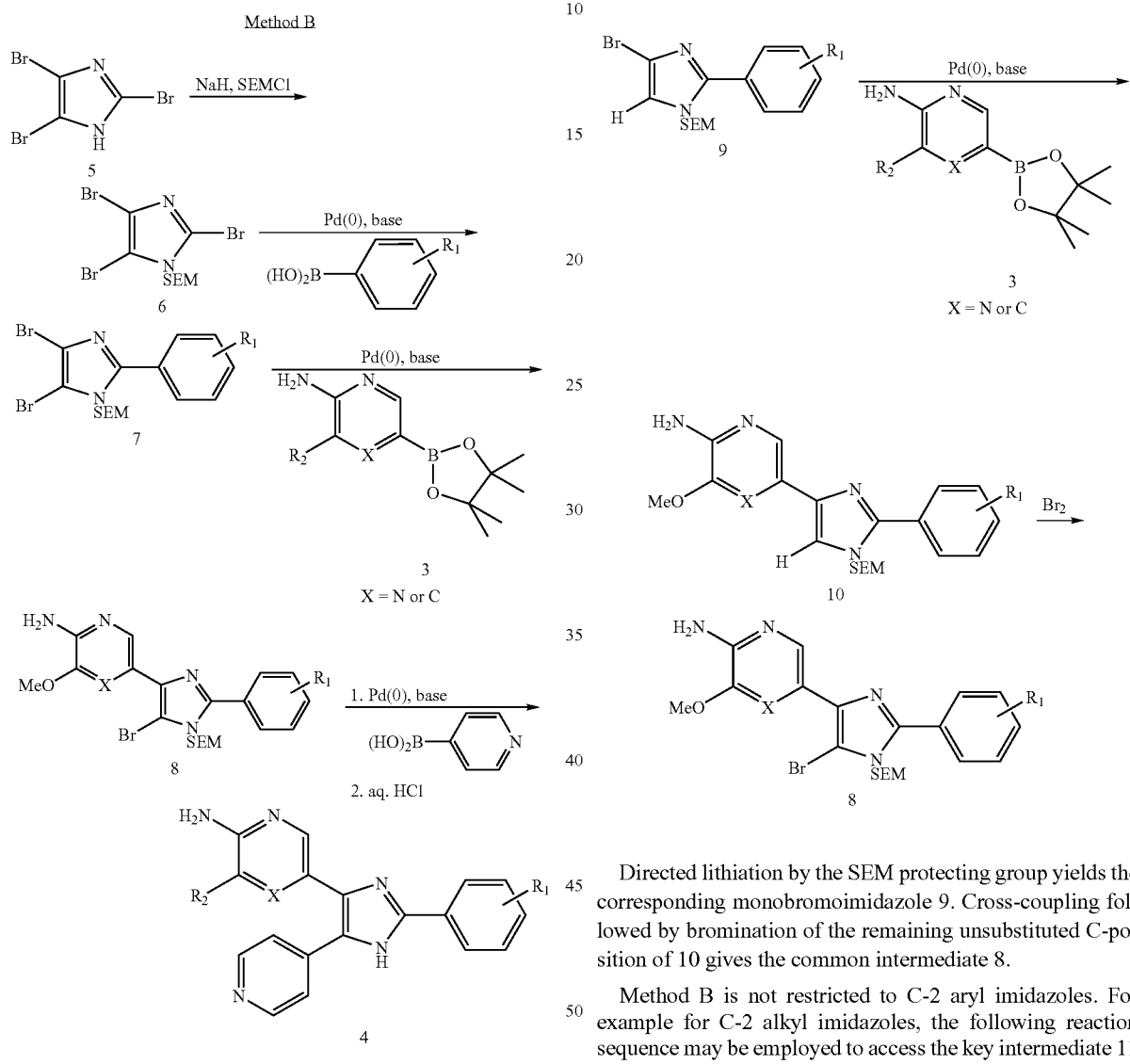

SEM protected 2,4,5-tribromoimidazole 6 can be selectively C-2 arylated using the Suzuki cross-coupling reaction (Revesz, L.; Bonne, F.; Makavou, P. *Tetrahedron Letters*, 1998, 39, 5171) to provide the substituted dibromoimidazole 7. A second Suzuki cross-coupling with boronate ester 3 gives the monobrominated imidazole 8 as a mixture of regioisomers. Final cross-coupling with 4-pyridyl boronic acid and SEM deprotection furnishes the trisubstituted imidazole 4. The Suzuki cross couplings described in this route may be generally substituted with the corresponding Stille reactions where by the boronate ester or boronic acid is replaced with the corresponding stannane.

A variation of Method B that involves a more circuitous route from dibromoimidazole 7 to monobrominated imidazole 8 is described below.

Directed lithiation by the SEM protecting group yields the corresponding monobromoimidazole 9. Cross-coupling followed by bromination of the remaining unsubstituted C-position of 10 gives the common intermediate 8.

Method B is not restricted to C-2 aryl imidazoles. For example for C-2 alkyl imidazoles, the following reaction sequence may be employed to access the key intermediate 11 which then follows the rest of Method B.

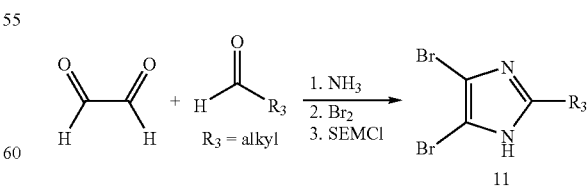

A general approach to functionalized C-5 pyrimidinyl imidazoles such as 12 can be realized using Method C (Bursavich, M. G.; Lombardi, S.; Gilbert, A. M. *Organic Letters*, 2005, 4113).

Method C

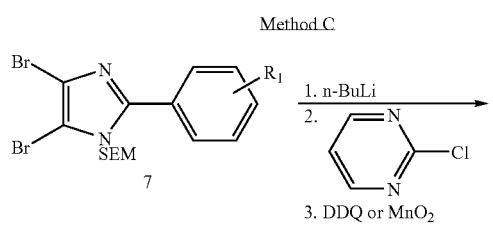

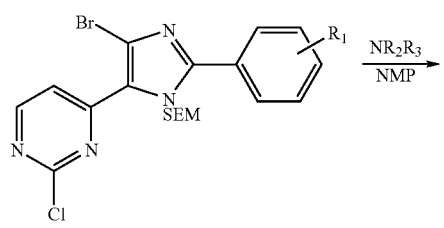

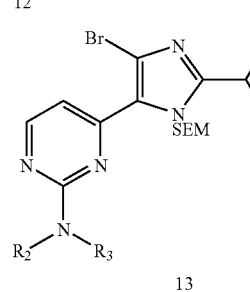

Monolithiation of dibromoimidazole 7 by one equivalent of n-BuLi followed by treatment with 2-chloropyrimidine results in the dihydrochlorpyrimidine adduct which is oxidized by DDQ or MnO$_2$ to furnish the 4-bromo-5-(2-chloropyrimidin-3-yl)imidazole 12. Displacement of the chloro group by simple primary and secondary amines afford amino substituted pyrimidines as depicted by 13. 2-Methylthiopyrimidine may be used instead (Itami, K.; Yamazaki, D.; Yoshida, J. *JACS*, 2004, 126, 15396.) The thiomethyl group can be readily oxidized to the sulfone or sulfoxide in preparation for amine displacement. Further elaboration of 13 may be completed in accordance with Method A.

Conversely, in Method D, chloropyrimidine 12 may be coupled to anilines and aminoheterocycles under Buchwald conditions to provide substituted pyrimidines with the general structure 14. Subsequent cross-coupling and deprotection can be effected as per Method A.

Method D

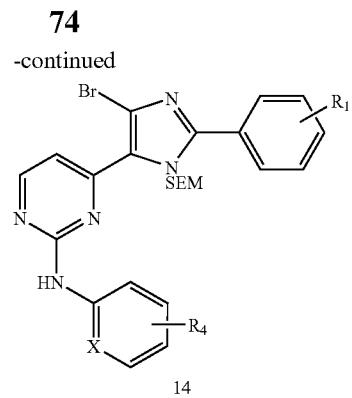

For oxazoles with the general structure as illustrated by 19, the synthetic approach depicted by Method E may be used.

Method E

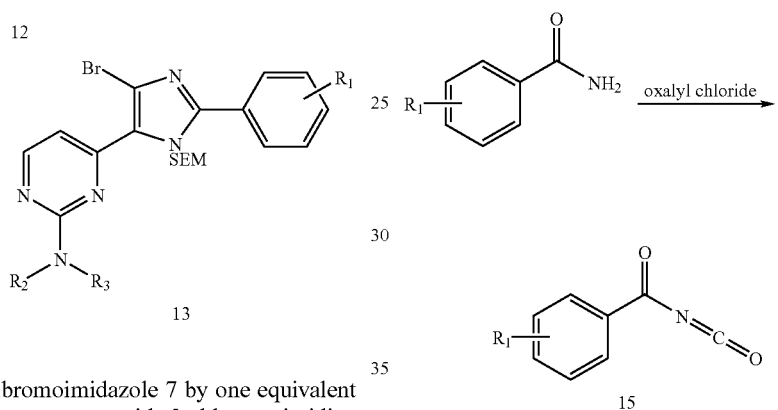

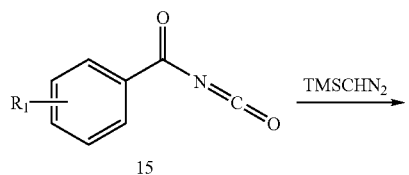

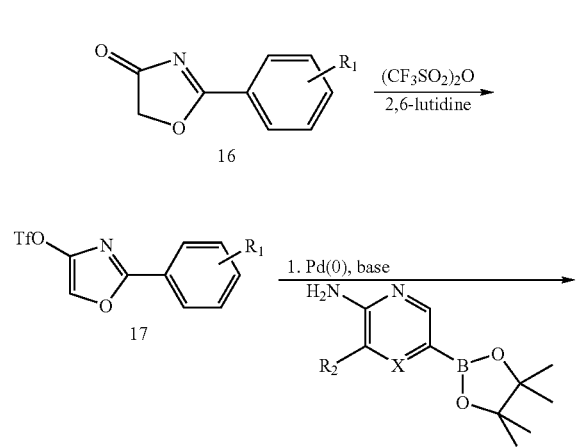

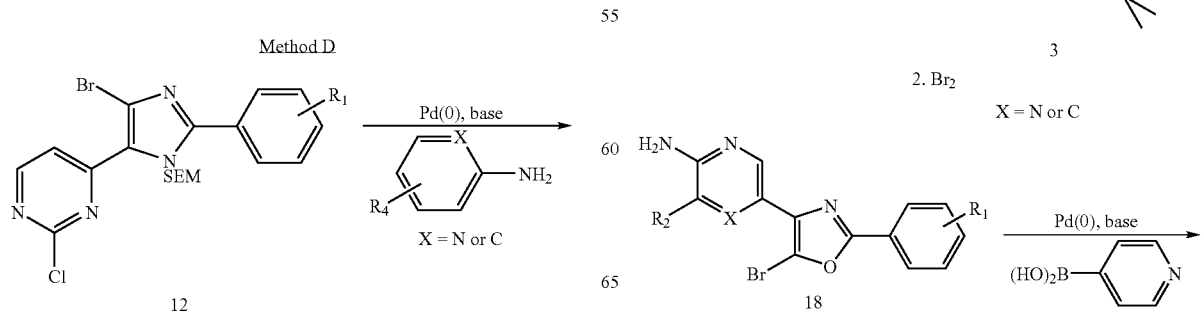

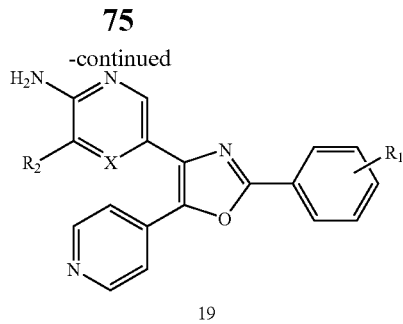

Treatment of a benzamidine with oxalyl chloride generates an acyl isocyanate 15 (McGrew, L. A.; Sweeny, W.; Campbell, T. W.; Foldi, V. S. *J. Org. Chem.* 1964, 29, 3002) which followed by reaction with TMSCHN$_2$ furnishes the oxazolone 16 (Hari, Y.; Iguchi, T.; Aoyama, T. *Synthesis* 2004, 1359). Exposure to triflic anhydride furnishes the coupling partner 17. The subsequent. Suzuki reaction (Flegeau, E. F.; Popkin, M. E.; Greaney, M. F. *Org. Lett.* 2006, 8, 2495) and bromination of the remaining unsubstituted C-5 position affords 18. Final elaboration to 19 is accomplished by Suzuki cross-coupling with 4-pyridyl boronic acid. The converse oxazole regioisomer may be accessed by simply reversing the order of the cross-coupling reactions.

For access to C-5 pyrimidinyl oxazoles, as depicted by intermediate 20, the reaction sequence illustrated in Method F may be employed.

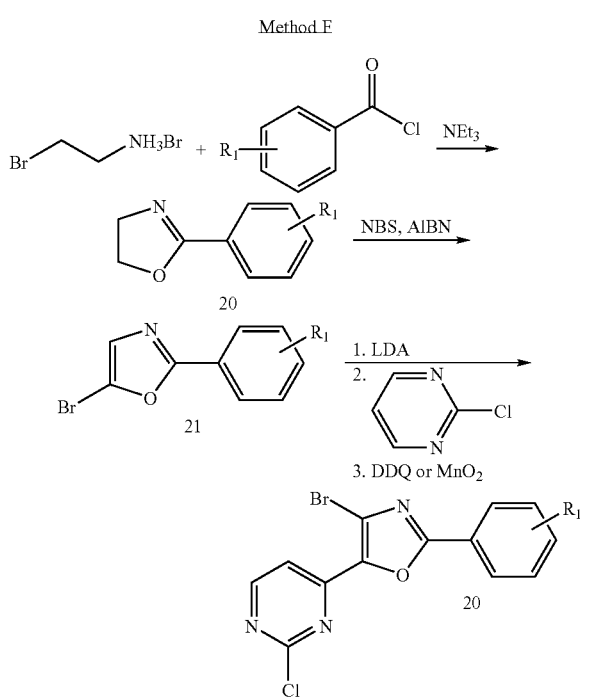

The precursor oxazoline 20 can be prepared by treatment of an aryl acid chloride with 2-bromoethylamine hydrobromide (Kajima, C.; Arao, H. *Synthesis* 1989, 873). Concomitant oxidation and bromination can be achieved by using NBS in the presence of AIBN to yield 21. Deprotonation using LDA results in a halogen migration (Stanetty, P.; Spina, M.; Mihovilovic, M. D. *Synthesis* 2005, 1433), which followed by addition into 2-chloropyrimidine and oxidation furnishes the C-5 pyrimidinyl oxazole 22. Further elaboration may be achieved using Method A.

Preparative separations are carried out using a CombiFlash Rf system (Teledyne Isco Inc. Lincoln, Nebr.) in combination with RediSep Normal-Phase Silica Flash Columns (4 g-120 g, 35-70 micron particle size; Teledyne Isco Inc.), or by flash column chromatography using silica gel (230-400 mesh) packing material, or by HPLC using a Waters 2767 Sample Manager, C-18 reversed phase column, 30×50 mm, flow 75 mL/min. Typical solvents employed for the CombiFlash system and flash column chromatography are dichloromethane, methanol, ethyl acetate, hexane, acetone, aqueous ammonia (or ammonium hydroxide), and triethyl amine. Typical solvents employed for the reverse phase HPLC are varying concentrations of acetonitrile and water with 0.1% trifluoroacetic acid.

Microwave reactions conducted in a Creator or Initiator microwave system (Biotage, Charlottesville, Va.)

EXAMPLES

The present invention will be understood more readily by reference to the following examples, which are provided by way of illustration and are not intended to be limiting of the present invention.

Example 1

3-Methoxy-5-(2-phenyl-5-(pyridine-4-yl)-1H-imidazol-4-yl)pyridine-2-amine

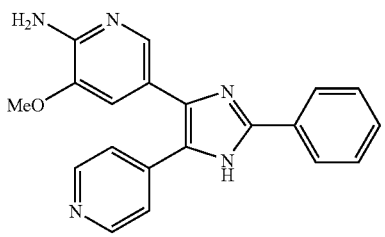

Step 1. Preparation of 4-(2-phenyl-1H-imidazol-4-yl)pyridine: 2-Bromo-1-(pyridin-4-yl)ethanone hydrobromide (6.4 g, 23 mmol) was added portionwise to a solution of benzamidine (11.2 g, 93 mmol) in dry DMF (50 mL) at 0° C., maintaining an internal temperature of <5° C. The stirred reaction was allowed to warm to rt over 2 h and then heated to 40° C. for 16 h. The crude reaction was poured into saturated aqueous NaHCO$_3$ solution (600 mL), and partition and extracted with EtOAc (3×300 mL). The combined organic layers were dried (Na$_2$SO$_4$) and evaporated. The resulting crude residue was purified by flash chromatography (SiO$_2$, 100:0-90:10 DCM-MeOH) to give 3.68 g (72%) of 4-(2-phenyl-1H-imidazol-4-yl)pyridine: $^1$H NMR (CDCl$_3$) δ 9.73 (broad s, 1H), 8.61 (d, J=6.0, 1.2 Hz, 2H), 7.91 (d, J=8.0, 1.6 Hz, 2H), 7.77 (d, J=6.0, 1.2 Hz, 2H), 7.57 (s, 1H), 7.48 (m, 3H).

Step 2. Preparation of 4-(2-phenyl-1-((2-(trimethylsilyl)ethoxy)methyl)-1H-imidazol-4-yl)pyridine: 60% Sodium hydride (200 mg, 5.0 mmol) was added slowly into a solution of 4-(2-phenyl-1H-imidazol-4-yl)pyridine (1.0 g, 4.5 mmol; Example 1, Step 1) in dry DMF (5 mL) at 0° C. The reaction mixture was stirred at rt for 1 h and re-cooled to 0° C. and 2-(trimethylsilyl)ethoxymethyl chloride (SEM chloride; 0.88 mL, 0.83 g, 5.0 mmol) was added. The reaction was stirred at 10° C. for 2 h and quenched with water (40 mL). The mixture was partitioned and extracted with EtOAc (3×60 mL) and the organic layers were combined, dried (Na$_2$SO$_4$), and concentrated. The resulting residue was purified by flash chromatography (SiO$_2$, 100:0-90:10 DCM-MeOH) to give 1.2 g (75%) of 4-(2-phenyl-1-((2-(trimethylsilyl)ethoxy)methyl)-1H-imidazol-4-yl)pyridine: $^1$H NMR (CDCl$_3$) δ 8.61 (d, J=6.0, 1.2 Hz, 2H), 7.81 (d, J=8.0, 1.6 Hz, 2H), 7.74 (d, J=6.0, 1.2 Hz, 2H), 7.58 (s, 1H), 7.49 (m, 3H), 5.30 (s, 2H), 3.60 (t, J=8.0 Hz, 2H), 0.94 (t, J=8.0 Hz, 2H), 0.00 (s, 9H).

Step 3. Preparation of 4-(5-bromo-2-phenyl-1-((2-(trimethylsilyl)ethoxy)methyl)-1H-imidazol-4-yl)pyridine: Bromine (0.2 mL, 3.8 mmol) was added slowly to a solution of 4-(2-phenyl-1-((2-(trimethylsilyl)ethoxy)methyl)-1H-imidazol-4-yl)pyridine (1.2 g, 3.41 mmol; Example 1, Step 2) in dry DCM at 0° C., followed by saturated aqueous Na$_2$CO$_3$ solution (40 µL). The reaction mixture was then stirred at rt for 16 h. The reaction was then allowed to partition and the layers separated. The aqueous phase was extracted with EtOAc (2×20 mL) and the combined organic phases were dried (Na$_2$SO$_4$). The resulting residue was purified by flash chromatography (SiO$_2$, 100:0-90:10 DCM-MeOH) to furnish 1.06 g (72%) of 4-(5-bromo-2-phenyl-1-((2-(trimethylsilyl)ethoxy)methyl)-1H-imidazol-4-yl)pyridine: $^1$H NMR (400 MHz, CDCl$_3$) δ 8.62-8.70 (m, 2H), 7.78-8.05 (m, 2H), 7.77-7.86 (m, 2H), 7.45-7.54 (m, 3H), 5.37 (s, 2H), 3.60-3.70 (m, 2H), 0.92-1.02 (m, 2H), 0.003 (s, 9H).

Step 4. Preparation of 3-methoxy-5-(2-phenyl-5-(pyridine-4-yl)-1H-imidazol-4-yl)pyridine-2-amine: A mixture of 4-(5-bromo-2-phenyl-1-((2-(trimethylsilyl)ethoxy)methyl)-1H-imidazol-4-yl)pyridine (620 mg, 1.4 mmol; Example 1, Step 3), 3-methoxy-5-(4,4,5,5-tetramethyl-1,3,2-dioxoborolan-2-yl)pyridine-2-amine (570 mg, 2.3 mmol, Example 17, Step 3), and aqueous 2.0 M Na$_2$CO$_3$ solution (2 mL, 4 mmol) in DME (8 mL) was purged with Ar for 3 min. Pd(dppf)Cl$_2$-DCM (34 mg, 0.04 mmol) was added and the reaction mixture was purged with Ar for another 5 min. The reaction mixture was then heated to and maintained at 90° C. for 18 h under Ar. The reaction was allowed to cool to rt and was concentrated. The resulting residue was suspended in EtOAc (15 mL) and passed through a syringe filter. The filtrate was concentrated, treated with aqueous 3 M HCl solution (6 mL), and heated at 60° C. for 2 h. The reaction was allowed to cool to rt and was evaporated in vacuo. The resulting residue was purified by reverse-phase HPLC and lyophilized to afford 160 mg (33%) of 3-methoxy-5-(2-phenyl-5-(pyridine-4-yl)-1H-imidazol-4-yl)pyridine-2-amine as the TFA salt: LCMS (m/z): 344.2 (MH$^+$); t$_R$=0.46 min; $^1$H NMR (CD$_3$OD) δ 3.88 (s, 3H), 6.22 (br s, 2H), 7.16 (m, 1H), 7.38 (t, J=7.2 Hz, 1H), 7.47 (t, J=7.2 Hz, 2H), 7.61 (m, 2H), 7.67 (m, 1H), 8.05 (d, J=6.0 Hz, 2H), 8.48 (d, J=6.0 Hz, 2H).

Example 2

3-methoxy-5-(5-(pyridine-4-yl)-2-(4-(trifluoromethyl)phenyl)-1H-imidazol-4-yl)pyridin-2-amine

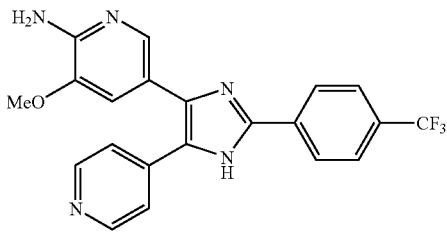

Step 1. Preparation of 2,4,5-tribromo-1-((2-(trimethylsilyl)ethoxy)methyl)-1H-imidazole: A dried 500 mL round bottom flask was charged with 2,4,5-tribromoimidazole (20.0 g, 65.62 mmol) and anhydrous DMF (100 mL), the resulting solution was cooled to 0° C. To this cold solution was added NaH (60% in mineral oil, 2.80 g, 70.0 mmol) portionwise with gas evolution under control and an internal temperature maintained below 10° C. After addition, the cold bath was removed and the resulting mixture was stirred at ambient temperature for 30 minutes. The reaction mixture was cooled back to 0° C., and SEM chloride (12.2 mL, 69.5 mmol) was added to the reaction via syringe pump over 30 minutes. The reaction was stirred at 0° C. for an additional 30 minutes and at ambient temperature for another 30 minutes. The reaction was deemed complete by LCMS and the mixture was partitioned between EtOAc (150 mL) and water (300 mL), and the layers separated. The organic phase was sequentially washed with dilute aqueous NaCl (5% w/w, 2×), then brine (100 mL), dried (Na$_2$SO$_4$), concentrated and a light yellow solid was obtained. The crude material was recrystallized from hot petroleum ether (30 mL) and the solids were harvested from the mother liquor at 0° C. The product was washed with cold petroleum ether (30 mL) and dried under vacuum to afford 2,4,5-tribromo-1-((2-(trimethylsilyl)ethoxy)methyl)-1H-imidazole (26.3 g, 92% yield): $^1$H NMR (400 MHz, CDCl$_3$) δ 5.31 (s, 2H), 3.59 (t, J=7.2 Hz, 2H), 0.92 (t, J=7.2 Hz, 2H), −0.01 (s, 9H, —Si(CH$_3$)$_3$).

Step 2. Preparation of 4,5-dibromo-2-(4-(trifluoromethyl)phenyl)-1-((2-trimethylsilyl)ethoxy)methyl-1H-imidazole: A mixture of 2,4,5-tribromo-1-((2-(trimethylsilyl)ethoxy)methyl)-1H-imidazole (10.2 g, 23.5 mmol), 4-(trifluoromethyl)phenylboronic acid (5.4 g, 28.4 mmol), and 2.0 M aqueous sodium carbonate solution (20 mL, 40 mmol) in DME (70 mL). was sparged with Ar. Pd(PPh$_3$)$_4$ (746 mg, 0.65 mmol) was added in one portion, and the reaction mixture was sparged again with Ar, then heated to 95° C. for 16 h. LCMS indicated only 70% conversion. Another charge of 4-(trifluoromethyl)phenylboronic acid (2.0 g, 10.5 mmol) was added and the reaction was maintained at 95° C. for 24 h. The reaction was allowed to cool to rt and was then partitioned between water and EtOAc. The aqueous layer was separated and extracted with EtOAc (2×). The combined organic phases were then dried (Na$_2$SO$_4$), concentrated, and adsorbed onto silica gel. Purification by flash chromatography (SiO$_2$; 100: 0-50:50 hexanes-EtOAc) afforded 9.9 g (19.3 mmol, 82%) of 4,5-dibromo-2-(4-(trifluoromethyl)phenyl)-1-((2-trimethylsilyl)ethoxy)methyl-1H-imidazole: LCMS (m/z): 500.9

(MH⁺); t_R=1.33 min; ¹H NMR (400 MHz, CDCl₃) δ 7.98 (d, J=9.0 Hz, 2H), 7.72 (d, J=9.0 Hz, 2H), 5.32 (s, 2H), 3.74 (t, J=7.2 Hz, 2H), 0.99 (t, J=7.2 Hz, 2H), 0.03 (s, 9H).

Step 3. Preparation of 5-(5-bromo-2-(4-trifluoromethyl) phenyl)-1-((2-(trimethylsilyl)ethoxy)methyl)-1H-imidazol-4-yl)-3-methoxypyridin-2-amine: A mixture 4,5-dibromo-2-(4-(trifluoromethyl)phenyl)-1-((2-trimethylsilyl)ethoxy) methyl-1H-imidazole (730 mg, 1.5 mmol) and 3-methoxy-5-(4,4,5,5-tetramethyl-1,3,2-dioxaborolan-2-yl)pyridin-2-amine (400 mg, 1.6 mmol; Example 17, Step 3), and 2.0 M aqueous Na₂CO₃ solution (3 mL, 6.0 mmol) in DME (10 mL) was purged with Ar for 3 min. Pd(PPh₃)₄ (65 mg, 0.055 mmol) was added the reaction was heated to 100° C. by for 20 h. The reaction was allowed to cool to rt and phases partitioned. The organic portion was separated and concentrated. The resulting residue crude was purified by flash chromatography (SiO₂; 80:20-0:100 hexanes-EtOAc) to furnish 640 mg (1.2 mmol, 80%) of 5-(5-bromo-2-(4-trifluoromethyl)phenyl)-1-((2-(trimethylsilyl)ethoxy)methyl)-1H-imidazol-4-yl)-3-methoxypyridin-2-amine: LCMS (m/z): 545.0 (MH⁺), t_R=1.02 min.

Step 4. Preparation of 3-methoxy-5-(5-(pyridine-4-yl)-2-(4-(trifluoromethyl)phenyl)-1H-imidazol-4-yl)pyridin-2-amine: A mixture of 5-(5-bromo-2-(4-trifluoromethyl)phenyl)-1-((2-(trimethylsilyl)ethoxy)methyl)-1H-imidazol-4-yl)-3-methoxypyridin-2-amine (420 mg, 0.77 mmol), pyridin-4-ylboronic acid (186 mg, 1.54 mmol), and 2.0 M aqueous Na₂CO₃ solution (2 mL, 4.0 mmol) in DME (8 mL) was sparged with Ar for 3 min. Pd(PPh₃)₄ (78 mg, 0.067 mmol) was added and the reaction was irradiated at 110° C. for 20 min in a microwave reactor. The reaction was allowed to cool to rt and phases partitioned. The organic portion was separated, concentrated, and the resulting residue was treated with 4 M HCl aqueous solution at 60° C. for 2 h. The reaction was allowed to cool to rt and was directly purified by reverse phase HPLC, which after freeze drying, provide 96 mg of the title compound as the TFA salt: LCMS (m/z): 412.0 (MH⁺), t_R=0.61 min. ¹H NMR (400 MHz, CD₃OD): 8.67 (d, J=6.8 Hz, 2H); 8.29 (d, J=6.8 Hz, 2H); 8.26 (d, J=8.0 Hz, 2H); 7.84 (d, J=8.0 Hz, 2H); 7.78 (s, 1H); 7.60 (s, 1H); 4.02 (s, 3H).

Example 3

2-(4-(4-(6-amino-5-methoxypyridin-3-yl)-2-phenyl-1H-imidazol-5-yl)pyrimidin-2-ylamino)ethanol

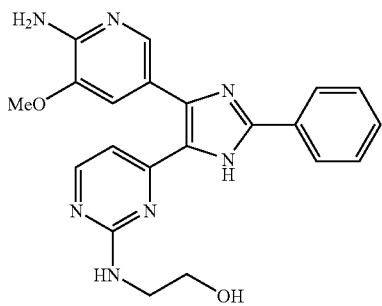

Step 1. Preparation of 4-(4-bromo-2-phenyl-1-((2-(trimethylsilyl)ethoxy)methyl-1H-imidazol-5-yl)-2-chloropyrimidine: n-BuLi (2.2 M in hexane, 3.1 mL, 6.8 mmol) was added dropwise to a stirring solution of 4,5-dibromo-2-phenyl-1-((2-(trimethylsilyl)ethoxy)methyl)-1H-imidazole (2.9 g, 6.8 mmol; prepared similarly as per Example 2, Steps 2-3) at –78° C. The reaction was maintained at –78° C. for 45 min, after which 2-chloropyrimidine (0.884 g, 7.72 mmol) was added in one portion, and the reaction was then allowed to warm to –40° C. over 20 min. The reaction was quenched at –40° C. by the addition of THF/H₂O (3 ml/0.2 ml) and the resulting mixture was allowed to warm to 5° C. over 20 min. The mixture was cooled to –40° C. and a solution of DDQ (1.86 g, 8.19 mmol) in THF (5 mL) was added and the resulting reaction was allowed to warm to 10° C. over 50 min. 3.0 M NaOH (20 mL, 60 mmol) was added followed by water (60 mL) and the resulting mixture was stirred for 10 min at rt. The layers were allowed to partition and then separated. The organic portion was washed with brine (30 mL), dried (Na₂SO₄), and concentrated. The resulting residue was purified by flash chromatography (SiO₂, 100:0-70:30 hexanes-EtOAc) to provide 2.70 g (85%) of 4-(4-bromo-2-phenyl-1-((2-(trimethylsilyl)ethoxy)methyl-1H-imidazol-5-yl)-2-chloropyrimidine: LCMS (m/z): 466.8 (MH⁺), t_R=1.33 min; ¹H NMR (400 MHz, CDCl₃) δ 8.66 (AB, J=5.2 Hz, 2H), 7.98 (AB, J=5.2 Hz, 2H), 7.70-7.80 (m, 2H), 7.42-7.56 (m, 3H), 5.77 (s, 2H), 3.34-3.40 (m, 2H), 0.72-0.77 (m, 2H), –0.12 (s, 9H).

Step 2. Preparation of 2-(4-(4-bromo-2-phenyl-1-((2-(trimethylsilyl)ethoxy)methyl)-1H-imidazol-5-yl)pyrimidin-2-ylamino)ethanol: A solution of 4-(4-bromo-2-phenyl-1-((2-(trimethylsilyl)ethoxy)methyl-1H-imidazol-5-yl)-2-chloropyrimidine (145 mg; 0.31 mmol; Example 3, Step 1) and ethanolamine (0.30 ml, 4.97 mmol) in dry NMP (1 ml) was heated at 120° C. for 1 h. The reaction was allowed to cool to rt and water (5 mL) was added. The resulting suspension was centrifuged and the remaining solid was washed with water and dried under vacuum to furnish 150 mg (98%) of 2-(4-(4-bromo-2-phenyl-1-((2-(trimethylsilyl)ethoxy)methyl)-1H-imidazol-5-yl)pyrimidin-2-ylamino)ethanol: LCMS (m/z): 492.0 (MH⁺), t_R=0.96 min.

Step 3. Preparation of 2-(4-(4-(6-amino-5-methoxypyridin-3-yl)-2-phenyl-1H-imidazol-5-yl)pyrimidin-2-ylamino) ethanol: A mixture of 2-(4-(4-bromo-2-phenyl-1-((2-trimethylsilyl)ethoxy)methyl)-1H-imidazol-5-yl)pyrimidin-2-ylamino)ethanol (38 mg, 0.08 mmol; Example 3, Step 2), 3-methoxy-5-(4,4,5,5-tetramethyl-1,3,2-dioxaborolan-2-yl) pyridin-2-amine (0.39 M in 1,4-dioxane, 0.51 mL, 0.2 mmol), and aqueous 2.0 M Na₂CO₃ solution (1 mL, 1 mmol) in DME (1.2 mL) was sparged with Ar. Pd(PPh₃)₄ (27 mg, 0.023 mmol) was added in one portion and the reaction mixture was sparged again and sealed. The reaction was irradiated at 115° C. for 20 min in a microwave reactor. The reaction was allowed to cool to rt and partitioned between EtOAc (2 mL) and saturated aqueous Na₂CO₃ solution (1 mL). The layers were separated and the organic phase was washed with brine (1 ml), dried (Na₂SO₄), and concentrated. The resulting residue was treated with ethanol (1 ml) and conc. HCl (0.2 ml) and heated to 60° C. for 1 h. After allowing to cool to rt, the reaction was concentrated in vacuo and the resulting residue was purified by reverse phase HPLC, and after lypholization, afforded 19 mg of 2-(4-(4-(6-amino-5-methoxypyridin-3- yl)-2-phenyl-1H-imidazol-5-yl)pyrimidin-2-ylamino)etha-
nol as the TFA salt: LCMS (m/z): 404.1 (MH⁺), $t_R$=0.54 min.

Example 4

(S)—N-(1-(4-(4-(5-amino-6-methoxypyrazin-2-yl)-
2-(4-(trifluoromethyl)phenyl)-1H-imidazol-5-yl)
pyrimidin-2-ylamino)propan-2-yl)-2-methoxyaceta-
mide

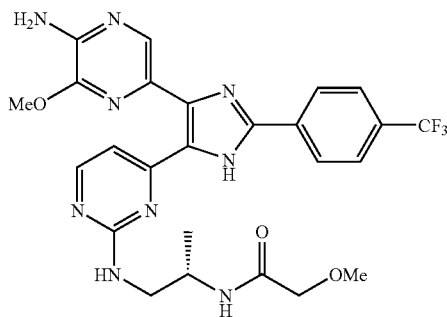

Step 1. Preparation of 4-(4-bromo-2-(4-(trifluoromethyl)
phenyl)-1-((2-(trimethylsilyl)ethoxy)methyl)-1H-imidazol-
5-yl)-2-chloropyrimidine: A solution of 4,5-dibromo-2-(4-
(trifluoromethyl)phenyl)-1-((2-(trimethylsilyl)ethoxy)
methyl)-1H-imidazole (1.0 g, 2.0 mmol, Example 2, Step 2)
in dry THF (10 mL) was cooled to −78° C. under Ar. n-BuLi
(1.0 mL, 2.5 M in hexane, 2.5 mmol) was added dropwise,
afterwards the reaction was maintained below −70° C. for an
additional 45 min. A solution of 2-chloropyrimidine (0.29 g,
2.5 mmol) in dry THF (2 mL) was added dropwise at −78° C.
After addition, the reaction was allowed to warm to −40° C.
over 25 min and maintained at −40° C. for 20 min. The
reaction was then warmed to −5° C. in a brine-ice bath,
quenched with water (30 mL), and stirred at rt for 30 min. The
reaction mixture was concentrated and partitioned between
EtOAc and water. The organic phase was separated, dried
($Na_2SO_4$), and concentrated. The resulting residue was fur-
ther purified by flash chromatography ($SiO_2$, 100:0-20:80,
hexanes-EtOAc) to afford 1.1 g (2.05 mmol, 82%) of 6-(4-
bromo-2-(4-(trifluoromethyl)phenyl)-1-((2-trimethylsilyl)
ethoxy)methyl)-1H-imidazol-5-yl)-2-chloro-1,6-dihydropy-
rimidine. A solution of 6-(4-bromo-2-(4-(trifluoromethyl)
phenyl)-1-((2-(trimethylsilyl)ethoxy)methyl)-1H-imidazol-
5-yl)-2-chloro-1,6-dihydropyrimidine (410 mg, 0.8 mmol) in
EtOAc (20 mL) was treated with $MnO_2$ (920 mg, 10.6 mmol)
and the resulting reaction mixture was heated to and main-
tained at reflux for 18 h. The reaction was allowed to cool to
rt and was then filtered through Celite. The filter cake was
washed with EtOAc (2×20 mL) and the combined filtrates
were concentrated to give 400 mg (0.75 mmol, 98%) of 4-(4-
bromo-2-(4-(trifluoromethyl)phenyl)-1-((2-(trimethylsilyl)
ethoxy)methyl)-1H-imidazol-5-yl)-2-chloropyrimidine: ¹H
NMR (400 MHz, $CDCl_3$) δ 8.71 (d, J=5.4 Hz, 1H), 8.02 (d,
J=5.4 Hz, 1H), 7.96 (d, J=8.1 Hz, 2H), 7.77 (d, J=8.1 Hz, 2H),
5.77 (s, 2H), 3.49 (t, J=7.5 Hz, 2H), 0.83 (t, J=7.5 Hz, 2H),
0.01 (s, 9H).

Step 2. Preparation of (S)-tert-butyl-1-(4-(4-bromo-2-(4-
trifluoromethyl)phenyl)-1-((2-(trimethylsilyl)ethoxy)me-
thyl)-1H-imidazol-5-yl)pyrimidin-2-ylamino)propan-2-yl-
carbamate: A solution of 4-(4-bromo-2-(4-trifluoromethyl)
phenyl)-1-((2-(trimethylsilyl)ethoxy)methyl)-1H-imidazol-
5-yl)-2-chloropyrimidine (4.1 g, 7.7 mmol) in dry NMP (10
mL) was treated with (S)-tert-butyl-1-aminopropan-2-ylcar-
bamate (1.9 g, 11.0 mmol; Example 23, Step 2), followed by
$Na_2CO_3$ (0.82, 7.7 mmol). The resulting mixture was heated
to 80° C. for 4 h whereupon the reaction was deemed com-
plete by LCMS, and allowed to cool to rt. Water was added
and the resulting suspension was compacted by centrifuga-
tion. The filtrate was decanted, the remaining solids were
washed with water, and dried under vacuum to provide 4.6 g
(6.9 mmol, 90%) as (S)-tert-butyl-1-(4-(4-bromo-2-(4-trif-
luoromethyl)phenyl)-1-((2-(trimethylsilyl)ethoxy)methyl)-
1H-imidazol-5-yl)pyrimidin-2-ylamino)propan-2-ylcar-
bamate, which was carried forward without further
purification.

Step 3. Preparation of (S)—N-(1-(4-(4-bromo-2-(4-(trif-
luoromethyl)phenyl)-1H-imidazol-5-yl)pyrimidin-2-
ylamino)propan-2-yl)-2-methoxyacetamide: A solution of
(S)-tert-butyl-1-(4-(4-bromo-2-(4-trifluoromethyl)phenyl)-
1-((2-(trimethylsilyl)ethoxy)methyl)-1H-imidazol-5-yl)py-
rimidin-2-ylamino)propan-2-ylcarbamate (4.7 g, 6.9 mmol)
in dry ethanol (8 mL) was treated with aqueous 4 N HCl
solution (4 mL, 16 mmol) and the resulting reaction mixture
was heated to 60° C. for 4 h. After the reaction was judged
complete, the mixture was allowed to cool to rt and evapo-
rated to dryness. The resulting residue was carried forward
without further purification. The preceding residue (2.0 g, 4.6
mmol) was dissolved in dry DCM (60 mL) and treated with
diisopropylethylamine (DIPEA, 1.0 mL, 5.7 mmol). The
resulting mixture was stirred at rt for 5 min until the reaction
became homogenous. A solution of 2-methoxyacetyl chlo-
ride (0.46 mL, 4.6 mmol) in dry DCM (5 mL) was added
dropwise and the resulting reaction was maintained at rt for 4
h. An additional charge of 2-methoxyacetyl chloride (0.03
mL 0.3 mmol) was added to complete the reaction. After-
wards, the reaction was partitioned between DCM and water,
and the layers were separated. The aqueous phase was
extracted with DCM (2×30 mL) and the combined organic
layers were dried ($Na_2SO_4$), and concentrated to furnish
(S)—N-(1-(4-(4-bromo-2-(4-(trifluoromethyl)phenyl)-1H-
imidazol-5-yl)pyrimidin-2-ylamino)propan-2-yl)-2-meth-
oxyacetamide: LCMS (m/z): 513.1 (MH⁺), $t_R$=0.88 min.

Step 4. Preparation of (S)—N-(1-(4-(4-(5-amino-6-meth-
oxypyrazin-2-yl)-2-(4-(trifluoromethyl)phenyl)-1H-imida-
zol-5-yl)pyrimidin-2-ylamino)propan-2-yl)-2-methoxyac-
etamide: A 20 mL microwave vial containing (S)—N-(1-(4-
(4-bromo-2-(4-(trifluoromethyl)phenyl)-1H-imidazol-5-yl)
pyrimidin-2-ylamino)propan-2-yl)-2-methoxyacetamide
(0.8 g, 1.6 mmol), 3-methoxy-5-(4,4,5,5-tetramethyl-1,3,2-
dioxaborolan-2-yl)pyrazin-2-amine (0.52 g, 3.1 mmol,
Example 18, Step 2), and 2.0 M $Na_2CO_3$ aqueous solution
(5.0 mL, 10.0 mmol) in DME (17 mL) was sparged with Ar
for 15 min. Pd(PPh₃)₄ (0.16 g, 0.14 mmol) was added in one
portion and the reaction vial sealed, and irradiated at 120° C.
for 30 min in a microwave reactor. The reaction was allowed
to cool to rt and the organic and aqueous phases partitioned
upon standing. The layers were separated and the aqueous
phase was back extracted with EtOAc (2×). The combined
organic phases were concentrated, and the resulting residue
was suspended in DMSO (20 mL) and filtered through a
plastic membrane. The filtrate was purified by preparative
reverse-phase HPLC and the combined isolated fractions
were partitioned with EtOAc and saturated aqueous $Na_2CO_3$
solution. The layers were separated and the organic phase was washed with saturated aqueous Na$_2$CO$_3$ solution (2×), brine, dried (Na$_2$SO$_4$), and concentrated. The resulting free base was suspended in acetonitrile-water (1:4), acidified with one equivalent of 1.0 M aqueous HCl solution, and lyophilized to give the title compound as the HCl salt: LCMS (m/z): 558.2 (MH$^+$), t$_R$=0.72 min; $^1$H NMR (400 MHz, CD$_3$COOD, 45° C.) δ 8.43 (d, J=8.1 Hz, 2H), 8.26-8.36 (m, 2H), 7.82 (d, J=8.1 Hz, 2H), 7.67 (d, J=5.7 Hz, 1H), 4.31 (m, 1H), 4.13 (s, 3H), 3.95 (m, 2H), 3.79 (dd, J=13, 5.0 Hz, 1H), 3.68 (dd, J=13, 6.5 Hz, 1H), 3.35 (s, 3H), 1.30 (d, J=6.6 Hz, 3H).

Example 5

(S)—N-(1-(4-(4-(5-amino-6-methoxylpyrazin-2-yl)-2-(4-fluorophenyl)-1H-imidazol-5-yl)pyrimidin-2-ylamino)propan-2-yl)-2-methoxyacetamide

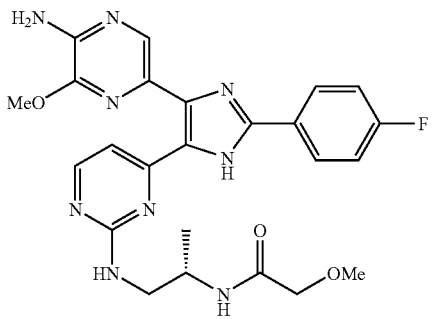

Step 1. Preparation of 4,5-dibromo-2-(4-fluorophenyl)-1-((2-(trimethylsilyl)ethoxy)methyl)-1H-imidazole: A microwave vial was charged with 2,4,5-tribromo-1-((2-(trimethylsilyl)ethoxy)methyl)-1H-imidazole (881 mg, 2.0 mmol, Example 2, Step 2), 4-fluorophenyl boronic acid (308 mg, 2.2 mmol), aqueous Na$_2$CO$_3$ solution (6 ml, 2.0 M, 12.0 mmol) and DME (12 ml). The mixture was sparged with argon for 15 min, followed by addition of Pd(PPh$_3$)$_4$ (120 mg, 0.1 mmol). The reaction vial was sealed and heated at 110° C. for 20 minutes in a microwave reactor; the reaction was deemed complete by LCMS. The reaction mixture was partitioned between saturated Na$_2$CO$_3$ solution and EtOAc (10 ml/30 ml), the organic layer was separated, washed with brine (10 ml), dried (Na$_2$SO$_4$), and concentrated. The resulting residue was purified by flash column chromatography (SiO$_2$; 100:0-80:20 hexanes-EtOAc) to furnish 4,5-dibromo-2-(4-fluorophenyl)-1-((2-(trimethylsilyl)ethoxy)methyl)-1H-imidazole (780 mg, 1.73 mmol, 87%) as a solid: $^1$H NMR (400 MHz, DMSO-d$_6$) δ 7.80-7.70 (m, 2H), 7.37 (app t, J=9.0 Hz, 2H), 5.33 (s, 2H), 3.52 (t, J=8.2 Hz, 2H), 0.83 (t, J=8.2 Hz, 2H), −0.06 (s, 9H).

Step 2. Preparation of (S)—N-(1-(4-(4-(5-amino-6-methoxylpyrazin-2-yl)-2-(4-fluorophenyl)-1H-imidazol-5-yl)pyrimidin-2-ylamino)propan-2-yl)-2-methoxyacetamide: 4,5-dibromo-2-(4-fluorophenyl)-1-((2-(trimethylsilyl)ethoxy)methyl)-1H-imidazole was elaborated to the title compound following Example 4, Steps 1-4: $^1$H NMR (400 MHz, CD$_3$COOD): δ 8.20-8.32 (m, 3H), 8.16 (s, 1H), 7.50 (d, J=6.7 Hz, 1H), 7.25 (t, J=8.6 Hz, 2H), 4.24-4.35 (m, 1H), 4.04 (s, 3H), 3.93 (s, 2H), 3.75 (dd, J=13.3, 1.5 Hz, 1H), 3.59 (dd, J=13.3, 7.0 Hz, 1H), 3.33 (s, 3H), 1.25 (d, J=7.0 Hz, 3H).

Example 6

(S)-1-(4-(4-6-amino-5-methoxypyrdin-3-yl)-2-tert-butyl-1H-imidazol-5-yl)pyrimidin-2-ylamino)propan-2-ol

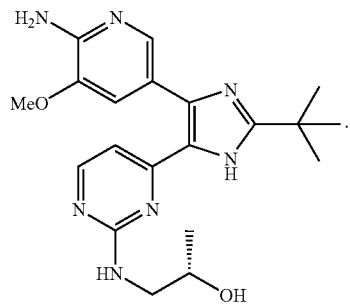

Step 1. Preparation of 2-t-butylimidazole: A solution of glyoxal (40% in water, 16.4 g, 113.4 mmol) in water (180 ml) was added to trimethylacetaldehyde (12.4 ml, 112.6 mmol) and the resultant solution was cooled to 10° C. in an ice/water bath. To this solution was added ammonium hydroxide solution (28% in water, 56 mL) with stirring. The reaction mixture was stirred overnight and the resulting precipitate was filtered and dried to afford 12.1 grams of the title compound as a white crystalline solid. LCMS (m/z): 125.10 (MH$^+$), t$_R$=0.26 min; $^1$H NMR (300 MHz, CD$_3$OD) δ 6.86 (2H, s), 1.32 (9H, s).

Step 2. Preparation of 4,5-dibromo-2-tert-butyl-1H-imidazole: Bromine (8.4 grams, 52.42 mmol) was added dropwise to a mixture of 2-t-butylimidazole (2.6 grams, 20.97 mmol) and potassium bicarbonate (5.4 grams, 52.42 mmol) in dry DMF (25 ml). The reaction mixture was then stirred at 70° C. for 4 h. The reaction was allowed to cool to rt and was then filtered through a sintered funnel. The collected filtrate was cooled in an ice bath and diluted with cold water (100 mL) with stirring.

The resultant precipitate was collected by filtration, washed with cold water (3×) and dried under vacuum to furnish 2.79 g of 4,5-dibromo-2-tert-butyl-1H-imidazole as a light yellow solid: LCMS (m/z): 283.0 (MH$^+$), t$_R$=0.63 min; $^1$H NMR (300 MHz, DMSO-d$_6$) δ 1.23 (9H, s).

Step 3. Preparation of 4,5-Dibromo-2-tert-butyl-1-((2-(trimethylsilyl)ethoxy)methyl)-1H-imidazole: To a cooled solution of 2-t-butyl-4,5-dibromoimidazole (1.4 grams, 5.0 mmol; Example 5, Step 2) in dry THF (10 ml) at 0° C. was added sodium hydride (95%, 0.15 grams, 6.0 mmol) portion wise. The reaction mixture was stirred for 10 min at 0° C., at rt for 40 min. The reaction was re-cooled to 0° C. and SEM-chloride (0.97 ml, 5.5 mmol) was added in dropwise. The reaction mixture was stirred overnight allowing the ice bath to expire and poured into a mixture of water (30 mL) and EtOAc (50 ml). The resulting layers were partitioned and separated. The organic portion was washed with brine, then water, dried (Na$_2$SO$_4$), and concentrated. The remaining residue was purified by flash chromatography (SiO$_2$, 100:0-90:10 hexanes-EtOAc) to provide 2.1 g of 4,5-dibromo-2-tert-butyl-1-((2-(trimethylsilyl)ethoxy)methyl)-1H-imidazole: LCMS (m/z): 447.10 (MH$^+$), t$_R$=1.30 min; $^1$H NMR (400 MHz, CDCl$_3$) δ

8.75 (dd, 1H), 7.92 (dd, 1H), 5.90 (s, 2H), 3.51 (m, 2H), 1.55 (s, 9H), 0.82 (m, 2H), 0.08 (s, 9H).

Step 4. Preparation of 4-(4-bromo-2-tert-butyl-1H-imidazol-5-yl)-2-chloropyrimidine: n-BuLi (1.5 M in hexane, 40 mL, 60 mmol) was added dropwise to a cooled solution of 4,5-dibromo-2-tert-butyl-1-((2-(trimethylsilyl)ethoxy)methyl)-1H-imidazole (23.6 g, 57.2 mmol) in anhydrous THF (250 mL) at −78° C. After 30 min at −78° C., a solution of 2-chloropyrimidine (7.21 g, 63.0 mmol) in anhydrous THF (2 mL) was added dropwise and the reaction was stirred at −78° C. for 1 h. The reaction was quenched by the addition of saturated aqueous NH$_4$Cl solution and allowed to warm to rt. The mixture was partitioned with EtOAc and the layers separated. The aqueous portion was extracted with EtOAc (3×) and the combine organic layers were washed with water, brine, dried (MgSO$_4$), and concentrated. The resulting residue was dissolved in dry EtOAc, treated with MnO$_2$ (5.2 g, 60 mmol), and heated to reflux for 3 h. The reaction was allowed to cool to rt and filtered through Celite. The filter cake was washed thoroughly with EtOAc and the combine filtrates were concentrated. The remaining residue was purified by flash chromatography (SiO$_2$, 100:0-90:10 hexanes-EtOAc) to give 10 g (37%) of 4-(4-bromo-2-tert-butyl-1H-imidazol-5-yl)-2-chloropyrimidine: LCMS (m/z): 447.10 (MH$^+$), $t_R$=1.30 min. $^1$H NMR (400 MHz, CDCl$_3$) δ 8.64 (d, J=5.3 Hz, 1H), 7.83 (d, J=5.3 Hz, 1H), 5.85 (s, 2H), 3.45 (m, 2H), 0.76 (m, 2H), −0.08 (s, 9H).

Step 5. Preparation of (S)-1-(4-(4-bromo-2-tert-butyl-1-((2-(trimethylsilyl)ethoxy)methyl)-1H-imidazol-5-yl)pyrimidin-2-ylamino)propan-2-ol: The subtitled compound was prepared similarly to Example 3, Step 2 using (S)-1-aminopropanol-2-ol instead of ethanolamine: LCMS (m/z): 486.1 (MH$^+$), $t_R$=0.96 min Step 6. Preparation of (S)-1-(4-(4-6-amino-5-methoxypyridin-3-yl)-2-tert-butyl-1H-imidazol-5-yl)pyrimidin-2-ylamino)propan-2-ol: The title compound was prepared from (S)-1-(4-(4-bromo-2-tert-butyl-1-((2-(trimethylsilyl)ethoxy)methyl)-1H-imidazol-5-yl)pyrimidin-2-ylamino)propan-2-ol, utilizing the procedure from Example 3, Step 3: LCMS (m/z): 398.1 (MH$^+$), $t_R$=0.40 min.

Example 7

(S)—N-(1-(4-(4-(5-amino-6-methoxypyrazin-2-yl)-2-tert-butyl-1H-imidazol-5-yl)pyrimidin-2-ylamino)propan-2-yl)-2-methoxyacetamide

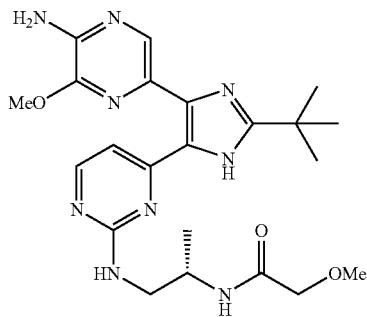

Step 1. Preparation of (S)-tert-butyl 1-(4-(4-bromo-2-tert-butyl-1H-imidazol-5-yl)pyrimidin-2-ylamino)propan-2-ylcarbamate: A mixture of 4-(4-bromo-2-tert-butyl-1H-imidazol-5-yl)-2-chloropyrimidine (2.0 g, 4.5 mmol; Example 6, Step 4), (S)-tert-butyl-1-aminopropan-2-ylcarbamate (1.0 g, 5.8 mmol; Example 23, Step 2), and diisopropylethyl amine (2.4 mL, 13.5 mmol) in dry acetonitrile was heated at 85° C. for 16 h. An additional charge of (S)-tert-butyl-1-aminopropan-2-ylcarbamate (145 mg, 0.8 mmol) was added and the reaction was maintained at 85° C. for 5 h. After allowing to cool to rt, the reaction was diluted with EtOAc (40 mL), washed with water (2×15 mL), dried (Na$_2$SO$_4$), and concentrated to provide 2.6 g of (S)-tert-butyl 1-(4-(4-bromo-2-tert-butyl-1H-imidazol-5-yl)pyrimidin-2-ylamino)propan-2-ylcarbamate which was carried forward without further purification: LCMS (m/z): 585.0 (MH$^+$), $t_R$=1.07 min.

Step 2. Preparation of (S)—N-(1-(4-(4-bromo-2-tert-butyl-1H-imidazol-5-yl)pyrimidin-2-ylamino)propan-2-yl)-2-methoxyacetamide: A solution of (S)-tert-butyl 1-(4-(4-bromo-2-tert-butyl-1H-imidazol-5-yl)pyrimidin-2-ylamino)propan-2-ylcarbamate (2.6 g, 4.4 mmol) in methanol was treated with aqueous 12 N HCl (1.4 mL. 16.8 mmol). The reaction was heated at 60° C. for 1 h, and allowed to cool to rt. The reaction was then concentrated and dried in vacuo to give 1.6 g of a crude residue which was carried forward without further purification. The residue was treated with diisopropylethyl amine (4.6 mL, 26.3 mmol) in dry DCM (18 mL), followed by the dropwise addition of methoxyacetyl chloride (0.44 mL, 4.8 mmol). The reaction mixture was stirred at rt for 1 h, then concentrated, in vacuo, to dryness. The remaining residue was dissolved in EtOAc (40 mL) was washed with water (2×), dried (Na$_2$SO$_4$), and concentrated. The crude residue was purified by flash chromatography (SiO$_2$, 90:10-50:50 hexanes-EtOAc) to afford 1.3 g of (S)—N-(1-(4-(4-bromo-2-tert-butyl-1H-imidazol-5-yl)pyrimidin-2-ylamino)propan-2-yl)-2-methoxyacetamide: LCMS (m/z): 427.0 (MH$^+$), $t_R$=0.61 min.

Step 3. Preparation of (S)—N-(1-(4-(4-(5-amino-6-methoxypyrazin-2-yl)-2-tert-butyl-1H-imidazol-5-yl)pyrimidin-2-ylamino)propan-2-yl)-2-methoxyacetamide: A 20 mL microwave vial containing (S)—N-(1-(4-(4-bromo-2-tert-butyl-1H-imidazol-5-yl)pyrimidin-2-ylamino)propan-2-yl)-2-methoxyacetamide (1.17 g, 2.75 mmol), 3-methoxy-5-(4,4,5,5-tetramethyl-1,3,2-dioxaborolan-2-yl)pyrazin-2-amine (0.97 g, 3.9 mmol, Example 18, Step 2), 2.0 M Na$_2$CO$_3$ aqueous solution (14 mL, 28 mmol), and Pd(PPh$_3$)$_4$ (0.16 g, 0.14 mmol) in DME (20 mL) was sparged with Ar for. The reaction vial was sealed, and irradiated at 115° C. for 10 min in a microwave reactor. The reaction was allowed to cool to rt and the organic and aqueous phases partitioned upon standing. The layers were separated and the aqueous phase was extracted with EtOAc (2×). The combined organic phases were concentrated, and the resulting residue was suspended in DMSO (10 mL), sonicated, and filtered through a plastic membrane. The filtrate was purified by preparative reverse-phase HPLC and the combined isolated fractions were partitioned with EtOAc and saturated aqueous Na$_2$CO$_3$ solution. The layers were separated and the organic phase was washed with saturated aqueous Na$_2$CO$_3$ solution (2×), brine, dried (Na$_2$SO$_4$), and concentrated. The resulting free base was suspended in acetonitrile-water (1:4), acidified with one equivalent of 1.0 M aqueous HCl solution, and lyophilized to give the title compound as the HCl salt: LCMS (m/z): 470.2 (MH$^+$), $t_R$=0.50 min; $^1$H NMR (400 MHz, CD$_3$COOD): δ 8.29 (br d, J=5.6 Hz, 1H), 8.07 (br s, 1H), 7.30 (d, J=6.0 Hz, 1H), 4.26 (m, 1H), 4.02 (s, 3H), 3.93 (s, 2H), 3.75 (m, 1H), 3.61 (dd, J=14.0, 7.2 Hz, 1H), 3.34 (s, 3H), 1.61 (s, 9H), 1.26 (d, J=6.8 Hz, 3H).

Example 8

(S)-methyl 1-(4-(4-(5-amino-6-methoxypyrazin-2-yl)-2-tert-butyl-1H-imidazol-5-yl)pyrimidin-2-ylamino)propan-2-ylcarbamate

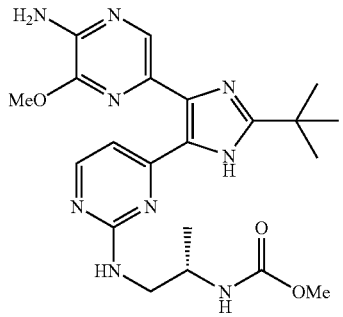

Step 1. Preparation of (S)-methyl 1-(4-(4-bromo-2-tert-butyl-1H-imidazol-5-yl)pyrimidin-2-ylamino)propan-2-ylcarbamate: To a solution of (S)-tert-butyl 1-(4-(4-bromo-2-tert-butyl-1-((2-(trimethylsilyl)ethoxy)methyl)-1H-imidazol-5-yl)pyrimidin-2-ylamino)propan-2-ylcarbamate (2.66 g, 3.94 mmol, Example 7, Step 1) in MeOH (17 ml) was added aqueous concentrated HCl (1.97 ml, 23.65 mmol) and the resulting reaction was stirred at 60° C. for 1 h. The reaction was allowed to cool to rt and concentrated in vacuo to give 2.28 g of crude residue. This material was then suspended in 1:1 THF-water (100 mL) followed by the addition of NaHCO$_3$ (1.66 g, 19.70 mmol). The mixture was cooled to 5° C. and methyl chloroformate (1.0 M in THF, 4.33 ml, 4.33 mmol) was added dropwise. After 50 min, an additional charge of methyl chloroformate (1.0 M in THF, 4.33 ml, 4.33 mmol) was added and the reaction maintained for 45 min at 0° C. The reaction was quenched with water (300 mL) and the resulting layers were separated. The aqueous phase was extracted with EtOAc (2×200 mL) and the combined organic portions were washed with brine (2×400 mL), dried (Na$_2$SO$_4$), and concentrated. The resulting residue was triturated with 1:4 EtOAc-hexanes (10 mL) and washed with ether to provide 958 mg of (S)-methyl 1-(4-(4-bromo-2-tert-butyl-1H-imidazol-5-yl)pyrimidin-2-ylamino)propan-2-ylcarbamate: LCMS (m/z): 411.0 (MH$^+$), t$_R$=0.65 min.

Step 2. Synthesis of (S)-methyl 1-(4-(4-(5-amino-6-methoxypyrazin-2-yl)-2-tert-butyl-1H-imidazol-5-yl)pyrimidin-2-ylamino)propan-2-ylcarbamate: (S)-methyl 1-(4-(4-bromo-2-tert-butyl-1H-imidazol-5-yl)pyrimidin-2-ylamino)propan-2-ylcarbamate was elaborated as per Example 7, Step 3 to give (S)-methyl 1-(4-(4-(5-amino-6-methoxypyrazin-2-yl)-2-tert-butyl-1H-imidazol-5-yl)pyrimidin-2-ylamino)propan-2-ylcarbamate as the HCl salt: LCMS (m/z): 456.2 (MH$^+$), t$_R$=0.52 min; $^1$H NMR (300 MHz, CD$_3$COOD): δ 8.30 (d, J=6.6 Hz, 1H), 8.08 (br s, 1H), 7.33 (d, J=6.6, 1H), 4.05 (s, 3H), 4.00 (m, 1H), 3.87 (m, 1H), 3.67 (s, 3H), 3.41 (m, 1H), 1.65 (s, 9H), 1.23 (d, J=6.9 Hz, 3H).

Example 9

4-(4-(5-amino-6-methoxypyrazin-2-yl)-2-tert-butyl-1H-imidazol-5-yl)-N-(2-methoxypyridin-4-yl)pyrimidin-2-amine

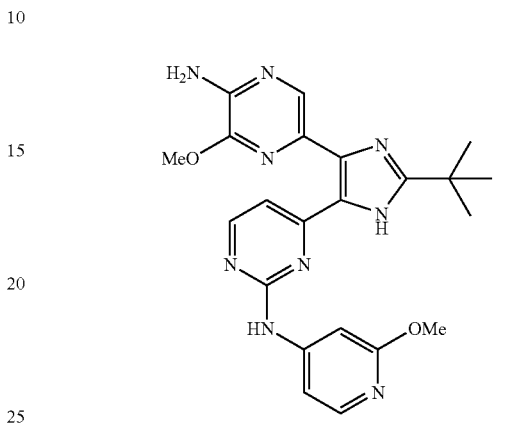

Step 1. Synthesis of 4-(4-bromo-2-tert-butyl-1-((2-(trimethylsilyl)ethoxy)methyl)-1H-imidazol-5-yl)-N-(2-methoxypyridin-4-yl)pyrimidin-2-amine:

A mixture of 4-(4-bromo-2-tert-butyl-1-((2-(trimethylsilyl)ethoxy)methyl)-1H-imidazol-5-yl)-2-chloropyrimidine (500 mg, 1.1 mmol; Example 6, Step 4), 2-methoxypyridin-4-amine (153 mg, 1.2 mmol), Pd(OAc)$_2$ (30 mg, 0.14 mmol), XANTPHOS (117 mg, 0.20 mmol), cesium carbonate (731 mg, 2.2 mmol) in dry dioxane (9 ml) was sparged with N$_2$ for 5 min. The reaction was sealed and heated at 100° C. for 2 hr. The reaction was allowed to cool to rt and partitioned between EtOAc and water. The layers were separated and the aqueous portion was extracted with EtOAc. The combined organic portions were dried (MgSO$_4$) and concentrated to an orange residue which as purified by column chromatography (SiO$_2$, 100:0-0:100, hexanes-EtOAc) to provide 386 mg of 4-(4-bromo-2-tert-butyl-1-((2-(trimethylsilyl)ethoxy)methyl)-1H-imidazol-5-yl)-N-(2-methoxypyridin-4-yl)pyrimidin-2-amine: LCMS (m/z): 533.2 (MH$^+$), t$_R$=0.92 min.

Step 2. Preparation of 4-(4-(5-amino-6-methoxypyrazin-2-yl)-2-tert-butyl-1H-imidazol-5-yl)-N-(2-methoxypyridin-4-yl)pyrimidin-2-amine: A mixture of 4-(4-bromo-2-tert-butyl-1-((2-(trimethylsilyl)ethoxy)methyl)-1H-imidazol-5-yl)-N-(2-methoxypyridin-4-yl)pyrimidin-2-amine (100 mg, 0.19 mmol), 3-methoxy-5-(4,4,5,5-tetramethyl-1,3,2-dioxaborolan-2-yl)pyrazin-2-amine (118 mg, 0.47 mmol, Example 18, Step 2), aqueous 2.0 M Na$_2$CO$_3$ solution (1 ml, 2.0 mmol), and Pd(PPh$_3$)$_4$ (22 mg, 0.019 mmol) in DME (2 mL) was sparged with N$_2$ for 5 min. The reaction was sealed and heated to 100° C. for 2 h. The reaction was allowed to cool to rt, poured into EtOAc and partitioned with water. The layers were separated and the organic portion was washed with water, dried (MgSO$_4$), and concentrated. The resulting residue was purified by flash chromatography (SiO$_2$, 100:0-0:100, hexanes-25% MeOH in EtOAc) to afford 102 mg (69% purity) of 4-(4-(6-amino-5-methoxypyridin-3-yl)-2-tert-butyl-1-((2-(trimethylsilyl)ethoxy)methyl)-1H-imidazol-5-yl)-N-(2-methoxypyridin-4-yl)pyrimidin-2-amine: LCMS (m/z): 578.5 (MH$^+$), t$_R$=0.74 min.

Step 3. Synthesis of 4-(4-(5-amino-6-methoxypyrazin-2-yl)-2-tert-butyl-1H-imidazol-5-yl)-N-(2-methoxypyridin-4-yl)pyrimidin-2-amine: A solution of 4-(4-(6-amino-5-methoxypyridin-3-yl)-2-tert-butyl-1-((2-(trimethylsilyl)ethoxy)methyl)-1H-imidazol-5-yl)-N-(2-methoxypyridin-4-yl)pyrimidin-2-amine (12 mg, 0.021 mmol) in dry MeOH (1 mL) was treated with aqueous 4 N HCl (0.26 mL, 1.04 mmol) and the resulting reaction was maintained at rt for 2 h. The reaction was then concentrated and the resulting residue was triturated with ether to give 8.2 mg of the title compound as the HCl salt: LCMS (m/z): 447.1 (MH$^+$), $t_R$=0.39 min.

Example 10

5-(2-(4-fluorophenyl)-5-(tetrahydro-2H-pyran-4-yl)-1H-imidazol-4-yl)-3-methoxypyridin-2-amine

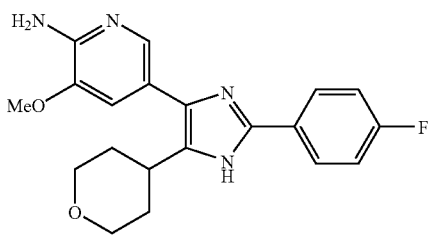

Step 1. Preparation of 3,6-dihydro-2H-pyran-4-yl trifluoromethanesulfonate: A solution of LiHMDS (1.0 M in THF, 11 mL, 11 mmol) was added dropwise to a cooled solution of 4-tetrahydropyranone (1 g, 10 mmol) in dry THF (5 mL) at −78° C. and the resulting reaction was maintained at −78° C. for 1 h. A solution of 2-[N,N-bis(trifluoromethanesulfonyl)amino]-5-chloropyridine (3.93 g, 10 mmol) in dry THF (6 mL) was added dropwise and the reaction maintained overnight, allowing the cooling bath to expire. The reaction was quenched with water (10 mL) and partitioned with DCM. The layers were separated and the aqueous portion was extracted with DCM (2×). The combined organic portions were dried (Na$_2$SO$_4$) and evaporated. The crude residue was purified by flash chromatography (neutral alumina, 80:20 DCM-hexanes) to provide 800 mg of 3,6-dihydro-2H-pyran-4-yl trifluoromethanesulfonate as a colorless oil: $^1$H NMR (400 MHz, CDCl$_3$) δ 5.82-5.81 (m, 1H), 4.27-4.25 (m, 2H), 3.91-3.88 (m, 2H), 2.48-2.45 (m, 2H).

Step 2. Preparation of 2-(3,6-dihydro-2H-pyran-4-yl)-4,4,5,5-tetramethyl-1,3,2-dioxaborolane: A mixture of 3,6-dihydro-2H-pyran-4-yl trifluoromethanesulfonate (250 mg, 1.1 mmol), bis(pinacolato)diboron (410 mg, 1.6 mmol), and KOAc (323 mg, 3.3 mmol) dioxane (3 mL) was sparged with Ar for 5 min. Then PdCl$_2$dppf.DCM (45 mg, 0.05 mmol) was added and reaction was sparged again with Ar for 5 min. The reaction was sealed and heated to and maintained at 80° C. for overnight. The reaction mixture was allowed to cool rt and was filtered through Celite, washing the filter cake with EtOAc. The combined filtrate was concentrated and the resulting residue was purified by flash chromatography (SiO$_2$, 100:0-80:20 hexanes-EtOAc) to furnish 150 mg of 2-(3,6-dihydro-2H-pyran-4-yl)-4,4,5,5-tetramethyl-1,3,2-dioxaborolane: LCMS (m/z): 211.0 (MH$^+$), $t_R$=0.89 min; $^1$H NMR (400 MHz, CDCl$_3$) δ 6.48 (br s, 1H); 4.15-4.14 (app dd, J=2.8, 5.6 Hz, 2H); 3.72-3.69 (app t, 5.2, 2H); 2.19-2.17 (m, 2H); 1.22 (s, 12H).

Step 3. Preparation of 5-(2-(4-fluorophenyl)-5-(tetrahydro-2H-pyran-4-yl)-1H-imidazol-4-yl)-3-methoxypyridin-2-amine: A mixture of 2-(3,6-dihydro-2H-pyran-4-yl)-4,4,5,5-tetramethyl-1,3,2-dioxaborolane (53 mg, 0.25 mmol), 5-(5-bromo-2-(4-fluorophenyl)-1H-imidazol-4-yl)-3-methoxypyridin-2-amine (123 mg, 0.25 mmol; prepared similarly as per Example 2, Steps 2-3), and aqueous 2.0 M Na$_2$CO$_3$ solution (0.5 mL, 1.0 mmol) in DME (3 mL) was sparged with Ar for 5 min. A catalytic amount of Pd(PPh$_3$)$_4$ was added and the mixture was purged with Ar again. Then the reaction was heated to and maintained at 90° C. for 16 h. The reaction mixture was allowed cool to rt and partitioned between EtOAc and water. The layers were separated and the aqueous phase was extracted with EtOAc (2×). The combined organic layers were dried (Na$_2$SO$_4$) and concentrated. The resulting residue was dissolved in dry MeOH (5 mL) and treated with Pd/C (10% w/w, 5.7 mg, 0.005 mmol). The reaction mixture was placed and maintained under a H2 atmosphere for 2 d. The reaction was then filtered through Celite, the filter cake was washed thoroughly with EtOAc. The combined filtrate was concentrated and the resulting residue was purified by flash chromatography (SiO$_2$, 50:50-0:100 hexanes-EtOAc). The isolated material was treated with 3 N HCl at 60° C. for 1 h. The reaction was allowed to cool to rt and was directly purified on reverse phase HPLC, as after freeze drying, provided 6.0 mg of 5-(2-(4-fluorophenyl)-5-(tetrahydro-2H-pyran-4-yl)-1H-imidazol-4-yl)-3-methoxypyridin-2-amine as the TFA salt: LCMS (m/z): 369.0 (MH$^+$), $t_R$=0.44 min Example 11

5-(2-(4-fluorophenyl)-5-(thiazol-5-yl)-1H-imidazol-4-yl)-3-methoxypyridin-2-amine

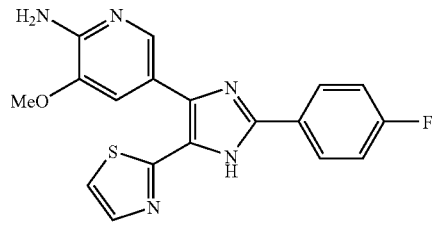

Step 1. Preparation of 5-(2-(4-fluorophenyl)-5-(thiazol-5-yl)-1H-imidazol-4-yl)-3-methoxypyridin-2-amine: A mixture of 5-(5-bromo-2-(4-fluorophenyl)-1-((2-(trimethylsilyl)ethoxy)methyl)-1H-imidazol-4-yl)-3-methoxypyridin-2-amine (0.10 g, 0.20 mmol; prepared similarly as per Example 2, Steps 2-3), 5-(tributyl)stannyl)thiazole (0.10 g, 0.27 mmol) and triethylamine (0.14 mL, 1.0 mmol) in DMF (1 mL) was purged with N$_2$ for 10 min. Pd(dppf)Cl$_2$.CH$_2$Cl$_2$ (17 mg, 0.02 mmol) was added in one portion and the reaction vial was sealed, heated to and maintained at 100° C. overnight. LCMS indicated slow conversion, additional stannane (excess) and catalyst (excess) were then added, and the reaction was heated again to 100° C. overnight. The reaction was allowed to cool to rt and was triturated with hexanes (2×). The hexane layers were discarded and the DMF layer was directly purified by reverse phase HPLC, and upon lypholization, provided 5-(2-(4-fluorophenyl)-5-(thiazol-2-yl)-1-((2-(trimethylsilyl)ethoxy)methyl)-1H-imidazol-4-yl)-3-methoxypyridin-2-amine as the TFA salt, which was dissolved in ethanol (3 mL) and treated with aqueous 12 N HCl solution (0.5 mL). The reaction mixture was heated to 60° C. for 40 min and was then allowed to cool to rt. The reaction mixture was concentrated and the resulting residue was purified by reverse-phase HPLC to furnish the title compound as the TFA after freeze drying: LCMS (m/z)=368.0 (MH+), $t_R$=0.52 min.

Example 12

3-chloro-5-(2-(4-fluorophenyl)-4-(pyridine-4-yl)-1H-imidazol-5-yl)-1H-pyrrolo[2,3-b]pyridine

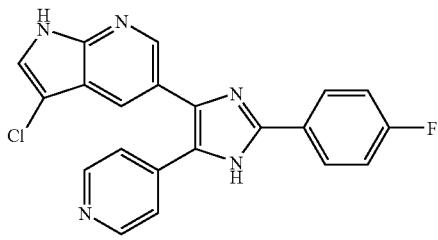

To a solution of 5-(2-(4-fluorophenyl)-4-(pyridin-4-yl)-1-((2-(trimethylsilyl)ethoxy)methyl)-1H-imidazol-5-yl)-1H-pyrrolo[2,3-b]pyridine (18 mg, 0.04 mmol) in ACN (0.6 mL) was added NCS (5 mg, 0.04 mmol). After stirring for 18 h, the reaction mixture was partitioned between EtOAc (20 mL) and aqueous saturated NaHCO$_3$ (10 mL). The layers were separated and the organic phase was washed with aqueous 0.1 M HCl solution (10 mL), brine (10 mL), and dried (Na$_2$SO$_4$). After concentrating in vacuo, the resulting crude product was dissolved in ethanol (1.5 mL) and conc. HCl (0.25 mL, 3 mmol) was added and the reaction was heated at 60° C. for 20 min and then concentrated in vacuo. The crude material was dissolved in DMSO (1.3 mL) and purified by reverse phase HPLC, which after lypholization, yielded 7 mg (38%) of the title compound as the TFA salt: —LC/MS (m/z): 390.1 (MH+), $t_R$=0.67 min.

Example 13

5-(2-(4-fluorophenyl)-5-(pyridin-4-yl)oxazol-4-yl)-3-methoxypyridin-2-amine

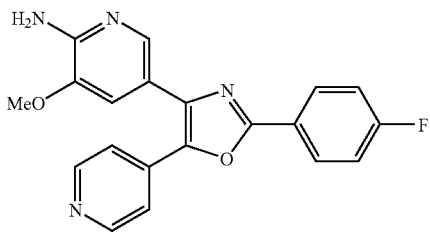

Step 1. Synthesis of 4-fluorobenzoyl isocyanate: To a solution of 4-fluorobenzamide (1 g, 7.2 mmol) in DCM (25 mL) was added slowly oxalylchloride (0.76 mL, 8.62 mmol). The mixture was heated to 50° C. for ~18 hr. The mixture was allowed to cool to room temperature and concentrated in vacuo to afford crude 4-fluorobenzoyl isocyanate (1.2 g). The crude material was used in the next step without further purification.

Step 2. Synthesis of 2-(4-fluorophenyl)oxazol-4(5H)-one: To a solution of 4-fluorobenzoyl isocyanate (1.2 g, 7.2 mmol) in DCM (25 mL) was added (trimethylsilyl)diazomethane (2.0 M in hexane, 4.3 mL, 8.6 mmol) at 0° C. The reaction mixture was stirred for 45 min at rt. The mixture was diluted with water and the separated aqueous phase was extracted with DCM (3×). The combined organic layers were dried over (Na$_2$SO$_4$), filtered and concentrated in vacuo. The resulting residue was purified by column chromatography (SiO$_2$, 100:0-80:20 DCM-methanol) to afford 870 mg of 2-(4-fluorophenyl)oxazol-4(5H)-one: LCMS (m/z): 180.0 (MH+), $t_R$=0.39 min Step 3. Synthesis of 2-(4-fluorophenyl)oxazol-4-yl trifluoromethanesulfonate: To a solution of 2-(4-fluorophenyl)oxazol-4(5H)-one (870 mg, 4.9 mmol) in DCM (25 mL) was added 2,6-lutidine (0.91 mL, 7.8 mmol) and trifluoromethanesulfonic anhydride (1.8 mL, 7.3 mmol) at 0° C. The reaction mixture was allowed to warm up to rt over ~18 hr. The mixture was concentrated in vacuo and the residue was purified by flash chromatography (SiO$_2$, 100% DCM) to give 1.40 g of 2-(4-fluorophenyl)oxazol-4-yl trifluoromethanesulfonate.

Step 4. Synthesis of 5-(2-(4-fluorophenyl)oxazol-4-yl)-3-methoxypyridin-2-amine: A mixture of 3-methoxy-5-(4,4,5,5-tetramethyl-1,3,2-dioxaborolan-2-yl)pyridin-2-amine (200 mg, 0.8 mmol) and 2-(4-fluorophenyl)oxazol-4-yl trifluoromethanesulfonate (250 mg, 0.8 mmol), and 2.0 M aqueous Na$_2$CO$_3$ (1.2 mL, 2.4 mmol) in DME (2.0 mL) was sparged with Ar. Dichlorobis(triphenylphosphine)palladium (0) (281 mg, 0.4 mmol) was added and the reaction mixture was irradiated at 150° C. for 15 min in a microwave reactor. After cooling to rt, the reaction mixture was diluted with water and extracted with EtOAc (3×). The combined organic layers were dried over sodium sulfate, filtered and concentrated in vacuo. The residue was purified by flash chromatography over (SiO$_2$, 100:0-0:100 hexanes-EtOAc) to provide 145 mg of 5-(2-(4-fluorophenyl)oxazol-4-yl)-3-methoxypyridin-2-amine: LCMS (m/z): 286.1 (MH+), $t_R$=0.68 min.

Step 5. Synthesis of 5-(5-bromo-2-(4-fluorophenyl)oxazol-4-yl)-3-methoxypyridin-2-amine: To a solution of 5-(2-(4-fluorophenyl)oxazol-4-yl)-3-methoxypyridin-2-amine (145 mg, 0.5 mmol) in chloroform (20 mL) at 0° C. was added a pre-cooled solution of bromine (40 µL, 0.7 mmol) in CHCl$_3$ (5 mL). The reaction mixture was stirred for <5 min, concentrated in vacuo, and the resulting residue was azeotroped with CHCl$_3$ (2×). Purification by flash chromatography (SiO$_2$, 100:0-95:5 DCM-MeOH) provided 135 mg of 5-(5-bromo-2-(4-fluorophenyl)oxazol-4-yl)-3-methoxypyridin-2-amine as a yellow solid: LCMS (m/z): 365.8 (MH+), $t_R$=0.83 min.

Step 6. 5-(2-(4-fluorophenyl)-5-(pyridin-4-yl)oxazol-4-yl)-3-methoxypyridin-2-amine: A mixture of 4-pyridineboronic acid (113 mg, 0.9 mmol) and 5-(5-bromo-2-(4-fluorophenyl)oxazol-4-yl)-3-methoxypyridin-2-amine (135 mg, 0.4 mmol), and in DME (1.0 mL) and 2.0 M aqueous Na$_2$CO$_3$ (1.0 mL, 2.0 mmol) was sparged with Ar. Tetrakis(triphenylphosphine)palladium(0) (21 mg, 0.018 mmol) was added and the mixture was again sparged with Ar. The reaction was irradiated at 120° C. for 15 min in a microwave reactor. The reaction mixture was diluted with water and extracted with EtOAc (3×). The combined organic layers were dried over sodium sulfate, filtered and concentrated in vacuo. The residue was purified by flash chromatography over (SiO$_2$, 100:0-0:100 hexanes-EtOAc). Enriched fractions were concentrated in vacuo and further purified by column chromatography (SiO$_2$, 100:0-80:20 DCM-MeOH) to afford 82 mg of the title compound: LC/MS (m/z): 362.9 (MH+), $t_R$=0.54 min.

Example 14

(S)—N-(1-(4-(4-(6-amino-5-methoxypyridin-3-yl)-2-(4-(trifluoromethyl)phenyl)oxazol-5-yl)pyrimidin-2-ylamino)propan-2-yl)-2-methoxyacetamidine

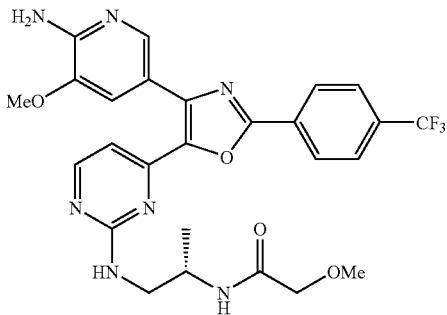

Step 1. Preparation of 2-(4-(trifluoromethyl)phenyl)-4,5-dihydrooxazole: 4-(trifluoromethyl)benzoyl chloride (4.6 mL, 31 mmol) was slowly added to a solution of 2-bromoethanamine hydrobromide (6.27 g, 30.6 mmol) and triethylamine (23 mL, 165 mmol) in dry DCM (150 mL) at 0° C. The reaction was stirred for 18 h, allowing the cooling bath to expire. The resulting mixture was filtered through a Buechner funnel and the filter cake was washed thoroughly with DCM. The collected filtrate was washed with water (100 mL), brine (75 mL), and dried ($Na_2SO_4$). The volume was reduced in vacuo to 5 mL and the resulting crystals were harvested. The remaining filtrate was again reduced in volume to provide a second crop of crystals to give a total of 4.8 g of 2-(4-(trifluoromethyl)phenyl)-4,5-dihydrooxazole. The combined crop of crystals were dissolved in $CCl_4$ (200 mL) and the resulting solution was decanted away from a dark oily residue and was carried forward without further purification: LC/MS (m/z): 216.1 ($MH^+$), $t_R$=0.60 min.

Step 2. Preparation of 5-bromo-2-(4-(trifluoromethyl)phenyl)oxazole: The above solution of 2-(4-(trifluoromethyl)phenyl)-4,5-dihydrooxazole (4.8 g, 22 mmol), NBS (11.9 g, 66.9 mmol), and AIBN (0.18 g, 1.12 mmol) in $CCl_4$ (200 mL) was refluxed for 16 h. The resulting solution was filtered and the filtrate was washed with aqueous 10% $Na_2S_2O_3$ (3×150 mL), brine (100 mL), dried ($Na_2SO_4$), and concentrated. The resulting residue was recrystallized from hexanes (350 mL) to provide 3.2 g of 5-bromo-2-(4-(trifluoromethyl)phenyl)oxazole as a crystalline solid. The filtrate and mother liquor was concentrated and purified by flash chromatography over ($SiO_2$, 100:0-90:10 hexanes-EtOAc). to furnish an additional 1.8 g: LCMS (m/z): 294.0 ($MH^+$), $t_R$=1.14 min.

Step 3. Synthesis of 4-bromo-5-(2-chloropyrimidin-4-yl)-2-(4-(trifluoromethyl)phenyl)oxazole: A solution of lithium diisopropylamide (1.8 M in THF-heptane-ethylbenzene, 1.4 mL, 2.6 mmol) was added dropwise into a cooled solution of 5-bromo-2-(4-(trifluoromethyl)phenyl)oxazole (620 mg, 2.1 mmol) in dry THF (20 mL) at −78° C. After 2.5 h, 2-chloropyrimidine (292 mg, 2.6 mmol) was added. After 10 min, the reaction flask was raised half way out of the acetone-dry ice bath and maintained for 30 min, after which the reaction was warmed to 10° C. in an ice-water bath and maintained for 1 h. The reaction was quenched with water (1 mL) and concentrated. The resulting mixture was partitioned between EtOAc (70 mL) and water (40 mL), and the layers were separated. The organic phase was washed with water, brine, dried ($Na_2SO_4$), and concentrated to give 859 mg of a residue as 4-bromo-5-(2-chloro-4,5-dihydropyrimidin-4-yl)-2-(4-(trifluoromethyl)phenyl)oxazole which was used in the next step without further purification: LCMS (m/z): 407.9 ($MH^+$), $t_R$=0.83 min. A suspension of 4-bromo-5-(2-chloro-4,5-dihydropyrimidin-4-yl)-2-(4-(trifluoromethyl)phenyl)oxazole (859 mg, 2.12 mmol) and $MnO_2$ (1.8 g, 21.2 mmol) in EtOAc (10 mL) was irradiated at 110° C. for 10 min in a microwave reactor. The reaction was allowed to cool to rt and was filtered through a plastic membrane. The filtrate was concentrated and resulting residue was triturated with EtOAc to afford 234 mg of 4-bromo-5-(2-chloropyrimidin-4-yl)-2-(4-(trifluoromethyl)phenyl)oxazole: LCMS (m/z): 406.0 ($MH^+$), $t_R$=1.19 min.

Step 4. Synthesis of (S)—N-(1-(4-(4-(6-amino-5-methoxypyridin-3-yl)-2-(4-(trifluoromethyl)phenyl)oxazol-5-yl)pyrimidin-2-ylamino)propan-2-yl)-2-methoxyacetamidine: The elaboration of 4-bromo-5-(2-chloropyrimidin-4-yl)-2-(4-(trifluoromethyl)phenyl)oxazole follows that of Example 4, Steps 2-4.

Example 15

3-methoxy-5-(2-phenyl-4-(pyridine-4-yl)thiazol-5-yl)pyridine-2-amine

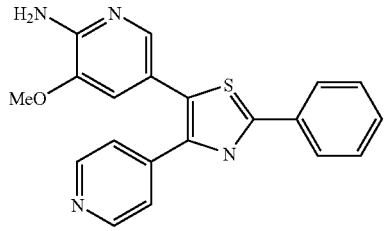

Step 1. Synthesis of 2-phenyl-4-(pyridin-4-yl)thiazole: To the solution of 4-(bromoacetyl)pyridine hydrobromide (500 mg, 1.8 mmol) in dry DMF (5 mL) was added thiobenzamide (242 mg, 1.8 mmol) and the resulting reaction was stirred at rt for 12 h. Thereafter, the reaction quenched with saturated aqueous $NaHCO_3$ solution (25 mL) and the mixture extracted with EtOAc (3×25 mL). The combined organic extracts were washed with water (25 mL), dried ($Na_2SO_4$), and concentrated. The resulting residue was purified by flash chromatography ($SiO_2$, 100:0-0-100 hexanes-EtOAc) furnished 2-phenyl-4-(pyridin-4-yl)thiazole: LCMS (m/z): 239.0 ($MH^+$), $t_R$=0.64 min.

Step 2. Synthesis of 5-bromo-2-phenyl-4-(pyridin-4-yl)thiazole. To the solution of 2-phenyl-4-(pyridin-4-yl)thiazole (70 mg, 0.3 mmol) in $CHCl_3$ was added $Na_2CO_3$ (311 mg, 2.9 mmol) and $Br_2$ (75 μL, 1.470 mmol) at rt. After 1 h, additional charges of $Na_2CO_3$ (1 g, 9.4 mmol) and $Br_2$ (0.5 mL, 1 mmol) were added and the reaction maintained for another hour. The reaction was diluted with CHCl3 and filtered through a pad of Celite, washing the filter cake thoroughly with $CHCl_3$. The combined filtrates were concentrated of provide 0.5-bromo-2-phenyl-4-(pyridin-4-yl)thiazole which was carried forward without further purification: LCMS (m/z): 318.9 ($MH^+$), $t_R$=0.75 min.

Step 3. Synthesis of 3-methoxy-5-(2-phenyl-4-(pyridin-4-yl)thiazol-5-yl)pyridin-2-amine: A mixture of 5-bromo-2-phenyl-4-(pyridin-4-yl)thiazole (20 mg, 0.062 mmol), 3-methoxy-5-(4,4,5,5-tetramethyl-1,3,2-dioxaborolan-2-yl)pyridin-2-amine (39 mg, 0.157 mmol), and aqueous 2.0 M $K_2CO_3$ solution (0.5 ml, 1 mmol) in dioxane (0.5 mL) was sparged with Ar. Pd(PPh₃)₄ (181 mg, 0.157 mmol) was added, the reaction was sealed and irradiated at 120° C. for 15 min. While allowing to cool to rt, the reaction partitioned and the resulting layers were separated. The aqueous phase was extracted with EtOAc (3×) and the combined organic phases were washed with brine, dried (Na2SO4), and concentrated. The resulting residue was purified by reverse phase HPLC to give, after freeze drying, 3-methoxy-5-(2-phenyl-4-(pyridin-4-yl)thiazol-5-yl)pyridin-2-amine as the TFA salt: LCMS (m/z): 361.0 (MH⁺), $t_R$=0.58 min.

Example 16

5-(2-(4-fluorophenyl)-5-(pyridin-4-yl)thiazol-4-yl)-3-methoxypyridin-2-amine

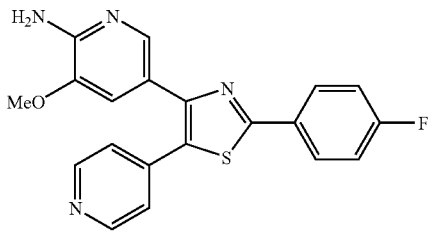

Step 1. Preparation of 4-bromo-2-(4-fluorophenyl)thiazole: Following a modified procedure (Bach, T.; Heuser, S. *Tetrahedron Lett.* 2000, 41, 1707), a mixture of 2,4-dibromothiazole (486 mg, 2.0 mmol), 4-fluorophenyl boronic acid (266 mg, 1.9 mmol), and aqueous 2.0 M Na₂CO₃ solution (2.3 mL, 4.6 mmol) in DME (6.8 mL) was sparged with Ar for 3 min. Tetrakis(triphenylphosphine)palladium(0) (150 mg) was added and the reaction mixture was sparged with Ar for 1 min. The reaction was sealed and irradiated at 105° C. for 12 min in a microwave reactor. The reaction mixture was partitioned with EtOAc (50 mL) and saturated aqueous NaHCO₃ solution (10 mL). The layers were separated and the organic layer was washed with saturated aqueous NaHCO₃ solution (10 mL), brine (20 mL), dried (Na₂SO₄), and concentrated in vacuo. The crude material was purified by column chromatography over silica gel to provide 450 mg of 4-bromo-2-(4-fluorophenyl)thiazole which was directly used in the next step without further purification: LCMS (m/z): 259.9 (MH⁺), $t_R$=1.08 min.

Step 2: A mixture of 4-bromo-2-(4-fluorophenyl)thiazole (450 mg, 1.7 mmol), 3-methoxy-5-(4,4,5,5-tetramethyl-1,3,2-dioxaborolan-2-yl)pyridin-2-amine (400 mg, 1.6 mmol), and aqueous 2.0 M Na₂CO₃ solution (2.3 mL, 4.6 mmol) in DME (6.8 mL) was sparged with Ar for 3 min. Tetrakis(triphenylphosphine)palladium(0) (120 mg, 0.1 mmol) was added and the reaction mixture was sparged with Ar for 1 min. The reaction was sealed and irradiated at 115° C. for 25 min in a microwave reactor. The reaction mixture was partitioned with EtOAc (50 mL) and saturated aqueous NaHCO₃ solution (100 mL). The separated organic layer was washed with saturated aqueous NaHCO₃ solution (50 mL). The organic layer was extracted with aqueous 0.5 N HCl solution (2×25 mL). The combined acidic aqueous portions were washed with EtOAc (30 mL), neutralized with saturated aqueous NaHCO₃ solution and extracted with EtOAc (3×50 mL). The organic layer was dried (Na₂SO₄), filtered, and concentrated in vacuo. The crude material was purified by column chromatography over silica gel (SiO₂, 100% EtOAc) to furnish 145 mg (88% purity) of 5-(2-(4-fluorophenyl)thiazol-4-yl)-3-methoxypyridin-2-amine which was directly used in the next step: LCMS (m/z): 302.1 (MH⁺), $t_R$=0.75 min.

Step 3. Preparation of 5-(5-bromo-2-(4-fluorophenyl)thiazol-4-yl)-3-methoxypyridin-2-amine: To a solution of 5-(2-(4-fluorophenyl)thiazol-4-yl)-3-methoxypyridin-2-amine (68 mg, 0.23 mmol) in chloroform (3.6 mL) at 0° C. was added a solution of bromine (2.0 M in CHCl₃, 0.17 mL, 0.34 mmol). The reaction was stirred at rt for 6-10 min and concentrated in vacuo. The resulting residue was azeotroped with 5% methanol in DCM solution (5 mL) and purified by prep TLC (SiO2, 1.0 mm, 95:5 DCM-methanol) to give 67 mg of 5-(5-bromo-2-(4-fluorophenyl)thiazol-4-yl)-3-methoxypyridin-2-amine was isolated as a tan solid: LCMS (m/z): 380.0 (MH⁺), $t_R$=0.85 min.

Step 4: A mixture of 5-(5-bromo-2-(4-fluorophenyl)thiazol-4-yl)-3-methoxypyridin-2-amine (40 mg, 0.11 mmol), 4-pyridineboronic acid (39 mg, 0.32 mmol), and, and aqueous 2.0 M Na₂CO₃ solution (0.6 mL) in DME (1.8 mL) was sparged with Ar for 3 min. Tetrakis(triphenylphosphine)palladium(0) (20 mg, 0.02 mmol) was added and the reaction mixture was sparged with Ar for 1 min. The reaction was sealed and irradiated at 115° C. for 15 min in a microwave reactor. The reaction mixture was partitioned with EtOAc (25 mL) and saturated aqueous NaHCO₃ solution (25 mL). The separated organic layer was washed with saturated aqueous NaHCO₃ solution (25 mL), brine (25 mL), dried (Na₂SO₄), filtered and concentrated in vacuo. The resulting residue was purified by reverse phase HPLC, which after lypholization, provided 23 mg of the titled compound as the TFA salt: LCMS (m/z): 378.9 (MH⁺), $t_R$=0.57 min.

Example 17

2-amino-3-methoxy-5-(4,4,5,5-tetramethyl-1,3,2-dioxaborolan-2-yl)pyridine

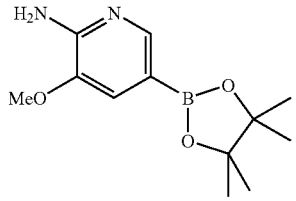

Step 1. Preparation of 2-amino-3-methoxypyridine: To a solution of 2-nitro-3-methoxypyridine (32 g, 208 mmol) in EtOAc (150 mL) and MeOH (35 mL) under a nitrogen atmosphere was added 10% palladium on carbon (1.5 g, 1.4 mmol). This mixture was purged with H₂ three times and the mixture was stirred for 3 h under a hydrogen atmosphere. The reaction mixture was purged with N₂ three times, filtered through Celite, and the filter cake was washed with EtOAc (2×35 ml). The combined filtrate were concentrated and dried over high vacuum to afford 25.8 grams (100%) of 2-amino-3-methoxypyridine: LCMS (m/z): 125.0 (MH⁺); ¹H NMR (300 MHz, CDCl₃): 7.66 (m, 1H), 6.90 (m, 1H), 6.61 (m, 2H), 4.64 (s, br, 2H), 3.83 (s, 3H).

Step 2. Preparation of 2-amino-3-methoxy-5-bromopyridine: A 2 L Erlenmeyer flask was charged with 10% sulfuric acid (800 ml). At ambient temperature, 2-amino-3-methoxypyridine (25.8 grams, 206 mmol) was added portionwise with stirring. After a clear solution was obtained, the solution was cooled in an ice/water bath until the solution temperature reached 3° C. A solution of bromine (10.8 ml, 210 mmol) in acetic acid (140 ml) was added dropwise while maintaining the internal temperature at 3-5° C. After the addition was complete, the mixture was stirred at 5° C. for 2 h. This mixture was poured into 800 grams of ice with stirring and saturated ammonium hydroxide solution (30% w/w) was added slowly to the resultant mixture until the pH=8 was reached. A dark solid precipitates and the mixture was stirred for additional 30 min at 3-5° C. The solid was obtained by filtration and was washed with cold water (2×30 ml) and dried to afford 39.0 grams of crude product. The crude was suspended in EtOAc (500 ml) and the resulting dark mixture was stirred vigorously for 30 min and filtered through Celite. The filter cake was washed with EtOAc (2×) and the combined filtrates were washed with 10% sodium thiosulfite solution (100 ml), brine and dried ($Na_2SO_4$). Concentration of this mixture afforded 29.0 grams (68%) of 2-amino-3-methoxyl-5-bromopyridine: LCMS (m/z): 204.9.0 ($MH^+$); $^1H$ NMR (300 MHz, $CDCl_3$): 7.71 (d, J=2.1 Hz, 1H), 7.01 (d, J=2.1 Hz, 1H), 4.69 (br s, 2H), 3.84 (s, 3H).

Step 3. Preparation of 2-amino-3-methoxy-5-(4,4,5, 5-tetramethyl-1,3,2-dioxaborolan-2-yl)pyridine A mixture of 2-amino-3-methoxy-5-bromopyridine (8.5 g, 41.6 mmol), bis(pinacolato)diboron (11.1 g, 43.7 mmol), potassium acetate (8.2 g, 83.6 mmol), $Pd_2(dba)_3$ (774 mg, 0.8 mmol), and $PCy_3$ (827 mg, 2.9 mmol) in dry dioxane (60 mL) was sparged with argon for 20 min. The reaction flask was sealed and the reaction was heated to 110° C. and maintained for 6 h. The reaction was allowed to cool to rt and diluted with EtOAc. The mixture was filtered through neutral alumina, washing the filter cake thoroughly with EtOAc (3×). The combined filtrates were then filtered through Celite. The resulting homogenous filtrate was concentrated. The resulting residue was triturated with hexanes to provide 7.39 g (71%) of the title compound: LCMS (m/z): 169.0 ($MH^+$, boronic acid), $t_R$=0.22 min; $^1H$ NMR (300 MHz, $CDCl_3$ δ 8.07 (d, J=1.2 Hz, 1H), 7.20 (d, J=1.2 Hz, 1H), 4.88 (br s, 2H), 3.86 (s, 3H), 1.33 (s, 12H).

Example 18

3-methoxy-5-(4,4,5,5-tetramethyl-1,3,2-dioxaborolan-2-yl)pyrazin-2-amine

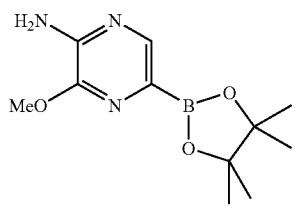

Step 1. Preparation of 5-bromo-3-methoxypyrazin-2-amine: A 30% w/w solution of NaOMe in MeOH (8.4 mL, 44.8 mmol) was added to a stirring suspension of 3,5-dibromo-2-aminopyrazine (10 g, 39.5 mmol) in dry MeOH (40 mL). The reaction mixture was heated to reflux and maintained for 3 h. The reaction was allowed to cool to rt and concentrate to ⅓ volume. The reaction was then partitioned between DCM and saturated aqueous $NaHCO_3$ solution. The layers were separated and the organic phase was washed with saturated aqueous $NaHCO_3$ solution (3×). The combined aqueous portions were back extracted with DCM (3×). The combined organic portions were washed with brine, dried ($Na_2SO_4$), and concentrated to provide 8.1 g of 5-bromo-3-methoxypyrazin-2-amine: $^1H$ NMR (300 MHz, $CDCl_3$): 7.64 (s, 1H), 4.79 (br s, 2H), 4.01 (s, 3H).

Step 2. Preparation of 3-methoxy-5-(4,4,5,5-tetramethyl-1,3,2-dioxaborolan-2-yl)pyrazin-2-amine: 5-bromo-3-methoxypyrazin-2-amine was elaborated to the title compound in an identical manner as described in Example 17, Step 3: LCMS (m/z): 169.9 ($MH^+$, boronic acid), $t_R$=0.18 min; $^1H$ NMR (300 MHz, DMSO-$d_6$) δ 7.78 (s, 1H), 6.69 (br s, 1H), 3.86 (s, 3H), 1.25 (s, 12H).

Example 19

3-$d_3$-methoxy-5-(4,4,5,5-tetramethyl-1,3,2-dioxaborolan-2-yl)pyrazin-2-amine

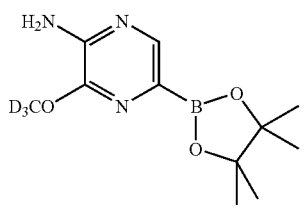

Step 1. Preparation of 5-bromo-3-$d_3$-methoxypyrazin-2-amine: Sodium (0.55 g, 23.7 mmol) was added to dry methanol-$d_3$ (20 ml) the reaction was stirred until homogeneity. 2-Amino-3,5-dibromo-aminopyrazine (5 g, 19.8 mmol) was added and the resulting reaction mixture was heated to reflux for 1 hr. The reaction was allowed cool to rt and concentrated to ~⅓ volume. The reaction was then partitioned between DCM (100 mL) and brine (100 mL). The layers were separated and the aqueous portion was extracted with DCM (50 mL). The combined organic portions were washed with brine (100 mL), dried ($MgSO_4$), and concentrated in vacuo to give 4.1 g of 5-bromo-3-$d_3$-methoxypyrazin-2-amine: LCMS (m/z): 207.0 ($MH^+$), $t_R$=0.55 min; $^1H$ NMR (400 MHz, $CDCl_3$) δ 7.65 (s, 1H), 4.69 (br s, 1H).

Step 2. Preparation of 3-$d_3$-methoxy-5-(4,4,5,5-tetramethyl-1,3,2-dioxaborolan-2-yl)pyrazin-2-amine: 5-bromo-3-$d_3$-methoxypyrazin-2-amine was elaborated to the title compound as per Example 17 Step 3: LCMS (m/z): 173.0 ($MH^+$, boronic acid), $t_R$=0.19 min; $^1H$ NMR (300 MHz, $CDCl_3$): 8.03 (s, 1H), 5.05 (br s, 2H), 1.36 (s, 12H).

Example 20

3-methoxy-6-methyl-5-(4,4,5,5-tetramethyl-1,3,2-dioxaborolan-2-yl)pyrazin-2-amine

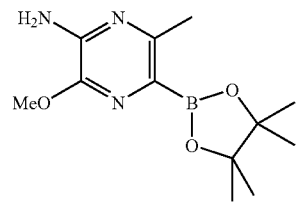

Step 1. Preparation of 6-Methylpyrazin-2-amine: Following a literature procedure (Walters, I. A. S. *Tetrahedron Lett.* 2006, 47, 341), a solution of dimethylzinc (2.0 M in toluene, 75.0 mL, 150.0 mmol) was carefully added in 25 mL portions to a solution of 2-amino-6-chloropyrazine (10.0 g, 77.0 mmol) and 1,3-bis(diphenylphosphino)propane-nickel (II) chloride (4.2 g, 7.8 mmol) were dry in dioxane (400 mL) under a nitrogen atmosphere. The reaction was stirred at rt for 2 h and then heated to 50° C. for 1 h and 95° C. overnight. The reaction was allowed to cool to rt and an additional charge of dimethylzinc was added (22 mL, 44 mmol) and the reaction was then maintained at 95° C. overnight. The reaction was cooled to rt, quenched over 15 min with MeOH and then concentrated to a brown solid. Water and EtOAc were added to the solid, and the mixture was sonicated. The solid was removed by filtration and brine was added to the EtOAc-water mixture. The layers were separated, and the organic layer was dried ($Na_2SO_4$), and concentrated to give 9.72 g (~70 purity) of 6-methylpyrazin-2-amine, which was carried forward without further purification: LCMS (m/z): 110.0 ($MH^+$), $t_R$=0.21 min.

Step 2. Synthesis of 3,5-dibromo-6-methylpyrazin-2-amine: Following a literature procedure (WO 2007/035154, p 29), bromine (12 mL, 231.0 mmol) was added portion-wise over 5 minutes into a cooled solution of 6-methylpyrazin-2-amine (9.72 g, 89.0 mmol) and lutidine (31.0 mL, 266.0 mmol) in dry acetonitrile at 10° C. The reaction was maintained overnight, allowing the cooling bath to expire. The reaction was quenched with aqueous 2.0 M sodium sulfite solution and the pH was adjusted to 8 with the addition of 6 M NaOH. The mixture was concentrated in vacuo and the remaining aqueous portion was cooled to 5° C. overnight. The resulting brown solid was isolated by filtration and triturated with a 9:1 EtOAc-hexanes solution to furnish 11.9 g of 3,5-dibromo-6-methylpyrazin-2-amine. The collected filtrate was concentrated and the resulting solid triturated again to provide an additional 2.2 g of product: LCMS (m/z): 267.9 ($MH^+$+2), $t_R$=0.80 min.

Step 3. Preparation of 5-bromo-3-methoxy-6-methylpyrazin-2-amine: A solution of NaOMe (~4.4 M in MeOH, 14.0 mL, 61.6 mmol) was added to solution of 3,5-sibromo-6-methylpyrazin-2-amine (14.1 g, 52.7 mmol) in dry MeOH. The reaction was heated to 70° C. for 18 h and then cooled to rt and stirred for 48 h. Water then added to reaction, and mixture cooled at 5° C. for 3 h. The resulting solid was isolated by filtration to give 10.1 g of 5-bromo-3-methoxy-6-methylpyrazin-2-amine: LCMS (m/z): 218.0 ($MH^+$), $t_R$=0.59 min; $^1$H NMR (300 MHz, $CDCl_3$) δ 6.42 (bs, 2H), 3.83 (s, 3H), 2.24 (s, 3H).

Step 4. Synthesis of 3-methoxy-6-methyl-5-(4,4,5,5-tetramethyl-1,3,2-dioxaborolan-2-yl)pyrazin-2-amine: 5-Bromo-3-methoxy-6-methylpyrazin-2-amine was converted to the title compound in a manner identical to Example 17, Step 3: LCMS (m/z): 184.0 ($MH^+$, boronic acid), $t_R$=0.23 min.

Example 21

3-ethyl-5-(4,4,5,5-tetramethyl-1,3,2-dioxaborolan-2-yl)pyridine-2-amine

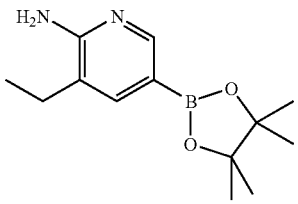

Step 1. Synthesis of tert-butyl 3-methylpyridin-2-ylcarbamate: BOC anhydride (9.6 g, 44 mmol) was added slowly to a solution of 3-methylpyridin-2-amine (4 g, 37 mmol) and cesium carbonate (7.2 g) dry in DMF (20 mL) and the reaction was maintained at rt for 2 d. The reaction mixture was poured into water (300 mL) with stirring. The resulting white precipitate was collected by filtration and dried under vacuum to give 4.45 g of tert-butyl 3-methylpyridin-2-ylcarbamate: $^1$H NMR (300 MHz, $CDCl_3$) δ 8.26 (m, 1H); 7.52 (m, 1H); 7.02 (m, 1H); 6.88 (br s, 1H); 2.29 (s, 3H); 1.52 (s, 9H).

Step 2. Preparation of tert-butyl 3-ethylpyridin-2-ylcarbamate: Following a literature procedure (*Synthesis* 1996, 877), n-BuLi (2.2 M in hexane, 9.1 mL, 20 mmol) was added dropwise to solution of tert-butyl 3-methylpyridin-2-ylcarbamate (1.98 g, 9.5 mmol) in dry THF (21 mL) at −5° C. The reaction was maintained at −5° C. for 1 h, then cooled to −78° C. in a dry ice-acetone bath. A solution of MeI (0.62 mL, 10 mmol) in dry THF (3 mL) was added over 20 min. The reaction was maintained at −78° C. for 1 h and then raised slowly to −55° C. The reaction was quenched with water (20 mL) and the resulting mixture was partitioned and the layers separated. The aqueous phase was extracted with EtOAc (2×20 mL) and the combined organic portions were washed with brine, dried ($Na_2CO_3$), and concentrated to furnish 1.8 g of tert-butyl 3-ethylpyridin-2-ylcarbamate: LCMS (m/z): 223.1 ($MH^+$), $t_R$=0.54 min Step 3. Preparation of 5-bromo-3-ethylpyridin-2-amine: Following a literature procedure (*Journal of Molecular Catalysis A: Chemical* 2007, 267, 30) tert-butyl 3-ethylpyridin-2-ylcarbamate (820 mg, 3.68 mmol) was treated with 4.0 M HCl in dioxane (4 mL, 4 mmol) and the reaction was maintained at rt for 2 h. Water (2 mL) was added and $K_2CO_3$ was added until pH>10. The resulting suspension was filtered and the isolated solid was washed with EtOAc (2 mL). The organic filtrates were concentrated and the resulting residue was dissolved in acetonitrile (4 mL). A portion (2 mL) was treated with $NH_4OAc$ (100 mg), followed by NBS (280 mg, 1.57 mmol). The reaction was maintained at rt for 15 min. The reaction was then partitioned between EtOAc and water and the resulting layers separated. The aqueous portion was extract with EtOAc (2×5 mL) and the combined organic layers were concentrated. The resulting residue was purified by reverse phase HPLC. The collected fractions were basified to pH>10 by the addition of saturated aqueous $Na_2CO_3$ solution. Extraction with EtOAc (2×20 mL) followed by concentration provided 240 mg of 5-bromo-3-ethylpyridin-2-amine: $^1$H NMR (400 MHz, CDCl$_3$) δ 7.99 (d, J=2.4 Hz, 1H); 7.39 (d, J=2.4 Hz, 1H); 4.41 (br s, 2H); 2.42 (q, J=7.2 Hz, 2H); 1.26 (t, J=7.2 Hz, 3H).

Step 4. Preparation of 3-ethyl-5-(4,4,5,5-tetramethyl-1,3,2-dioxaborolan-2-yl)pyridine-2-amine: 5-Bromo-3-ethylpyridin-2-amine (230 mg, 1.5 mmol), bis(pinacolato)diboron (500 mg, 1.97 mmol) and KOAc (210 mg, 2.1 mmol) were suspended in dry dioxane (15 mL). The mixture was sparged with Ar for 3 min followed by the addition of Pd(PPh$_3$)$_4$ (42 mg, 0.036 mmol). The reaction mixture was sparged again with Ar. The reaction was sealed and heat to and maintained at 100° C. for 18 hr under Ar. The reaction was allowed to cool to rt and to settle. The supernatant was decanted and used in the next step without further purification: LCMS (m/z): 166.9 (MH$^+$, boronic acid), $t_R$=0.32 min.

Example 22

3-methyl-5-(4,4,5,5-tetramethyl-1,3,2-dioxaborolan-2-yl) 1-1-((2-(trimethylsilyl)ethoxy)methyl)-1H-pyrrolo[2,3-b]pyridine

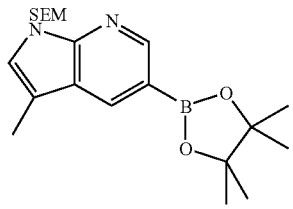

Step 1. Preparation of 5-bromo-3-iodo-1-((2-(trimethylsilyl)ethoxy)methyl)-1H-pyrrolo[2,3,-b]pyridine: 60% NaH in oil (150 mg, 3.74 mmol) was added to a solution of 5-bromo-3-iodo-1H-pyrrolo[2,3-b]pyridine (1.0 g, 3.12 mmol) in dry DMF (6 mL) at 0° C. The reaction mixture was allowed to warm to rt over 1 h and cooled again to 0° C. 2-(chloromethoxy)ethyl)trimethylsilane (661 uL, 3.74 mmol) was then added and the reaction was maintained for 1.5 h. The reaction was then quenched with water and the mixture was concentrated in vacuo. The resulting crude solid was dissolved in EtOAc (75 mL) and washed sequentially with water (2×25 mL), aqueous 2.0 M HCl (50 mL), water (25 mL), and then brine (50 mL). The solution was dried (Na$_2$SO$_4$) and concentrated to yield 1.48 g of 5-bromo-3-iodo-1-((2-(trimethylsilyl)ethoxy)methyl)-1H-pyrrolo[2,3,-b]pyridine: LCMS (m/z): 455.0 (MH$^+$), $t_R$=1.47 min.

Step 2. Preparation of 5-bromo-3-methyl-1-((2-(trimethylsilyl)ethoxy)methyl)-1H-pyrrolo[2,3-b]pyridine: A mixture of 5-bromo-3-iodo-1-((2-(trimethylsilyl)ethoxy)methyl)-1H-pyrrolo[2,3-b]pyridine (1.05 g, 2.33 mmol), 2,4,6-trimethyl-1,3,5,2,4,6-trioxatriborinane (2.6 mL, 18.6 mmol), and potassium carbonate (0.97 g, 7.0 mmol) in 10% aqueous dioxane (19 mL) was sparged with Ar. Pd(PPh$_3$)$_4$ (134 mg, 0.12 mmol) was added and the reaction was sealed and heated to 90° C. for 6.5 h. The reaction was allowed to cool to rt and concentrated in vacuo. The remaining residue was dissolved in EtOAc (250 mL), washed sequentially with water (100 mL), aqueous 0.1 M HCl solution (150 mL), and brine (100 mL). The resulting solution was dried (Na$_2$SO$_4$) and concentrated. Purification by reverse phase HPLC yielded 23 mg of 5-bromo-3-methyl-1-((2-(trimethylsilyl)ethoxy)methyl)-1H-pyrrolo[2,3-b]pyridine as the TFA salt: LCMS (m/z): 342.9 (MH$^+$), $t_R$=0.74 min Step 3. Preparation of 3-methyl-5-(4,4,5,5-tetramethyl-1,3,2-dioxaborolan-2-yl)-1-((2-(trimethylsilyl)ethoxy)methyl)-1H-pyrrolo[2,3-b]pyridine: A mixture of 5-bromo-3-methyl-1-((2-(trimethylsilyl)ethoxy)methyl)-1H-pyrrolo[2,3-b]pyridine (33 mg, 0.097 mmol) and bis(pinacolato)diboron (27 mg, 0.107 mmol) in 0.5 mL dioxane sparged with nitrogen was added KOAc (29 mg, 0.291 mmol) and Pd(dppf)Cl$_2$-DCM (8 mg, 0.010 mmol). This mixture was heated in an oil bath at 110° C. for 3 h. After cooling to rt the reaction mixture was centrifuged and the supernatant decanted, and used in the next step without further purification. LCMS (m/z): 307.0 (MH$^+$, boronic acid), $t_R$=0.80 min.

Example 23

(S)-tert-Butyl-1-aminopropan-2-ylcarbamate

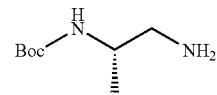

Step 1. Preparation of (S)-tert-butyl 1-(1,3-dioxoisoindolin-2-yl)propan-2-ylcarbamate: To a stirred solution of (S)-tert-butyl 1-hydroxypropan-2-ylcarbamate (7.4 g, 42.2 mmol) in dry THF (420 ml) were added phthalimide (6.83 g, 46.4 mmol) and PPh$_3$ (12.18 g, 46.4 mmol). DEAD (7.3 ml, 46.4 mmol) was then added dropwise to the stirred solution at rt, and maintained for 3 h. The reaction mixture was then concentrated and the residue was purified by flash chromatography (SiO$_2$, 70:30-50:50 hexanes-EtOAc) to provide 12.5 g of (S)-tert-butyl 1-(1,3-dioxoisoindolin-2-yl)propan-2-ylcarbamate: LCMS (m/z, M+H-Boc): 205.1, $t_R$=0.86 min; $^1$H NMR (CDCl$_3$, 400 MHz) δ 7.82-7.87 (m, 2H), 7.67-7.75 (m, 2H), 4.60-4.76 (br d, 1H), 4.03-4.20 (br s, 1H), 3.62-3.72 (m, 2H), 1.25 (s, 9H), 1.21 (d, J=6.64 Hz, 3H).

Step 2. Synthesis of (S)-tert-Butyl-1-aminopropan-2-ylcarbamate: Hydrazine monohydrate (20 ml, 642.7 mmol) was added to a suspension of (S)-tert-butyl 1-(1,3-dioxoisoindolin-2-yl)propan-2-ylcarbamate (12.50 g, 41.1 mmol) in dry MeOH (150 ml), and the resulting mixture was heated to 50° C. for 1 h. After cooling to rt, the reaction mixture was filtered through a sintered funnel, and the filtrate concentrated. The resulting residue was suspended in Et$_2$O (300 mL) and filtered, washing the filter cake thoroughly with Et$_2$O. The combine filtrates were filtered and concentrated to furnish 6.3 g of (S)-tert-Butyl-1-aminopropan-2-ylcarbamate: $^1$H NMR (CDCl$_3$, 400 MHz) δ 4.44-4.71 (br s, 1H), 3.53-3.74 (br m, 1H), 2.75 (dd, J=4.9, 12.9 Hz, 1H), 2.64 (dd, J=6.6, 12.9 Hz, 1H), 1.45 (s, 9H), 1.21 (d, J=6.6 Hz, 3H), 1.15-1.34 (br s, 2H), 1.12 (d, J=6.7 Hz, 3H).

Example 24

Synthesis of 5-(2-(4-(ethylsulfonyl)piperazin-1-yl)-5-(pyridin-4-yl)-1H-imidazol-4-yl)-3-methoxypyridin-2-amine

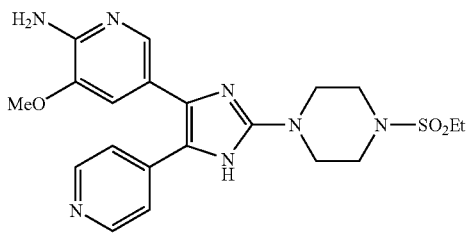

Step 1. Preparation of 1-(4,5-dibromo-1-((2-(trimethylsilyl)ethoxy)methyl)-1H-imidazol-2-yl)piperazine: A mixture of 2,4,5-tribromo-1-((2-(trimethylsilyl)ethoxy)methyl)-1H-imidazole (653 mg, 1.5 mmol) and piperazine (1.03 g, 12.0 mmol) under Ar was irradiated at 130° C. for 15 min in a microwave reactor. The reaction mixture was partitioned between DCM and water (100 mL, 1/1). The layers were separated and the aqueous layer was extracted with DCM (2×50 mL). The combined organic layers were dried (Na$_2$SO$_4$), filtered and concentrated in vacuo. The resulting was purified by flash chromatography (SiO$_2$, 100:0-90:10 DCM-MeOH) to provide 186 mg of 1-(4,5-dibromo-1-((2-(trimethylsilyl)ethoxy)methyl)-1H-imidazol-2-yl)piperazine as a colorless oil: LCMS (m/z): 441.0 (MH$^+$), t$_R$=0.86 min Step 2. Preparation of 5-(5-bromo-2-(piperazin-1-yl)-1-((2-(trimethylsilyl)ethoxy)methyl)-1H-imidazol-4-yl)-3-methoxypyridin-2-amine: A mixture of 3-methoxy-5-(4,4,5,5-tetramethyl-1,3,2-dioxaborolan-2-yl)pyridin-2-amine (66.5 mg, 0.27 mmol) and 1-(4,5-dibromo-1-((2-(trimethylsilyl)ethoxy)methyl)-1H-imidazol-2-yl)piperazine (90 mg, 0.20 mmol) in DME (2.4 ml) and 2.0 M aqueous Na$_2$CO$_3$ (0.8 ml) was sparged with Ar for 2 min. Pd(Ph$_3$P)$_4$ (47.2 mg, 0.041 mmol) was added. The mixture was sparged with Ar for an additional 2 min and was irradiated in a sealed tube in a microwave reactor at 115° C. for 20 min. The reaction mixture was extracted with EtOAc (3×15 mL). The combined organic layers were washed with brine (50 mL), dried (Na$_2$SO$_4$), filtered and concentrated in vacuo.

A mixture of 3-methoxy-5-(4,4,5,5-tetramethyl-1,3,2-dioxaborolan-2-yl)pyridin-2-amine (56.2 mg, 0.225 mmol) and 1-(4,5-dibromo-1-((2-(trimethylsilyl)ethoxy)methyl)-1H-imidazol-2-yl)piperazine (90 mg, 0.204 mmol) in DME (2.1 ml) and 2M aqueous Na$_2$CO$_3$ (0.7 ml) was sparged with Ar for 2 min. Pd(Ph$_3$P)$_4$ (23.6 mg, 0.02 mmol) was added. The mixture was sparged with Argon for an additional 2 min and was heated in a sealed tube in a microwave reactor at 115° C. for 15 min. The reaction mixture was extracted with EtOAc (3×15 mL). The combined organic layers were washed with brine (50 mL), dried (Na$_2$SO$_4$), filtered and concentrated in vacuo. The crude materials of both reactions were combined and purified by preparative TLC (SiO$_2$, 1.0 mm, 90:10 DCM-MeOH) to furnish 5-(5-bromo-2-(piperazin-1-yl)-1-((2-(trimethylsilyl)ethoxy)methyl)-1H-imidazol-4-yl)-3-methoxypyridin-2-amine was isolated as a white solid which was directly used in the next step: LCMS (m/z): 485.2 (MH$^+$), t$_R$=0.56 min.

Step 3. Preparation of 5-(5-bromo-2-(4-(ethylsulfonyl)piperazin-1-yl)-1-((2-(trimethylsilyl)ethoxy)methyl)-1H-imidazol-4-yl)-3-methoxypyridin-2-amine: In a 10 mL round-bottomed flask was 5-(5-bromo-2-(piperazin-1-yl)-1-((2-(trimethylsilyl)ethoxy)methyl)-1H-imidazol-4-yl)-3-methoxypyridin-2-amine (22 mg, 0.046 mmol) in THF (1.2 ml) and DMF (0.2 mL) under Ar at 0° C. to give a colorless solution. Ethanesulfonyl chloride (8.62 µl, 0.091 mmol) and triethylamine (0.014 ml, 0.100 mmol) were added. The ice bath was removed and the mixture was stirred at ambient temperature for 30 min. The mixture was quenched with water (3 mL) and diluted with EtOAc (10 mL). The aq layer was extracted with EtOAc (2×10 mL). The combined org layers were washed with sat aq NaHCO$_3$ solution (1×30 mL), brine (1×30 mL), dried over Na$_2$SO$_4$, filtered and conc in vacuo. The crude material was directly used in the next step without purification: LCMS (m/z): 577.2 (MH$^+$), t$_R$=0.82 min.

Step 4. Preparation of 5-(2-(4-(ethylsulfonyl)piperazin-1-yl)-5-(pyridine-4-yl)-1-((2-(trimethylsilyl)ethoxy)methyl)-1H-imidazol-4-yl)-3-methoxypyridin-2-amine: A mixture of pyridin-4-ylboronic acid (17.0 mg, 0.14 mmol) and 5-(5-bromo-2-(4-(ethylsulfonyl)piperazin-1-yl)-1-((2-(trimethylsilyl)ethoxy)methyl)-1H-imidazol-4-yl)-3-methoxypyridin-2-amine (26.5 mg, 0.05 mmol) in DME (1.5 mL) and 2.0 M aqueous Na$_2$CO$_3$ (0.5 mL) was sparged with Ar for 2 min. Tetrakis(triphenylphosphine)palladium(0) (10.6 mg, 9.2 µmol) was added. The mixture was sparged with Ar for an additional 2 min and was irradiated in a sealed tube in a microwave reactor at 115° C. for 15 min. The reaction mixture was extracted with EtOAc (3×10 mL). The combined organic layers were washed with sat aqueous NaHCO$_3$ (30 mL), brine (30 mL), dried over Na$_2$SO$_4$, filtered and concentrated in vacuo. The material purified by preparative TLC (SiO$_2$, 0.25 mm, 95:5 DCM-MeOH) to afford 5-(2-(4-(ethylsulfonyl)piperazin-1-yl)-5-(pyridin-4-yl)-1-((2-(trimethylsilyl)ethoxy)methyl)-1H-imidazol-4-yl)-3-methoxypyridin-2-amine was isolated as colorless solid: LCMS (m/z): 574.3 (MH$^+$), t$_R$=0.68 min.

Step 5. Synthesis of 5-(2-(4-(ethylsulfonyl)piperazin-1-yl)-5-(pyridin-4-yl)-1H-imidazol-4-yl)-3-methoxypyridin-2-amine: 5-(2-(4-(Ethylsulfonyl)piperazin-1-yl)-5-(pyridin-4-yl)-1-((2-(trimethylsilyl)ethoxy)-methyl)-1H-imidazol-4-yl)-3-methoxypyridin-2-amine (6.1 mg, 10.63 µmol) in MeOH (1.6 ml) and conc hydrochloric acid (0.4 ml) was heated at 60° C. for 50 min. The reaction mixture was concentrated in vacuo and purified by reverse phase HPLC, which after freeze drying, gave the title compound as the TFA salt: LCMS (m/z): 444.2 (MH$^+$), $t_R$=0.37 min.

Example 25

3-(difluoromethoxy)-5-(4,4,5,5-tetramethyl-1,3,2-dioxaborolan-2yl)pyridine-2-amine

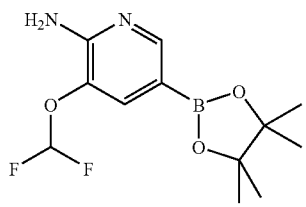

Step 1. Preparation of 2-bromo-3-(difluoromethoxy)pyridine: A mixture of 2-bromopyridin-3-ol (3.55 g, 20.4 mmol), sodium chlorodifluoroacetate (6.22 g, 40.8 mmol), and NaOH (0.90 g, 22.4 mmol) in DMF (20 ml) was heated at 55° C. for 111 h. The reaction was allowed to cool to rt and concentrated, and resulting residue was partitioned between EtOAc/sat. Na$_2$CO$_3$ (80 ml/40 ml). The organic phase was collected and washed with brine (40 ml), dried (Na$_2$SO$_4$), concentrated and the resulting residue was purified by flash chromatography (SiO$_2$, 100:0-0:100 hexanes-EtOAc) to provide 1.95 g (43%) of 2-bromo-3-(difluoromethoxy)pyridine: LCMS (m/z, MH$^+$): 225.9, $t_R$=0.74 min; $^1$H NMR (CDCl$_3$, 400 MHz) δ 8.23-8.33 (m, 1H), 7.52-7.60 (m, 1H), 7.27-7.35 (m, 1H), 6.60 (t, J=72.4 Hz, 1H).

Step 2. Preparation of 3-(difluoromethoxy)pyridin-2-amine: To a steel bomb were charged with 2-methoxyethanol (20 ml), 2-bromo-3-(difluoromethoxy)pyridine (1.95 g, 8.7 mmol), conc. aqueous NH$_4$OH (28-30%, 5 ml, 79 mmol) and Cu$_2$O (0.25 g, 1.7 mmol). The reaction mixture was heated at 100° C. for 23 h, then cooled to 0° C., and partitioned between mixture of EtOAc/aq. 3 N NaOH/H$_2$O (40 ml/10 ml/30 ml). The organic phase layer was collected, washed with saturated aqueous NaHCO$_3$ solution (30 ml), brine (40 ml), dried (Na$_2$SO$_4$), and concentrated to produce 1.12 g of 3-(difluoromethoxy)pyridin-2-amine which was carried forward without further purification: LCMS (m/z, MH$^+$): 161.0, $t_R$=0.31 min.

Step 3. Preparation of 5-bromo-3-(difluoromethoxy)pyridine-2-amine: N-Bromosuccinamide (1.00 g, 5.62 mmol) was added portionwise over 10 min to a cooled solution of 3-(difluoromethoxy)pyridin-2-amine (1.12 g) in dry acetonitrile (20 ml) at 0° C. The reaction mixture was further stirred at 0° C. for 10 min. The mixture was concentrated, and residue was partitioned between EtOAc/sat. Na$_2$CO$_3$/H$_2$O (30 ml/15 ml/15 ml). The organic phase was sequentially washed with sat. aqueous Na$_2$CO$_3$/H$_2$O (15 ml/15 ml) and brine (30 ml), dried (Na$_2$SO$_4$), and concentrated. The resulting residue was extracted with EtOAc/hexanes (6 ml/30 ml), and the resulting suspension was filtered through Celite, and the resulting filtrate was concentrated to provide 1.32 g (80%) of 5-bromo-3-(difluoromethoxy)pyridine-2-amine. LCMS (m/z, MH$^+$): 238.9, $t_R$=0.52 min; $^1$H NMR (CDCl$_3$, 400 MHz). δ 7.99 (d, J=2.0 Hz, 1H), 7.41 (m, 1H), 6.50 (t, J=72.8 Hz, 1H), 4.75 (br s, 2H).

Step 4. Preparation of 3-(difluoromethoxy)-5-(4,4,5,5-tetramethyl-1,3,2-dioxaborolan-2-yl)pyridine-2-amine: A mixture of 5-bromo-3-(difluoromethoxy)pyridine-2-amine (88 mg, 0.37 mmol), bis(pinacolato)diboron (102 mg, 0.40 mmol), potassium acetate (0.215 mg, 2.2 mmol), and Pd(dppf)-CH$_2$Cl$_2$ (30 mg, 0.037 mmol) in dry dioxane (2.0 mL) was sparged with argon, and heated at 120° C. for 30 min. After cooling to rt, the reaction mixture was centrifuged and the supernatant decanted, and used in the next step without further purification: LCMS (m/z, MH$^+$, boronic acid): 205.0, $t_R$=0.27 min.

Examples 26-290

The compounds of the present invention, including those shown in the following Table 1 (Compounds No. 1-265), have been prepared by these methods and modifications of these methods that are apparent to the person of ordinary skill. Compounds P1-P19 can be prepared similarly by the teachings of one or more procedures described in the Examples above and/or by general synthetic schemes described herein, and using the appropriate starting materials as readily determined by one of skill in the art.

TABLE 1

| Compound No. | STRUCTURE | mut-b-RAF (IC50 in uM) | retention time (min) | mass (MH$^+$) | Method | Compound Name |
|---|---|---|---|---|---|---|
| 1 | 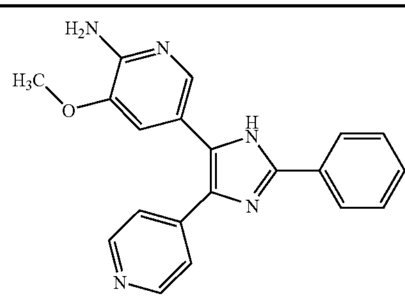 | 0.0010 | 0.46 | 344.2 | A | 3-methoxy-5-(2-phenyl-4-(pyridin-4-yl)-1H-imidazol-5-yl)pyridin-2-amine |

TABLE 1-continued

| Compound No. | STRUCTURE | mut-b-RAF (IC50 in uM) | retention time (min) | mass (MH+) | Method | Compound Name |
|---|---|---|---|---|---|---|
| 2 | 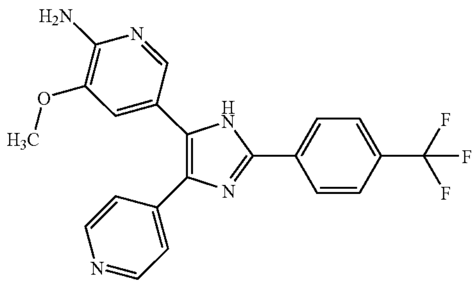 | 0.0004 | 0.57 | 412.0 | B | 3-methoxy-5-(4-(pyridin-yl)-2-(4-(trifluoromethyl)phenyl)-1H-imidazol-5-yl)pyridin-2-amine |
| 3 | 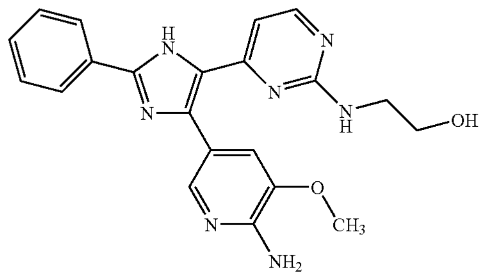 | 0.0013 | 0.52 | 404.1 | C | 2-(4-(4-(6-amino-5-methoxypyridin-3-yl)-2-phenyl-1H-imidazol-5-yl)pyrimidin-2-ylamino)ethanol |
| 4 | Chiral | 0.0001 | 0.65 | 508.1 | C | (S)-N-(1-(4-(4-(5-amino-6-methoxypyrazin-2-yl)-2-(4-(trifluoromethyl)phenyl)-1H-imidazol-5-yl)pyrimidin-2-ylamino)propan-2-yl)-2-methoxyacetamide |
| 5 | Chiral | 0.0002 | 0.72 | 558.2 | C | (S)-N-(1-(4-(4-(5-amino-6-methoxypyrazin-2-yl)-2-(4-fluorophenyl)-1H-imidazol-5-yl)pyrimidin-2-ylamino)propan-2-yl)-2-methoxyacetamide |

TABLE 1-continued

| Compound No. | STRUCTURE | mut-b-RAF (IC50 in uM) | retention time (min) | mass (MH+) | Method | Compound Name |
|---|---|---|---|---|---|---|
| 6 | Chiral | 0.0003 | 0.40 | 398.1 | C | (S)-1-(4-(4-(6-amino-5-methoxypyridin-3-yl)-2-tert-butyl-1H-imidazol-5-yl)pyrimidin-2-ylamino)propan-2-ol |
| 7 | Chiral | 0.0003 | 0.40 | 470.3 | C | (S)-N-(1-(4-(4-(5-amino-6-methoxypyrazin-2-yl)-2-tert-butyl-1H-imidazol-5-yl)pyrimidin-2-ylamino)propan-2-yl)-2-methoxyacetamide |
| 8 | Chiral | 0.0001 | 0.52 | 456.2 | C | (S)-methyl 1-(4-(4-(5-amino-6-methoxypyrazin-2-yl)-2-tert-butyl-1H-imidazol-5-yl)pyrimidin-2-ylamino)propan-2-ylcarbamate |
| 9 | 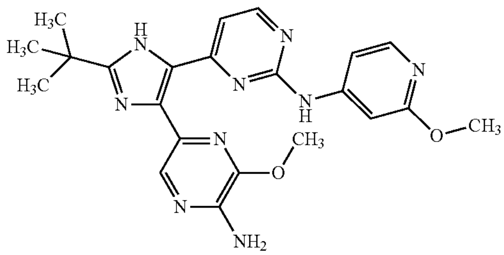 | 0.0001 | 0.45 | 448.1 | D | 4-(4-(5-amino-6-methoxypyrazin-2-yl)-2-tert-butyl-1H-imidazol-5-yl)-N-(2-methoxypyridin-4-yl)pyrimidin-2-amine |

TABLE 1-continued

| Compound No. | STRUCTURE | mut-b-RAF (IC50 in uM) | retention time (min) | mass (MH+) | Method | Compound Name |
|---|---|---|---|---|---|---|
| 10 | 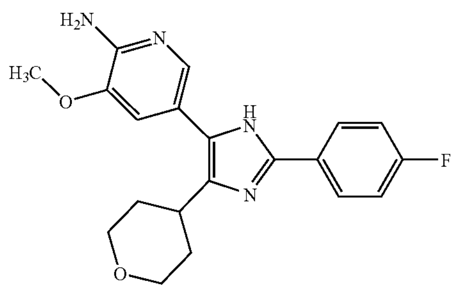 | 0.4053 | 0.44 | 369.0 | B | 5-(2-(4-fluorophenyl)-4-(tetrahydro-2H-pyran-4-yl)-1H-imidazol-5-yl)-3-methoxypyridin-2-amine |
| 11 | 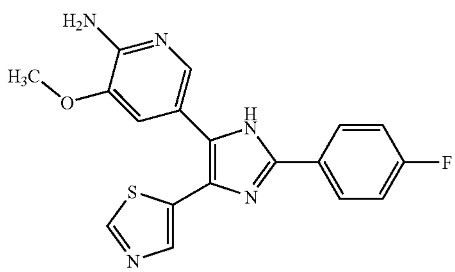 | 0.0365 | 0.52 | 368.0 | B | 5-(2-(4-fluorophenyl)-4-(thiazol-5-yl)-1H-imidazol-5-yl)-3-methoxypyridin-2-amine |
| 12 | 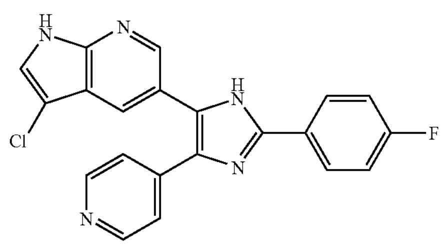 | 0.0020 | 0.67 | 390.1 | B | 3-chloro-5-(2-(4-fluorophenyl)-4-(pyridin-4-yl)-1H-imidazol-5-yl)-1H-pyrrolo[2,3-b]pyridine |
| 13 | 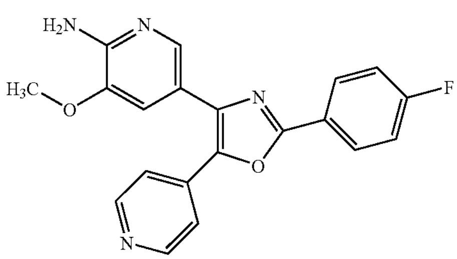 | 0.0005 | 0.54 | 362.9 | E | 5-(2-(4-fluorophenyl)-5-(pyridin-4-yl)oxazol-4-yl)-3-methoxypyridin-2-amine |
| 14 | 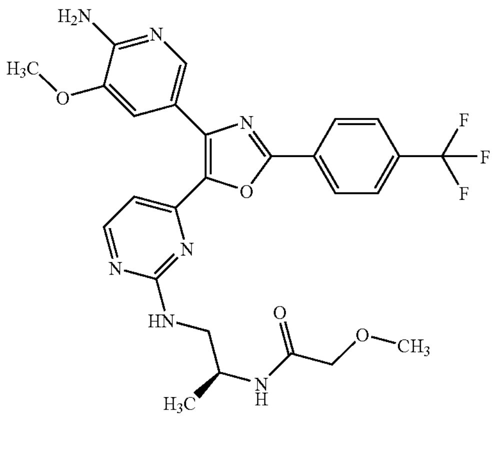 | Chiral 0.0030 | 0.77 | 558.3 | F | (S)-N-(1-(4-(4-(6-amino-5-methoxypyridin-3-yl)-2-(4-(trifluoromethyl)phenyl)-oxazol-5-yl)pyrimidin-2-ylamino)propan-2-yl)-2-methoxyacetamide |

TABLE 1-continued

| Compound No. | STRUCTURE | mut-b-RAF (IC50 in uM) | retention time (min) | mass (MH+) | Method | Compound Name |
|---|---|---|---|---|---|---|
| 15 | 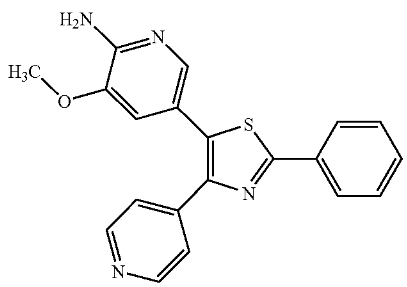 | 0.0019 | 0.57 | 361.0 | A | 3-methoxy-5-(2-phenyl-4-(pyridin-4-yl)thiazol-5-yl)pyridin-2-amine |
| 16 | 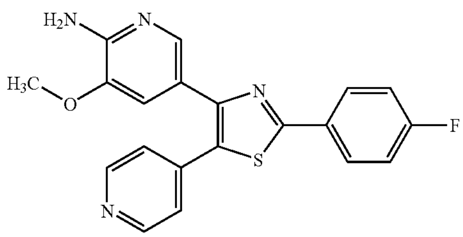 | 0.0143 | 0.57 | 378.9 | B Ex. 16 | 5-(2-(4-fluorophenyl)-5-(pyridin-4-yl)thiazol-4-yl)-3-methoxypyridin-2-amine |
| 24 | 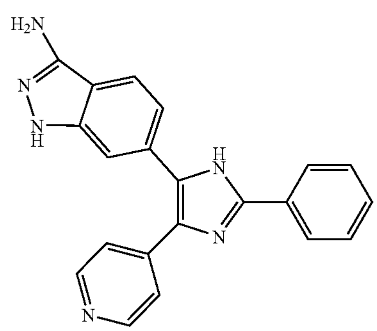 | 0.0580 | 1.76 | 353.1 | A | 6-(2-phenyl-4-(pyridin-4-yl)-1H-imidazol-5-yl)-1H-indazol-3-amine |
| 25 | 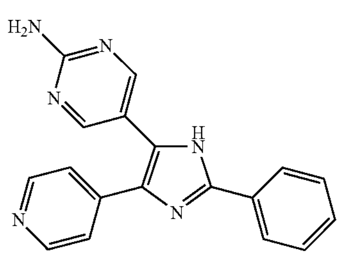 | 0.4890 | 1.74 | 315.1 | A | 5-(2-phenyl-4-(pyridin-4-yl)-1H-imidazol-5-yl)pyrimidin-2-amine |
| 26 | 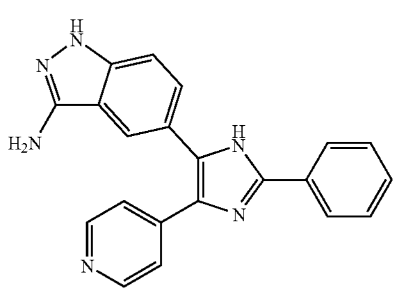 | 0.1730 | 1.76 | 353.1 | A | 5-(2-phenyl-4-(pyridin-4-yl)-1H-imidazol-5-yl)-1H-indazol-3-amine |

TABLE 1-continued

| Compound No. | STRUCTURE | mut-b-RAF (IC50 in uM) | retention time (min) | mass (MH+) | Method | Compound Name |
|---|---|---|---|---|---|---|
| 27 | 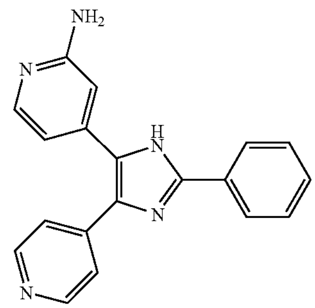 | 0.4170 | 0.43 | 314.1 | A | 4-(2-phenyl-4-(pyridin-4-yl)-1H-imidazol-5-yl)pyridin-2-amine |
| 28 | 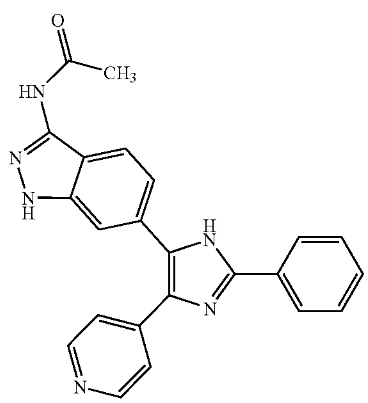 | 0.4490 | 1.84 | 395.2 | A | N-(6-(2-phenyl-4-(pyridin-4-yl)-1H-imidazol-5-yl)-1H-indazol-3-yl)acetamide |
| 29 | 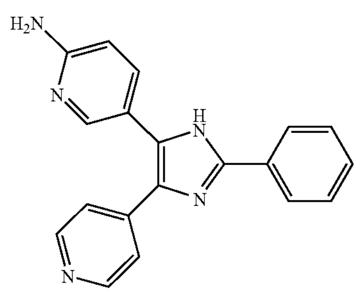 | 0.2600 | 1.63 | 314.2 | A | 5-(2-phenyl-4-(pyridin-4-yl)-1H-imidazol-5-yl)pyridin-2-amine |
| 30 | 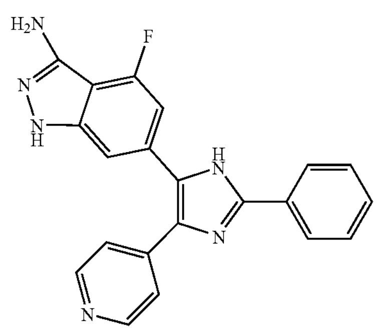 | 0.5280 | 1.89 | 371.2 | A | 4-fluoro-6-(2-phenyl-4-(pyridin-4-yl)-1H-imidazol-5-yl)-1H-indazol-3-amine |

TABLE 1-continued

| Compound No. | STRUCTURE | mut-b-RAF (IC50 in uM) | retention time (min) | mass (MH+) | Method | Compound Name |
|---|---|---|---|---|---|---|
| 32 | 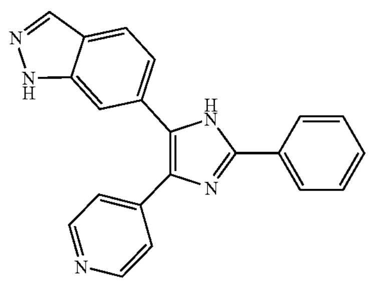 | 0.0170 | 0.57 | 338.1 | A | 6-(2-phenyl-4-(pyridin-4-yl)-1H-imidazol-5-yl)-1H-indazole |
| 33 | 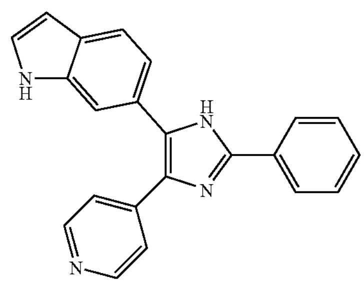 | 0.0540 | 0.61 | 337.1 | A | 6-(2-phenyl-4-(pyridin-4-yl)-1H-imidazol-5-yl)-1H-indole |
| 34 | 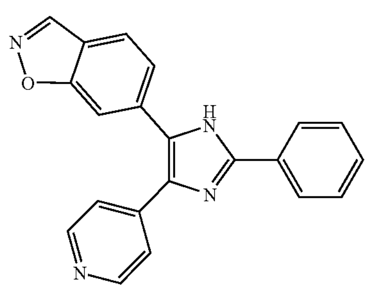 | 0.0050 | 0.59 | 339.1 | A | 6-(2-phenyl-4-(pyridin-4-yl)-1H-imidazol-5-yl)benzo[d]isoxazole |
| 35 | 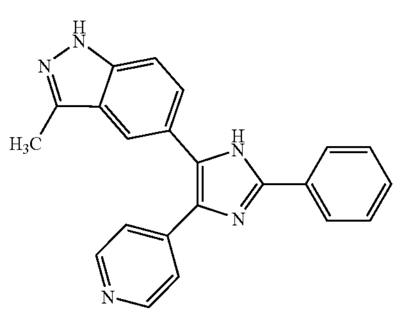 | 0.0990 | 0.55 | 352.0 | A | 3-methyl-5-(2-phenyl-4-(pyridin-4-yl)-1H-imidazol-5-yl)-1H-indazole |
| 36 | 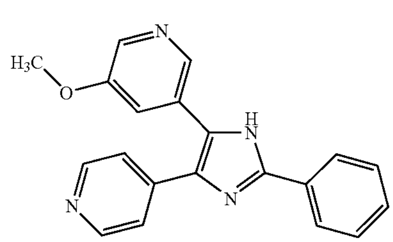 | 0.0130 | 0.47 | 329.1 | A | 3-methoxy-5-(2-phenyl-4-(pyridin-4-yl)-1H-imidazol-5-yl)pyridine |

TABLE 1-continued

| Compound No. | STRUCTURE | mut-b-RAF (IC50 in uM) | retention time (min) | mass (MH+) | Method | Compound Name |
|---|---|---|---|---|---|---|
| 37 | 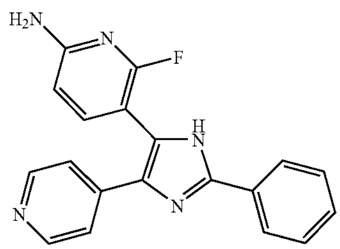 | 0.3870 | 0.49 | 332.1 | A | 6-fluoro-5-(2-phenyl-4-(pyridin-4-yl)-1H-imidazol-5-yl)pyridin-2-amine |
| 39 | 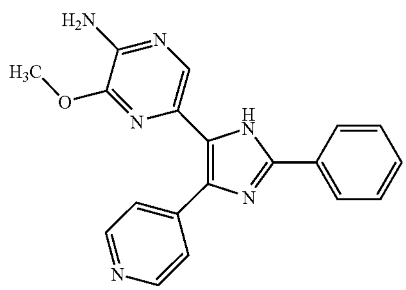 | 0.0060 | 0.47 | 345.2 | A | 3-methoxy-5-(2-phenyl-4-(pyridin-4-yl)-1H-imidazol-5-yl)pyrazin-2-amine |
| 40 | 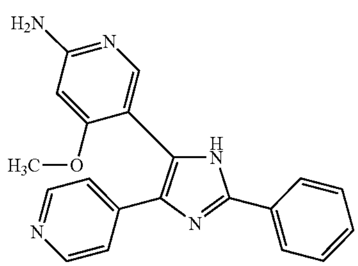 | 0.5020 | 0.44 | 344.2 | A | 4-methoxy-5-(2-phenyl-4-(pyridin-4-yl)-1H-imidazol-5-yl)pyridin-2-amine |
| 42 | 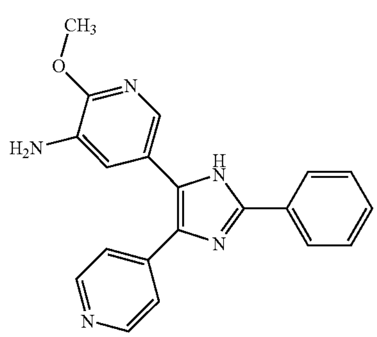 | 0.3490 | 0.49 | 344.2 | A | 2-methoxy-5-(2-phenyl-4-(pyridin-4-yl)-1H-imidazol-5-yl)pyridin-3-amine |
| 43 | 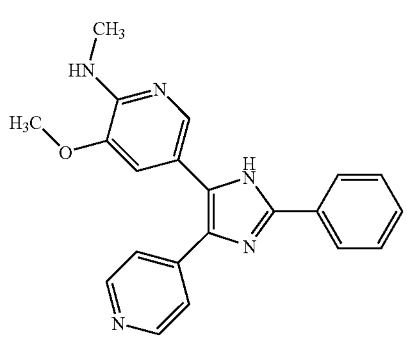 | 0.0250 | 0.44 | 358.2 | A | 3-methoxy-N-methyl-5-(2-phenyl-4-(pyridin-4-yl)-1H-imidazol-5-yl)pyridin-2-amine |

TABLE 1-continued

| Compound No. | STRUCTURE | mut-b-RAF (IC50 in uM) | retention time (min) | mass (MH+) | Method | Compound Name |
|---|---|---|---|---|---|---|
| 44 | 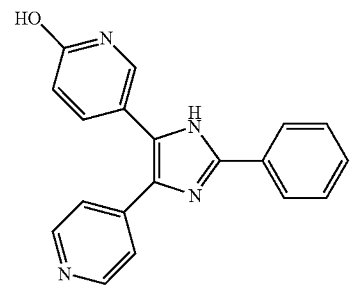 | 0.4650 | 0.43 | 314.9 | A | 5-(2-phenyl-4-(pyridin-4-yl)-1H-imidazol-5-yl)pyridin-2-ol |
| 45 | 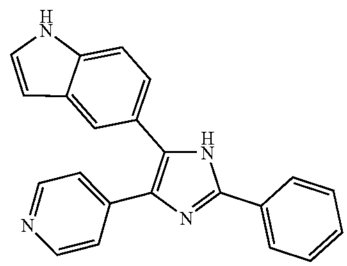 | 0.0046 | 0.51 | 338.2 | A | 5-(2-phenyl-4-(pyridin-4-yl)-1H-imidazol-5-yl)-1H-pyrrolo[2,3-b]pyridine |
| 46 | 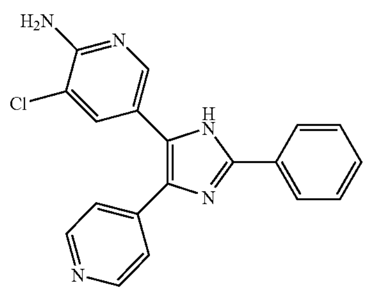 | 0.0287 | 0.51 | 348.1 | A | 3-chloro-5-(2-phenyl-4-(pyridin-4-yl)-1H-imidazol-5-yl)pyridin-2-amine |
| 47 | 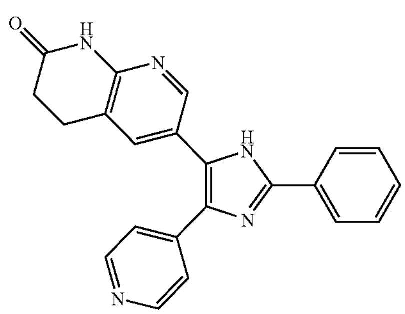 | 0.8848 | 0.50 | 368.0 | A | 6-(2-phenyl-4-(pyridin-4-yl)-1H-imidazol-5-yl)-3,4-dihydro-1,8-naphthyridin-2(1H)-one |
| 48 | 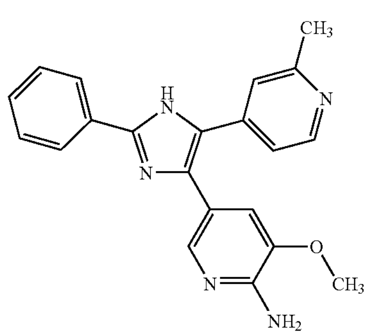 | 0.1201 | 0.48 | 358.1 | B | 3-methoxy-5-(5-(2-methylpyridin-4-yl)-2-phenyl-1H-imidazol-4-yl)pyridin-2-amine |

TABLE 1-continued

| Compound No. | STRUCTURE | mut-b-RAF (IC50 in uM) | retention time (min) | mass (MH+) | Method | Compound Name |
|---|---|---|---|---|---|---|
| 49 | 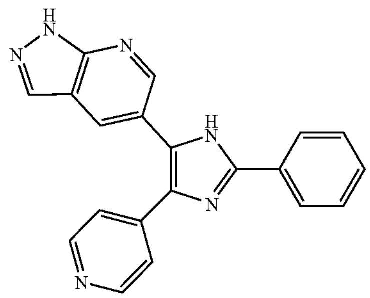 | 0.0222 | 0.50 | 339.0 | A | 5-(2-phenyl-4-(pyridin-4-yl)-1H-imidazol-5-yl)-1H-pyrazolo[3,4-b]pyridine |
| 50 | 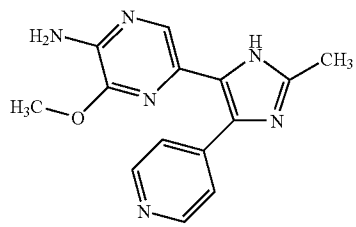 | 0.2591 | 0.27 | 283.0 | A | 3-methoxy-5-(2-methyl-4-(pyridin-4-yl)-1H-imidazol-5-yl)pyrazin-2-amine |
| 51 | 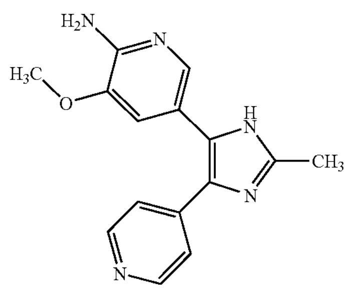 | 0.0196. | 0.22 | 282.2 | A | 3-methoxy-5-(2-methyl-4-(pyridin-4-yl)-1H-imidazol-5-yl)pyridin-2-amine |
| 52 | 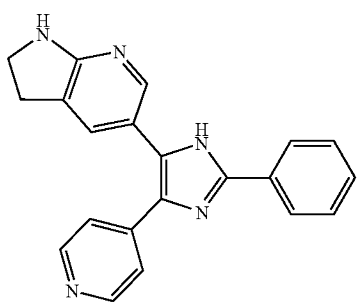 | 0.0123 | 0.43 | 340.2 | A | 5-(2-phenyl-4-(pyridin-4-yl)-1H-imidazol-5-yl)-2,3-dihydro-1H-pyrrolo[2,3-b]pyridine |
| 53 | 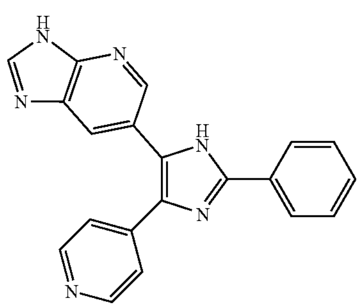 | 0.2901 | 0.43 | 339.0 | A | 6-(2-phenyl-4-(pyridin-4-yl)-1H-imidazol-5-yl)-3H-imidazo[4,5-b]pyridine |

TABLE 1-continued

| Compound No. | STRUCTURE | mut-b-RAF (IC50 in uM) | retention time (min) | mass (MH+) | Method | Compound Name |
|---|---|---|---|---|---|---|
| 55 | 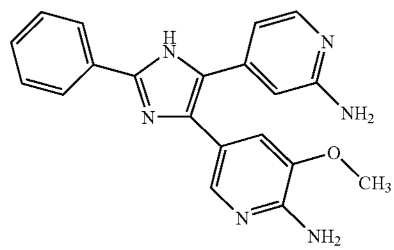 | 0.0098 | 0.44 | 359.0 | B | 5-(5-(2-aminopyridin-4-yl)-2-phenyl-1H-imidazol-4-yl)-3-methoxypyridin-2-amine |
| 56 | 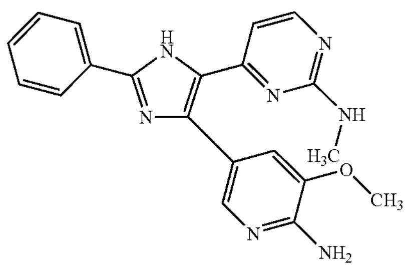 | 0.0029 | 0.48 | 374.1 | B | 4-(4-(6-amino-5-methoxypyridin-3-yl)-2-phenyl-1H-imidazol-5-yl)-N-methylpyrimidin-2-amine |
| 57 | 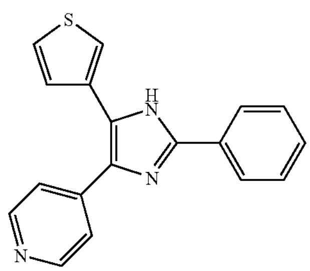 | 0.6200 | 0.55 | 304.0 | A | 4-(2-phenyl-5-(thiophen-3-yl)-1H-imidazol-4-yl)pyridine |
| 58 | Chiral | 0.0002 | 0.74 | 617.1 | C | (R)-4-(5-(6-amino-5-methoxypyridin-3-yl)-2-phenyl-1H-imidazol-4-yl)-N-(1-(4-chlorophenylsulfonyl)piperidin-3-yl)pyrimidin-2-amine |
| 59 | 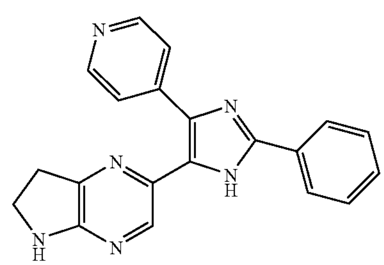 | 0.6803 | 0.45 | 341.0 | A | 2-(2-phenyl-4-(pyridin-4-yl)-1H-imidazol-5-yl)-6,7-dihydro-5H-pyrrolo[3,2-b]pyrazine |

TABLE 1-continued

| Compound No. | STRUCTURE | mut-b-RAF (IC50 in uM) | retention time (min) | mass (MH+) | Method | Compound Name |
|---|---|---|---|---|---|---|
| 60 | 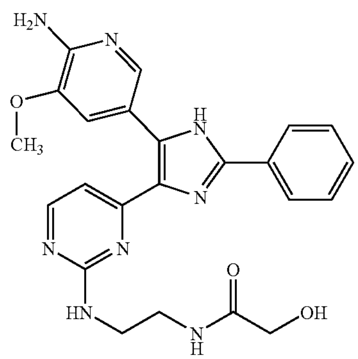 | 0.0001 | 0.53 | 4.61.1 | C | 2-(4-(4-(6-amino-5-methoxypyridin-3-yl)-2-phenyl-1H-imidazol-5-yl)pyrimidin-2-ylamino)-N-(2-hydroxyethyl)acetamide |
| 61 | 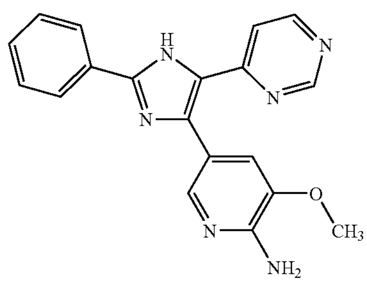 | 0.0049 | 0.54 | 345.0 | B | 3-methoxy-5-(2-phenyl-5-(pyrimidin-4-yl)-1H-imidazol-4-yl)pyridin-2-amine |
| 62 | Chiral | 0.0003 | 0.77 | 617.1 | B | (S)-4-(5-(6-amino-5-methoxypyridin-3-yl)-2-phenyl-1H-imidazol-4-yl)-N-(1-(4-chlorophenylsulfonyl)piperidin-3-yl)pyrimidin-2-amine |
| 63 | 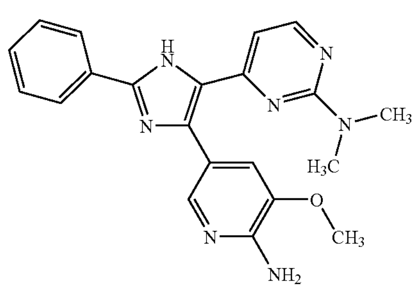 | 0.6407 | 0.55 | 388.0 | B | 4-(4-(6-amino-5-methoxypyridin-3-yl)-2-phenyl-1H-imidazol-5-yl)-N,N-dimethylpyrimidin-2-amine |

TABLE 1-continued

| Compound No. | STRUCTURE | mut-b-RAF (IC50 in uM) | retention time (min) | mass (MH+) | Method | Compound Name |
|---|---|---|---|---|---|---|
| 64 | Chiral | 0.0003 | 0.61 | 705.2 | C | (R)-4-(5-(6-amino-5-methoxypyridin-3-yl)-2-phenyl-1H-imidazol-4-yl)-N-(1-(4-(6-amino-5-methoxypyridin-3-yl)phenylsulfonyl)piperidin-3-yl)pyrimidin-2-amine |
| 65 | Chiral | 0.0599 | 0.43 | 443.1 | B | (R)-4-(5-(6-amino-5-methoxypyridin-3-yl)-2-phenyl-1H-imidazol-4-yl)-N-(piperidin-3-yl)pyrimidin-2-amine |
| 66 | 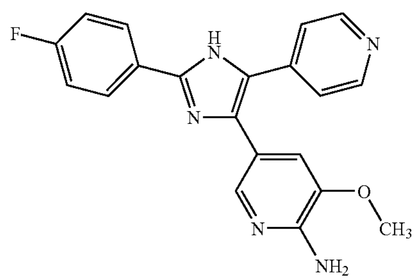 | 0.0006 | 0.47 | 362.1 | B | 5-(2-(4-fluorophenyl)-5-(pyridin-4-yl)-1H-imidazol-4-yl)-3-methoxypyridin-2-amine |
| 67 | 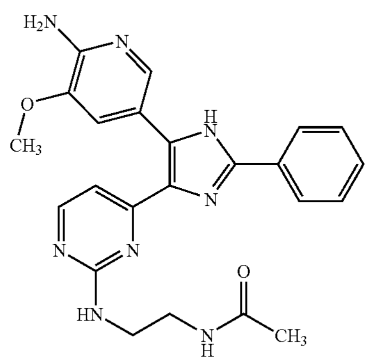 | 0.0001 | 0.47 | 445.0 | C | N-(2-(4-(5-(6-amino-5-methoxypyridin-3-yl)-2-phenyl-1H-imidazol-4-yl)pyrimidin-2-ylamino)ethyl)acetamide |

TABLE 1-continued

| Compound No. | STRUCTURE | mut-b-RAF (IC50 in uM) | retention time (min) | mass (MH+) | Method | Compound Name |
|---|---|---|---|---|---|---|
| 68 | 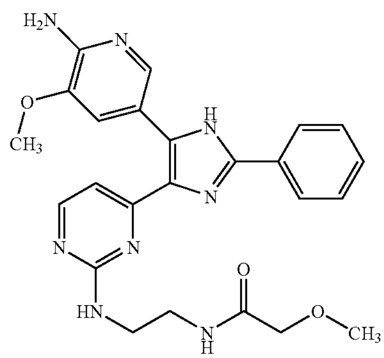 | 0.0001 | 0.47 | 475.1 | C | N-(2-(4-(5-(6-amino-5-methoxypyridin-3-yl)-2-phenyl-1H-imidazol-4-yl)pyrimidin-2-ylamino)ethyl)-2-methoxyacetamide |
| 69 | 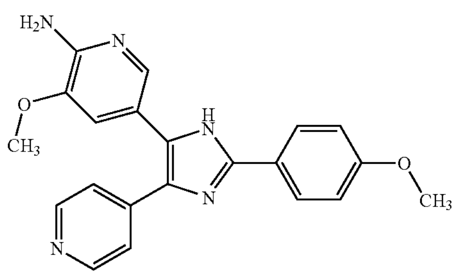 | 0.0003 | 0.43 | 374.1 | B | 3-methoxy-5-(2-(4-methoxyphenyl)-4-(pyridin-4-yl)-1H-imidazol-5-yl)pyridin-2-amine |
| 70 | 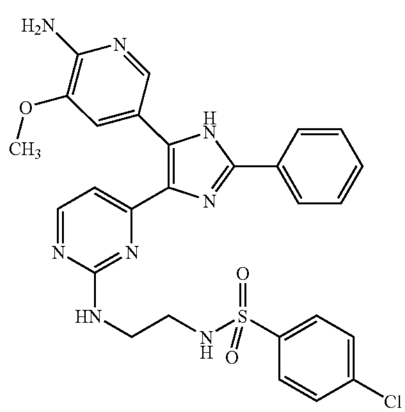 | 0.0004 | 0.64 | 577.0 | C | N-(2-(4-(5-(6-amino-5-methoxypyridin-3-yl)-2-phenyl-1H-imidazol-4-yl)pyrimidin-2-ylamino)ethyl)-4-chlorobenzenesulfonamide |
| 71 | 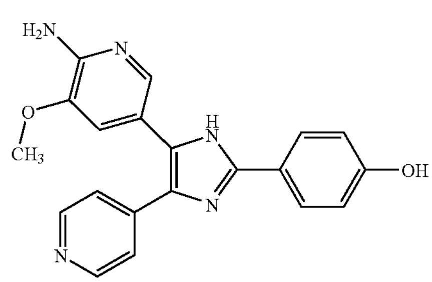 | 0.0003 | 0.34 | 360.0 | B | 4-(5-(6-amino-5-methoxypyridin-3-yl)-4-(pyridin-4-yl)-1H-imidazol-2-yl)phenol |

TABLE 1-continued

| Compound No. | STRUCTURE | mut-b-RAF (IC50 in uM) | retention time (min) | mass (MH+) | Method | Compound Name |
|---|---|---|---|---|---|---|
| 72 | 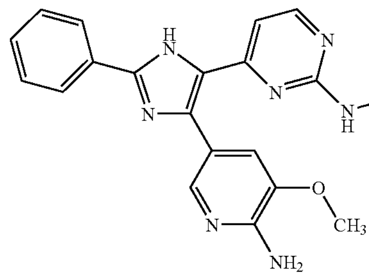 | 0.0016 | 0.49 | 400.1 | B | 4-(4-(6-amino-5-methoxypyridin-3-yl)-2-phenyl-1H-imidazol-5-yl)-N-cyclopropylpyrimidin-2-amine |
| 73 | 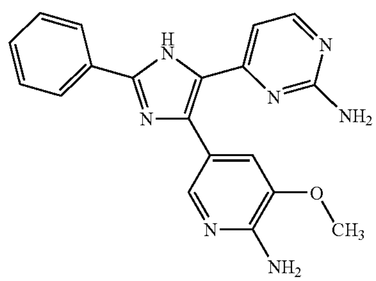 | 0.0011 | 0.44 | 360.0 | B | 4-(4-(6-amino-5-methoxypyridin-3-yl)-2-phenyl-1H-imidazol-5-yl)pyrimidin-2-amine |
| 74 | Chiral | 0.0006 | 0.46 | 418.1 | C | (S)-1-(4-(4-(6-amino-5-methoxypyridin-3-yl)-2-phenyl-1H-imidazol-5-yl)pyrimidin-2-ylamino)propan-2-ol |
| 75 | Chiral | 0.0011 | 0.47 | 418.1 | C | (R)-1-(4-(4-(6-amino-5-methoxypyridin-3-yl)-2-phenyl-1H-imidazol-5-yl)pyrimidin-2-ylamino)propan-2-ol |
| 76 | 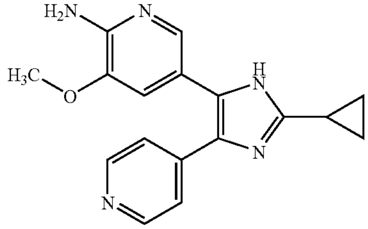 | 0.0015 | 0.29 | 307.9 | B | 5-(2-cyclopropyl-4-(pyridin-4-yl)-1H-imidazol-5-yl)-3-methoxypyridin-2-amine |

TABLE 1-continued

| Compound No. | STRUCTURE | mut-b-RAF (IC50 in uM) | retention time (min) | mass (MH+) | Method | Compound Name |
|---|---|---|---|---|---|---|
| 77 | 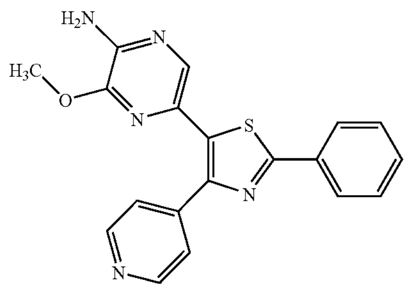 | 0.0890 | 0.70 | 362.0 | A | 3-methoxy-5-(2-phenyl-4-(pyridin-4-yl)thiazol-5-yl)pyrazin-2-amine |
| 78 | 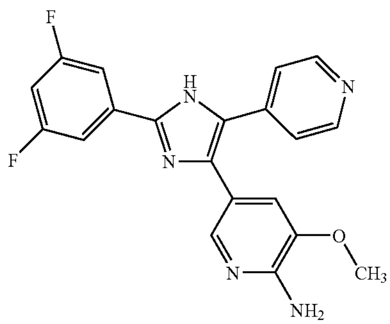 | 0.0010 | 0.54 | 380.0 | B | 5-(2-(3,5-difluorophenyl)-5-(pyridin-4-yl)-1H-imidazol-4-yl)-3-methoxypyridin-2-amine |
| 79 | 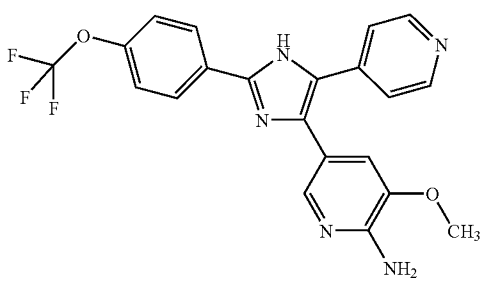 | 0.0020 | 0.64 | 428.0 | B | 3-methoxy-5-(5-(pyridin-4-yl)-2-(4-(trifluoromethoxy)phenyl)-1H-imidazol-4-yl)pyridin-2-amine |
| 80 | 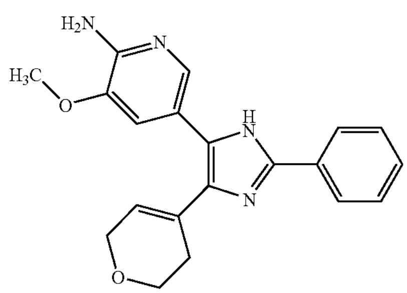 | 0.0380 | 0.44 | 349.0 | B | 5-(4-(3,6-dihydro-2H-pyran-4-yl)-2-phenyl-1H-imidazol-5-yl)-3-methoxypyridin-2-amine |
| 81 | 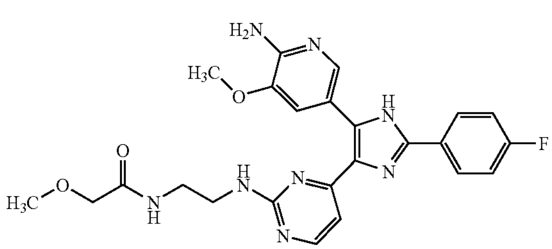 | 0.0001 | 0.54 | 493.0 | C | N-(2-(4-(5-(6-amino-5-methoxypyridin-3-yl)-2-(4-fluorophenyl)-1H-imidazol-4-yl)pyrimidin-2-ylamino)ethyl)-2-methoxyacetamide |

TABLE 1-continued

| Compound No. | STRUCTURE | mut-b-RAF (IC50 in uM) | retention time (min) | mass (MH+) | Method | Compound Name |
|---|---|---|---|---|---|---|
| 82 | 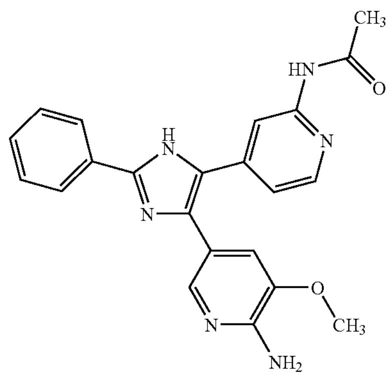 | 0.0020 | 0.48 | 401.1 | B | N-(4-(4-(6-amino-5-methoxypyridin-3-yl)-2-phenyl-1H-imidazol-5-yl)pyridin-2-yl)acetamide |
| 83 | 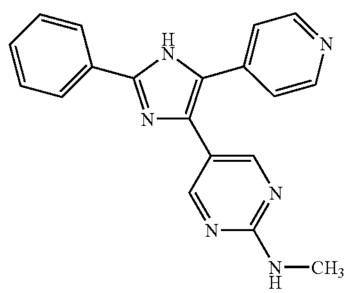 | 0.1970 | 0.49 | 329.0 | A | N-methyl-5-(2-phenyl-5-(pyridin-4-yl)-1H-imidazol-4-yl)pyrimidin-2-amine |
| 84 | 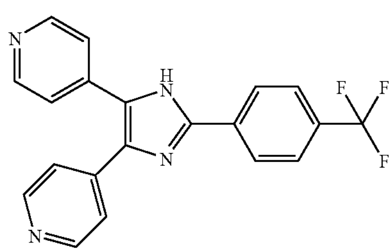 | 0.2290 | 0.61 | 367.0 | B | 4,4'-(2-(4-(trifluoromethyl)phenyl)-1H-imidazole-4,5-diyl)dipyridine |
| 85 | 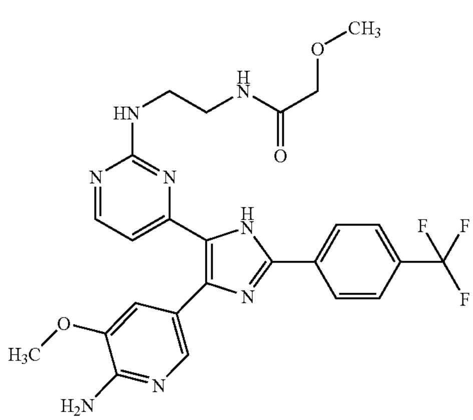 | 0.0002 | 0.68 | 543.1 | C | N-(2-(4-(4-(6-amino-5-methoxypyridin-3-yl)-2-(4-(trifluoromethyl)phenyl)-1H-imidazol-5-yl)pyrimidin-2-ylamino)ethyl)-2-methoxyacetamide |

TABLE 1-continued

| Compound No. | STRUCTURE | mut-b-RAF (IC50 in uM) | retention time (min) | mass (MH+) | Method | Compound Name |
|---|---|---|---|---|---|---|
| 86 | 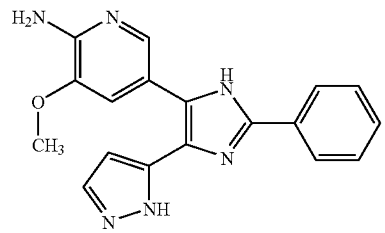 | 0.5370 | 0.42 | 333.0 | B | 3-methoxy-5-(2-phenyl-4-(1H-pyrazol-5-yl)-1H-imidazol-5-yl)pyridin-2-amine |
| 87 | 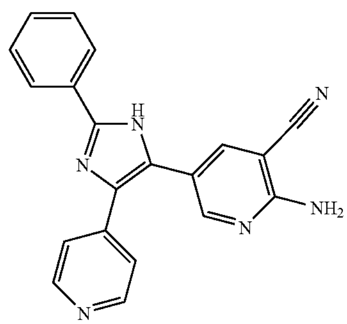 | 0.3910 | 0.51 | 339.1 | A | 2-amino-5-(2-phenyl-4-(pyridin-4-yl)-1H-imidazol-5-yl)nicotinonitrile |
| 88 | 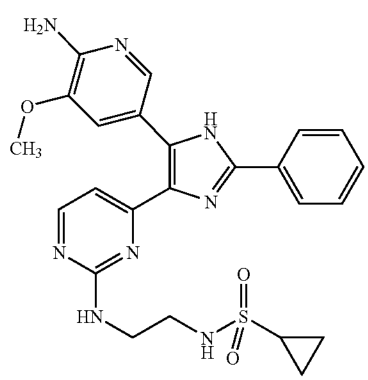 | 0.0001 | 0.55 | 507.1 | B | N-(2-(4-(5-(6-amino-5-methoxypyridin-3-yl)-2-phenyl-1H-imidazol-4-yl)pyrimidin-2-ylamino)ethyl)cyclopropanesulfonamide |
| 89 | 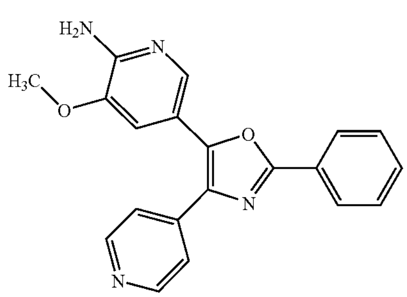 | 0.0137 | 0.57 | 344.9 | E | 3-methoxy-5-(2-phenyl-4-(pyridin-4-yl)oxazol-5-yl)pyridin-2-amine |
| 90 | 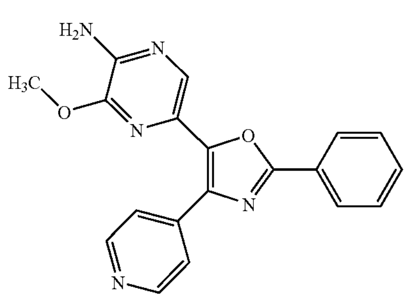 | 0.1128 | 0.68 | 345.9 | E | 3-methoxy-5-(2-phenyl-4-(pyridin-4-yl)oxazol-5-yl)pyrazin-2-amine |

TABLE 1-continued

| Compound No. | STRUCTURE | mut-b-RAF (IC50 in uM) | retention time (min) | mass (MH+) | Method | Compound Name |
|---|---|---|---|---|---|---|
| 91 | Chiral | 0.0044 | 0.59 | 547.2 | C | (R)-4-(5-(6-amino-5-methoxypyridin-3-yl)-2-phenyl-1H-imidazol-4-yl)-N-(1-(cyclopropylsulfonyl)piperidin-3-yl)pyrimidin-2-amine |
| 92 | 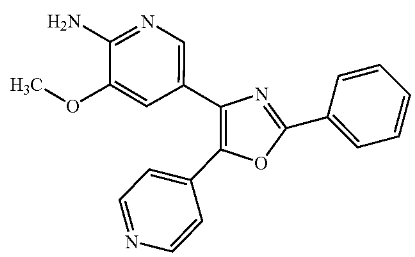 | 0.0003 | 0.58 | 345.1 | E | 3-methoxy-5-(2-phenyl-5-(pyridin-4-yl)oxazol-4-yl)pyridin-2-amine |
| 93 | 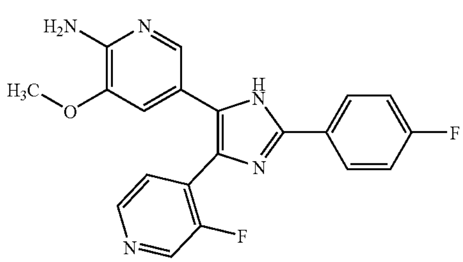 | 0.0038 | 0.53 | 379.9 | B | 5-(2-(4-fluorophenyl)-4-(3-fluoropyridin-4-yl)-1H-imidazol-5-yl)-3-methoxypyridin-2-amine |
| 94 | 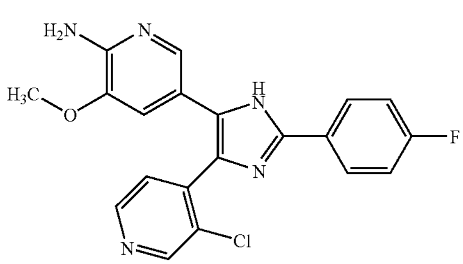 | 0.0606 | 0.56 | 395.9 | B | 5-(4-(3-chloropyridin-4-yl)-2-(4-fluorophenyl)-1H-imidazol-5-yl)-3-methoxypyridin-2-amine |

TABLE 1-continued

| Compound No. | STRUCTURE | mut-b-RAF (IC50 in uM) | retention time (min) | mass (MH+) | Method | Compound Name |
|---|---|---|---|---|---|---|
| 95 | 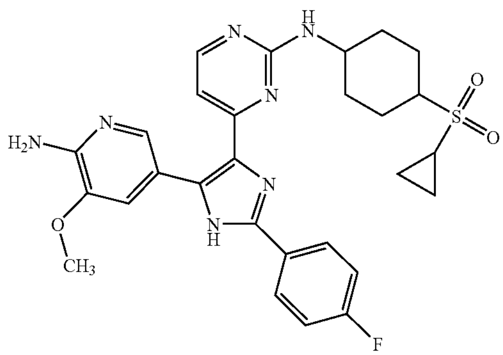 | 0.0025 | 0.63 | 565.1 | C | 4-(5-(6-amino-5-methoxypyridin-3-yl)-2-(4-fluorophenyl)-1H-imidazol-4-yl)-N-(1-(cyclopropylsulfonyl)piperidin-4-yl)pyrimidin-2-amine |
| 96 | 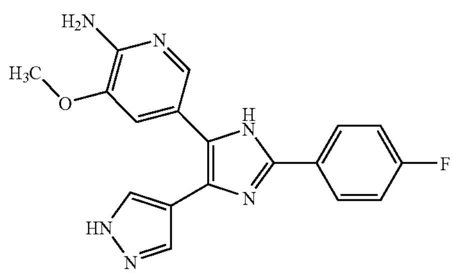 | 0.0321 | 0.43 | 350.9 | B | 5-(2-(4-fluorophenyl)-4-(1H-pyrazol-4-yl)-1H-imidazol-5-yl)-3-methoxypyridin-2-amine |
| 97 | Chiral | 0.0310 | 0.67 | 583.0 | C | (R)-1-(3-(4-(5-(6-amino-5-methoxypyridin-3-yl)-2-(4-(trifluoromethyl)phenyl)-1H-imidazol-4-yl)pyrimidin-2-ylamino)piperidin-1-yl)-2-methoxyethanone |
| 98 | 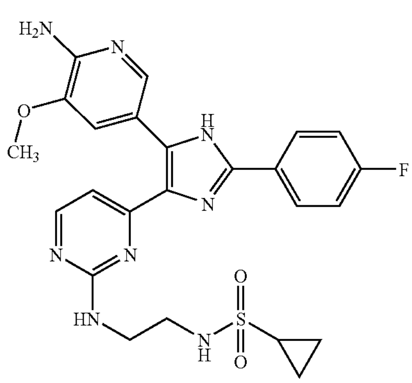 | 0.0001 | 0.58 | 525.1 | C | N-(2-(4-(5-(6-amino-5-methoxypyridin-3-yl)-2-(4-fluorophenyl)-1H-imidazol-4-yl)pyrimidin-2-ylamino)ethyl)cyclopropanesulfonamide |

TABLE 1-continued

| Compound No. | STRUCTURE | mut-b-RAF (IC50 in uM) | retention time (min) | mass (MH+) | Method | Compound Name |
|---|---|---|---|---|---|---|
| 99 | 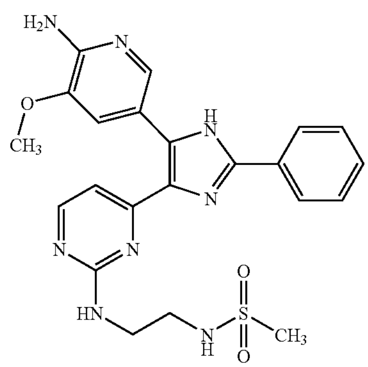 | 0.0001 | 0.51 | 481.1 | C | N-(2-(4-(5-(6-amino-5-methoxypyridin-3-yl)-2-phenyl-1H-imidazol-4-yl)pyrimidin-2-ylamino)ethyl)methanesulfonamide |
| 100 | Chiral | 0.0259 | 0.57 | 533.2 | C | (R)-1-(3-(4-(5-(6-amino-5-methoxypyridin-3-yl)-2-(4-fluorophenyl)-1H-imidazol-4-yl)pyrimidin-2-ylamino)piperidin-1-yl)-2-methoxyethanone |
| 101 | 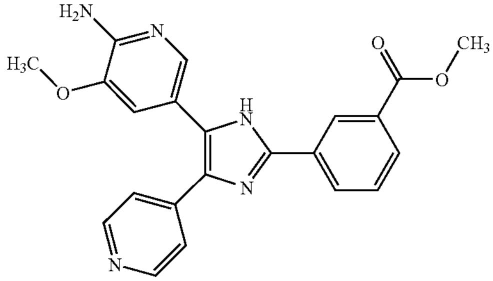 | 0.0013 | 0.49 | 402.1 | B | methyl 3-(5-(6-amino-5-methoxypyridin-3-yl)-4-(pyridin-4-yl)-1H-imidazol-2-yl)benzoate |
| 102 | 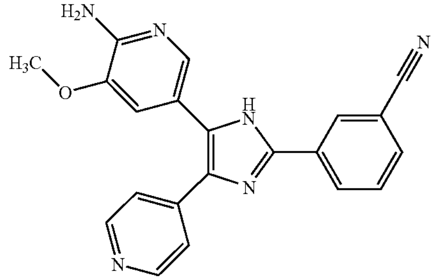 | 0.0011 | 0.45 | 369.2 | B | 3-(5-(6-amino-5-methoxypyridin-3-yl)-4-(pyridin-4-yl)-1H-imidazol-2-yl)benzonitrile |

TABLE 1-continued

| Compound No. | STRUCTURE | mut-b-RAF (IC50 in uM) | retention time (min) | mass (MH+) | Method | Compound Name |
|---|---|---|---|---|---|---|
| 103 | 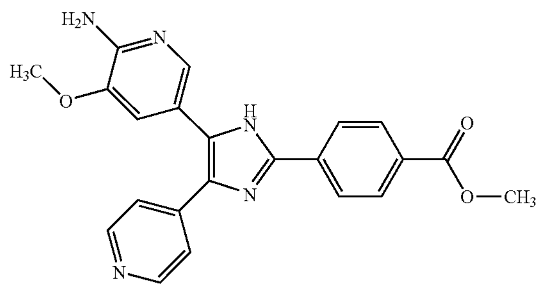 | 0.0007 | 0.48 | 402.1 | B | methyl 4-(5-(6-amino-5-methoxypyridin-3-yl)-4-(pyridin-4-yl)-1H-imidazol-2-yl)benzoate |
| 104 | 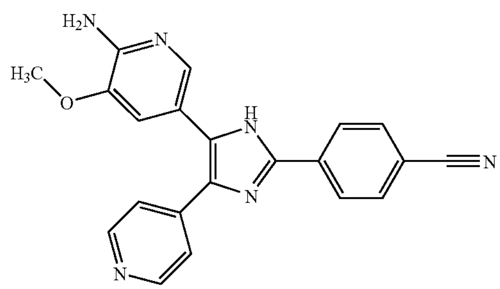 | 0.0014 | 0.47 | 369.2 | B | 4-(5-(6-amino-5-methoxypyridin-3-yl)-4-(pyridin-4-yl)-1H-imidazol-2-yl)benzonitrile |
| 105 | 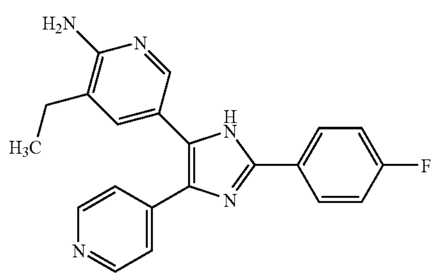 | 0.2145 | 0.53 | 360.0 | A | 3-ethyl-5-(2-(4-fluorophenyl)-4-(pyridin-4-yl)-1H-imidazol-5-yl)pyridin-2-amine |
| 106 | 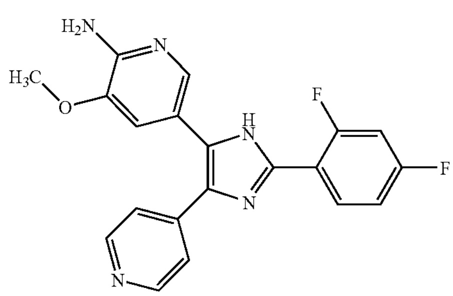 | 0.0010 | 0.49 | 379.9 | B | 5-(2-(2,4-difluorophenyl)-4-(pyridin-4-yl)-1H-imidazol-5-yl)-3-methoxypyridin-2-amine |
| 107 | 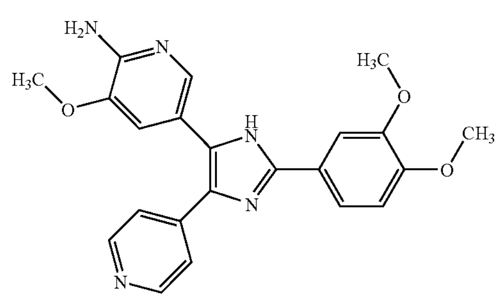 | 0.0007 | 0.48 | 404.0 | B | 5-(2-(3,4-dimethoxyphenyl)-4-(pyridin-4-yl)-1H-imidazol-5-yl)-3-methoxypyridin-2-amine |

TABLE 1-continued

| Compound No. | STRUCTURE | mut-b-RAF (IC50 in uM) | retention time (min) | mass (MH+) | Method | Compound Name |
|---|---|---|---|---|---|---|
| 108 | 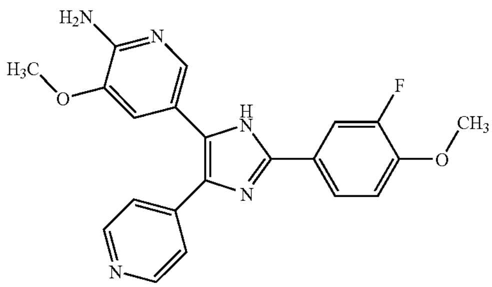 | 0.0007 | 0.57 | 392.0 | B | 5-(2-(3-fluoro-4-methoxyphenyl)-4-(pyridin-4-yl)-1H-imidazo-5-yl)-3-methoxypyridin-2-amine |
| 109 | 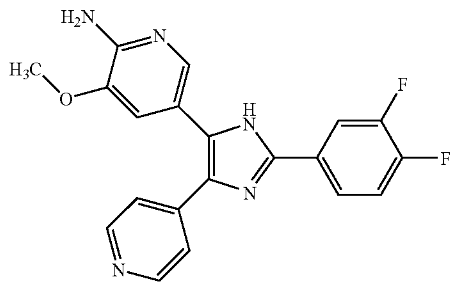 | 0.0012 | 0.53 | 380.1 | B | 5-(2-(3,4-difluorophenyl)-4-(pyridin-4-yl)-1H-imidazol-5-yl)-3-methoxypyridin-2-amine |
| 110 | 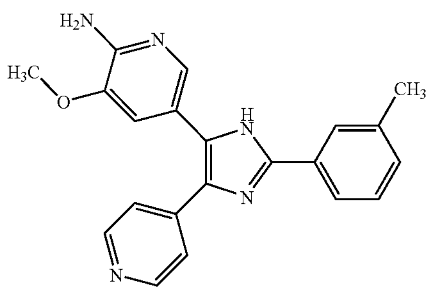 | 0.0005 | 0.55 | 358.0 | B | 3-methoxy-5-(4-(pyridin-4-yl)-2-tolyl-1H-imidazol-5-yl)pyridin-2-amine |
| 111 | 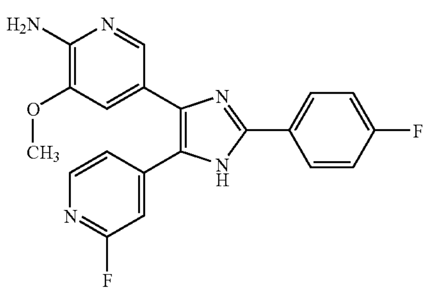 | 0.0292 | 0.57 | 380.1 | B | 5-(2-(4-fluorophenyl)-5-(2-fluoropyridin-4-yl)-1H-imidazol-4-yl)-3-methoxypyridin-2-amine |
| 112 | 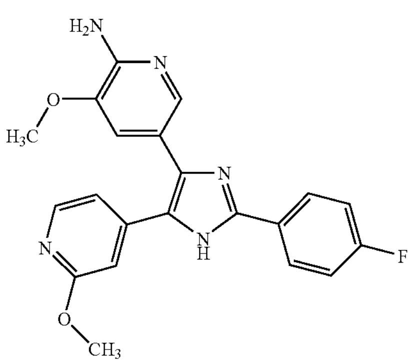 | 0.7370 | 0.62 | 392.2 | B | 5-(2-(4-fluorophenyl)-5-(2-methoxypyridin-4-yl)-1H-imidazol-4-yl)-3-methoxypyridin-2-amine |

TABLE 1-continued

| Compound No. | STRUCTURE | mut-b-RAF (IC50 in uM) | retention time (min) | mass (MH+) | Method | Compound Name |
|---|---|---|---|---|---|---|
| 113 | 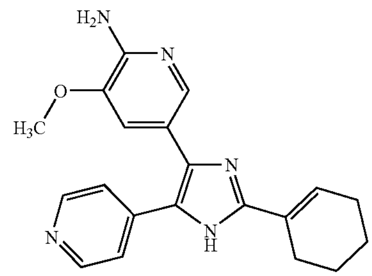 | 0.0026 | 0.50 | 348.0 | B | 5-(2-cyclohexenyl-5-(pyridin-4-yl)-1H-imidazol-4-yl)-3-methoxypyridin-2-amine |
| 114 | 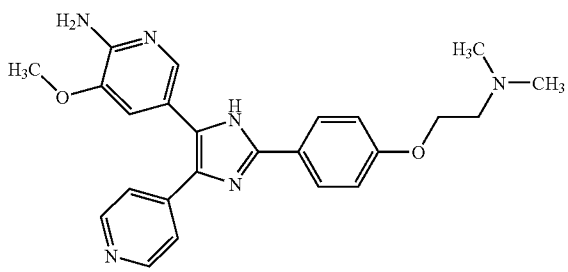 | 0.0064 | 0.31 | 431.2 | B | 5-(2-(4-(2-(dimethylamino)ethyl)-phenyl)-4-(pyridin-4-yl)-1H-imidazol-5-yl)-3-methoxypyridin-2-amine |
| 115 | 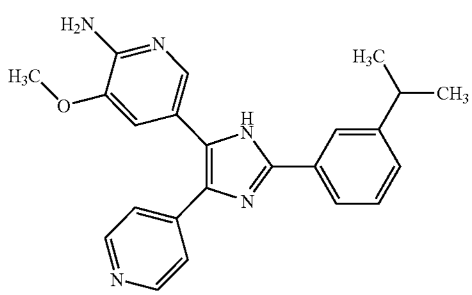 | 0.0030 | 0.65 | 386.1 | B | 5-(2-(3-isopropylphenyl)-4-(pyridin-4-yl)-1H-imidazol-5-yl)-3-methoxypyridin-2-amine |
| 116 | 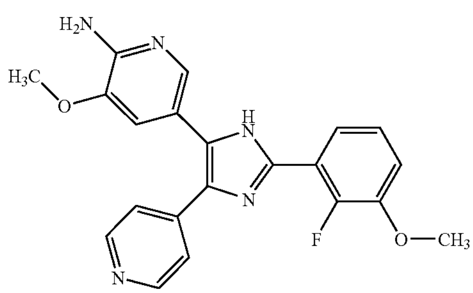 | 0.0017 | 0.47 | 392.0 | B | 5-(2-(2-fluoro-3-methoxyphenyl)-4-(pyridin-4-yl)-1H-imidazol-5-yl)-3-methoxypyridin-2-amine |
| 117 | 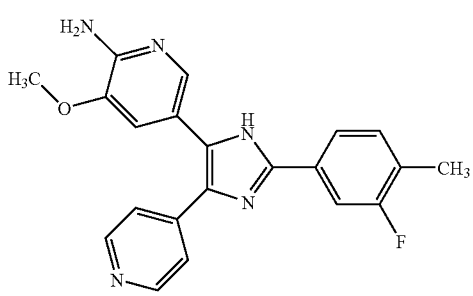 | 0.0007 | 0.56 | 450.1 | B | 5-(2-(3-fluoro-4-methylphenyl)-4-(pyridin-4-yl)-1H-imidazol-5-yl)-3-methoxypyridin-2-amine |

TABLE 1-continued

| Compound No. | STRUCTURE | mut-b-RAF (IC50 in uM) | retention time (min) | mass (MH+) | Method | Compound Name |
|---|---|---|---|---|---|---|
| 118 | 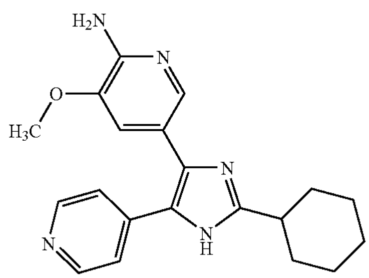 | 0.0020 | 0.55 | 350.1 | B | 5-(2-cyclohexyl-5-(pyridin-4-yl)-1H-imidazol-4-yl)-3-methoxypyridin-2-amine |
| 119 | 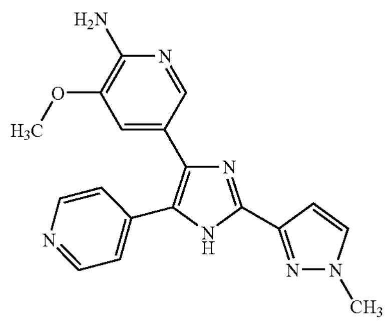 | 0.0019 | 0.33 | 375.9 | B | 3-methoxy-5-(2-(1-methyl-1H-pyrazol-3-yl)-5-(pyridin-4-yl)-1H-imidazol-4-yl)pyridin-2-amine |
| 120 | 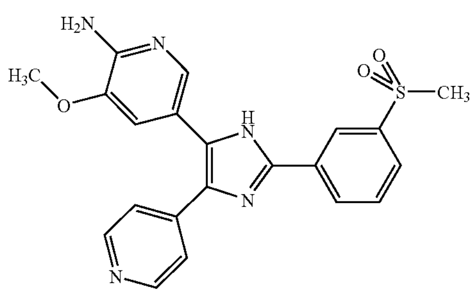 | 0.0088 | 0.44 | 421.9 | B | 3-methoxy-5-(2-(3-(methylsulfonyl)phenyl)-4-(pyridin-4-yl)-1H-imidazol-5-yl)pyridin-2-amine |
| 121 | 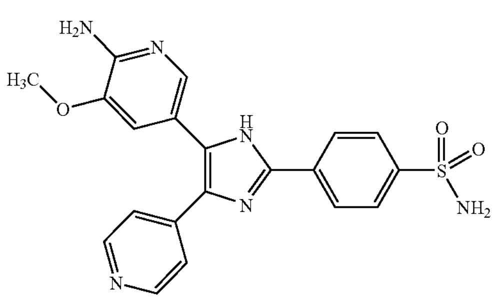 | 0.0017 | 0.39 | 422.9 | B | 4-(5-(6-amino-5-methoxypyridin-3-yl)-4-(pyridin-4-yl)-1H-imidazol-2-yl)benzenesulfonamide |
| 122 | 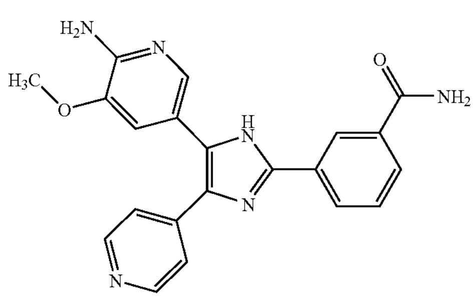 | 0.0021 | 0.38 | 386.9 | B | 3-(5-(6-amino-5-methoxypyridin-3-yl)-4-(pyridin-4-yl)-1H-imidazol-2-yl)benzamide |

TABLE 1-continued

| Compound No. | STRUCTURE | mut-b-RAF (IC50 in uM) | retention time (min) | mass (MH+) | Method | Compound Name |
|---|---|---|---|---|---|---|
| 123 | 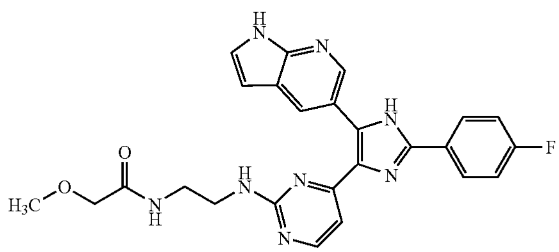 | 0.0013 | 0.61 | 487.1 | C | N-(2-(4-(2-(4-fluorophenyl)-5-(1H-pyrrolo[2,3-b]pyridin-5-yl)-1H-imidazaol-4-yl)pyrimidin-2-ylamino)ethyl)-2-methoxyacetamide |
| 124 | 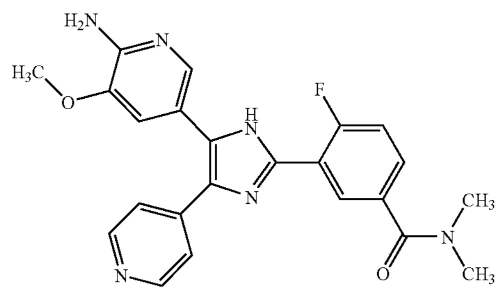 | 0.0166 | 0.43 | 433.0 | B | 3-(5-(6-amino-5-methoxypyridin-3-yl)-4-(pyridin-4-yl)-1H-imidazol-2-yl)-4-fluoro-N,N-dimethylbenzamide |
| 125 | 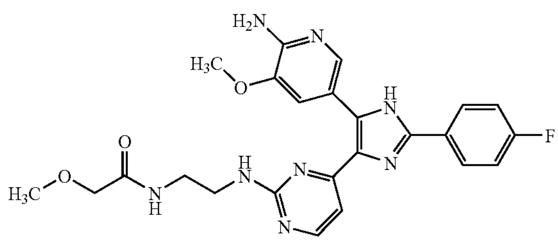 | 0.0005 | 0.60 | 494.0 | C | N-(2-(4-(5-(5-amino-6-methoxypyrazin-2-yl)-2-(4-fluorophenyl)-1H-imidazol-4-yl)pyrimidin-2-ylamino)ethyl)-2-methoxyacetamide |
| 126 | 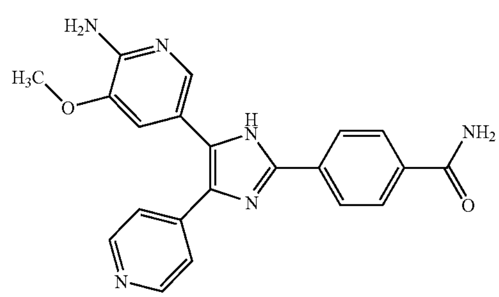 | 0.0035 | 0.35 | 387.0 | B | 4-(5-(6-amino-5-methoxypyridin-3-yl)-4-(pyridin-4-yl)-1H-imidazol-2-yl)benzamide |
| 127 | 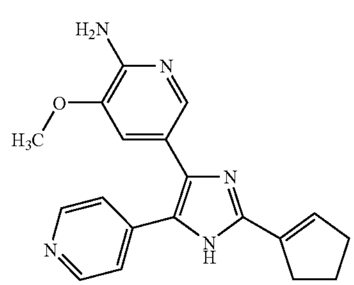 | 0.0018 | 0.44 | 334.0 | B | 5-(2-cyclopentenyl-5-(pyridin-4-yl)-1H-imidazol-4-yl)-3-methoxypyridin-2-amine |

TABLE 1-continued

| Compound No. | STRUCTURE | mut-b-RAF (IC50 in uM) | retention time (min) | mass (MH+) | Method | Compound Name |
|---|---|---|---|---|---|---|
| 128 | 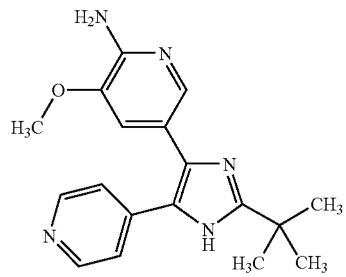 | 0.0010 | 0.38 | 324.2 | B | 5-(2-tert-butyl-5-(pyridin-4-yl)-1H-imidazol-4-yl)-3-methoxypyridin-2-amine |
| 129 | 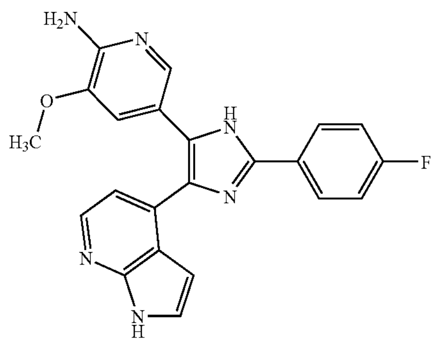 | 0.0088 | 0.55 | 401.0 | B | 5-(2-(4-fluorophenyl)-4-(1H-pyrrolo[2,3-b]pyridin-4-yl)-1H-imidazol-5-yl)-3-methoxypyridin-2-amine |
| 130 | 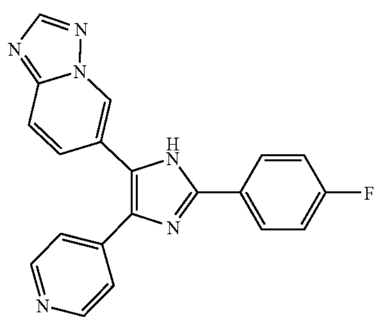 | 0.4160 | 0.54 | 357.2 | A | 6-(2-(4-fluorophenyl)-4-(pyridin-4-yl)-1H-imidazol-5-yl)-[1,2,4]triazolo[1,5-a]pyridine |
| 131 | 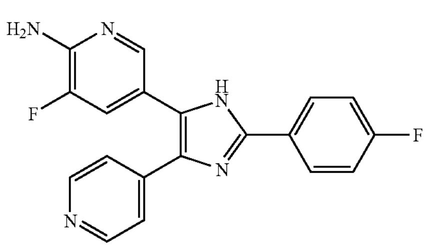 | 0.1740 | 0.52 | 351.0 | A | 3-fluoro-5-(2-(4-fluorophenyl)-4-(pyridin-4-yl)-1H-imidazol-5-yl)pyridin-2-amine |
| 132 | 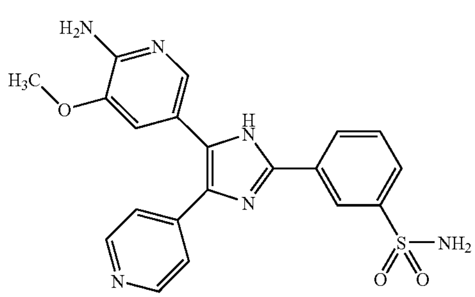 | 0.0010 | 0.39 | 423.1 | B | 3-(5-(6-amino-5-methoxypyridin-3-yl)-4-(pyridin-4-yl)-1H-imidazol-2-yl)benzenesulfonamide |

TABLE 1-continued

| Compound No. | STRUCTURE | mut-b-RAF (IC50 in uM) | retention time (min) | mass (MH+) | Method | Compound Name |
|---|---|---|---|---|---|---|
| 133 | 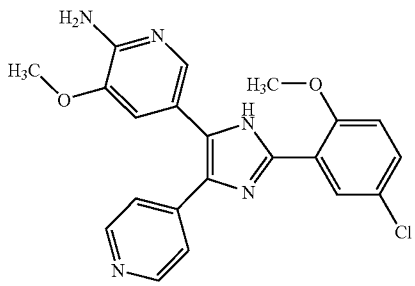 | 0.0005 | 0.60 | 408.1 | B | 5-(2-(5-chloro-2-methoxyphenyl)-4-(pyridin-4-yl)-1H-imidazol-5-yl)-3-methoxypyridin-2-amine |
| 134 | 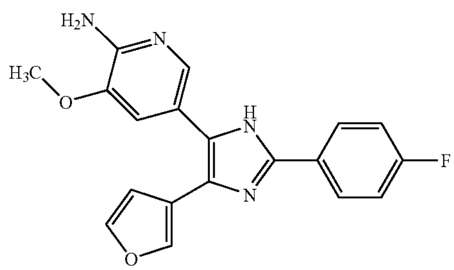 | 0.0014 | 0.50 | 483.2 | B | 5-(2-(4-fluorophenyl)-4-(furan-3-yl)-1H-imidazol-5-yl)-3-methoxypyridin-2-amine |
| 135 | 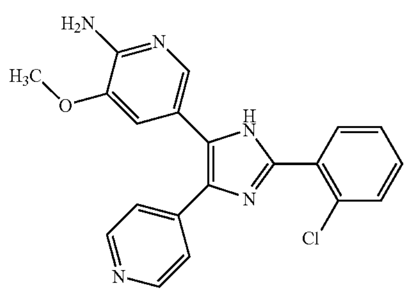 | 0.0004 | 0.45 | 378.0 | B | 5-(2-(2-chlorophenyl)-4-(pyridin-4-yl)-1H-imidazol-5-yl)-3-methoxypyridin-2-amine |
| 136 | 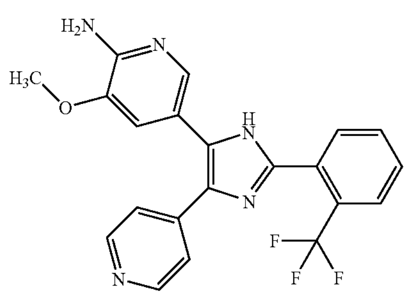 | 0.0028 | 0.48 | 412.0 | B | 3-methoxy-5-(4-(pyridin-4-yl)-2-(2-(trifluoromethyl)phenyl)-1H-imidazol-5-yl)pyridin-2-amine |
| 137 | 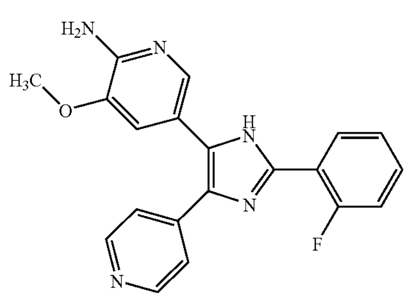 | 0.0017 | 0.44 | 362.2 | B | 5-(2-(2-fluorophenyl)-4-(pyridin-4-yl)-1H-imidazol-5-yl)-3-methoxypyridin-2-amine |

TABLE 1-continued

| Compound No. | STRUCTURE | mut-b-RAF (IC50 in uM) | retention time (min) | mass (MH+) | Method | Compound Name |
|---|---|---|---|---|---|---|
| 138 | 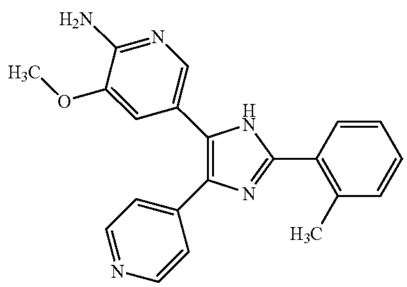 | 0.0012 | 0.45 | 358.0 | B | 3-methoxy-5-(4-(pyridin-4-yl)-2-o-tolyl-1H-imidazol-5-yl)pyridin-2-amine |
| 139 | 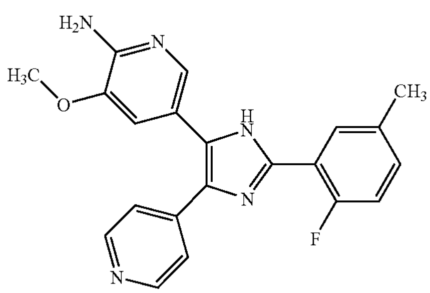 | 0.0012 | 0.50 | 376.0 | B | 5-(2-(2-fluoro-5-methylphenyl)-4-(pyridin-4-yl)-1H-imidazol-5-yl)-3-methoxypyridin-2-amine |
| 140 | 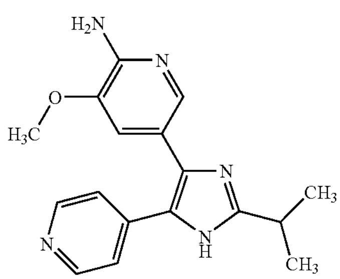 | 0.0016 | 0.33 | 310.2 | B | 5-(2-isopropyl-5-(pyridin-4-yl)-1H-imidazol-4-yl)-3-methoxypyridin-2-amine |
| 141 | 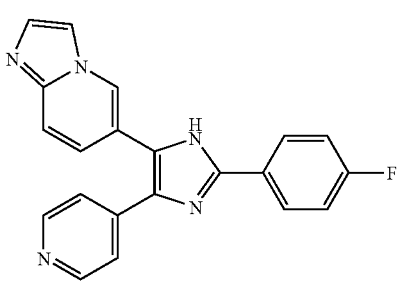 | 0.6180 | 0.49 | 356.2 | B | 6-(2-(4-fluorophenyl)-4-(pyridin-4-yl)-1H-imidazol-5-yl)imidazo[1,2-a]pyridine |
| 142 | 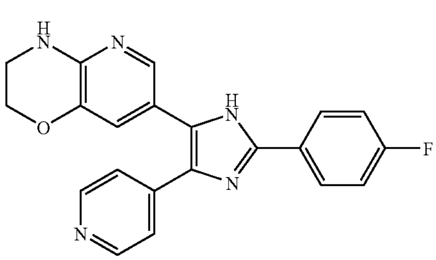 | 0.3820 | 0.52 | 374.2 | B | 7-(2-(4-fluorophenyl)-4-(pyridin-4-yl)-1H-imidazol-5-yl)-3,4-dihydro-2H-pyrido[3,2-b][1,4]oxazine |

TABLE 1-continued

| Compound No. | STRUCTURE | mut-b-RAF (IC50 in uM) | retention time (min) | mass (MH+) | Method | Compound Name |
|---|---|---|---|---|---|---|
| 143 | 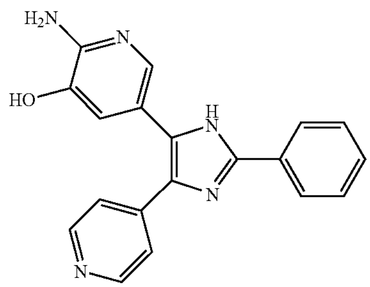 | 0.2151 | 0.42 | 330.0 | B | 2-amino-5-(2-phenyl-4-(pyridin-4-yl)-1H-imidazol-5-yl)pyridin-3-ol |
| 144 | 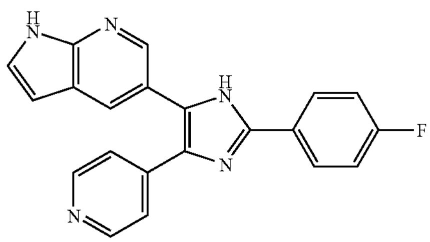 | 0.0030 | 0.56 | 356.1 | B | 5-(2-(4-fluorophenyl)-4-(pyridin-4-yl)-1H-imidazol-5-yl)-1H-pyrrolo[2,3-b]pyridine |
| 145 | 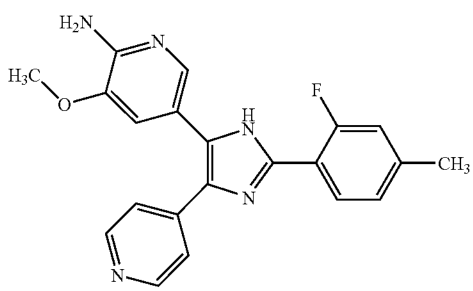 | 0.0009* | 0.49 | 376.0 | B | 5-(2-(2-fluoro-4-methylphenyl)-4-(pyridin-4-yl)-1H-imidazol-5-yl)-3-methoxypyridin-2-amine |
| 146 | 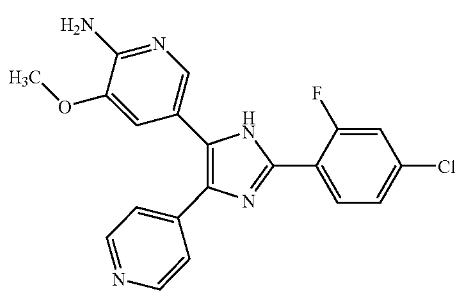 | 0.0023 | 0.54 | 396.1 | B | 5-(2-(4-chloro-2-fluorophenyl)-4-(pyridin-4-yl)-1H-imidazol-5-yl)-3-methoxypyridin-2-amine |
| 147 | 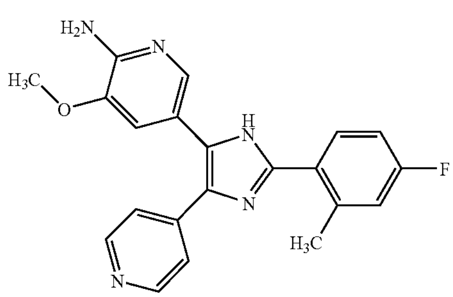 | 0.0016 | 0.49 | 376.0 | B | 5-(2-(4-fluoro-2-methylphenyl)-4-(pyridin-4-yl)-1H-imidazol-5-yl)-3-methoxypyridin-2-amine |

TABLE 1-continued

| Compound No. | STRUCTURE | mut-b-RAF (IC50 in uM) | retention time (min) | mass (MH+) | Method | Compound Name |
|---|---|---|---|---|---|---|
| 148 | 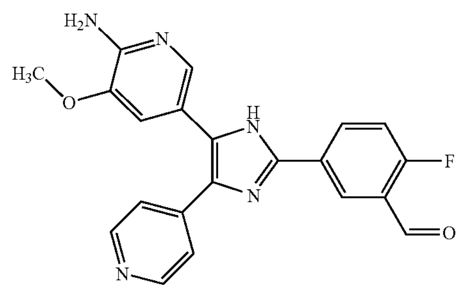 | 0.0015 | 0.46 | 390.0 | B | 5-(5-(6-amino-5-methoxypyridin-3-yl)-4-(pyridin-4-yl)-1H-imidazol-2-yl)-2-fluorobenzaldehyde |
| 149 | 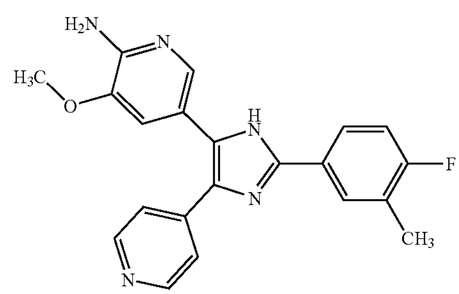 | 0.0006 | 0.54 | 376.0 | B | 5-(2-(4-fluoro-3-methylphenyl)-4-(pyridin-4-yl)-1H-imidazol-5-yl)-3-methoxypyridin-2-amine |
| 150 | 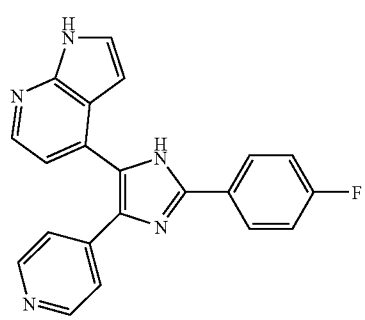 | 0.7751 | 0.53 | 355.9 | B | 4-(2-(4-fluorophenyl)-4-(pyridin-4-yl)-1H-imidazol-5-yl)-1H-pyrrolo[2,3-b]pyridine |
| 151 | 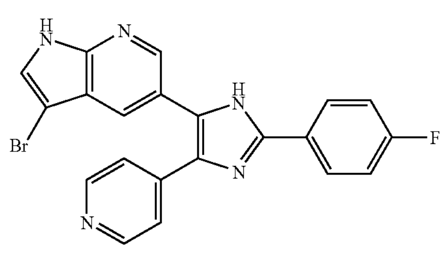 | 0.0007 | 0.71 | 436.1 | B | 3-bromo-5-(2-(4-fluorophenyl)-4-(pyridin-4-yl)-1H-imidazol-5-yl)-1H-pyrrolo[2,3-b]pyridine |
| 152 | 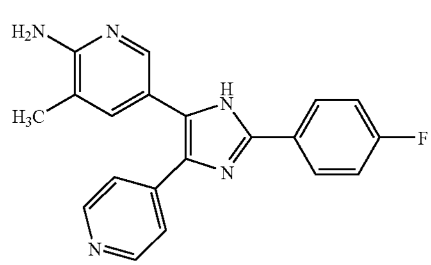 | 0.0658 | 0.51 | 346.1 | B | 5-(2-(4-fluorophenyl)-4-(pyridin-4-yl)-1H-imidazol-5-yl)-3-methylpyridin-2-amine |

TABLE 1-continued

| Compound No. | STRUCTURE | mut-b-RAF (IC50 in uM) | retention time (min) | mass (MH+) | Method | Compound Name |
|---|---|---|---|---|---|---|
| 153 | 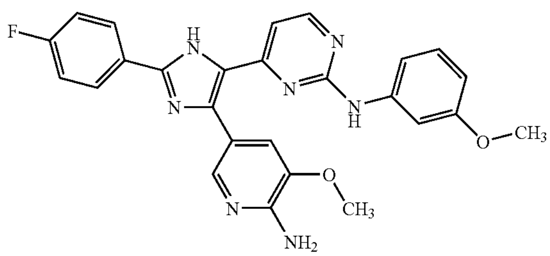 | 0.0002 | 0.63 | 484.1 | B | 4-(4-(6-amino-5-methoxypyridin-3-yl)-2-(4-fluorophenyl)-1H-imidazol-5-yl)-N-(3-methoxyphenyl)pyrimidin-2-amine |
| 154 | 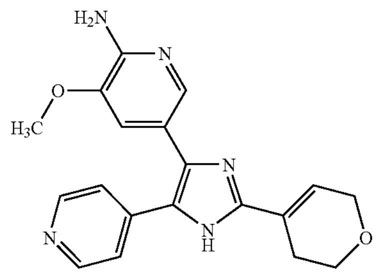 | 0.0033 | 0.36 | 350.2 | B | 5-(2-(3,6-dihydro-2H-pyran-4-yl)-5-(pyridin-4-yl)-1H-imidazol-4-yl)-3-methoxypyridin-2-amine |
| 155 | 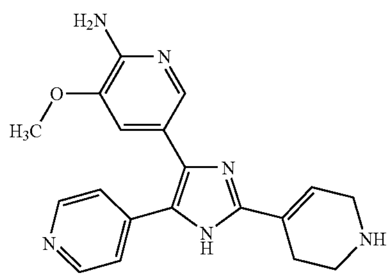 | 0.0162 | 0.23 | 349.2 | B | 3-methoxy-5-(5-(pyridin-4-yl)-2-(1,2,3,6-tetrahydropyridin-4-yl)-1H-imidazol-4-yl)pyridin-2-amine |
| 156 | 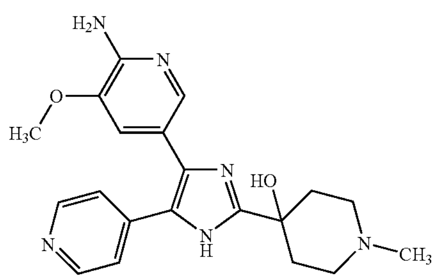 | 0.0093 | 0.24 | 381.2 | B | 4-(4-(6-amino-5-methoxypyridin-3-yl)-5-(pyridin-4-yl)-1H-imidazol-2-yl)-1-methylpiperidin-4-ol |
| 157 | 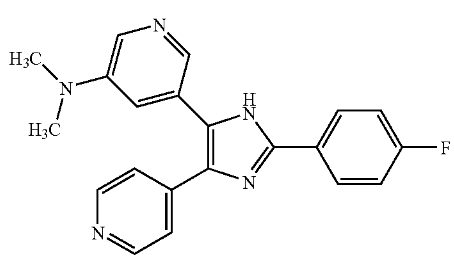 | 0.0170 | 0.52 | 360.1 | B | 5-(2-(4-fluorophenyl)-4-(pyridin-4-yl)-1H-imidazol-5-yl)-N,N-dimethylpyridin-3-amine |

TABLE 1-continued

| Compound No. | STRUCTURE | mut-b-RAF (IC50 in uM) | retention time (min) | mass (MH+) | Method | Compound Name |
|---|---|---|---|---|---|---|
| 158 | 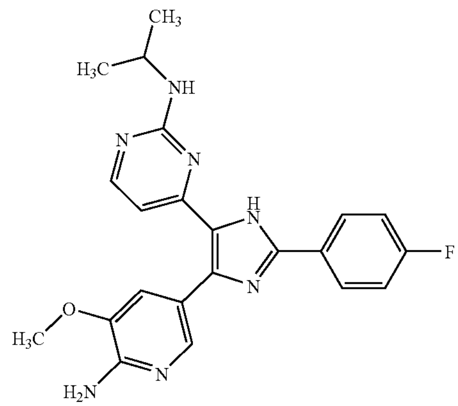 | 0.0051 | 0.58 | 420.0 | C | 4-(4-(6-amino-5-methoxypyridin-3-yl)-2-(4-fluorophenyl)-1H-imidazol-5-yl)-N-isopropylpyrimidin-2-amine |
| 159 | 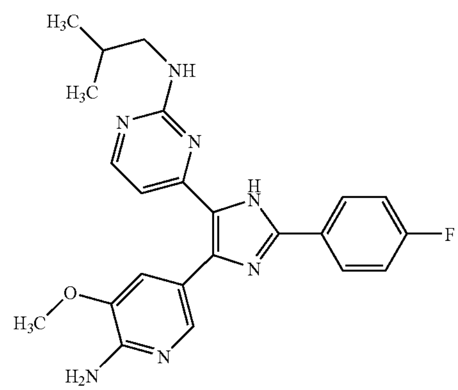 | 0.0015 | 0.62 | 434.0 | C | 4-(4-(6-amino-5-methoxypyridin-3-yl)-2-(4-fluorophenyl)-1H-imidazol-5-yl)-N-isobutylpyrimidin-2-amine |
| 160 | 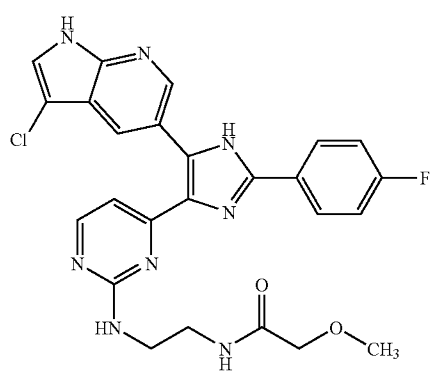 | 0.0003 | 0.70 | 521.1 | C | N-(2-(4-(5-(3-chloro-1H-pyrrolo[2,3-b]pyridin-5-yl)-2-(4-fluorophenyl)-1H-imidazol-4-yl)pyrimidin-2-ylamino)ethyl)-2-methoxyacetamide |
| 161 | 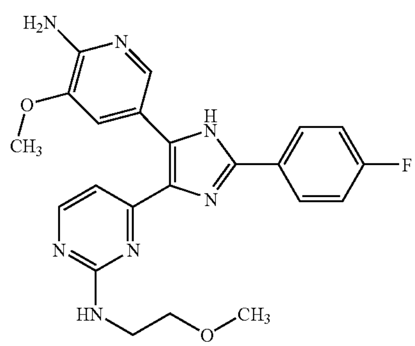 | 0.0022 | 0.55 | 436.1 | C | 4-(5-(6-amino-5-methoxypyridin-3-yl)-2-(4-fluorophenyl)-1H-imidazol-4-yl)-N-(2-methoxyethyl)pyrimidin-2-amine |

TABLE 1-continued

| Compound No. | STRUCTURE | mut-b-RAF (IC50 in uM) | retention time (min) | mass (MH+) | Method | Compound Name |
|---|---|---|---|---|---|---|
| 162 | 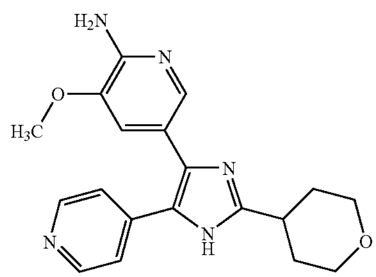 | 0.0055 | 0.32 | 352.2 | B | 3-methoxy-5-(5-(pyridin-4-yl)-2-(tetrahydro-2H-pyran-4-yl)-1H-imidazol-4-yl)pyridin-2-amine |
| 163 | Chiral | 0.0001 | 0.56 | 507.1 | C | (S)-N-(1-(4-(4-(6-amino-5-methoxypyridin-3-yl)-2-(4-fluorophenyl)-1H-imidazol-5-yl)pyrimidin-2-ylamino)propan-2-yl)-2-methoxyacetamide |
| 164 | 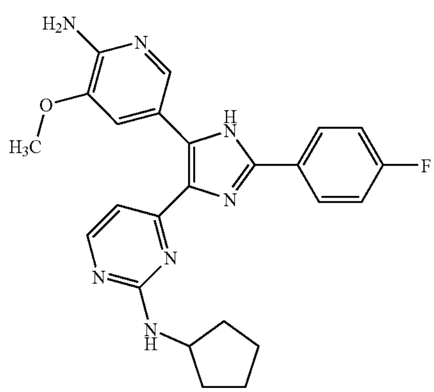 | 0.0163 | 0.63 | 446.1 | C | 4-(5-(6-amino-5-methoxypyridin-3-yl)-2-(4-fluorophenyl)-1H-imidazol-4-yl)-N-cyclopentylpyrimidin-2-amine |
| 165 | 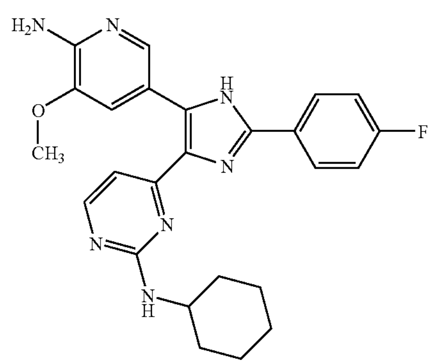 | 0.0483 | 0.69 | 460.1 | C | 4-(5-(6-amino-5-methoxypyridin-3-yl)-2-(4-fluorophenyl)-1H-imidazol-4-yl)-N-cyclohexylpyrimidin-2-amine |

TABLE 1-continued

| Compound No. | STRUCTURE | mut-b-RAF (IC50 in uM) | retention time (min) | mass (MH+) | Method | Compound Name |
|---|---|---|---|---|---|---|
| 166 | 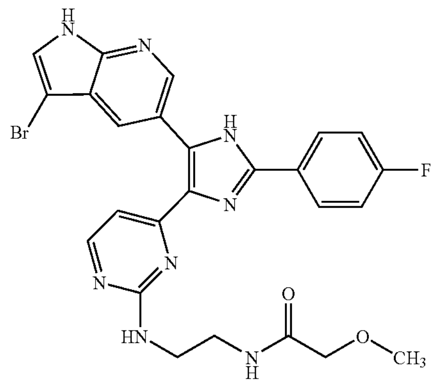 | 0.0001 | 0.71 | 567.0 | C | N-(2-(4-(5-(3-bromo-1H-pyrrolo[2,3-b]pyridin-5-yl)-2-(4-fluorophenyl)-1H-imidazol-4-yl)pyrimidin-2-ylamino)ethyl)-2-methoxyacetamide |
| 167 | 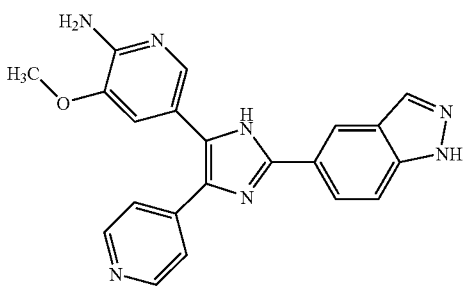 | 0.0007 | 0.37 | 384.0 | B | 5-(2-(1H-indazol-5-yl)-4-(pyridin-4-yl)-1H-imidazol-5-yl)-3-methoxypyridin-2-amine |
| 168 | 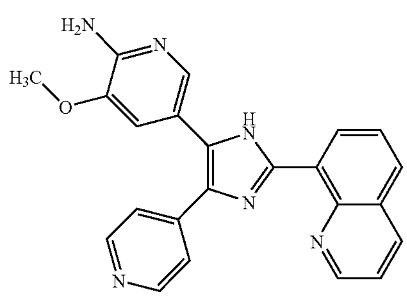 | 0.0009 | 0.41 | 395.1 | B | 3-methoxy-5-(4-(pyridin-4-yl)-2-quinolin-8-yl)-1H-imidazol-5-yl)pyridin-2-amine |
| 169 | 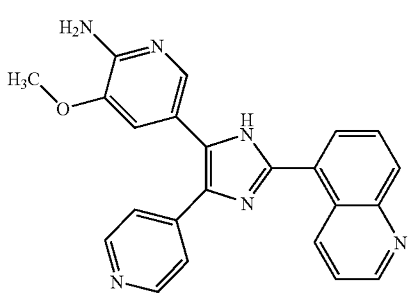 | 0.0016 | 0.32 | 395.0 | B | 3-methoxy-5-(4-(pyridin-4-yl)-2-(quinolin-5-yl)-1H-imidazol-5-yl)pyridin-2-amine |

TABLE 1-continued

| Compound No. | STRUCTURE | mut-b-RAF (IC50 in uM) | retention time (min) | mass (MH+) | Method | Compound Name |
|---|---|---|---|---|---|---|
| 170 | 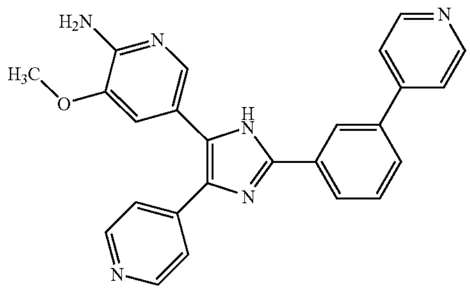 | 0.0002 | 0.38 | 421.1 | B | 3-methoxy-5-(4-(pyridin-4-yl)-2-(3-(pyridin-4-yl)phenyl)-1H-imidazol-5-yl)pyridin-2-amine |
| 171 | 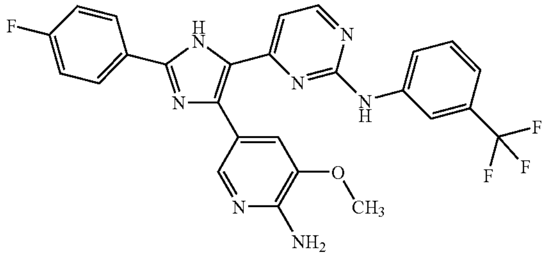 | 0.0013 | 0.76 | 522.1 | D | 4-(4-(6-amino-5-methoxypyridin-3-yl)-2-(4-fluorophenyl)-1H-imidazol-5-yl)-N-(3-(trifluoromethyl)phenyl)pyrimidin-2-amine |
| 172 | 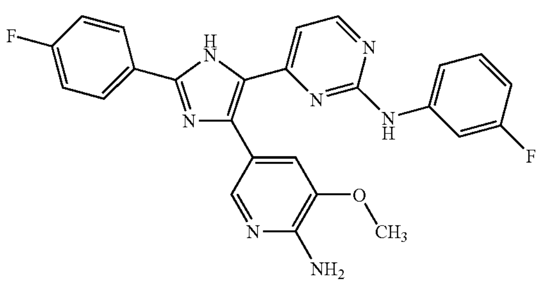 | 0.0014 | 0.67 | 472.1 | D | 4-(4-(6-amino-5-methoxypyridin-3-yl)-2-(4-fluorophenyl)-1H-imidazol-5-yl)-N-(3-fluorophenyl)pyrimidin-2-amine |
| 173 | 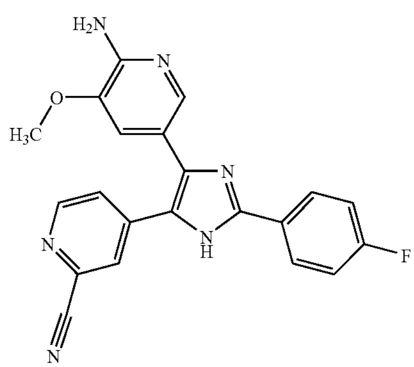 | 0.1970 | 0.63 | 387.0 | B | 4-(4-(6-amino-5-methoxypyridin-3-yl)-2-(4-fluorophenyl)-1H-imidazol-5-yl)picolinonitrile |
| 174 | 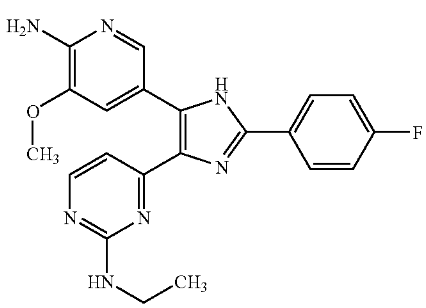 | 0.0023 | 0.53 | 406.0 | C | 4-(5-(6-amino-5-methoxypyridin-3-yl)-2-(4-fluorophenyl)-1H-imidazol-4-yl)-N-ethylpyrimidin-2-amine |

TABLE 1-continued

| Compound No. | STRUCTURE | mut-b-RAF (IC50 in uM) | retention time (min) | mass (MH+) | Method | Compound Name |
|---|---|---|---|---|---|---|
| 175 | 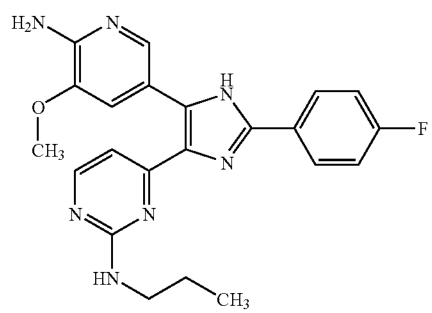 | 0.0012 | 0.56 | 420.0 | C | 4-(5-(6-amino-5-methoxypyridin-3-yl)-2-(4-fluorophenyl)-1H-imidazol-4-yl)-N-propylpyrimidin-2-amine |
| 176 | Chiral | 0.0046 | 0.58 | 434.0 | C | (S)-4-(5-(6-amino-5-methoxypyridin-3-yl)-2-(4-fluorophenyl)-1H-imidazol-4-yl)-N-sec-butylpyrimidin-2-amine |
| 177 | 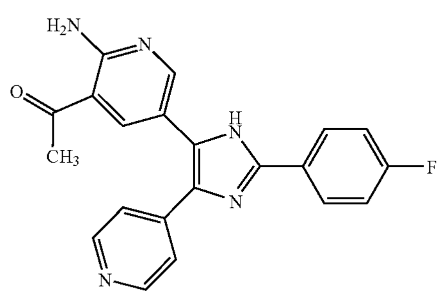 | 0.0030 | 0.51 | 374.1 | B | 1-(2-amino-5-(2-(4-fluorophenyl)-4-(pyridin-4-yl)-1H-imidazol-5-yl)pyridin-3-yl)ethanone |
| 178 | 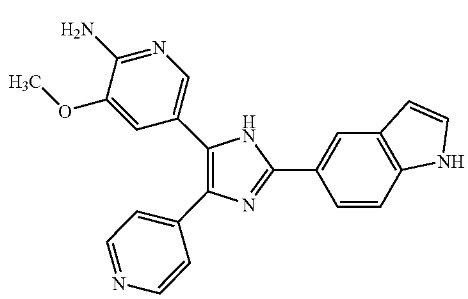 | 0.0009 | 0.40 | 383.2 | E | 5-(2-(1H-indol-5-yl)-4-(pyridin-4-yl)-1H-imidazol-5-yl)-3-methoxypyridin-2-amine |

TABLE 1-continued

| Compound No. | STRUCTURE | mut-b-RAF (IC50 in uM) | retention time (min) | mass (MH+) | Method | Compound Name |
|---|---|---|---|---|---|---|
| 179 | 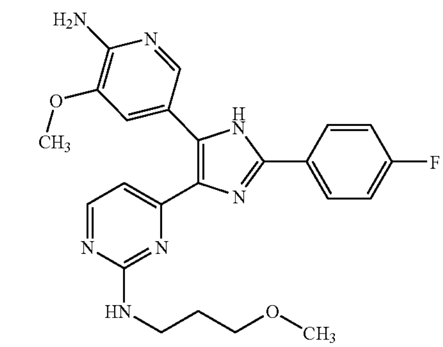 | 0.0010 | 0.56 | 450.1 | B | 4-(5-(6-amino-5-methoxypyridin-3-yl)-2-(4-fluorophenyl)-1H-imidazol-4-yl)-N-(3-methoxypropyl)pyrimidin-2-amine |
| 180 | 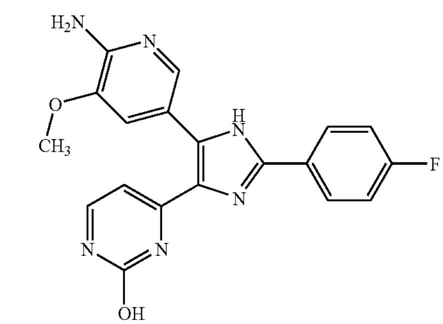 | 0.8916 | 0.48 | 378.9 | B | 4-(5-(6-amino-5-methoxypyridin-3-yl)-2-(4-fluorophenyl)-1H-imidazol-4-yl)pyrimidin-2-ol |
| 181 | Chiral | 0.0099 | 0.57 | 434.2 | C | (R)-4-(5-(6-amino-5-methoxypyridin-3-yl)-2-(4-fluorophenyl)-1H-imidazol-4-yl)-N-sec-butylpyrimidin-2-amine |
| 182 | 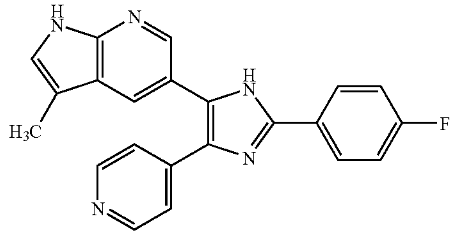 | 0.0002 | 0.59 | 370.0 | B | 5-(2-(4-fluorophenyl)-4-(pyridin-4-yl)-1H-imidazol-5-yl)-3-methyl-1H-pyrrolo[2,3-b]pyridine |

TABLE 1-continued

| Compound No. | STRUCTURE | mut-b-RAF (IC50 in uM) | retention time (min) | mass (MH+) | Method | Compound Name |
|---|---|---|---|---|---|---|
| 183 | 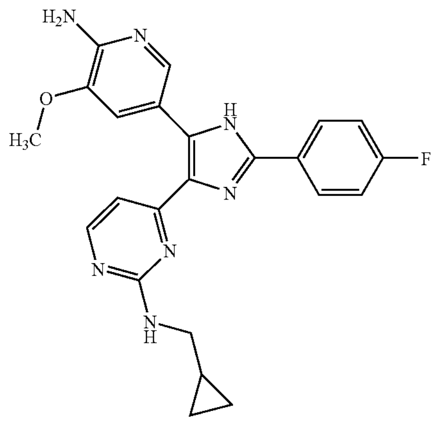 | 0.0007 | 0.56 | 432.0 | C | 4-(5-(6-amino-5-methoxypyridin-3-yl)-2-(4-fluorophenyl)-1H-imidazol-4-yl)-N-(cyclopropylmethyl)pyrimidin-2-amine |
| 184 | Chiral | 0.0003 | 0.46 | 530.2 | D | 4-(4-(6-amino-5-methoxypyridin-3-yl)-2-tert-butyl-1H-imidazol-5-yl)-N-(6-((2R,6S)-2,6-dimethylmorpholino)-pyridin-3-yl)pyrimidin-2-amine |
| 185 | Chiral | 0.0032 | 0.41 | 451.1 | D | (R)-1-(3-(4-(4-(6-amino-5-methoxypyridin-3-yl)-2-tert-butyl-1H-imidazol-5-yl)pyrimidin-2-ylamino)pyrrolidin-1-yl)ethanone |

TABLE 1-continued

| Compound No. | STRUCTURE | | mut-b-RAF (IC50 in uM) | retention time (min) | mass (MH+) | Method | Compound Name |
|---|---|---|---|---|---|---|---|
| 186 | 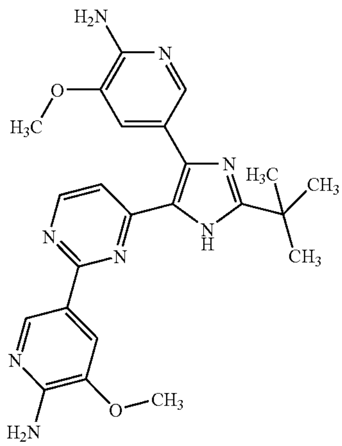 | Chiral | 0.0299 | 0.41 | 447.1 | D | 5-(4-(4-(6-amino-5-methoxypyridin-3-yl)-2-tert-butyl-1H-imidazol-5-yl)pyrimidin-2-yl)-3-methoxypyridin-2-amine |
| 187 | 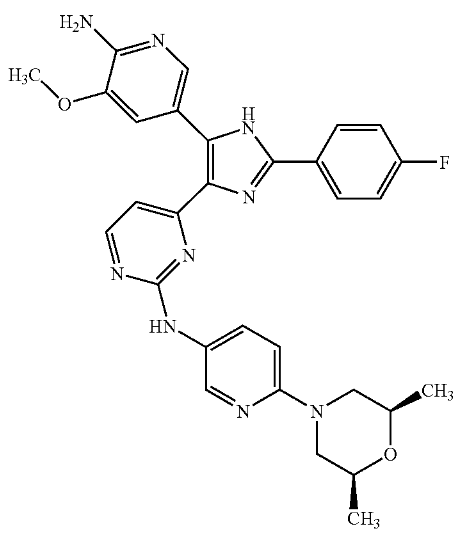 | Chiral | 0.0005 | 0.58 | 568.2 | D | 4-(5-(6-amino-5-methoxypyridin-3-yl)-2-(4-fluorophenyl)-1H-imidazol-4-yl)-N-(6-((2S,6R)-2,6-dimethylmorpholino)-pyridin-3-yl)pyrimidin-2-amine |
| 189 | 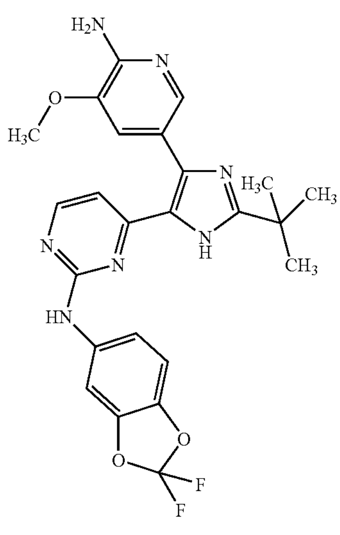 | | 0.0003 | 0.62 | 496.1 | D | 4-(4-(6-amino-5-methoxypyridin-3-yl)-2-tert-butyl-1H-imidazol-5-yl)-N-(2,2-difluorobenzo[d][1,3]dioxol-5-yl)pyrimidin-2-amine |

TABLE 1-continued

| Compound No. | STRUCTURE | mut-b-RAF (IC50 in uM) | retention time (min) | mass (MH+) | Method | Compound Name |
|---|---|---|---|---|---|---|
| 190 | 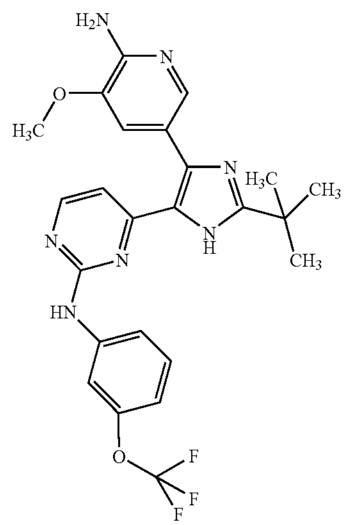 | 0.0003 | 0.65 | 500.2 | D | 4-(4-(6-amino-5-methoxypyridin-3-yl)-2-tert-butyl-1H-imidazol-5-yl)-N-(3-(trifluoromethoxy)phenyl)pyrimidin-2-amine |
| 191 | 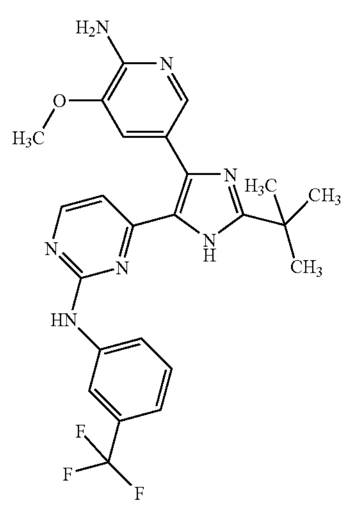 | 0.0004 | 0.63 | 484.1 | D | 4-(4-(6-amino-5-methoxypyridin-3-yl)-2-tert-butyl-1H-imidazol-5-yl)-N-(3-(trifluoromethyl)phenyl)pyrimidin-2-amine |

| Compound No. | STRUCTURE | mut-b-RAF (IC50 in uM) | retention time (min) | mass (MH+) | Method | Compound Name |
|---|---|---|---|---|---|---|
| 192 | 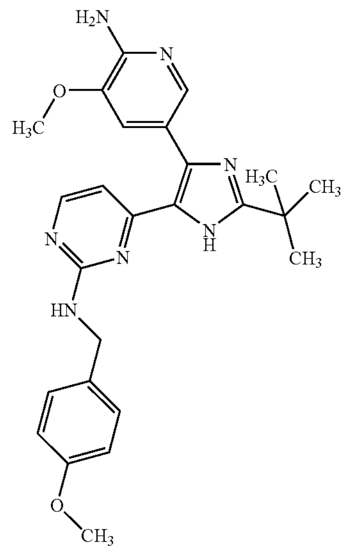 | 0.0002 | 0.54 | 460.2 | D | 4-(4-(6-amino-5-methoxypyridin-3-yl)-2-tert-butyl-1H-imidazol-5-yl)-N-(4-methoxybenzyl)pyrimidin-2-amine |
| 193 | 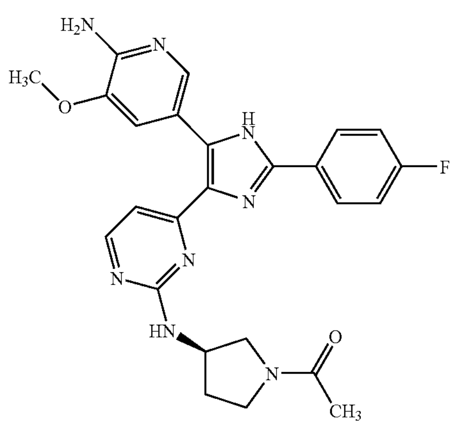 | Chiral 0.0380 | 0.51 | 489.1 | D | (R)-1-(3-(4-(5-(6-amino-5-methoxypyridin-3-yl)-2-(4-fluorophenyl)-1H-imidazol-4-yl)pyrimidin-2-ylamino)pyrrolidin-1-yl)ethanone |
| 194 | 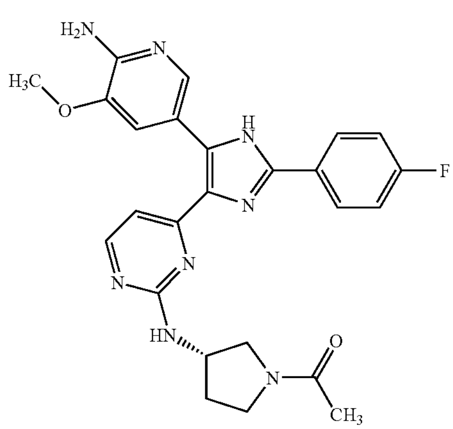 | Chiral 0.0080 | 0.51 | 489.1 | D | (S)-1-(3-(4-(5-(6-amino-5-methoxypyridin-3-yl)-2-(4-fluorophenyl)-1H-imidazol-4-yl)pyrimidin-2-ylamino)pyrrolidin-1-yl)ethanone |

TABLE 1-continued

| Compound No. | STRUCTURE | mut-b-RAF (IC50 in uM) | retention time (min) | mass (MH+) | Method | Compound Name |
|---|---|---|---|---|---|---|
| 195 | 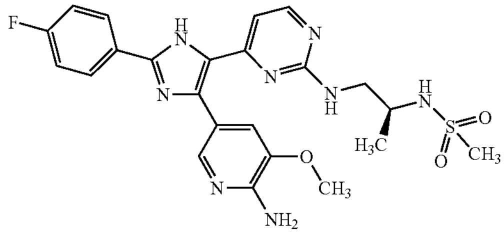 | Chiral 0.0001 | 0.52 | 513.1 | C | (S)-N-(1-(4-(4-(6-amino-5-methoxypyridin-3-yl)-2-(4-fluorophenyl)-1H-imidazol-5-yl)pyrimidin-2-ylamino)propan-2-yl)methanesulfonamide |
| 196 | 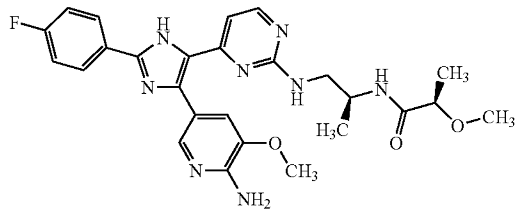 | Chiral 0.0002 | 0.57 | 521.9 | C | (R)-N-((S)-1-(4-(4-(6-amino-5-methoxypyridin-3-yl)-2-(4-fluorophenyl)-1H-imidazol-5-yl)pyrimidin-2-ylamino)propan-2-yl)-2-methoxypropanamide |
| 197 | 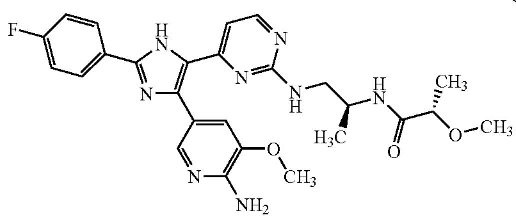 | Chiral 0.0001 | 0.57 | 521.2 | C | (S)-N-((S)-1-(4-(4-(6-amino-5-methoxypyridin-3-yl)-2-(4-fluorophenyl)-1H-imidazol-5-yl)pyrimidin-2-ylamino)propan-2-yl)-2-methoxypropanamide |
| 198 | 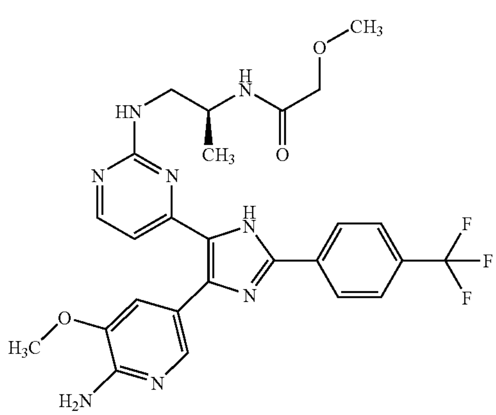 | Chiral 0.0003 | 0.;64 | 557.2 | C | (S)-N-(1-(4-(4-(6-amino-5-methoxypyridin-3-yl)-2-(4-(trifluoromethyl)phenyl)-1H-imidazol-5-yl)pyrimidin-2-ylamino)propan-2-yl)-2-methoxyacetamide |

TABLE 1-continued

| Compound No. | STRUCTURE | mut-b-RAF (IC50 in uM) | retention time (min) | mass (MH+) | Method | Compound Name |
|---|---|---|---|---|---|---|
| 199 | 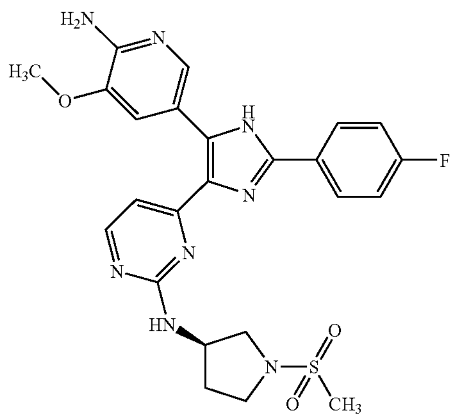 | Chiral 0.0150 | 0.55 | 525.1 | C | (R)-4-(5-(6-amino-5-methoxypyridin-3-yl)-2-(4-fluorophenyl)-1H-imidazol-4-yl)-N-(1-(methylsulfonyl)pyrrolidin-3-yl)pyrimidin-2-amine |
| 200 | 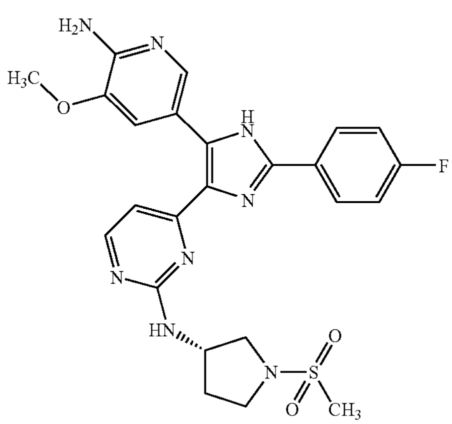 | Chiral 0.0040 | 0.55 | 525.1 | C | (S)-4-(5-(6-amino-5-methoxypyridin-3-yl)-2-(4-fluorophenyl)-1H-imidazol-4-yl)-N-(1-(methylsulfonyl)pyrrolidin-3-yl)pyrimidin-2-amine |
| 201 | 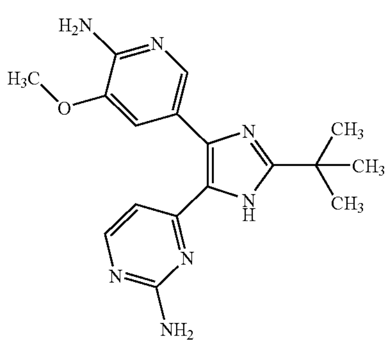 | 0.0005 | 0.36 | 340.1 | C | 4-(4-(6-amino-5-methoxypyridin-3-yl)-2-tert-butyl-1H-imidazol-5-yl)pyrimidin-2-amine |

TABLE 1-continued

| Compound No. | STRUCTURE | mut-b-RAF (IC50 in uM) | retention time (min) | mass (MH+) | Method | Compound Name |
|---|---|---|---|---|---|---|
| 202 | 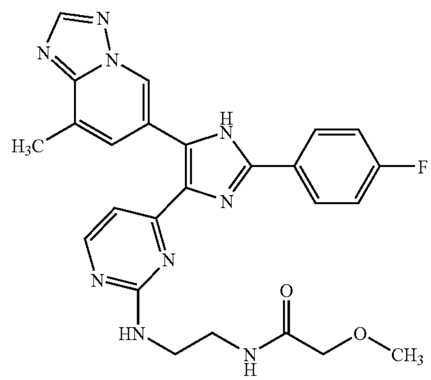 | 0.0250 | 0.62 | 502.1 | C | N-(2-(4-(2-(4-fluorophenyl)-5-(8-methyl-[1,2,4]triazolo[1,5-a]pyridin-6-yl)-1H-imidazol-4-yl)pyrimidin-2-ylamino)ethyl)-2-methoxyacetamide |
| 203 | Chiral | 0.0035 | 0.44 | 487.1 | C | (R)-4-(4-(6-amino-5-methoxypyridin-3-yl)-2-tert-butyl-1H-imidazol-5-yl)-N-(1-(methylsulfonyl)pyrrolidin-3-yl)pyrimidin-2-amine |
| 204 | Chiral | 0.0008 | 0.46 | 469.2 | C | (S)-N-(2-(4-(5-(6-amino-5-methoxypyridin-3-yl)-2-tert-butyl-1H-imidazol-4-yl)pyrimidin-2-ylamino)propyl)-2-methoxyacetamide |

TABLE 1-continued

| Compound No. | STRUCTURE | mut-b-RAF (IC50 in uM) | retention time (min) | mass (MH+) | Method | Compound Name |
|---|---|---|---|---|---|---|
| 205 | Chiral | 0.0004 | 0.45 | 469.3 | C | (S)-N-(1-(4-(4-(6-amino-5-methoxypyridin-3-yl)-2-tert-butyl-1H-imidazol-5-yl)pyrimidin-2-ylamino)propan-2-yl)-2-methoxyacetamide |
| 206 | Chiral | 0.0003 | 0.53 | 493.1 | C | (S)-N-(1-(4-(4-(6-amino-5-methoxypyridin-3-yl)-2-tert-butyl-1H-imidazol-5-yl)pyrimidin-2-ylamino)propan-2-yl)-2,2,2-trifluoroacetamide |
| 207 | Chiral | 0.0158 | 0.50 | 483.2 | C | (S)-N-((S)-2-(4-(5-(6-amino-5-methoxypyridin-3-yl)-2-tert-butyl-1H-imidazol-4-yl)pyrimidin-2-ylamino)propyl)-2-methoxypropanamide |

TABLE 1-continued

| Compound No. | STRUCTURE | mut-b-RAF (IC50 in uM) | retention time (min) | mass (MH+) | Method | Compound Name |
|---|---|---|---|---|---|---|
| 208 | 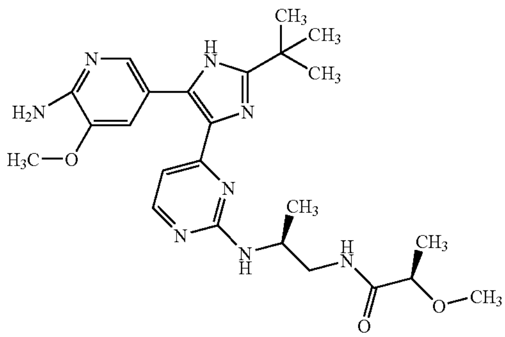 | Chiral 0.0014 | 0.50 | 483.0 | C | (R)-N-((S)-2-(4-(5-(6-amino-5-methoxypyridin-3-yl)-2-tert-butyl-1H-imidazol-4-yl)pyrimidin-2-ylamino)propyl)-2-methoxypropanamide |
| 209 | 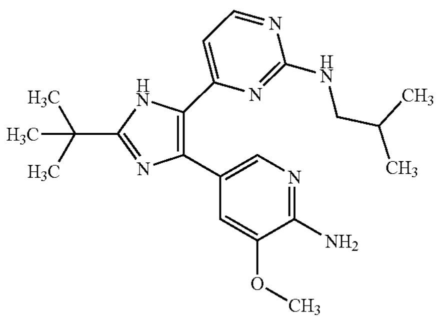 | 0.0001 | 0.50 | 396.3 | C | 4-(4-(6-amino-5-methoxypyridin-3-yl)-2-tert-butyl-1H-imidazol-5-yl)-N-isobutylpyrimidin-2-amine |
| 210 | 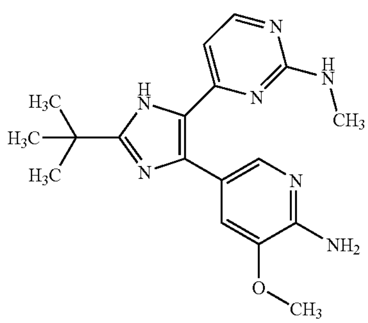 | 0.0001 | 0.40 | 354.2 | C | 4-(4-(6-amino-5-methoxypyridin-3-yl)-2-tert-butyl-1H-imidazol-5-yl)-N-methylpyrimidin-2-amine |
| 211 | 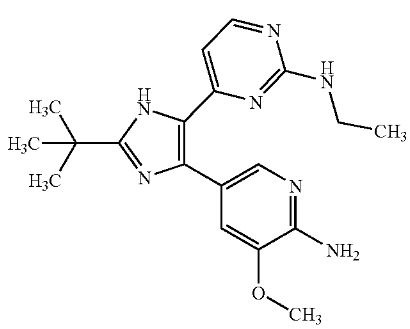 | 0.0001 | 0.43 | 368.3 | C | 4-(4-(6-amino-5-methoxypyridin-3-yl)-2-tert-butyl-1H-imidazol-5-yl)-N-ethylpyrimidin-2-amine |

TABLE 1-continued

| Compound No. | STRUCTURE | mut-b-RAF (IC50 in uM) | retention time (min) | mass (MH+) | Method | Compound Name |
|---|---|---|---|---|---|---|
| 212 | 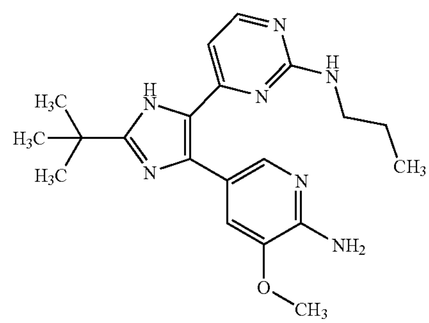 | 0.0001 | 0.47 | 382.3 | C | 4-(4-(6-amino-5-methoxypyridin-3-yl)-2-tert-butyl-1H-imidazol-5-yl)-N-propylpyrimidin-2-amine |
| 213 | 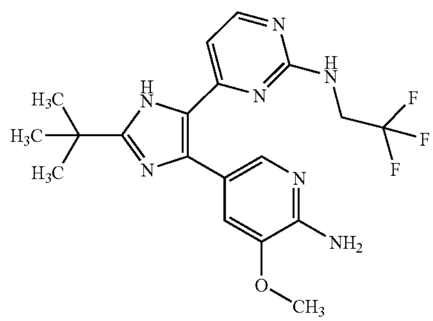 | 0.0001 | 0.49 | 422.2 | C | 4-(4-(6-amino-5-methoxypyridin-3-yl)-2-tert-butyl-1H-imidazol-5-yl)-N-(2,2,2-trifluoroethyl)pyrimidin-2-amine |
| 214 | 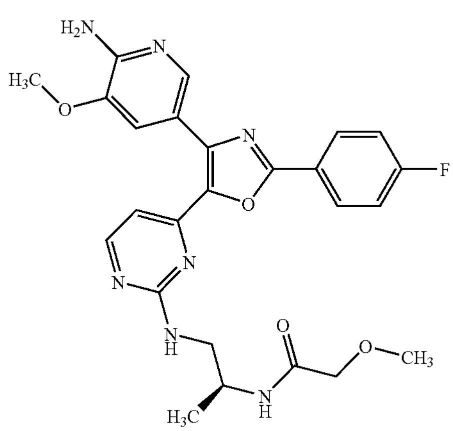 | Chiral 0.0010 | 0.67 | 508.2 | F | (S)-N-(1-(4-(4-(6-amino-5-methoxypyridin-3-yl)-2-(4-fluorophenyl)oxazol-5-yl)pyrimidin-2-ylamino)propan-2-yl)-2-methoxyacetamide |
| 215 | 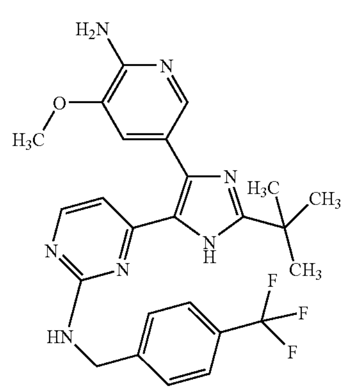 | 0.0005 | 0.63 | 498.1 | C | 4-(4-(6-amino-5-methoxypyridin-3-yl)-2-tert-butyl-1H-imidazol-5-yl)-N-(4-(trifluoromethyl)benzyl)-pyrimidin-2-amine |

TABLE 1-continued

| Compound No. | STRUCTURE | mut-b-RAF (IC50 in uM) | retention time (min) | mass (MH+) | Method | Compound Name |
|---|---|---|---|---|---|---|
| 216 | 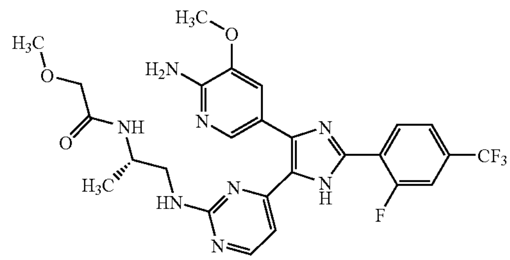 | Chiral 0.0002 | 0.65 | 575.2 | C | (S)-N-(1-(4-(6-(6-amino-5-methoxypyridin-3-yl)-2-(2-fluoro-4-(trifluoromethyl)phenyl)-1H-imidazol-5-yl)pyrimidin-2-ylamino)propan-2-yl)-2-methoxyacetamide |
| 217 | 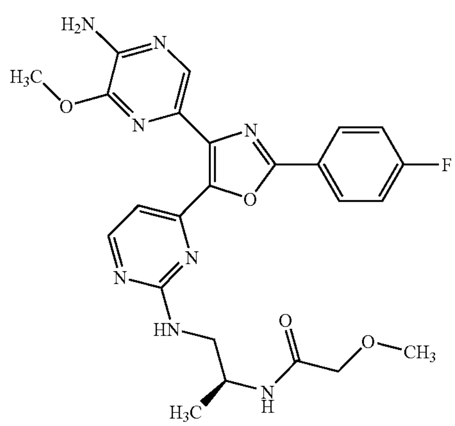 | Chiral 0.0020 | 0.67 | 509.3 | F | (S)-N-(1-(4-(4-(5-amino-6-methoxypyrazin-2-yl)-2-(4-fluorophenyl)oxazol-5-yl)pyrimidin-2-ylamino)propan-2-yl)-2-methoxyacetamide |
| 218 | 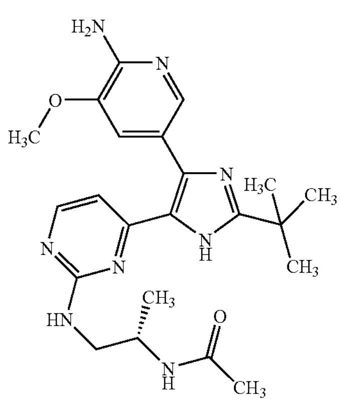 | Chiral 0.0003 | 0.43 | 439.2 | C | (S)-N-(1-(4-(4-(6-amino-5-methoxypyridin-3-yl)-2-tert-butyl-1H-imidazol-5-yl)pyrimidin-2-ylamino)propan-2-yl)acetamide |

TABLE 1-continued

| Compound No. | STRUCTURE | mut-b-RAF (IC50 in uM) | retention time (min) | mass (MH+) | Method | Compound Name |
|---|---|---|---|---|---|---|
| 219 | Chiral | 0.0003 | 0.41 | 454.2 | C | (S)-1-(1-(4-(4-(6-amino-5-methoxypyridin-3-yl)-2-tert-butyl-1H-imidazol-5-yl)pyrimidin-2-ylamino)propan-2-yl)-3-methylurea |
| 220 | 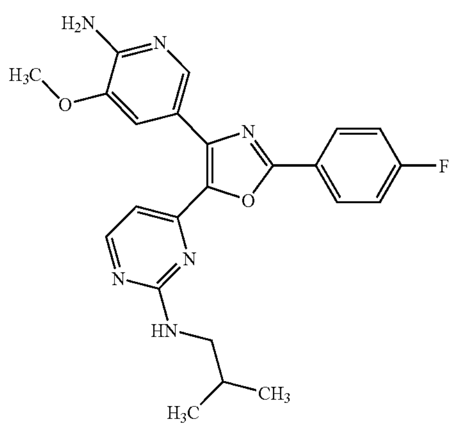 | 0.0020 | 0.69 | 435.1 | F | 4-(4-(6-amino-5-methoxypyridin-3-yl)-2-(4-fluorophenyl)oxazol-5-yl)-N-isobutylpyrimidin-2-amine |
| 221 | 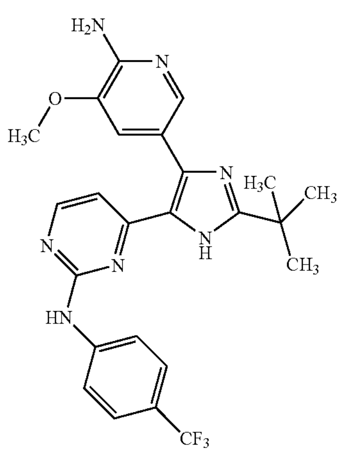 | 0.0002 | 0.70 | 484.1 | D | 4-(4-(6-amino-5-methoxypyridin-3-yl)-2-tert-butyl-1H-imidazol-5-yl)-N-(4-(trifluoromethyl)phenyl)-pyrimidin-2-amine |

TABLE 1-continued

| Compound No. | STRUCTURE | mut-b-RAF (IC50 in uM) | retention time (min) | mass (MH+) | Method | Compound Name |
|---|---|---|---|---|---|---|
| 222 | 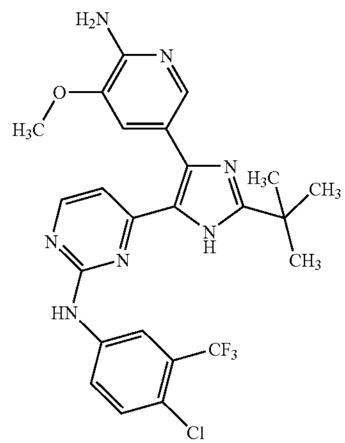 | 0.0002 | 0.76 | 518.1 | D | 4-(4-(6-amino-5-methoxypyridin-3-yl)-2-tert-butyl-1H-imidazol-5-yl)-N-(4-chloro-3-(trifluoromethyl)phenyl)pyrimidin-2-amine |
| 223 | 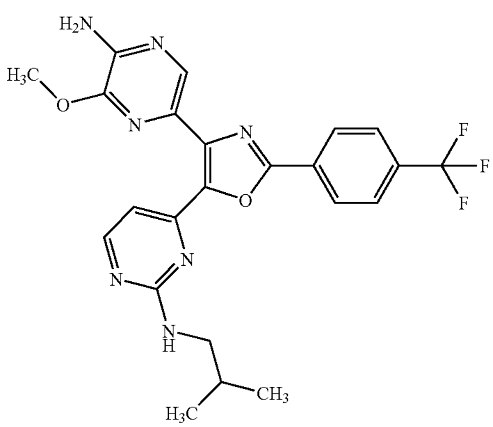 | 0.0110 | 0.89 | 486.2 | F | 4-(4-(5-amino-6-methoxypyrazin-2-yl)-2-(4-(trifluoromethyl)phenyl)oxazol-5-yl)-N-isobutylpyrimidin-2-amine |
| 224 | 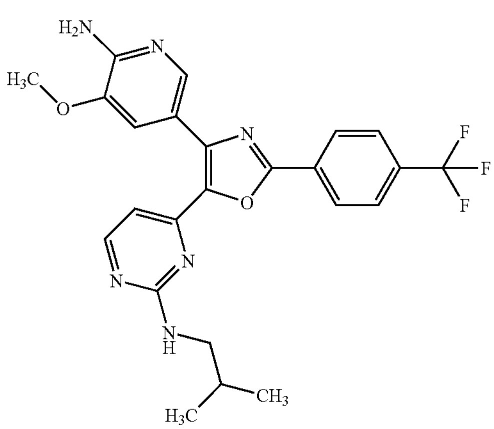 | 0.0140 | 0.81 | 485.2 | F | 4-(4-(6-amino-5-methoxypyridin-3-yl)-2-(4-(trifluoromethyl)phenyl)oxazol-5-yl)-N-isobutylpyrimidin-2-amine |

TABLE 1-continued

| Compound No. | STRUCTURE | mut-b-RAF (IC50 in uM) | retention time (min) | mass (MH+) | Method | Compound Name |
|---|---|---|---|---|---|---|
| 225 | 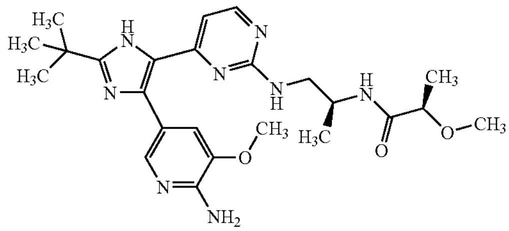 | Chiral 0.0013 | 0.45 | 483.2 | C | (R)-N-((S)-1-(4-(4-(6-amino-5-methoxypyridin-3-yl)-2-tert-butyl-1H-imidazol-5-yl)pyrimidin-2-ylamino)propan-2-yl)-2-methoxypropanamide |
| 226 | 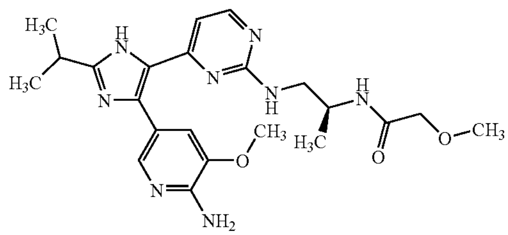 | Chiral 0.0003 | 0.40 | 455.2 | C | (S)-N-(1-(4-(4-(6-amino-5-methoxypyridin-3-yl)-2-isopropyl-1H-imidazol-5-yl)pyrimidin-2-ylamino)propan-2-yl)-2-methoxyacetamide |
| 227 | 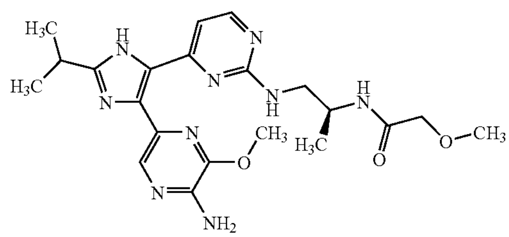 | Chiral 0.0003 | 0.45 | 456.2 | C | (S)-N-(1-(4-(4-(5-amino-6-methoxypyrazin-2-yl)-2-isopropyl-1H-imidazol-5-yl)pyrimidin-2-ylamino)propan-2-yl)-2-methoxyacetamide |
| 228 | 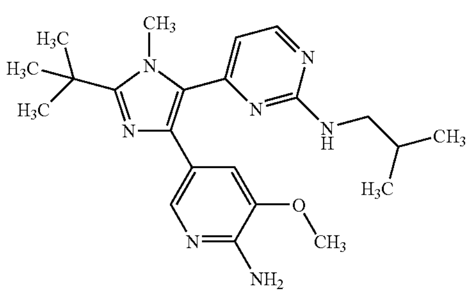 | 0.0006 | 0.55 | 410.4 | C | 4-(4-(6-amino-5-methoxypyridin-3-yl)-2-tert-butyl-1-methyl-1H-imidazol-5-yl)-N-isobutylpyrimidin-2-amine |
| 229 | 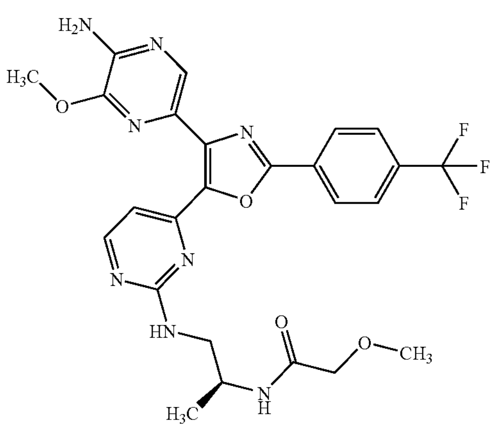 | Chiral 0.0030 | 0.82 | 559.2 | F | (S)-N-(1-(4-(4-(5-amino-6-methoxypyrazin-2-yl)-2-(4-(trifluoromethyl)phenyl)-oxazol-5-yl)pyrimidin-2-ylamino)propan-2-yl)-2-methoxyacetamide |

TABLE 1-continued

| Compound No. | STRUCTURE | mut-b-RAF (IC50 in uM) | retention time (min) | mass (MH+) | Method | Compound Name |
|---|---|---|---|---|---|---|
| 230 | 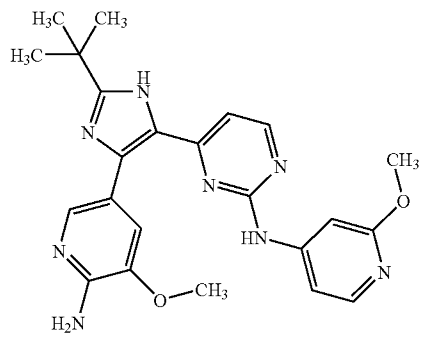 | 0.0001 | 0.40 | 447.2 | D | 4-(4-(6-amino-5-methoxypyridin-3-yl)-2-tert-butyl-1H-imidazol-5-yl)-N-(2-methoxypyridin-4-yl)pyrimidin-2-amine |
| 231 | 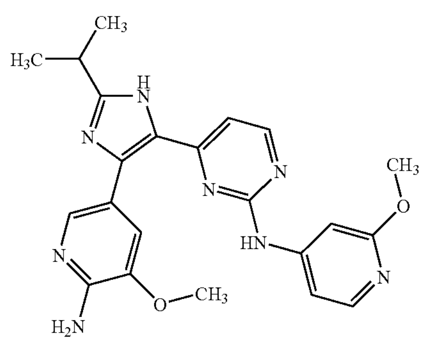 | 0.0002 | 0.37 | 433.1 | D | 4-(4-(6-amino-5-methoxypyridin-3-yl)-2-isopropyl-1H-imidazol-5-yl)-N-(2-methoxypyridin-4-yl)pyrimidin-2-amine |
| 232 | 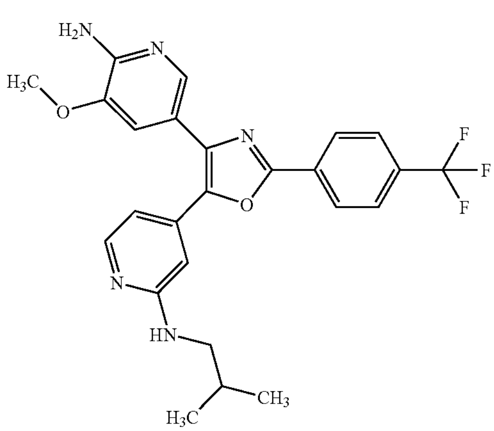 | 0.0084 | 0.75 | 484.3 | F | 4-(4-(6-amino-5-methoxypyridin-3-yl)-2-(4-(trifluoromethyl)phenyl)-oxazol-5-yl)-N-isobutylpyridin-2-amine |

TABLE 1-continued

| Compound No. | STRUCTURE | mut-b-RAF (IC50 in uM) | retention time (min) | mass (MH+) | Method | Compound Name |
|---|---|---|---|---|---|---|
| 233 | 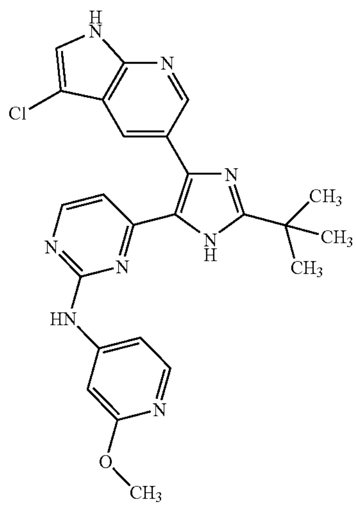 | 0.0003 | 0.52 | 475.2 | D | 4-(2-tert-butyl-4-(3-chloro-1H-pyrrolo[2,3-b]pyridin-5-yl)-1H-imidazol-5-yl)-N-(2-methoxypyridin-4-yl)pyrimidin-2-amine |
| 235 | 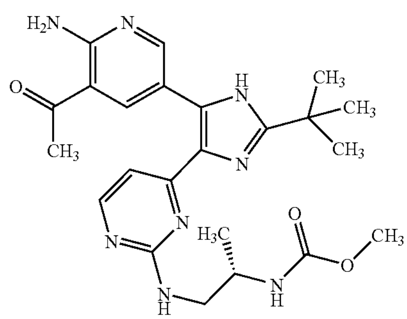 | Chiral 0.0004 | 0.50 | 467.3 | C | (S)-methyl-1-(4-(5-(5-acetyl-6-aminopyridin-3-yl)-2-tert-butyl-1H-imidazol-4-yl)pyrimidin-2-ylamino)propan-2-ylcarbamate |
| 236 | 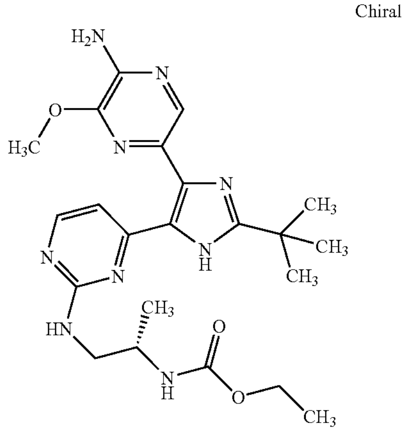 | Chiral 0.0001 | 0.55 | 470.2 | C | (S)-ethyl 1-(4-(4-(5-amino-6-methoxypyrazin-2-yl)-2-tert-butyl-1H-imidazol-5-yl)pyrimidin-2-ylamino)propan-2-ylcarbamate |

TABLE 1-continued

| Compound No. | STRUCTURE | | mut-b-RAF (IC50 in uM) | retention time (min) | mass (MH+) | Method | Compound Name |
|---|---|---|---|---|---|---|---|
| 237 | 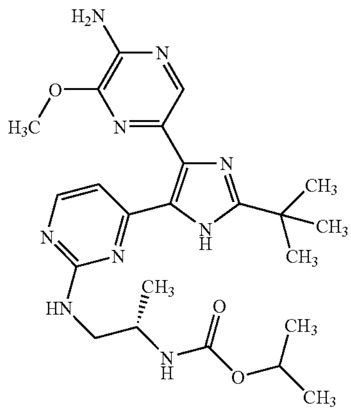 | Chiral | 0.0001 | 0.60 | 484.2 | C | (S)-isopropyl 1-(4-(4-(5-amino-6-methoxypyrazin-2-yl)-2-tert-butyl-1H-imidazol-5-yl)pyrimidin-2-ylamino)propan-2-ylcarbamate |
| 238 | 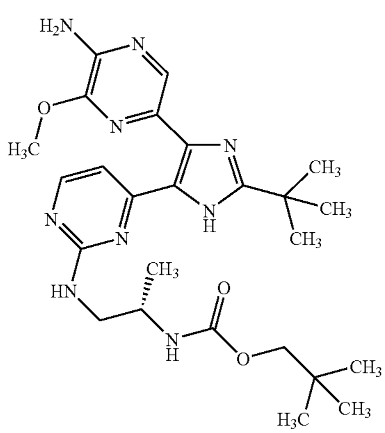 | Chiral | 0.0001 | 0.70 | 512.2 | D | (S)-neopentyl 1-(4-(4-(5-amino-6-methoxypyrazin-2-yl)-2-tert-butyl-1H-imidazol-5-yl)pyrimidin-2-ylamino)propan-2-ylcarbamate |
| 239 | 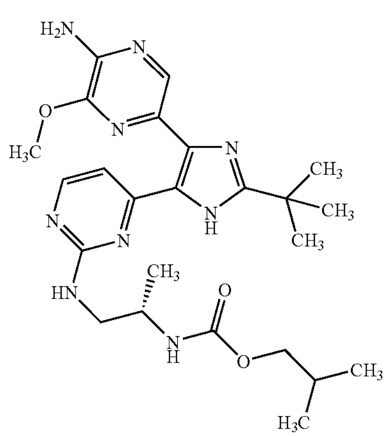 | Chiral | 0.0001 | 0.66 | 498.2 | C | (S)-isobutyl 1-(4-(4-(5-amino-6-methoxypyrazin-2-yl)-2-tert-butyl-1H-imidazol-5-yl)pyrimidin-2-ylamino)propan-2-ylcarbamate |

TABLE 1-continued

| Compound No. | STRUCTURE | mut-b-RAF (IC50 in uM) | retention time (min) | mass (MH+) | Method | Compound Name |
|---|---|---|---|---|---|---|
| 240 | Chiral | 0.0138 | 0.63 | 448.3 | C | (S)-methyl 1-(4-(2-tert-butyl-5-(1H-indol-5-yl)-1H-imidazol-4-yl)pyrimidin-2-ylamino)propan-2-ylcarbamate |
| 241 | 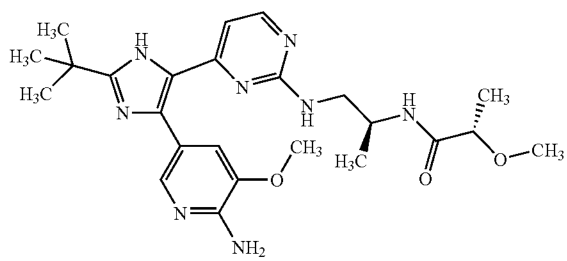 | 0.0007 | 0.49 | 483.3 | C | (S)-N-((S)-1-(4-(4-(6-amino-5-methoxypyridin-3-yl)-2-tert-butyl-1H-imidazol-5-yl)pyrimidin-2-ylamino)propan-2-yl)-2-methoxypropanamide |
| 242 | 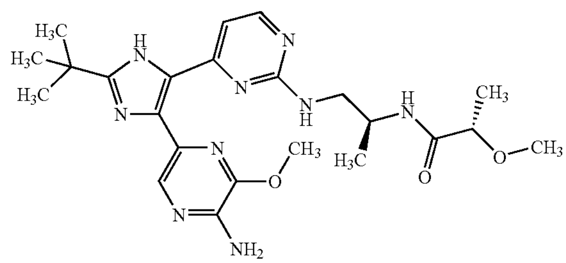 | 0.0002 | 0.54 | 484.3 | C | (S)-N-((S)-1-(4-(4-(5-amino-6-methoxypyrazin-2-yl)-2-tert-butyl-1H-imidazol-5-yl)pyrimidin-2-ylamino)propan-2-yl)-2-methoxypropanamide |
| 243 | 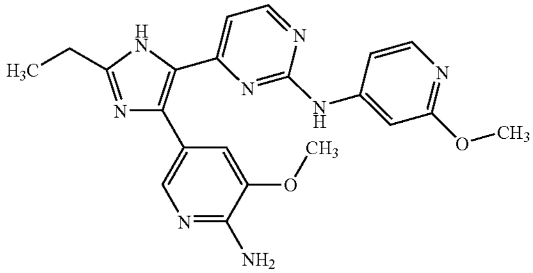 | 0.0004 | 0.34 | 419.1 | D | 4-(4-(6-amino-5-methoxypyridin-3-yl)-2-ethyl-1H-imidazol-5-yl)-N-(2-methoxypyridin-4-yl)pyrimidin-2-amine |
| 244 | 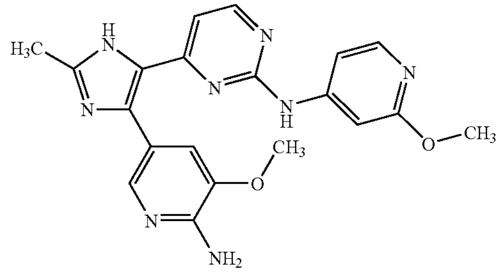 | 0.0030 | 0.32 | 405.1 | D | 4-(4-(6-amino-5-methoxypyridin-3-yl)-2-methyl-1H-imidazol-5-yl)-N-(2-methoxypyridin-4-yl)pyrimidin-2-amine |

TABLE 1-continued

| Compound No. | STRUCTURE | mut-b-RAF (IC50 in uM) | retention time (min) | mass (MH+) | Method | Compound Name |
|---|---|---|---|---|---|---|
| 245 | 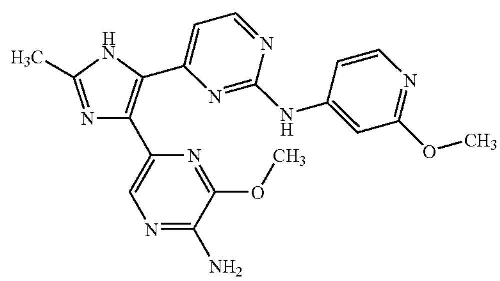 | 0.0110 | 0.38 | 406.1 | D | 4-(4-(5-amino-6-methoxypyrazin-2-yl)-2-methyl-1H-imidazol-5-yl)-N-(2-methoxypyridin-4-yl)pyrimidin-2-amine |
| 246 | 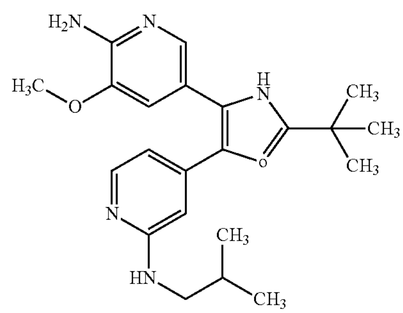 | 0.0001 | 0.62 | 396.2 | E | 4-(4-(6-amino-5-methoxypyridin-3-yl)-2-tert-butyloxazol-5-yl)-N-isobutylpyridin-2-amine |
| 247 | 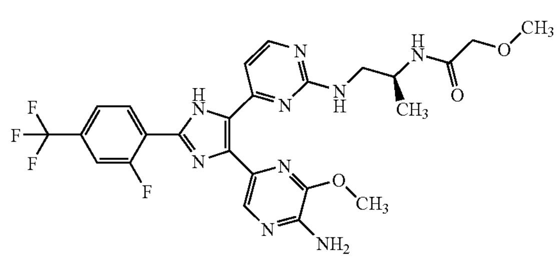 | 0.0001 | 0.73 | 576.3 | C | (S)-N-(1-(4-(4-(5-amino-6-methoxypyrazin-2-yl)-2-(2-fluoro-4-(trifluoromethyl)phenyl)-1H-imidazol-5-yl)pyrimidin-2-ylamino)propan-2-yl)-2-methoxyacetamide |
| 248 | 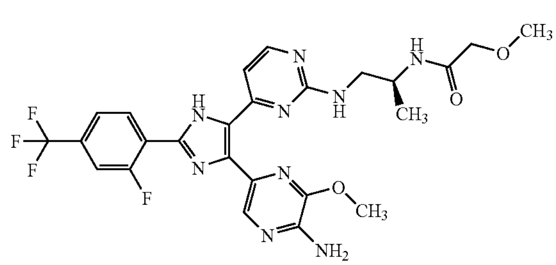 | 0.0001 | 0.73 | 576.3 | C | (S)-N-(1-(4-(4-(5-amino-6-methoxypyrazin-2-yl)-2-(2-fluoro-4-(trifluoromethyl)phenyl)-1H-imidazol-5-yl)pyrimidin-2-ylamino)propan-2-yl)-2-methoxyacetamide |
| 249 | 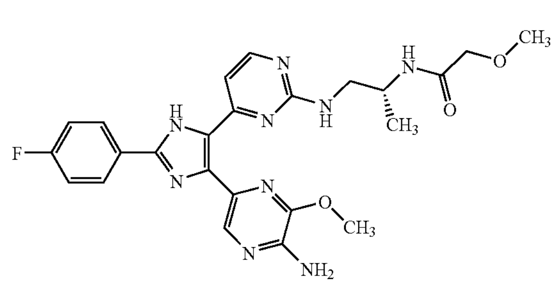 | 0.0120 | 0.59 | 508.3 | C | (R)-N-(1-(4-(4-(5-amino-6-methoxypyrazin-2-yl)-2-(4-fluorophenyl)-1H-imidazol-5-yl)pyrimidin-2-ylamino)propan-2-yl)-2-methoxyacetamide |

TABLE 1-continued

| Compound No. | STRUCTURE | mut-b-RAF (IC50 in uM) | retention time (min) | mass (MH+) | Method | Compound Name |
|---|---|---|---|---|---|---|
| 250 | Chiral | 0.0001 | 0.45 | 454.1 | C | (S)-N-(1-(4-(4-(5-amino-6-methoxypyrazin-2-yl)-2-cyclopropyl-1H-imidazol-5-yl)pyrimidin-2-ylamino)propan-2-yl)-2-methoxyacetamide |
| 251 | Chiral | 0.00004 | 0.57 | 454.1 | C | (S)-methyl 1-(4-(4-(5-amino-6-methoxypyrazin-2-yl)-2-(1-methylcyclopropyl)-1H-imidazol-5-yl)pyrimidin-2-ylamino)propan-2-ylcarbamate |
| 252 | Chiral | 0.0024 | 0.59 | 522.3 | C | (S)-N-(1-(4-(4-(5-amino-6-methoxy-3-methylpyrazin-2-yl)-2-(4-fluorophenyl)-1H-imidazol-5-yl)pyrimidin-2-ylamino)propan-2-yl)-2-methoxyacetamide |

TABLE 1-continued

| Compound No. | STRUCTURE | mut-b-RAF (IC50 in uM) | retention time (min) | mass (MH+) | Method | Compound Name |
| --- | --- | --- | --- | --- | --- | --- |
| 253 | 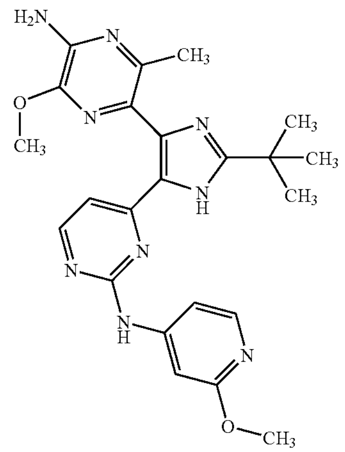 | 0.0062 | 0.44 | 462.3 | C | 4-(4-(5-amino-6-methoxy-3-methylpyrazin-2-yl)-2-tert-butyl-1H-imidazol-5-yl)-N-(2-methoxypyridin-4-yl)pyrimidin-2-amine |
| 254 | Chiral | 0.0038 | 0.52 | 498.3 | C | (S)-N-((S)-1-(4-(4-(5-amino-6-methoxy-3-methylpyrazin-2-yl)-2-tert-butyl-1H-imidazol-5-yl)pyrimidin-2-ylamino)propan-2-yl)-2-methoxypropanamide |
| 255 | Chiral | 0.0039 | 0.45 | 468.3 | C | (S)-N-(1-(4-(4-(5-amino-6-methoxy-3-methylpyrazin-2-yl)-2-cyclopropyl-1H-imidazol-5-yl)pyrimidin-2-ylamino)propan-2-yl)-2-methoxyacetamide |

TABLE 1-continued

| Compound No. | STRUCTURE | mut-b-RAF (IC50 in uM) | retention time (min) | mass (MH+) | Method | Compound Name |
|---|---|---|---|---|---|---|
| 256 | 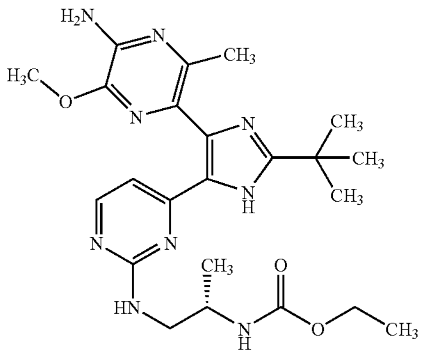 | Chiral 0.0011 | 0.55 | 484.4 | C | (S)-ethyl 1-(4-(4-(5-amino-6-methoxy-3-methylpyrazin-2-yl)-2-tert-butyl-1H-imidazol-5-yl)pyrimidin-2-ylamino)propan-2-ylcarbamate |
| 257 | 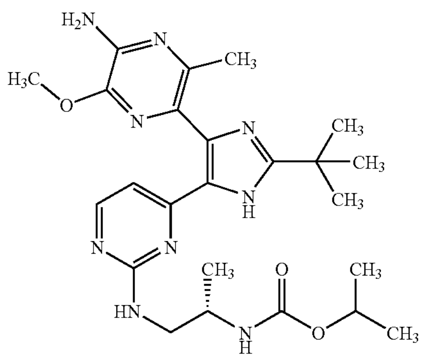 | Chiral 0.0012 | 0.58 | 498.4 | C | (S)-isopropyl 1-(4-(4-(5-amino-6-methoxy-3-methylpyrazin-2-yl)-2-tert-butyl-1H-imidazol-5-yl)pyrimidin-2-ylamino)propan-2-ylcarbamate |
| 258 | 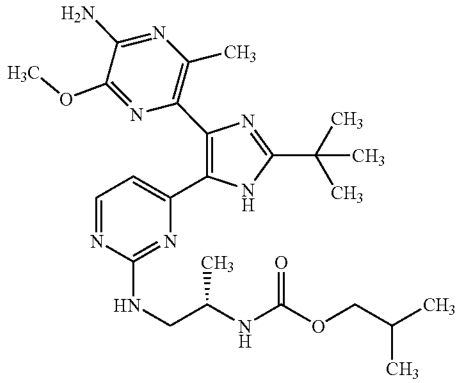 | Chiral 0.0011 | 0.64 | 512.4 | C | (S)-isobutyl 1-(4-(4-(5-amino-6-methoxy-3-methylpyrazin-2-yl)-2-tert-butyl-1H-imidazol-5-yl)pyrimidin-2-ylamino)propan-2-ylcarbamate |

TABLE 1-continued

| Compound No. | STRUCTURE | mut-b-RAF (IC50 in uM) | retention time (min) | mass (MH+) | Method | Compound Name |
|---|---|---|---|---|---|---|
| 259 | 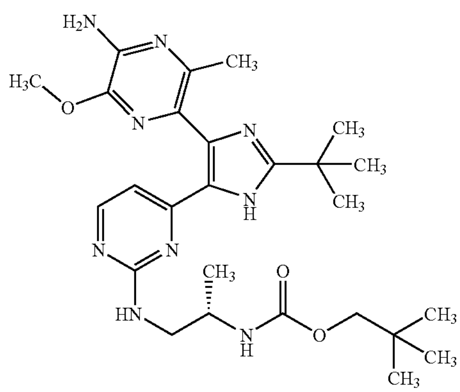 | Chiral 0.0015 | 0.70 | 525.65 | C | (S)-neopentyl 1-(4-(4-(5-amino-6-methoxy-3-methylpyrazin-2-yl)-2-tert-butyl-1H-imidazol-5-yl)pyrimidin-2-ylamino)propan-2-ylcarbamate |
| 260 | 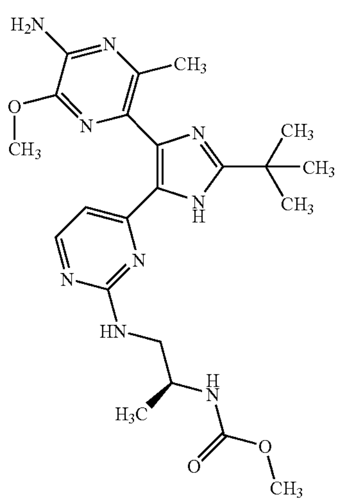 | Chiral 0.001 | 0.49 | 470.3 | C | (S)-methyl 1-(4-(4-(5-amino-6-methoxy-3-methylpyrazin-2-yl)-2-tert-butyl-1H-imidazol-5-yl)pyrimidin-2-ylamino)propan-2-ylcarbamate |
| 261 | 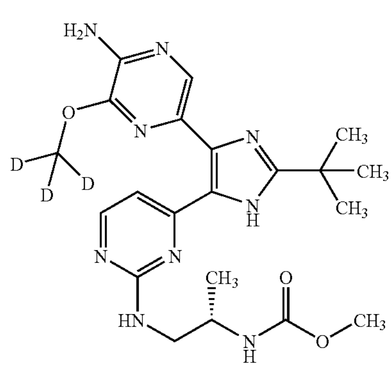 | Chiral 0.0001 | 0.52 | 459.1 | C | (S)-methyl 1-(4-(4-(5-amino-6-(D$_3$-methoxy)pyrazin-2-yl)-2-tert-butyl-1H-imidazol-5-yl)pyrimidin-2-ylamino)propan-2-ylcarbamate |

TABLE 1-continued

| Compound No. | STRUCTURE | mut-b-RAF (IC50 in uM) | retention time (min) | mass (MH+) | Method | Compound Name |
|---|---|---|---|---|---|---|
| 262 | 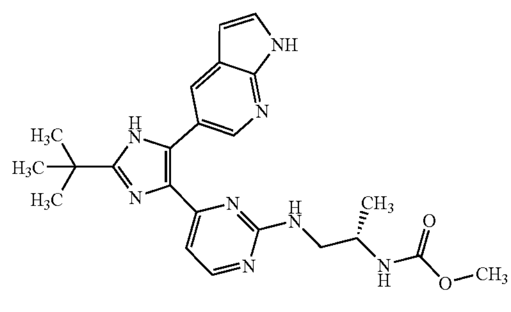 | Chiral 0.0002 | 0.53 | 449.3 | C | (S)-methyl 1-(4-(2-tert-butyl-5-(1H-pyrrolo[2,3-b]pyridin-5-yl)-1H-imidazol-4-yl)pyrimidin-2-ylamino)propan-2-ylcarbamate |
| 263 | 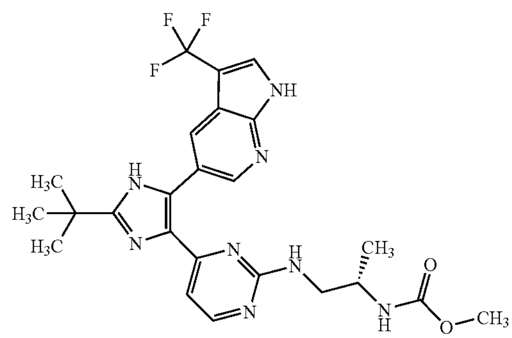 | Chiral 0.065 | 0.68 | 517.2 | C | (S)-methyl 1-(4-(2-tert-butyl-5-(3-(trifluoromethyl)-1H-pyrrolo[2,3-b]pyridin-5-yl)-1H-imidazol-4-yl)pyrimidin-2-ylamino)propan-2-ylcarbamate |
| 264 | 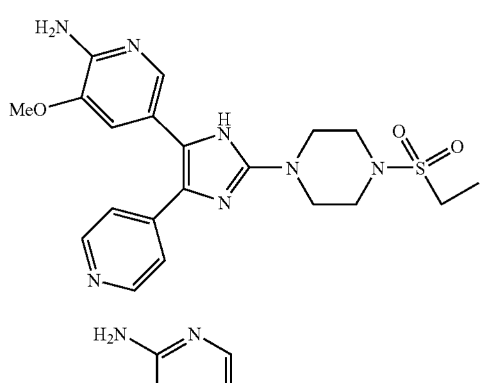 | 0.040 | 1.32 | 444.2 | C | 5-(2-(4-(ethylsulfonyl)piperazin-1-yl)-4-(pyridin-4-yl)-1H-imidazol-5-yl)-3-methoxypyridin-2-amine |
| 265 | 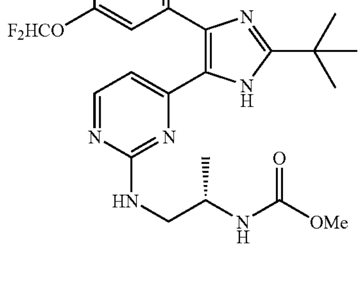 | 0.00001 | 0.55 | 491.0 | C | (S)-methyl 1-(4-(4-(6-amino-5-(difluoromethoxy)pyridin-3-yl)-2-tert-butyl-1H-imidazol-5-yl)pyrimidin-2-ylamino)propan-2-ylcarbamate |

TABLE 1-continued

| Compound No. | STRUCTURE | mut-b-RAF (IC50 in uM) | retention time (min) | mass (MH+) | Method | Compound Name |
|---|---|---|---|---|---|---|
| P1 | 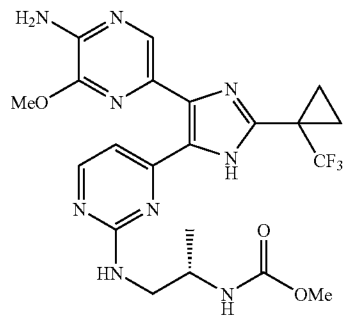 | | | | | (S)-methyl 1-(4-(4-(5-amino-6-methoxypyrazin-2-yl)-2-(1-(trifluoromethyl)cyclopropyl)-1H-imidazol-5-yl)pyrimidin-2-ylamino)propan-2-ylcarbamate |
| P2 | 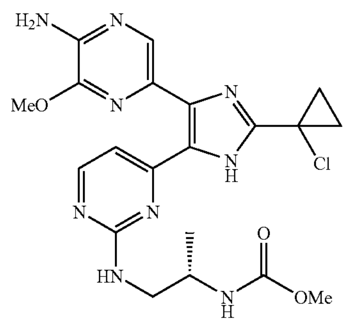 | | | | | (S)-methyl 1-(4-(4-(5-amino-6-methoxypyrazin-2-yl)-2-(1-chlorocyclopropyl)-1H-imidazol-5-yl)pyrimidin-2-ylamino)propan-2-ylcarbamate |
| P3 | 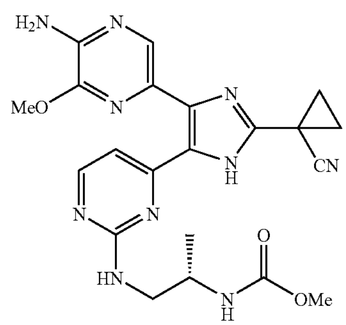 | | | | | (S)-methyl 1-(4-(4-(5-amino-6-methoxypyrazin-2-yl)-2-(1-cyanocyclopropyl)-1H-imidazol-5-yl)pyrimidin-2-ylamino)propan-2-ylcarbamate |
| P4 | 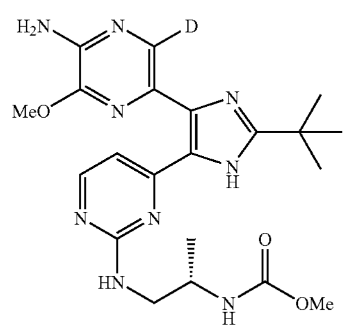 | | | | | (S)-methyl 1-(4-(4-(5-amino-6-methoxy-3-deuteriopyrazin-2-yl)-2-tert-butyl-1H-imidazol-5-yl)pyrimidin-2-ylamino)propan-2-ylcarbamate |

TABLE 1-continued

| Compound No. | STRUCTURE | mut-b-RAF (IC50 in uM) | retention time (min) | mass (MH+) | Method | Compound Name |
|---|---|---|---|---|---|---|
| P5 | 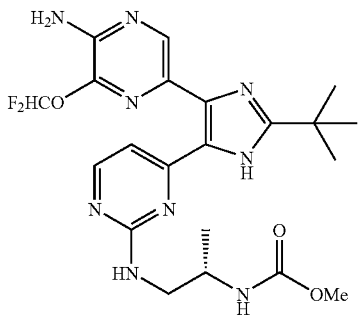 | | | | | (S)-methyl 1-(4-(4-(5-amino-6-(difluoromethoxy)pyrazin-2-yl)-2-tert-butyl-1H-imidazol-5-yl)pyrimidin-2-ylamino)propan-2-ylcarbamate |
| P6 | 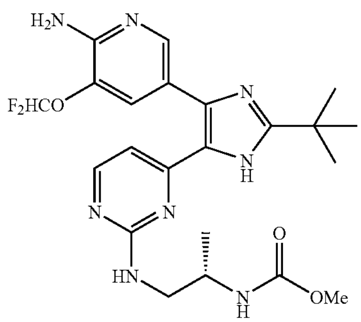 | | | | | (S)-methyl 1-(4-(4-(6-amino-5-(difluoromethoxy)pyridin-3-yl)-2-tert-butyl-1H-imidazol-5-yl)pyrimidin-2-ylamino)propan-2-ylcarbamate |
| P7 | 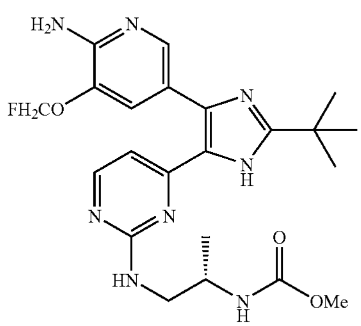 | | | | | (S)-methyl 1-(4-(4-(6-amino-5-(fluoromethoxy)pyridin-3-yl)-2-tert-butyl-1H-imidazol-5-yl)pyrimidin-2-ylamino)propan-2-ylcarbamate |
| P8 | 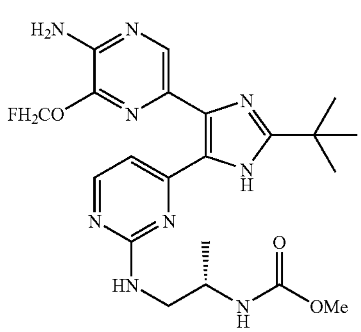 | | | | | (S)-methyl 1-(4-(4-(5-amino-6-(fluoromethoxy)pyrazin-2-yl)-2-tert-butyl-1H-imidazol-5-yl)pyrimidin-2-ylamino)propan-2-ylcarbamate |

TABLE 1-continued

| Compound No. | STRUCTURE | mut-b-RAF (IC50 in uM) | retention time (min) | mass (MH+) | Method | Compound Name |
|---|---|---|---|---|---|---|
| P9 | 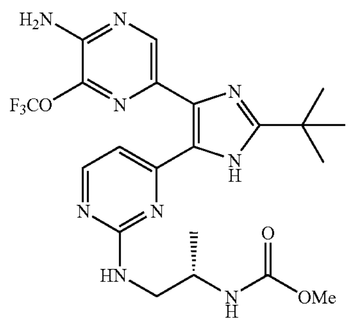 | | | | | (S)-methyl 1-(4-(4-(5-amino-6-(trifluoromethoxy)pyrazin-2-yl)-2-tert-butyl-1H-imidazol-5-yl)pyrimidin-2-ylamino)propan-2-ylcarbamate |
| P10 | 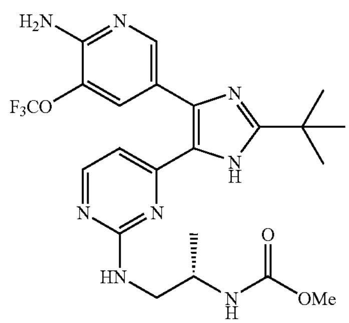 | | | | | (S)-methyl 1-(4-(4-(6-amino-5-(trifluoromethoxy)pyridin-3-yl)-2-tert-butyl-1H-imidazol-5-yl)pyrimidin-2-ylamino)propan-2-ylcarbamate |
| P11 | 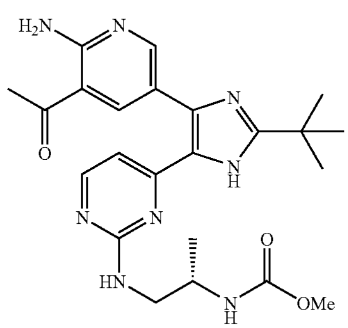 | | | | | (S)-methyl 1-(4-(4-(6-acetyl-5-aminopyrazin-2-yl)-2-tert-butyl-1H-imidazol-5-yl)pyrimidin-2-ylamino)propan-2-ylcarbamate |
| P12 | 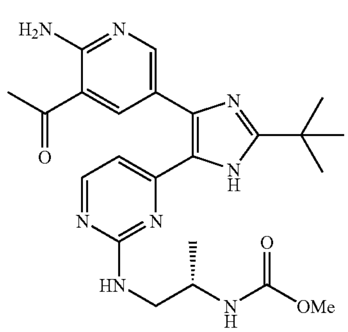 | | | | | (S)-methyl 1-(4-(4-(5-acetyl-6-aminopyridin-3-yl)-2-tert-butyl-1H-imidazol-5-yl)pyrimidin-2-ylamino)propan-2-ylcarbamate |

TABLE 1-continued

| Compound No. | STRUCTURE | mut-b-RAF (IC50 in uM) | retention time (min) | mass (MH+) | Method | Compound Name |
|---|---|---|---|---|---|---|
| P13 | 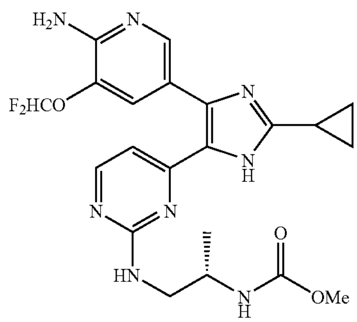 | | | | | (S)-methyl 1-(4-(4-(6-amino-5-(difluoromethoxy)pyridin-3-yl)-2-cyclopropyl-1H-imidazol-5-yl)pyrimidin-2-ylamino)propan-2-ylcarbamate |
| P14 | 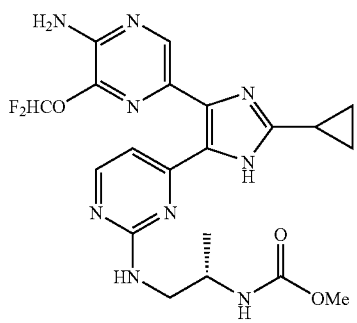 | | | | | (S)-methyl 1-(4-(4-(5-amino-6-(difluoromethoxy)pyrazin-2-yl)-2-cyclopropyl-1H-imidazol-5-yl)pyrimidin-2-ylamino)propan-2-ylcarbamate |
| P15 | 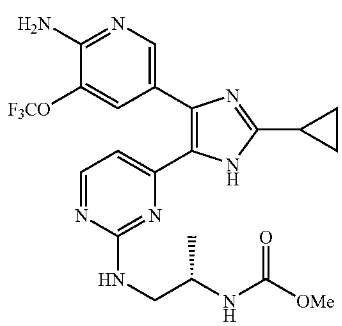 | | | | | (S)-methyl 1-(4-(4-(6-amino-5-(trifluoromethoxy)pyridin-3-yl)-2-cyclopropyl-1H-imidazol-5-yl)pyrimidin-2-ylamino)propan-2-ylcarbamate |
| P16 | 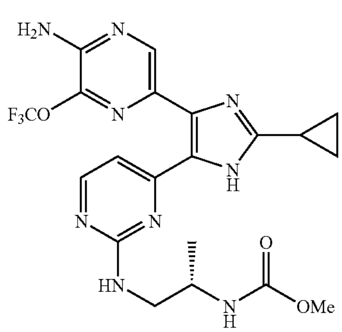 | | | | | (S)-methyl 1-(4-(4-(5-amino-6-(trifluoromethoxy)pyrazin-2-yl)-2-cyclopropyl-1H-imidazol-5-yl)pyrimidin-2-ylamino)propan-2-ylcarbamate |

TABLE 1-continued

| Compound No. | STRUCTURE | mut-b-RAF (IC50 in uM) | retention time (min) | mass (MH+) | Method | Compound Name |
|---|---|---|---|---|---|---|
| P17 | 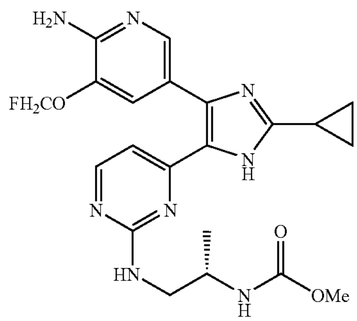 | | | | | (S)-methyl 1-(4-(4-(6-amino-5-(fluoromethoxy)pyridin-3-yl)-2-cyclopropyl-1H-imidazol-5-yl)pyrimidin-2-ylamino)propan-2-ylcarbamate |
| P18 | 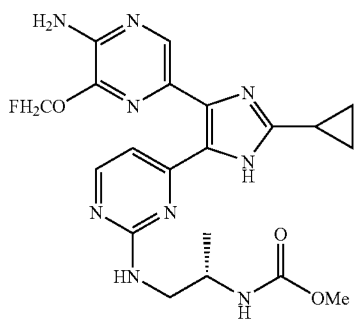 | | | | | (S)-methyl 1-(4-(4-(5-amino-6-(fluoromethoxy)pyrazin-2-yl)-2-cyclopropyl-1H-imidazol-5-yl)pyrimidin-2-ylamino)propan-2-ylcarbamate |
| P19 | 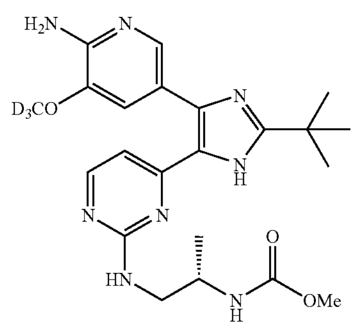 | | | | | (S)-methyl 1-(4-(4-(6-amino-5-(trideuteriomethoxy)pyridin-3-yl)-2-tert-butyl-1H-imidazol-5-yl)pyrimidin-2-ylamino)propan-2-ylcarbamate |

Example 291

Cell Viability Assay Protocol

The Cell Titer-Glo® assay (Promega) was used to measure cell viability. Cells were plated into 96-well black walled tissue culture plates in complete growth media. The plates were then incubated under standard growth conditions of 37° C. and 5% $CO_2$ until the cells had attached to the plates (3-6 hours), then compounds were added to the cells. Compounds were serially diluted in DMSO using 3-fold dilutions and then diluted in complete media before being added to the cells (final DMSO concentration on cells was 0.1-0.2%). The cell number plated per well and the compound incubation time for each cell line are shown in Table 2.

TABLE 2

|  | A375 | G361 | Malme3M | Capan1 | SU86.86 | PC3MM | K1 |
|---|---|---|---|---|---|---|---|
| # Cells/Well Plated | 1000 | 1000 | 1000 | 2000 | 1000 | 1500 | 1500 |
| # Days Compound Incubation | 3 | 4 | 5 | 5 | 5 | 5 | 4 |

After compound incubation, the cell plates were equilibrated to room temperature, culture media was removed, and 200 uL of Cell Titer-Glo® reagent mix was added to each well (1:1 mixture of Cell Titer-Glo® reagent and complete growth media, equilibrated to room temperature). The plates were shaken for 5-10 minutes, then sealed and luminescence was measured (using Trilux plate reader, Perkin Elmer).

Assay background luminescence values were determined from wells which were treated with a potent control compound that completely inhibited cell growth or caused cell death at the highest concentration of 10 uM. Analysis of data was done by subtracting the background luminescence value from each data point, then determining the percent inhibition of total growth (as determined by the values for DMSO-treated wells).

To determine the $EC_{50}$ for each compound, the data were fit using the Levenburg Marquardt algorithm, represented in the XLfit software as $y=A+((B-A)/(1+((C/x)\hat{\ }D)))$, the four parameter dose response model 205, where A is the minimum Y value, B is the maximum Y value, C is the Log $IC_{50}$ and D is the slope. Results for selected compounds are shown in Table 3.

15 mM $MgCl_2$, 0.01% BSA and 1 mM DTT) and dispensed 10 µl per well in assay plates (Greiner white 384 well assay plates #781207) containing 0.5 µl of 40× of a raf kinase inhibitor test compound diluted in 100% DMSO. The plate was incubated for 60 min at room temperature.

The Raf kinase activity reaction was started by the addition of 10 µl per well of 2×ATP diluted in assay buffer. After 3 hours (bRaf(V600E)) or 1 hour (c-Raf), the reactions were stopped with the addition of 10 µl of stop reagent (60 mM EDTA). Phosphorylated product was measured using a rabbit anti-p-MEK (Cell Signaling, #9121) antibody and the Alpha Screen IgG (Protein A) detection Kit (PerkinElmer #6760617R), by the addition of 30 µL to the well of a mixture of the antibody (1:2000 dilution) and detection beads (1:2000 dilution of both beads) in bead buffer (50 mM Tris, pH 7.5, 0.01% Tween20). The additions were carried out under dark conditions to protect the detection beads from light. A lid was placed on top of the plate and incubated for 1 hour at room temperature, then the luminescence was read on a PerkinElmer Envision instrument. The concentration of each compound for 50% inhibition ($IC_{50}$) was calculated by non-linear regression using XL Fit data analysis software.

TABLE 3

| Compound No. | Melanoma | | | Pancreatic | | Prostate | Papillary Thyroid |
| | A375 | G361 | Malme3M | Capan1 | SU86.86 | PC3MM | K1 |
| | | | | $EC_{50}$ (uM) | | | |
|---|---|---|---|---|---|---|---|
| 1 | 0.376 | 0.070 | 0.429 | 0.570 | 0.116 | | |
| 66 | 0.623 | 1.016 | 0.816 | | | | |
| 81 | 0.547 | 0.305 | 0.194 | 0.319 | | | |
| 85 | | | | 0.163 | 0.111 | | |
| 106 | | | | 0.674 | 0.118 | | |
| 163 | | | | 0.535 | 0.028 | 0.083 | |
| 5 | | | | | 0.354 | | 0.892 |
| 198 | | | | | | | 0.787 |
| 9 | | | | | | 0.250 | |

Example 292

Raf/Mek Amplified Luminescence Proximity Homogeneous Assay (Alpha Screen)

Buffers
Assay buffer: 50 mM Tris, pH 7.5, 15 mM $MgCl_2$, 0.01% BSA, 1 mM DTT
Stop buffer: 60 mM EDTA, 0.01% Tween20
Bead buffer: 50 mM Tris, pH 7.5, 0.01% Tween20
Materials
b-Raf(V600E), active: Recombinant in-house material
biotinylated Mek, kinase dead: Recombinant in-house material
Alpha Screen detection kit PerkinElmer, #6760617R
Anti phospho-MEK½ Cell signaling #9121
384 well assay plates: White Greiner plates, #781207
Assay Conditions
b-Raf(V600E) approximately 4 pM
c-Raf approximately 4 nM
biotinylated Mek, Kinase dead approximately 10 nM
ATP 10 µM
Pre-incubation time with compounds 60 min at room temperature
Reaction time 1 or 3 hours at room temperature
Assay Protocol
Raf and biotinylated Mek, kinase dead, were combined at 2× final concentrations in assay buffer (50 mM Tris, pH 7.5, The Raf/Mek Amplified Luminescence Proximity Homogeneous Assay described was used to generate the luminescence and mutant b-Raf(V600E) $IC_{50}$ data for selected Raf Kinase Inhibitors shown in Table 1 above.

The invention claimed is:

1. A compound of the following Formula:

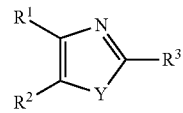

wherein Y is $NR^4$;
$R^1$ is an optionally substituted heteroaryl ring selected from pyrimidine, triazine, pyrazine, pyridazine, or an optionally substituted bicyclic heteroaryl ring system, comprising pyrazinyl, pyridazinyl, triazinyl, or pyrimidinyl fused to a second ring selected from phenyl, pyrrole, pyrazole, triazole, imidazole, piperidine, piperidinone, pyrrolidine, and pyrrolidinone;
$R^2$ is an optionally substituted pyrimidine, or an optionally substituted bicyclic group, comprising a pyrimidinyl ring fused to an additional cyclopentyl, cyclohexyl, pyrrole, imidazole, pyrazole, or piperidine ring;
$R^3$ is optionally substituted alkyl, optionally substituted aryl, optionally substituted heteroaryl, or optionally substituted cycloalkyl; and R⁴ is hydrogen or optionally substituted alkyl,
including tautomers of the central imidazole ring when Y is NH
or a stereoisomer or pharmaceutically acceptable salt thereof.

2. The compound of claim 1, wherein R¹ is optionally substituted pyrazinyl.

3. The compound of claim 1, wherein R³ is optionally substituted phenyl, optionally substituted C1-C6 alkyl, optionally substituted C3-C6 cycloalkyl, or optionally substituted heteroaryl.

4. The compound of claim 3, wherein R³ is unsubstituted phenyl or phenyl substituted with one, two or three substituents.

5. The compound of claim 3, wherein R³ is substituted or unsubstituted C1-C6 alkyl, or R³ is optionally substituted C3-C6 cycloalkyl.

6. The compound of claim 1, which is a compound of the formula:

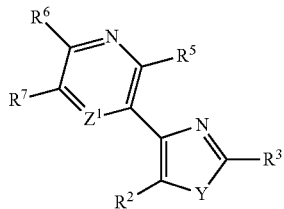

wherein Z¹ is N; and
R⁵, R⁶, R⁷, and R⁸ are independently selected from the group consisting of hydrogen, deuterium, halo, cyano, hydroxy, —C(O)R', —NR"C(O)R', —C(O)NR"₂, —OS(O)₂NR"₂, optionally substituted C1-C6 alkyl, optionally substituted amino, and optionally substituted C1-C6 alkoxy;
R' is optionally substituted alkyl and each R" is independently hydrogen or optionally substituted C1-C4 alkyl;
R², R³, and Y are as defined in claim 1;
R⁶ and R⁷ can be taken together to form an optionally substituted ring selected from selected from phenyl, pyrrole, pyrazole, triazole, imidazole, piperidine, piperidinone, pyrrolidine, and pyrrolidinone;
or a pharmaceutically acceptable salt, isomer, deuterated version or tautomer thereof.

7. The compound of claim 1, which a compound of the formula:

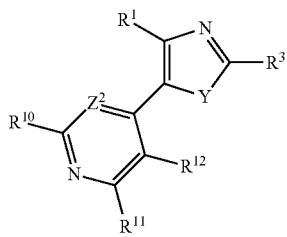

wherein Z² is N; and
R⁹, R¹⁰, R¹¹, and R¹² are independently selected from the group consisting of hydrogen, halo, D, cyano, hydroxy, —NR"C(O)R', optionally substituted alkyl, optionally substituted amino, optionally substituted heteroaryl, and optionally substituted alkoxy;
R' is optionally substituted C1-C4 alkyl and R" is hydrogen or optionally substituted C1-C4 alkyl;
R¹, R³, and Y are as defined in claim 1;
and R¹¹ and R¹² can be taken together to form an additional optionally substituted cyclopentyl, cyclohexyl, pyrrole, imidazole, pyrazole, or piperidine ring
or a pharmaceutically acceptable salt, isomer, deuterated version or tautomer thereof.

8. The compound of claim 7, wherein R¹⁰ is —NHR¹³, wherein R¹³ is selected from the group consisting of optionally substituted alkyl, optionally substituted heterocyclyl, —C(O)R', optionally substituted cycloalkyl, optionally substituted amino, optionally substituted aryl, and optionally substituted heteroaryl.

9. A compound of Formula IV:

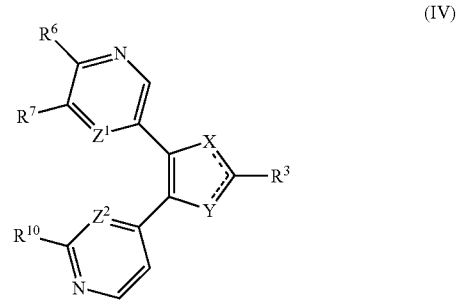

wherein Z¹ and Z² are both N;

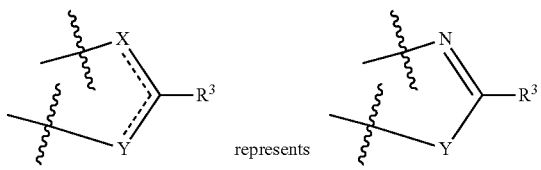

represents where Y is NR⁴;
R³ is optionally substituted phenyl, or a C1-C6 hydrocarbyl group;
R⁴ is H or optionally substituted C1-C6 alkyl;
R⁶ is NHR¹⁴, where R¹⁴ is H or optionally substituted C1-C6 alkyl;
R⁷ is H, D, halo, optionally substituted amino or optionally substituted C1-C4 alkoxy; and
R¹⁰ is NHR¹⁵, wherein R¹⁵ is selected from the group consisting of optionally substituted C1-C6 alkyl, optionally substituted heterocyclyl, —C(O)R', optionally substituted C3-C6 cycloalkyl, optionally substituted amino, optionally substituted aryl, and optionally substituted heteroaryl;
R' is H or optionally substituted C1-C4 alkyl;
or a pharmaceutically acceptable salt thereof, a deuterated version thereof, or a tautomer or stereoisomer thereof.

10. The compound of claim 9, wherein Y is NH or NMe.

11. The compound of claim 1, which is selected from the group consisting of:
(S)—N-(1-(4-(4-(5-amino-6-methoxypyrazin-2-yl)-2-(4-(trifluoromethyl)phenyl)-1H-imidazol-5-yl)pyrimidin-2-ylamino)propan-2-yl)-2-methoxyacetamide;
(S)—N-(1-(4-(4-(5-amino-6-methoxypyrazin-2-yl)-2-(4-fluorophenyl)-1H-imidazol-5-yl)pyrimidin-2-ylamino)propan-2-yl)-2-methoxyacetamide;

(S)—N-(1-(4-(4-(5-amino-6-methoxypyrazin-2-yl)-2-tert-butyl-1H-imidazol-5-yl)pyrimidin-2-ylamino)propan-2-yl)-2-methoxyacetamide;

(S)-methyl 1-(4-(4-(5-amino-6-methoxypyrazin-2-yl)-2-tert-butyl-1H-imidazol-5-yl)pyrimidin-2-ylamino)propan-2-ylcarbamate;

4-(4-(5-amino-6-methoxypyrazin-2-yl)-2-tert-butyl-1H-imidazol-5-yl)-N-(2-methoxypyridin-4-yl)pyrimidin-2-amine;

N-(2-(4-(5-(5-amino-6-methoxypyrazin-2-yl)-2-(4-fluorophenyl)-1H-imidazol-4-yl)pyrimidin-2-ylamino)ethyl)-2-methoxyacetamide;

(S)—N-(1-(4-(4-(5-amino-6-methoxypyrazin-2-yl)-2-(4-fluorophenyl)oxazol-5-yl)pyrimidin-2-ylamino)propan-2-yl)-2-methoxyacetamide;

4-(4-(5-amino-6-methoxypyrazin-2-yl)-2-(4-(trifluoromethyl)phenyl)oxazol-5-yl)-N-isobutylpyrimidin-2-amine;

(S)—N-(1-(4-(4-(5-amino-6-methoxypyrazin-2-yl)-2-isopropyl-1H-imidazol-5-yl)pyrimidin-2-ylamino)propan-2-yl)-2-methoxyacetamide;

(S)—N-(1-(4-(4-(5-amino-6-methoxypyrazin-2-yl)-2-(4-(trifluoromethyl)phenyl)oxazol-5-yl)pyrimidin-2-ylamino)propan-2-yl)-2-methoxyacetamide;

(S)-ethyl 1-(4-(4-(5-amino-6-methoxypyrazin-2-yl)-2-tert-butyl-1H-imidazol-5-yl)pyrimidin-2-ylamino)propan-2-ylcarbamate;

(S)-isopropyl 1-(4-(4-(5-amino-6-methoxypyrazin-2-yl)-2-tert-butyl-1H-imidazol-5-yl)pyrimidin-2-ylamino)propan-2-ylcarbamate;

(S)-neopentyl 1-(4-(4-(5-amino-6-methoxypyrazin-2-yl)-2-tert-butyl-1H-imidazol-5-yl)pyrimidin-2-ylamino)propan-2-ylcarbamate;

(S)-isobutyl 1-(4-(4-(5-amino-6-methoxypyrazin-2-yl)-2-tert-butyl-1H-imidazol-5-yl)pyrimidin-2-ylamino)propan-2-ylcarbamate;

(S)—N—((S)-1-(4-(4-(5-amino-6-methoxypyrazin-2-yl)-2-tert-butyl-1H-imidazol-5-yl)pyrimidin-2-ylamino)propan-2-yl)-2-methoxypropanamide;

4-(4-(5-amino-6-methoxypyrazin-2-yl)-2-methyl-1H-imidazol-5-yl)-N-(2-methoxypyridin-4-yl)pyrimidin-2-amine;

(S)—N-(1-(4-(4-(5-amino-6-methoxypyrazin-2-yl)-2-(2-fluoro-4-(trifluoromethyl)phenyl)-1H-imidazol-5-yl)pyrimidin-2-ylamino)propan-2-yl)-2-methoxyacetamide;

(S)—N-(1-(4-(4-(5-amino-6-methoxypyrazin-2-yl)-2-(2-fluoro-4-(trifluoromethyl)phenyl)-1H-imidazol-5-yl)pyrimidin-2-ylamino)propan-2-yl)-2-methoxyacetamide;

(R)—N-(1-(4-(4-(5-amino-6-methoxypyrazin-2-yl)-2-(4-fluorophenyl)-1H-imidazol-5-yl)pyrimidin-2-ylamino)propan-2-yl)-2-methoxyacetamide;

(S)—N-(1-(4-(4-(5-amino-6-methoxypyrazin-2-yl)-2-cyclopropyl-1H-imidazol-5-yl)pyrimidin-2-ylamino)propan-2-yl)-2-methoxyacetamide;

(S)-methyl 1-(4-(4-(5-amino-6-methoxypyrazin-2-yl)-2-(1-methylcyclopropyl)-1H-imidazol-5-yl)pyrimidin-2-ylamino)propan-2-ylcarbamate;

(S)—N-(1-(4-(4-(5-amino-6-methoxy-3-methylpyrazin-2-yl)-2-(4-fluorophenyl)-1H-imidazol-5-yl)pyrimidin-2-ylamino)propan-2-yl)-2-methoxyacetamide;

4-(5-amino-6-methoxy-3-methylpyrazin-2-yl)-2-tert-butyl-1H-imidazol-5-yl)-N-(2-methoxypyridin-4-yl)pyrimidin-2-amine;

(S)—N—((S)-1-(4-(4-(5-amino-6-methoxy-3-methylpyrazin-2-yl)-2-tert-butyl-1H-imidazol-5-yl)pyrimidin-2-ylamino)propan-2-yl)-2-methoxypropanamide;

(S)—N-(1-(4-(4-(5-amino-6-methoxy-3-methylpyrazin-2-yl)-2-cyclopropyl-1H-imidazol-5-yl)pyrimidin-2-ylamino)propan-2-yl)-2-methoxyacetamide;

(S)-ethyl 1-(4-(4-(5-amino-6-methoxy-3-methylpyrazin-2-yl)-2-tert-butyl-1H-imidazol-5-yl)pyrimidin-2-ylamino)propan-2-ylcarbamate;

(S)-isopropyl 1-(4-(4-(5-amino-6-methoxy-3-methylpyrazin-2-yl)-2-tert-butyl-1H-imidazol-5-yl)pyrimidin-2-ylamino)propan-2-ylcarbamate;

(S)-isobutyl 1-(4-(4-(5-amino-6-methoxy-3-methylpyrazin-2-yl)-2-tert-butyl-1H-imidazol-5-yl)pyrimidin-2-ylamino)propan-2-ylcarbamate;

(S)-neopentyl 1-(4-(4-(5-amino-6-methoxy-3-methylpyrazin-2-yl)-2-tert-butyl-1H-imidazol-5-yl)pyrimidin-2-ylamino)propan-2-ylcarbamate;

(S)-methyl 1-(4-(4-(5-amino-6-methoxy-3-methylpyrazin-2-yl)-2-tert-butyl-1H-imidazol-5-yl)pyrimidin-2-ylamino)propan-2-ylcarbamate;

(S)-methyl 1-(4-(4-(5-amino-6-(D$_3$-methoxy)pyrazin-2-yl)-2-tert-butyl-1H-imidazol-5-yl)pyrimidin-2-ylamino)propan-2-ylcarbamate;

(S)-methyl 1-(4-(4-(5-amino-6-methoxypyrazin-2-yl)-2-(1-(trifluoromethyl)cyclopropyl)-1H-imidazol-5-yl)pyrimidin-2-ylamino)propan-2-ylcarbamate;

(S)-methyl 1-(4-(4-(5-amino-6-methoxypyrazin-2-yl)-2-(1-chlorocyclopropyl)-1H-imidazol-5-yl)pyrimidin-2-ylamino)propan-2-ylcarbamate;

(S)-methyl 1-(4-(4-(5-amino-6-methoxypyrazin-2-yl)-2-(1-cyanocyclopropyl)-1H-imidazol-5-yl)pyrimidin-2-ylamino)propan-2-ylcarbamate;

(S)-methyl 1-(4-(4-(5-amino-6-methoxy-3-deuteriopyrazin-2-yl)-2-tert-butyl-1H-imidazol-5-yl)pyrimidin-2-ylamino)propan-2-ylcarbamate;

(S)-methyl 1-(4-(4-(5-amino-6-(difluoromethoxy)pyrazin-2-yl)-2-tert-butyl-1H-imidazol-5-yl)pyrimidin-2-ylamino)propan-2-ylcarbamate;

(S)-methyl 1-(4-(4-(6-amino-5-(difluoromethoxy)pyridin-3-yl)-2-tert-butyl-1H-imidazol-5-yl)pyrimidin-2-ylamino)propan-2-ylcarbamate;

(S)-methyl 1-(4-(4-(6-amino-5-(fluoromethoxy)pyridin-3-yl)-2-tert-butyl-1H-imidazol-5-yl)pyrimidin-2-ylamino)propan-2-ylcarbamate;

(S)-methyl 1-(4-(4-(5-amino-6-(fluoromethoxy)pyrazin-2-yl)-2-tert-butyl-1H-imidazol-5-yl)pyrimidin-2-ylamino)propan-2-ylcarbamate;

(S)-methyl 1-(4-(4-(5-amino-6-(trifluoromethoxy)pyrazin-2-yl)-2-tert-butyl-1H-imidazol-5-yl)pyrimidin-2-ylamino)propan-2-ylcarbamate;

(S)-methyl 1-(4-(4-(6-acetyl-5-aminopyrazin-2-yl)-2-tert-butyl-1H-imidazol-5-yl)pyrimidin-2-ylamino)propan-2-ylcarbamate;

(S)-methyl 1-(4-(4-(5-amino-6-(difluoromethoxy)pyrazin-2-yl)-2-cyclopropyl-1H-imidazol-5-yl)pyrimidin-2-ylamino)propan-2-ylcarbamate;

(S)-methyl 1-(4-(4-(5-amino-6-(trifluoromethoxy)pyrazin-2-yl)-2-cyclopropyl-1H-imidazol-5-yl)pyrimidin-2-ylamino)propan-2-ylcarbamate;

(S)-methyl 1-(4-(4-(6-amino-5-(fluoromethoxy)pyridin-3-yl)-2-cyclopropyl-1H-imidazol-5-yl)pyrimidin-2-ylamino)propan-2-ylcarbamate;

(S)-methyl 1-(4-(4-(5-amino-6-(fluoromethoxy)pyrazin-2-yl)-2-cyclopropyl-1H-imidazol-5-yl)pyrimidin-2-ylamino)propan-2-ylcarbamate;

or a pharmaceutically acceptable salt thereof.

12. The compound of claim 1, which is selected from the group consisting of

- (S)—N-(1-(4-(4-(5-amino-6-methoxypyrazin-2-yl)-2-(4-(trifluoromethyl)phenyl)-1H-imidazol-5-yl)pyrimidin-2-ylamino)propan-2-yl)-2-methoxyacetamide;
- (S)—N-(1-(4-(4-(5-amino-6-methoxypyrazin-2-yl)-2-(4-fluorophenyl)-1H-imidazol-5-yl)pyrimidin-2-ylamino)propan-2-yl)-2-methoxyacetamide;
- (S)—N-(1-(4-(4-(5-amino-6-methoxypyrazin-2-yl)-2-tert-butyl-1H-imidazol-5-yl)pyrimidin-2-ylamino)propan-2-yl)-2-methoxyacetamide;
- (S)-methyl 1-(4-(4-(5-amino-6-methoxypyrazin-2-yl)-2-tert-butyl-1H-imidazol-5-yl)pyrimidin-2-ylamino)propan-2-ylcarbamate;
- (S)—N—((S)-1-(4-(4-(5-amino-6-methoxypyrazin-2-yl)-2-tert-butyl-1H-imidazol-5-yl)pyrimidin-2-ylamino)propan-2-yl)-2-methoxypropanamide;
- 4-(4-(6-amino-5-methoxypyridin-3-yl)-2-ethyl-1H-imidazol-5-yl)-N-(2-methoxypyridin-4-yl)pyrimidin-2-amine;
- 4-(4-(5-amino-6-methoxypyrazin-2-yl)-2-tert-butyl-1H-imidazol-5-yl)-N-(2-methoxypyridin-4-yl)pyrimidin-2-amine;
- (S)—N-(1-(4-(4-(5-amino-6-methoxypyrazin-2-yl)-2-cyclopropyl-1H-imidazol-5-yl)pyrimidin-2-ylamino)propan-2-yl)-2-methoxyacetamide;
- (S)-methyl 1-(4-(4-(5-amino-6-methoxypyrazin-2-yl)-2-(1-methylcyclopropyl)-1H-imidazol-5-yl)pyrimidin-2-ylamino)propan-2-ylcarbamate; and
- (S)—N-(1-(4-(4-(5-amino-6-methoxypyrazin-2-yl)-2-(4-fluorophenyl)oxazol-5-yl)pyrimidin-2-ylamino)propan-2-yl)-2-methoxyacetamide.

13. A pharmaceutical composition comprising a compound of claim 1, admixed with at least one pharmaceutically acceptable excipient.

* * * * *